(12) United States Patent
Cicortas Gunnarsson et al.

(10) Patent No.: US 9,145,461 B2
(45) Date of Patent: *Sep. 29, 2015

(54) ANTIBODIES

(71) Applicant: Affitech Research AS, Oslo (NO)

(72) Inventors: Lavinia Diana Cicortas Gunnarsson, Oslo (NO); Didrik Paus, Oslo (NO)

(73) Assignee: Affitech Research AS, Oslo (NO)

(*) Notice: Subject to any disclaimer, the term of this patent is extended or adjusted under 35 U.S.C. 154(b) by 0 days.

This patent is subject to a terminal disclaimer.

(21) Appl. No.: 13/870,058

(22) Filed: Apr. 25, 2013

(65) Prior Publication Data

US 2013/0236535 A1  Sep. 12, 2013

Related U.S. Application Data

(63) Continuation of application No. 12/797,184, filed on Jun. 9, 2010, now Pat. No. 8,461,304.

(60) Provisional application No. 61/185,448, filed on Jun. 9, 2009, provisional application No. 61/302,768, filed on Feb. 9, 2010.

(30) Foreign Application Priority Data

Jun. 9, 2009  (GB) .................................. 0909906.0

(51) Int. Cl.
| | |
|---|---|
| *C07K 16/00* | (2006.01) |
| *C12P 21/08* | (2006.01) |
| *A61K 39/395* | (2006.01) |
| *A61K 39/40* | (2006.01) |
| *C07K 16/28* | (2006.01) |
| *A61K 45/06* | (2006.01) |
| *C07K 1/00* | (2006.01) |
| *A61K 39/00* | (2006.01) |

(52) U.S. Cl.
CPC ......... *C07K 16/2866* (2013.01); *A61K 39/3955* (2013.01); *A61K 45/06* (2013.01); *A61K 2039/505* (2013.01); *C07K 2316/96* (2013.01); *C07K 2317/21* (2013.01); *C07K 2317/41* (2013.01); *C07K 2317/56* (2013.01); *C07K 2317/565* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 6,989,145 B2 | 1/2006 | Shitara et al. |
|---|---|---|
| 8,039,595 B2 | 10/2011 | Kanda et al. |
| 8,461,304 B2 * | 6/2013 | Cicortas Gunnarsson et al. ............ 530/387.1 |
| 2003/0175273 A1 | 9/2003 | Shitara et al. |
| 2006/0246062 A1 | 11/2006 | Wu et al. |
| 2007/0031896 A1 | 2/2007 | Wu et al. |

FOREIGN PATENT DOCUMENTS

| AU | 2004201168 A1 | 4/2004 |
|---|---|---|
| EP | 1270595 A1 | 1/2003 |
| EP | 1449850 A1 | 8/2004 |
| EP | 1688436 A1 | 8/2006 |
| EP | 1992644 A1 | 11/2008 |
| WO | 0042074 A1 | 7/2000 |
| WO | 0067791 A1 | 11/2000 |
| WO | 02067771 A2 | 9/2002 |
| WO | 2009037454 A2 | 3/2009 |
| WO | 2009086514 A1 | 7/2009 |
| WO | 2010142952 A2 | 12/2010 |

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:11.*

Agrawal, Lokesh, et al., "Multiple determinants are involved in HIV coreceptor use as demonstraed by CCR4/CCL22 interaction in peripheral blood mononuclear cells (PBMCs)," Journal of Leukocyte Biology, 72: 1063-1074 (Nov. 2002).

Andrew, David P., et al., "C—C Chemokine Receptor 4 Expression Defines a Major Subset of Circulating Nonintestinal Memory T Cells of Both Th1 and Th2 Potential," The Journal of Immunology, 166: 103-111 (2001).

Baatar, Dolgor, et al., "Human Peripheral Blood T Regulatory Cells (Tregs), Functionally Primed CCR4+ Tregs and Unprimed CCR4- Tregs, Regulate Effector T Cells Using FasL," The Journal of Immunology, 178: 4891-4900 (2007).

Baatar, Dolgor, et al., "CCR4-Expressing T Cell Tumors Can Be Specifically Controlled via Delivery of Toxins to Chemokine Receptors," The Journal of Immunology, 179: 1996-2004 (2007).

Bayry, Jagadeesh, et al., "In silico identified CCR4 antagonists target regulatory T cells and exert adjuvant activity in vaccination," PNAS, 105(29): 10221-10226 (Jul. 22, 2008).

Burdi, Douglas F., et al., "Small molecule antagonists of the CC chemokine receptor 4 (CCR4)," Bioorganic & Medicinal Chemistry Letters, 17: 3141-3145 (2007).

Chvatchko, Yolande, et al., "A Key Role for CC Chemokine Receptor 4 in Lipopolysaccharide-induced Endotoxic Shock," J. Exp. Med., 191(10): 1755-63 (May 15, 2000).

(Continued)

*Primary Examiner* — Chun Dahle
(74) *Attorney, Agent, or Firm* — Rothwell, Figg, Ernst & Manbeck, p.c.

(57) ABSTRACT

The present invention provides antibodies which bind to an epitope in the extracellular domain of human CC chemokine receptor 4 (CCR4) and which are capable of inhibiting the binding of macrophage-derived chemokine (MDC) and/or thymus and activation regulated chemokine (TARC) to CCR4. Also provided are inter alia immunoconjugates and compositions comprising such antibodies and methods and uses involving such antibodies, particularly in the medical and diagnostic fields.

12 Claims, 32 Drawing Sheets

(56) References Cited

OTHER PUBLICATIONS

Figure 5:
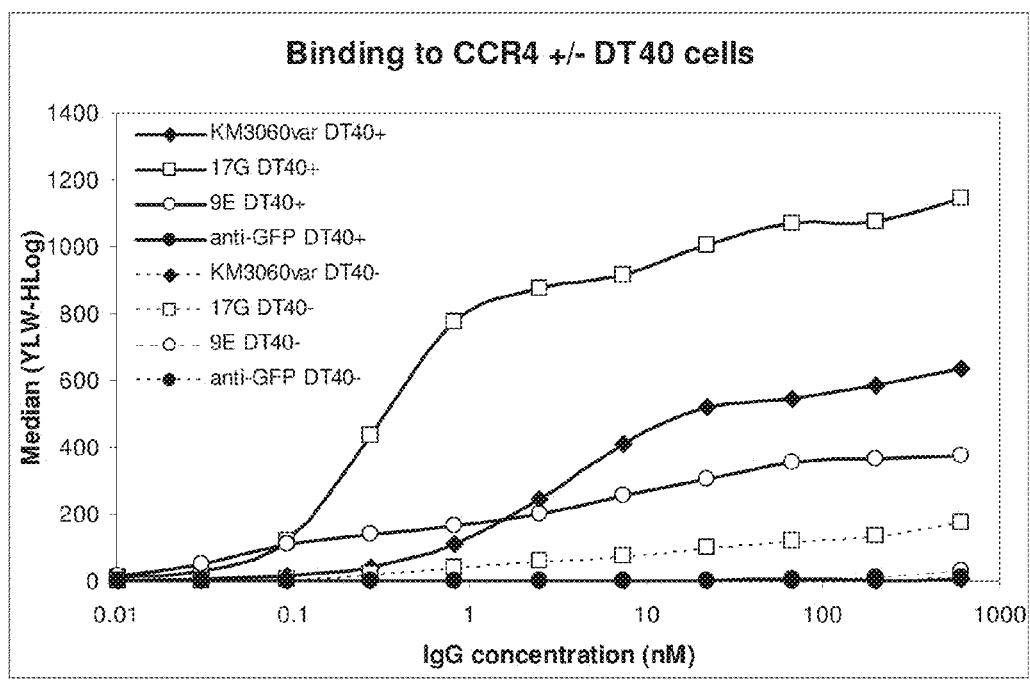

Davies, Matthew N., et al., "Toward the Discovery of Vaccine Adjuvants: Coupling In Silico Screening and In Vitro Analysis of Antagonist Binding to Human and Mouse CCR4 Receptors," PLoS One, 4(11); e8084, 12 pages (2009).

Hoogenboom, Hennie R., et al., "Selection-dominant and nonaccessible epitopes on cell-surface receptors revealed by cell-panning with a large phage antibody library," Eur. J. Biochem., 260: 774-784 (1999).

Ishida, Takashi, et al., "Specific Recruitment of CC Chemokine Receptor 4-Positive Regulatory T Cells in Hodgkin Lymphoma Fosters Immune Privilege," Cancer Research, 66(11): 5716-5722 (Jun. 1, 2006).

Ishida, T., et al., "Defucosylated Humanized Anti-CCR4 MAB KW-0761 As a Novel Immunotherapeutic Agent for Peripheral T-Cell Lymphoma," Annals of Oncology, 19(Supp. 4), No. 513 (Jun. 2008).

Ishida, Takashi, et al., "CXC Chemokine Receptor 3 and CC Chemokine Receptor 4 Expression in T-Cell and NK-Cell Lymphomas with Special Reference to Clinicopathological Significance for Peripheral T-Cell Lymphoma, Unspecified," Clinical Cancer Research, 10: 5494-5500 (Aug. 15, 2004).

Ishida, Takashi, et al., "Clinical Significance of CCR4 Expression in Adult -Cell Leukemia/Lymphoma: Its Close Association with Skin Involvement and Unfavorable Outcome," Clinical Cancer Research, 9: 3625-3634 (Sep. 1, 2003).

Ishida, Takashi, et al., "CCR4 as a novel molecular target for immunotherapy of cancer," Cancer Sci, 97(11): 1139-1146 (Nov. 2006).

Kawasaki. Shin, et al., "Intervention of Thymus and Activation-Regulated Chemokine Attenuates the Development of Allergic Airway Inflammation and Hyperresponsiveness in Mice," The Journal of Immunology, 166:2055-2062 (2001).

Niwa, Rinpei, et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma," Cancer Research, 64: 2127-33 (2004).

Panina-Bordignon, Paola, et al., "The C—C chemokine receptors CCR4 and CCR8 identify airway T cells of allergen-challenged atopic asthmatics," The Journal of Clinical Investigtion, 107(11): 1357-64 (Jun. 2001).

Purandare, Ashok V., et al., "Core exploration in optimization of chemokine receptor CCR4 antagonists," Bioorganic & Medicinal Chemistry Letters, 17: 679-682 (2007).

Sui, Jianhua, et al., "Identification of CD4 and transferrin receptor antibodies by CXCR4 antibody-guided Pathfinder selection," Eur. J. Biochem., 270: 4497-4506 (2003).

Yokoyama, Kazuhiro, et al., "Potent CCR4 antagonists: Synthesis, evaluation, and docking study of 2,4-diaminoquinazolines," Bioorganic & Medicinal Chemistry, 16: 7968-7974 (2008).

Yokoyama, Kazuhiro, et al., "Potent and orally bioavailable CCR4 antagonists: Synthesis and structure-activity relationship study of 2-aminoquinazolines," Bioorganic & Medicinal Chemistry, 17: 64-73 (2009).

Jopling, Louise A., et al., "The Identification, Characterization, and Distribution of Guinea Pig CCR4 and Epitope Mapping of a Blocking Antibody," The Journal of Biological Chemistry, 277(9): 6864-6873 (Mar. 1, 2002).

Perros, F., et al., "Blockade of CCR5 in a humanized model of asthma reveals a critical role for DC-derived CCL17 and CCL22 in attracting Th2 cells and inducing airway inflammation," Allergy, 64:993-1002 (2009).

Ishida, Takasha, et al., "The CC Chemokine Receptor 4 as a Novel Specific Molecular Target for Immunotherapy in Adult T-Cell Leukemia/Lymphoma," Clinical Cancer Research, 10: 7529-7539 (Nov. 15, 2004).

Fletcher, Liz, "PDL's mAb technology finds right timing," Nature Biotechnology, 19: 395-396 (May 2001).

Ménétrier-Caux,Christine, et al., "Differences in Tumor Regulatory T-Cell Localization and Activation Status Impact Patient Outcome," Cancer Res., 69(20): 7895-7898 (Oct. 15, 2009).

GB Combined Search and Examination Report dated Oct. 27, 2009 for GB Application No. 0909906.0.

Jopling, Louise A., "The Identification, Characterization, and Distribution of Guinea Pig CCR4 and Epitope Mapping of a Blocking Antibody," The Journal of Biological Chemistry, 272(9): 6864-6873 (Mar. 1, 2002).

PCT International Search Report for PCT/GB2011/052421 dated Feb. 15, 2012.

Nallet, et al., New Biotechnology, 29:471-47, 2012.

Lund et al., The Journal of Immunology, 157:4963-4969, 1996.

Rudikoff, et al., PNAS, 79:1979-83, 1982.

MacCallum et al., J. Mol. Biol., 262: 732-745, 1996.

Pascalis et al., The Journal of Immunology, 262:732-745, 1996.

Casset,et al., BBRC, 307:198-205, 2003.

Vajdos, et al., JMB, 320: 416-428, 2002.

Holm, et al., Molecular Immunology, 44: 1075-1084, 2007.

\* cited by examiner scFv 17G Nucleotide sequence

CCATGGCCCAGGTGCAGCTGGTGGAGTCTGGGGGAGGCTTGGTACAGCCTGGGGGGTCC
  NcoI    |----------V_H Start (SEQ ID No.34 Start)

CTGAGACTCTCCTGTGCAGCCTCTGGATTCACCTTTAGCAGCTATGCCATGAGCTGGGT

CCGCCAGGCTCCAGGGAAGGGGCTGGAGTGGGTCTCAGCTATTAGTGGTAGTGGTGGTA

GCACATACTACGCAGACTCCGTGAAGGGCCGGTTCACCATCTCCAGAGACAATTCCAAG

AACACGCTGTATCTGCAAATGAACAGCCTGAGAGCCGAGGACACGGCCGTATATTACTG

TGCGAATATTAGGTATAGTGCAGGCTACTGGGGCCAGGGAACCCTGGTCACCGTCTCCT
                                                     V_H End-----
CAAAGCTTTCAGGGAGTGCATCCGCCCCAAAACTTGAAGAAGGTGAATTTTCAGAAGCA
---|HindIII--Linker Start                          Linker End --------
CGCGTATCCTATGTGCTGACACAGCCACCCTCAGCGTCTGGGACCCCCGGGCAGAGGGT
--MluI-  |--------V_L Start
CACCATCTCTTGTTCTGGAAGCAGCTCCAACATCGGAAGTAATTATGTATACTGGTACC

AGCAGCTCCCAGGAACGGCCCCCAAACTCCTCATCTATAGGAATAATCAGCGGCCCTCA

GGGGTCCCTGACCGATTCTCTGGCTCCAAGTCTGGCACCTCAGCCTCCCTGGCCATCAG

TGGGCTCCGGTCCGAGGATGAGGCTGATTATTACTGTGCAGCATGGGATGACCGCCTGA

GTGGTTGGGTGTTCGGCGGAGGGACCAAGCTGACCGTCCTAGCGGCCGCTGGATCCGAA
                (SEQ ID No. 34 End)V_LEnd-------|   NotI
CAAAAGCTGATCTCAGAACAAGACCTAAACTCACATCACCATCACCATCAC
       cMyc-tag                          His_6-tag scFv 17G Amino acid sequence QVQLVESGGGLVQPGGSLRLSCAASGFTFSSYAMSWVRQAPGKGLEWVSAISGS
|----------V_H Start (SEQ ID No.35 Start)

GGSTYYADSVKGRFTISRDNSKNTLYLQMNSLRAEDTAVYYCANIRYSAGYWGQG

TLVTVSS*KLSGSASAPKLEEGEFSEARV*SYVLTQPPSASGTPGQRVTISCSGSSSNI
 V_H End-|--------------Linker----------|--------V_L Start
GSNYVYWYQQLPGTAPKLLIYRNNQRPSGVPDRFSGSKSGTSASLAISGLRSEDE ADYYCAAWDDRLSGWVFGGGTKLTVLAAAGSEQKLISEEDLNSHHHHHH
   (SEQ ID No. 35 end) V_LEnd-------|

Figure 1 scFv 9E Nucleotide sequence

<u>CCATGGCC</u>CAGGTCCAGCTTGTACAGTCTGGGGCTGAGGTGAAGAAGCCTGGGTCCTCG
   NcoI    |----------V_H Start (SEQ ID No.45 Start)

GTGAAGGTCTCCTGCAAGGCTTCTGGAGGCACCTTCAGCAACTATGCTATCAGCTGGGT

GCGACAGGCCCCTGGACAAGGGCTTGAGTGGATGGGAGGGATCATCCCTATCTTTGGTA

CAGCAAACTACGCACAGAAGTTCCAGGGCAGAGTCACGATTACCGCGGACGAATCCACG

AGCACAGCCTACATGGAGCTGAGCAGCCTGAGATCTGAGGACACGGCCGTGTATTACTG

TGCGAGACGCGGTGGGAGCTACTTTGACTACTGGGGCCAGGGAACCCTGGTCACCGTCT
                                                                                 V_H End------
CTTCA<u>AAGCTT</u>CAGGGAGTGCATCCGCCCCAAAACTTGAAGAAGGTGAATTTTCAGAA
--|HindIII---Linker Start                                  Linker End----
GC<u>ACGCGT</u>ATCCTATGTGCTGACTCAGCCACCCTCAGCGTCTGGGACCCCCGGGCAGAG
-----MluI--|-------V_L Start
CGTCACCATCTCTTGTTCTGGAAGCACCTCCAACATCGGAAGTCATTATGTGTTCTGGT

ACCAGCAGCTCCCAGGAACGGCCCCCAGACTCCTCATCTATAGGAATCATCAGCGGCCC

TCAGGGGTCCCTGACCGACTCTCTGGCTCCAAGTCTGGCACCTCAGCCTCCCTGGCCAT

CAGTGGGCTCCGGTCCGAGGATGAGGCTGATTATTACTGTGCAGTGTGGGATGACACCC

TGAGTGGCTGGGTGTTCGGCGGAGGGACCAAGCTGACCGTCCTA<u>GCGGCCGC</u>TGGATCC
                           (SEQ ID No. 45 End)V_LEnd------|  NotI
<u>GAACAAAAGCTGATCTCAGAAGAAGACCTAAACTCA</u><u>CATCACCATCACCATCAC</u>
         cMyc-tag                               His_6-tag scFv 9E Amino acid sequence

QVQLVQSGAEVKKPGSSVKVSCKASGGTFSNYAISWVRQAPGQGLEWMGGIIPIF
|----------V_H Start (SEQ ID No.46 Start)
GTANYAQKFQGRVTITADESTSTAYMELSSLRSEDTAVYYCARRGGSYFDYWGQ GTLVTVSS*KLSGSASAPKLEEGEFSEAR*SYVLTQPPSASGTPGQSVTISCSGSTS
  V_H End-|------------Linker----------|------V_L Start
NIGSHYVFWYQQLPGTAPRLLIYRNHQRPSGVPDRLSGSKSGTSASLAISGLRSED EADYYCAVWDDTLSGWVFGGGTKLTVLAAAGSEQKLISEEDLNSHHHHHH
   (SEQ ID No. 46 end) V_LEnd-------|

Figure 2 scFv 10 Nucleotide sequence

CCATGGCCCAGGTGCAGCTGGTGGAATCTGGGGGAGGCTTGGTACAGCCTGGCAGGTCC
 NcoI      |----------V$_H$ Start (SEQ ID No.56 Start)

CTGAGACTCTCCTGTGCAGCCTCTGGATTCACCTTTAGCAGCTATGCCATGAGCTGGGT

CCGCCAGGCTCCAGGGAAGGGGCTGGAGTGGGTCTCAGCTATTAGTGGTAGTGGTGGTA

GCACATACTACGCAGACTCCGTGAAGGGCCGGTTCACCATCTCCAGAGACAATTCCAAG

AACACGCTGTATCTGCAAATGAACAGCCTGAGAGCCGAGGACACGGCCGTATATTACTG

TGCGAAGGGGGCCGGCGAGGGTCGAGGGCTTGGAGTGGTTATGGGCCAGGGAACCCTGG

TCACCGTCTCCTCAAAGCTTTCAGGGAGTGCATCCGCCCCAAAACTTGAAGAAGGTGAA
    V$_H$ End--------|HindIII----Linker Start
TTTTCAGAAGCACGCGTACAGGCTGTGGTGACCCAGGAGCCCTCACTGACTGTGTCCCC
Linker End ----MluI----|--------V$_L$ Start
AGGAGGGACAGTCACTCTCACCTGTGCTTCCAGCACTGGAGCAGTCACCAGTGGTTACT

TTCCAAACTGGTTCCAGCAGAAACCTGGACAAGCACCCAGGGCACTCATTTATAGTACA

ACCAACAAACACTCCTGGACCCCTGCCCGGTTCTCAGGCTCCCTCCTTGGGGGCAAAGC

TGCCCTGACACTGTCAGGTGTGCAGCCTGAGGACGAGGCTGAGTATTACTGCCTGCTCT

ACTATGGTGGTGCTCGGGTGTTCGGCGGAGGGACCAAGCTCACCGTCCTAGCGGCCGCT
                          (SEQ ID No. 56 End)V$_L$End--------| NotI
GGATCCGAACAAAAGCTGATCTCAGAAGAAGACCTAAACTCACATCACCATCACCATCAC
           cMyc-tag                              His$_6$-tag scFv 10 Amino acid sequence QVQLVESGGGLVQPGRSLRLSCAASGFTFSSYAMSWVRQAPGKGLEWVSAISGS
|----------V$_H$ Start (SEQ ID No. 57 Start)
GGSTYYADSVKGRFTISRDNSKNTLYLQMNSLRAEDTAVYYCAKGAGEGRGLGVV MGQGTLVTVSSKLSGSASAPKLEEGEFSEARVQAVVTQEPSLTVSPGGTVTLTCA
    V$_H$ End-|--------------Linker------------|--------V$_L$ Start
SSTGAVTSGYFPNWFQQKPGQAPRALIYSTTNKHSWTPARFSGSLLGGKAALTLS GVQPEDEAEYYCLLYYGGARVFGGGTKLTVLAAAGSEQKLISEEDLNSHHHHHH
       (SEQ ID No. 57 end) V$_L$End--------|

Figure 3 scFv 11F Nucleotide sequence

CCATGGCCCAGGTCCAGCTTGTGCAGTCTGGGGCTGAGGTGAAGAAGCCTGGGGCCTCA
  NcoI   |----------V_H Start (SEQ ID No.67 Start)
GTGAAGGTCTCCTGCAAGGCTTCTGGATACACCTTCACCGGCTACTATATGCACTGGGT

GCGACAGGCCCCTGGACAAGGGCTTGAGTGGATGGGATGGATCAACCCTAACAGTGGTG

GCACAAACTATGCACAGAAGTTTCAGGGCAGGGTCACCATGACCAGGGACACGTCCATC

AGCACAGCCTACATGGAGCTGAGCAGGCTGAGATCTGACGACACGGCCGTGTATTACTG

TGCGAGAGGTACGGTGACTAGGATTCAGGGCCGCTCTCTACGGTATGGACGTCTGGG

GCCAAGGGACCACGGTCACCGTCTCTTCA*AAGCTTT*CAGGGAGTGCATCCGCCCCAAAA
                    V_H End--------|HindIII--Linker Start
*CTTGAAGAAGGTGAATTTTCAGAAGCACGCGT*AGAAACGACACTCACGCAGTCTCCAGG
      Linker End ---------MluI----|-------V_L Start
CACCCTGTCTTTGTCTCCAGGGGAAGGAGTCACCCTCTCCTGCAGGGCCAGTCAGAGTG

TTAACAGGAGGTACTTAGCCTGGTACCAGCAGAAACCTGGCCAGGCTCCCAGGCTCCTC

ATCTATGGGGCATCCAGCAGGGCCACTGGCATCCCTGACAGGTTCAGTGGCAGTGGGTC

TGGGACAGACTTCACTCTCACCATCAGCAGACTGGAGCCTGAAGATTTTGCAGTGTATT

ACTGTCAGCAGTATGGTAGCTCACCCCTCACTTTCGGCGGAGGGACCAAGGTGGAAATC
                                            (SEQ ID No. 67 End)V_L End----
AAA*GCGGCCGC*TGGATCCGAACAAAAGCTGATCTCAGAAGAAGACCTAAACTCACATCA
---| NotI                           cMyc-tag
CCATCACCATCAC
  His_6-tag scFv 11F amino acid sequence

QVQLVQSGAEVKKPGASVKVSCKASGYTFTGYYMHWVRQAPGQGLEWMGWIN
|----------V_H Start (SEQ ID No.68 Start)
PNSGGTNYAQKFQGRVTMTRDTSISTAYMELSRLRSDDTAVYYCARGTVTRIQGR

SLYGMDVWGQGTTVTVSSKLSGSASAPKLEEGEFSEARVETTLTQSPGTLSLSPG
         V_H End-|--------------Linker-------------|--------V_L Start
EGVTLSCRASQSVNRRYLAWYQQKPGQAPRLLIYGASSRATGIPDRFSGSGSGTD

FTLTISRLEPEDFAVYYCQQYGSSPLTFGGGTKVEIKAAAGSEQKLISEEDLNSHHH
                (SEQ ID No. 68 End)V_L End--------|
HHH

Figure 4

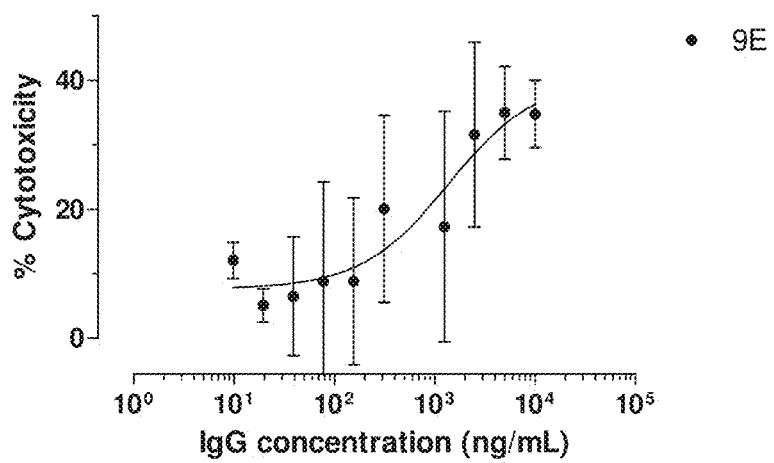
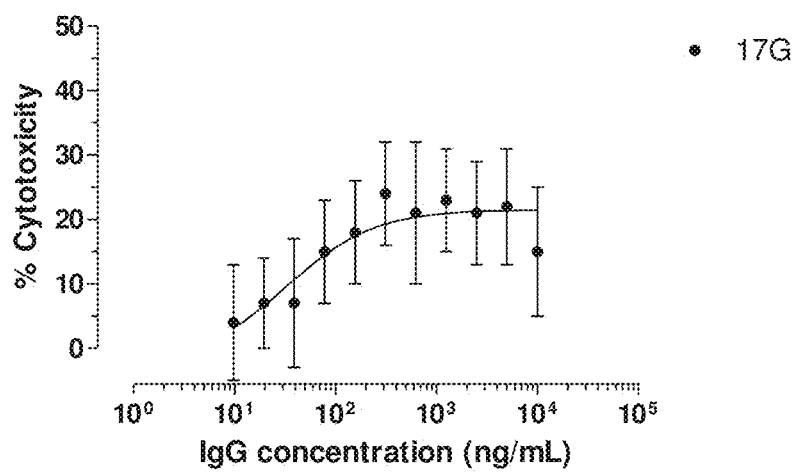
Figure 12

(a) bio-IgG 9E (0.7 nM) on DT40-CCR4+ cells
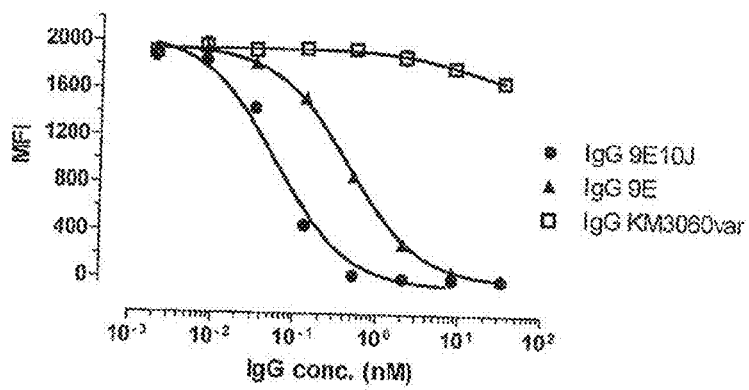
(b) bio-IgG 9E (3.3 nM) on DT40-CCR4+ cells
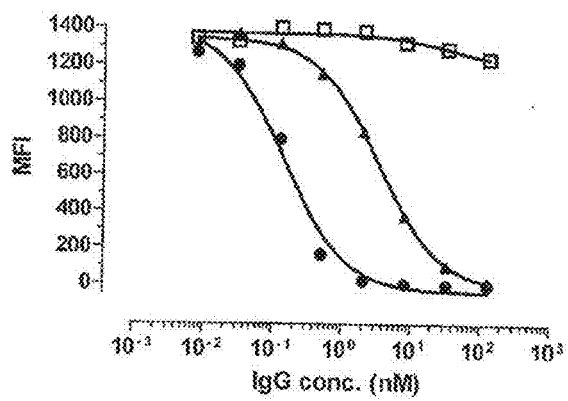
(c) bio-IgG 9E (0.7 nM) on CCRF-CEM cells
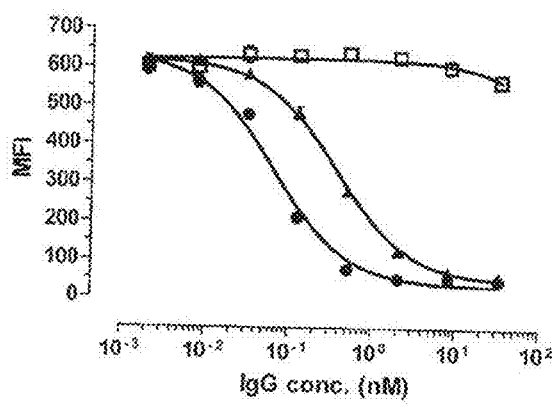
Figure 15 scFv 9E10J Nucleotide sequence

CCATGGCCCAGGTCCAGCTTGTACAGTCTGGGGCTGAGGTGAAGAAGCCTGGGTCCTCG
NcoI        |----------V_H Start (SEQ ID No.106 Start)

GTGAAGGTCTCCTGCAAGGCTTCTGGAGGCACCTTCAGCAGCTATGCTATCAGCTGGGT

GCGACAGGCCCCTGGACAAGGGCTTGAGTGGATGGGAGGGATCATCCCTATCTTTGGTA

CAGCAAACTACGCACAGAAGTTCCAGGGCAGAGTCACCATGACCAGGGACACGTCCACG

AGCACAGTCTACATGGAGCTGAGCAGCCTGAGATCTGAGGACACGGCCGTGTATTACTG

TGCGAGACGCGGTGGGAGCTACTTTGACTACTGGGGCCAAGGGACCCTGGTCACCGTCT
                                                    V_H End------
CCTCAAAGCTTTCAGGGAGTGCATCCGCCCCAAAACTTGAAGAAGGTGAATTTTCAGAA
-------|HindIII--Linker Start                       Linker End ------
GCACGCGTATCCTATGTGCTGACTCAGCCACCCTCAGCGTCTGGGACCCCCGGGCAGAG
----- MluI---|----------V_L Start
CGTCACCATCTCTTGTTCTGGAAGCACCTCCAACATCGGAAGTCATTATGTGTTCTGGT

ACCAGCAGCTCCCAGGAACGGCCCCCAGACTCCTCATCTATAGGAATCATCAGCGGCCC

TCAGGGGTCCCTGACCGACTCTCTGGCTCCAAGTCTGGCACCTCAGCCTCCCTGGCCAT

CAGTGGGCTCCGGTCCGAGGATGAGGCTGATTATTACTGTGCAGTGTGGGATGACACCC

TGAGTGGCTGGGTGTTCGGCGGAGGGACCAAGCTGACCGTCCTAGCGGCCGCTGGATCC
                    (SEQ ID No. 80 End)V_LEnd-----|      NotI
GAACAAAAGCTGATCTCAGAAGAAGACCTAAACTCACATCACCATCACCATCAC
         cMyc-tag                          His_6-tag scFv 9E10J Amino acid sequence QVQLVQSGAEVKKPGSSVKVSCKASGGTFSSYAISWVRQAPGQGLEWMGGIIPI
|-----------V_H Start (SEQ ID No.105 Start)
FGTANYAQKFQGRVTMTRDTSTSTVYMELSSLRSEDTAVYYCARRGGSYFDYWG QGTLVTVSS*KLSGSASAPKLEEGEFSEARV*SYVLTQPPSASGTPGQSVTISCSG
   V_H End- |-----------Linker--------|------V_L Start
STSNIGSHYVFWYQQLPGTAPRLLIYRNHQRPSGVPDRLSGSKSGTSASLAISG LRSEDEADYYCAVWDDTLSGWVFGGGTKLTVLAAAGSEQKLISEEDLNSHHHHHH
     (SEQ ID No. 72 End)V_LEnd-------|

Figure 27 scFv 9E1D Nucleotide sequence

<u>CCATGGCC</u>CAGGTCCAGCTTGTACAGTCTGGGGCTGAGGTGAAGAAGCCTGGGTCCTCG
  NcoI   |----------V<sub>H</sub> Start (SEQ ID No.79 Start)
GTGAAGGTCTCCTGCAAGGCTTCTGGAGGCACCTTCAGCAACTATGCTATCAGCTGGGT

GCGACAGGCCCCTGGACAAGGGCTTGAGTGGATGGGAGGGATCATCCCTATCTTTGGTA

CAGCAAACTACGCACAGAAGTTCCAGGGCAGAGTCACGATTACCGCGGACGAATCCACG

AGCACAGCCTACATGGAGCTGAGCAGCCTGAGATCTGAGGACACGGCCGTGTATTACTG

TGCGAGACGCGGTGGGAGCTACTTTGACTACTGGGGCCAGGGAACCCTGGTCACCGTCT
                                                                                                  V<sub>H</sub> End------
CTTCA*AAGCTTTCAGGGAGTGCATCCGCCCCAAAACTTGAAGAAGGTGAATTTTCAGAA*
---------|HindIII---Linker Start                                 Linker End --------
*GCACGCGTA*CAGCCTGTGCTGACTCAGCCCCCCTCAGCGTCTGGGACCCCCGGGCAGAGG
---- MluI---|--------V<sub>L</sub> Start
GTCACCATCTCTTGTTCTGGAGGCGGATCCAACATCGGAAGAAGGTTTGTAAACTGGTAC

CAGCAGCTCCCAGGAACGGCCCCCAAACTCCTCATCTATAGGAATAATCAGCGGCCCTCA

GGGGTCCCTGACCGATTCTCTGGCTCCAAGTCTGGCACCTCAGCCTCCCTGGTCATCAGT

GGGCTCCGGTCCGAGGATGAGGCTGATTATTACTGTGCAGCATGGGATGACAGCCTGAGT

GGTTGGGTGTTCGGCGGAGGGACCAAGCTGACCGTCCTA<u>GCGGCCGCTGGATCCGAACAA</u>
                 (SEQ ID No. 116 End)V<sub>L</sub>End------|  NotI
<u>AAGCTGATCTCAGAAGAAGACCTAAACTCA</u><u>CATCACCATCACCATCAC</u>
           cMyc-tag                    His<sub>6</sub>-tag scFv 9E1D Amino acid sequence QVQLVQSGAEVKKPGSSVKVSCKASGGTFSNYAISWVRQAPGQGLEWMGGIIPI
|------------V<sub>H</sub> Start (SEQ ID No.71 Start)
FGTANYAQKFQGRVTITADESTSTAYMELSSLRSEDTAVYYCARRGGSYFDYWG QGTLVTVSS*KLSGSASAPKLEEGEFSEARV*QPVLTQPPSASGTPGQRVTISCSG
  V<sub>H</sub> End-|------------Linker--------|-------V<sub>L</sub> Start
GGSNIGRRFVNWYQQLPGTAPKLLIYRNNQRPSGVPDRFSGSKSGTSASLVISG LRSEDEADYYCAAWDDSLSGWVFGGGTKLTVLAAAGSEQKLISEEDLNSHHHHHH
     (SEQ ID No. 115 End)V<sub>L</sub>End------|

Figure 28

ANTIBODIES

This application claims is a continuation application of U.S. Ser. No. 12/797,184, filed Jun. 9, 2010 which claims priority from U.S. provisional application No. 61/185,448, filed Jun. 9, 2009, U.S. provisional application No. 61/302,768, filed Feb. 9, 2010 and GB Application No. 0909906.0, filed Jun. 9, 2009. These prior applications are incorporated herein by reference.

FIELD OF THE INVENTION

The present invention relates generally to the fields of antibodies, CCR4 biology and related therapies. More particularly, it provides antibodies that bind to CCR4. Such anti-CCR4 antibodies have diagnostic and therapeutic uses in diseases and conditions associated with CCR4, such as in imaging tumour blood vessels, treating cancer and treating viral and other infections, and inflammatory and immune diseases. The antibody-based compositions and methods of the invention also extend to the use of immunoconjugates and other therapeutic combinations, kits and methods.

BACKGROUND

With more than 800 members, G-protein-coupled receptors (GPCRs) represent the largest family of cell surface molecules involved in signal transmission, accounting for >2% of the total genes encoded by human genome. Members of the GPCR superfamily share a common membrane topology: an extracellular N-terminus, an intracellular C-terminus and seven transmembrane (TM) helices, which are connected by three intracellular loops and three extracellular loops. On the basis of their shared topological structure, GPCRs are also referred to as seven transmembrane (7TM) receptors. These receptors control key physiological functions, including neurotransmission, hormone and enzyme release from endocrine and exocrine glands, immune responses, cardiac- and smooth-muscle contraction and blood pressure regulation. Their dysfunction contributes to some of the most prevalent human diseases. Emerging experimental and clinical data indicate that GPCRs have a crucial role in cancer progression and metastasis. Hence, there is the possibility that some GPCRs may be suitable targets for anti-cancer drugs.

Chemokines play an important role inter alia in immune and inflammatory responses in various diseases and disorders, including cancer, viral infections, asthma and allergic diseases, as well as autoimmune pathologies such as rheumatoid arthritis and atherosclerosis. These small, secreted molecules are a growing superfamily of 8-14 kDa proteins characterised by a conserved four cysteine motif.

Studies have demonstrated that the actions of chemokines are mediated by subfamilies of G protein-coupled receptors, among which is the receptor designated chemokine (C—C motif) receptor 4, or CC chemokine receptor 4 (CCR4). Specific ligands for CCR4 include the chemokines thymus and activation-regulated chemokine (TARC) (also known as CCL17) and macrophage-derived chemokine (MDC) (also known as CCL22). CCR4 may also bind to RANTES, MCP-1 and MIP-1 alpha, and CCR4 signalling in response to these ligands has also been reported.

CCR4 is believed to be important inter alia in the function of T cell chemotaxis and the migration of phagocytic cells to sites of inflammation. CCR4 is preferentially expressed on T-helper cell type 2 (Th2) cells and regulatory T (Treg) cells, whereas only limited expression on other healthy cells or tissues occurs.

Tumour cells, in particular adult T cell leukaemia/lymphoma cells, may be positive for CCR4. Expression of CCR4 by tumour cells is associated with skin involvement. Certain T-cell malignancies typically are located to the skin. For example, CCR4 is found at high levels in cutaneous T cell lymphoma lesions. More recently, CCR4 has also been found to be expressed by certain solid tumours (WO2009/037454). CCR4 expression is believed to be an early event in carcinogenesis of solid tumours, particularly cancer of the cervix, oesophagus, kidney, brain, breast, ovary, prostate, stomach and pancreas. Thus, both haematological and non-haematological cancer cells may express CCR4. Consequently, these cancers maybe diagnosed, monitored and treated using anti-CCR4 antibodies.

In addition, CCR4 has an important role in normal and tumour immunity. A significant fraction of $CD4^+$ $CD25^+$ regulatory T-cells (Tregs) are positive for CCR4 (Baatar et al, 2007b). These Tregs suppress immune responses through a variety of mechanisms, and it has been shown that they can inhibit tumour-specific immunity. Increased numbers of Tregs infiltrating the stroma, the tumour itself, or draining lymphnodes, correlate with worsened outcome in a variety of cancers. Studies in mouse model show that reducing Treg activity leads to increased endogenous anti-tumour immunity and increased efficacy of anti-tumour inventions by the immune system. Consequently, inhibiting Treg function is a promising strategy in immunotherapy of tumours. The inhibition can be achieved by killing the Tregs (depletion), interfering with their suppressor functions, changing their trafficking pattern or changing their differentiation.

In a subset of patients with CCR4+ T-cell leukaemia/lymphoma, the tumour cells themselves function as Treg cells, contributing to tumour survival in the face of host antitumour immune responses. In other types of cancers, MDC and TARC are produced by tumour cells and the tumour microenvironment and attract CCR4+ Treg cells to the tumour, where they create a favourable environment for tumour escape from the host immune responses. A higher frequency of Tregs in peripheral blood of patients with following cancers has been reported: Breast cancer, Colorectal cancer, Oesophageal cancer, Gastric cancer, Hepatocellular carcinoma, Lung cancer, Melanoma, Ovarian cancer and Pancreatic cancer. Treg cells have been reported to create a favourable environment for tumours. Hence, blocking the interaction between CCR4 and its ligands such as MDC could be useful in the treatment or prevention of cancers, especially the cancers listed above. It has been reported that in a SCID mouse model, antibody to human MDC/CCL22 was able to block infiltration of human Treg cells into transplanted human ovarian tumours. It is believed that the Treg cells present in human solid tumours prevent immune effector responses developing which could contribute to the slowing of tumour growth and metastasis. Thus, killing of Treg cells in the tumour mass, and/or prevention of migration of Treg cells to the tumour sites by using a neutralising MAb (monoclonal antibody) directed against CCR4 may result in enhanced immune responses towards solid tumours, and act as an adjunct to conventional cytotoxic or anti-hormonal therapies.

Cancer causes about 13% of all human deaths. According to the American Cancer Society, 7.6 million people died from cancer in the world during 2007, so there remains a strong and urgent need for further anti-cancer therapeutics.

CCR4 has been shown to play a role in inflammation and immune disorders. Th2 cells and basophils are key cells in the allergic response in the lung and skin. There are a number of reports which describe the presence of CCR4-expressing T cells and concomitant expression of CCR4 ligands (MDC, TARC) on airway epithelial cells in bronchial biopsies in allergen-challenged asthmatics (Panina-Bordignon et al, 2001). CCR4+ T cells are also found in increased numbers in patients with atopic dermatitis, with a marked reduction of CCR4+ T cells observed when the disease improved. Using a humanized SCID mouse model of asthma, it was shown that blockade of CCR4 with antibodies prior to allergen challenge reduced allergic airway inflammation, as well as the levels of Th2 cytokines in the lungs. Depletion of CCR4+ T cells via lung delivery of a blocking antibody may be a suitable treatment option for asthmatic patients. Targeted delivery of a CCR4 blocking antibody to the skin may also be an attractive treatment for atopic dermatitis.

In allergic asthma, the presence of high levels of allergen-specific IgE is a reflection of an aberrant Th2 cell immune response to commonly inhaled environmental allergens. Asthma is characterized by infiltration of Th2 lymphocytes and eosinophils and by the production of Th2 chemokines. Allergens are presented to T cells by dendritic cells (DCs) that continuously sample incoming foreign antigens. Upon proper activation by DCs, allergen-specific lymphocytes that are present in diseased airways produce Th2 cytokines interleukin (IL)-4, IL-5 and IL-13 that furthermore control leukocyte extravasation, goblet cell hyperplasia and bronchial hyper-reactivity (BHR). TARC and MDC produced by DCs induce the selective migration of Th2 cells but not Th1 cells through triggering CCR4 (Perros et al, 2009). It was shown in murine models of asthma, that treatment with anti-TARC antibodies reduced the number of CD4+ T cells and eosinophils in bronchoalveolar lavage (BAL) fluid, the production of Th2 cytokines and airway hyper-responsiveness after allergen challenge (Kawasaki et al, 2001). In contrast, CCR4-deficient mice showed no protection against airway inflammation and BHR (Chvatchko et al, 2000). Using a humanized SCID mouse model of asthma, it was shown that blockade of CCR4 with antibodies prior to allergen challenge reduced allergic airway inflammation as well as the levels of Th2 cytokines in the lungs (Perros et al, 2009). These data indicate that CCR4 blockade is a feasible strategy for inhibiting allergic inflammation in humans.

Treg cells may suppress dendritic cells (DCs), thereby facilitating the development and progression of diseases, particularly infectious diseases and cancer. Anti-CCR4 antibodies able to block the suppression of dendritic cells by Treg cells may therefore be useful as adjuvants in vaccines, particularly as adjuvants in tumour vaccination or vaccination against infectious disease. Thus, an anti-CCR4 antibody may enhance the therapeutic effect of a vaccine, particularly enhancing the vaccine-induced immune response.

CCR4 binding compounds have been reported to show efficacy in murine allergic inflammation (Purandare et al, 2007, Burdi et al. 2007). It has been reported that a CCR4-binding compound has reasonable potency in vivo, as CCR4 dependent recruitment of leucocytes to the peritoneum induced by TARC was inhibited by almost 90%. Yokoyama and colleagues presented a quinazoline derivative targeting CCR4 which proved in vivo to be effective in reducing hypersensitivity reactions in a mouse model (Yokoyama et al, 2008b); a derivative of this compound proved to be effective in a similar in vivo mouse model upon oral administration (Yokoyama et al, 2009). Recently, a group of scientists has identified a number CCR4 antagonists using in silico modelling approach (Bayry et al, 2008; Davies et al, 2009). By docking compounds to modelled CCR4, the authors found molecules able to bind within the transmembrane region. Sixteen compounds inhibited CCR4-mediated migration of CCRF-CEM cells. When CCR4 antagonists were tested for their adjuvant function in vivo with *Mycobacterium tuberculosis* and hepatitis B vaccines, enhanced immunogenicity was observed for both cellular and humoral immune responses. The observed effect was ascribed to inhibition of Treg activity (Bayry et al, 2008; Davies et al, 2009). The fact that a significant fraction of Treg cells are CCR4-positive is well known in the art (Baatar et al 2007b). The observed effect is believed to be useful not only in the context of vaccination against infectious diseases (caused, for example by a virus, a bacterium, a mycobacterium or a parasite such as protozoa), but also in the context of cancer vaccines.

As the cause for the efficacy of these compounds as adjuvants is based on inhibiting Tregs by blocking CCR4 mediated signaling, it is expected that antibodies binding to CCR4 in an antagonistic manner would work the same way; the pharmacological advantages of antibodies compared to small molecule drugs are well known in the art. The only antibody against CCR4 currently in development is to the best of our knowledge KW-0761 by Kyowa-Hakko. However, this antibody is effective only by ADCC; it does not prevent ligand-mediated signalling through CCR4 receptor. Therefore, the antibodies described in this invention are expected to be clearly superior in their modulation of immune reactions via Tregs.

Another application where modulating Tregs is of clinical use is cancer treatment. Tregs can inhibit tumour-specific immunity and their increased numbers correlate with unfavourable prognosis and disease progression in some cancers. Studies in mouse models demonstrate that reducing Treg activity boosts endogenous anti-tumour immunity, and increases the efficacy of active immune interventions. Consequently, inhibiting Treg function is a strategy worth considering in human cancer immunotherapy (Curiel, 2008; Ruter et al, 2009). This inhibition can be achieved both by modulating Tregs, or by directly killing them.

Examples for this approaches are described in the art by compounds targeting other surface of Treg like CD25. Daclizumab (Zenapax®; Roche)) and basiliximab (Simulect®; Novartis) are anti-human CD25 antibodies approved for use in autoimmune diseases, transplantation and cancers including HTLV-1 induced adult T-cell lymphoma/leukaemia (Church, 2003). Denileukin diftitox (Ontak®, DAB389IL-2; Ligand Pharmaceuticals Inc.) is a recombinant protein fusing the active domain of diphtheria toxin to human IL-2. In 1998, FDA has approved it to treat cutaneous T cell leukaemia/lymphoma (Olsen et al, 2001), which usually are CD4+ CD25+. Denileukin diftitox is targeted to the IL-2 receptor and is proposed to be internalized through CD25 by endocytosis. There is also evidence that Denileukin diftitox improves immunogenicity of a tumour vaccine in patients with renal cell cancer (Dannull et al, 2005). In addition, a recent report showed that denileukin diftitox reduces Treg numbers and function in melanoma with improved melanoma-specific immunity (Mahnke et al, 2007) Other molecules on Tregs which are targeted for cancer treatment or improved cancer vaccine effects include GITR (glucocorticoid-induced tumour necrosis factor receptor-related gene) (Levings et al, 2002), Toll-like receptors (TLR) are expressed ubiquitously on a variety of mammalian cells, including human Tregs (Yang et al, 2004, Rutter et al, 2009) and Cytotoxic T lymphocyte antigen-4 (CTLA-4; CD152) (Sutmuller et al. 2001). Currently, Phase II and III clinical trials of anti-CTLA-4 monoclonal antibody therapy are being conducted in melanoma, and Phase I and II trials are being conducted in other tumour types. Two human monoclonal antibodies are under investigation—ipilimumab (MDX-010; Bristol-Myers Squibb/Medarex) and tremelimumab (CP-675,206; Pfizer).

CCR4 has also been implicated inter alia in the following disorders: Adult T-cell leukemia/lymphoma, Peripheral T-cell lymphoma, Cutaneous T-Cell Lymphoma (CTCL), unspecified Diffuse large B-cell lymphoma, Hodgkin's lymphoma, B-cell chronic lymphocytic leukemia, Epstein-Barr virus (EBV) infection, Mycosis fungoides (a mature T-cell lymphoma), Sézary syndrome (a variant of mycosis fungoides), allergic bronchopulmonary aspergillosis (ABPA), Asthma, LPS-induced endotoxic shock, Allergic inflammation, T-cell mediated neurodegenerative diseases such as Multiple Sclerosis (MS), Autoimmune diseases such as Psoriasis, Castleman's disease and Rheumatoid arthritis (RA).

Due to their complex structures, GPCRs are considered as "difficult targets" for raising specific antibodies. They can neither be easily purified from the membrane fraction of lysed cells, nor be recombinantly produced in different expression systems as correctly folded soluble proteins. To the inventors' knowledge, to date all known attempts of others to generate anti-GPCR antibodies using phage display have proven to be unsuccessful.

The difficulties associated with generating antibodies against GPCRs are set out in Hoogenboom et al., 1999. Furthermore, Sui et al. (2003) explain the difficulties associated with trying to obtain human antibodies against the GPCR chemokine receptor CXCR4 and report that even using the pathfinder method combined with step-back selection no specific antibodies could be identified. Thus, in the field of GPCRs, the generation of specific antibodies remains a major challenge.

A murine monoclonal antibody called 1 G1 which reacts with human CCR4 is commercially available from BD Pharmingen. This antibody may be used for immunoflurescent staining, but the antibody is not a neutralising antibody.

A chimeric antibody to CCR4 designated KM2760 is disclosed in Ishida et al., 2006. The authors report that this antibody does not block the binding of CCR4 to its ligands MDC or TARC.

The inventors have recognized that the identification of additional antibodies that recognize CCR4 would be of benefit in expanding the number of therapeutic options. In particular, antibodies that block the binding of CCR4 to one or more of its ligands would offer further therapeutic avenues.

The inventors have also recognized that the development of therapeutic agents for the treatment of humans that are better tolerated from an immunological perspective would be advantageous. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system.

The art therefore still lacks anti-CCR4 antibodies that can be used in the safe and effective treatment of patients having disorders in which CCR4 is involved, including in long-term administration, and poses challenges to the development of such antibodies.

In particular, there is a need for human antibodies to CCR4. Although human antibodies are generally recognized to display advantages, it is known that the development of human antibodies that have high enough affinities and appropriate functional properties to make them candidates for successful human therapy is by no means straightforward. This is even more so the case with GPCRs, due to their complex and transmembrane nature.

There also remains a strong need for anti-CCR4 antibodies which can block the binding between CCR4 and one or more of its ligands such as MDC and/or TARC.

DESCRIPTION OF THE INVENTION

The present invention overcomes certain limitations in the prior art by providing new therapeutic compositions and methods for use in the safe and effective treatment of tumors, viral infections and other diseases and conditions in which CCR4+ cells are involved such as inflammatory or immune disorders. The invention is based on antibodies that bind to CCR4, preferably to an epitope within the extracellular domain of CCR4, particularly human antibodies. Such antibodies are effective in treating tumors and viral infections and other diseases and conditions in which CCR4+ cells are involved, such as inflammatory or immune disorders. The compositions and methods of the invention also extend to the use of immunoconjugates and combinations using this particular category of antibodies.

A particular advantage of the present invention is that the antibodies provided inhibit binding of MDC and/or TARC to CCR4. This contrasts with the leading antibodies in the clinical field, which do not inhibit binding of MDC and/or TARC to CCR4.

The present inventors have prepared CCR4-specific antibodies that bind to CCR4. For example, the antibodies bind to CCR4+ cells, in particular HEK293T-cells transfected with CCR4, DT40-cells transfected with CCR4 and CCRF-CEM cells which naturally express CCR4 (see Example 2). Importantly, the antibodies do not significantly bind to CCR4-cells, i.e. cells which do not express CCR4. Thus, the antibodies disclosed herein bind specifically to CCR4, making them suitable candidates for diagnostics and therapy of the conditions discussed herein.

Amino acid and/or DNA sequences of preferred antibody molecules of the invention which bind to an epitope in the extracellular domain of CCR4, their VH and VL domains including complementarity determining regions (CDRs), are set forth in the various SEQ ID NOs. listed herein.

Thus, the present invention provides an antibody which binds to CCR4 and which is capable of inhibiting the binding of MDC to CCR4.

Preferably, the antibody is isolated. Also preferably, the antibody is human. Preferably, the antibody binds to an epitope in the extracellular domain of CCR4. The CCR4 is preferably human. Thus, any reference to "binding to CCR4" includes the preferred embodiment of "binding to an epitope in the extracellular domain of CCR4".

Thus, the invention preferably provides an isolated human antibody which binds to an epitope in the extracellular domain of human CCR4 and which is capable of inhibiting the binding of MDC to CCR4.

In one embodiment, the present invention provides an antibody that binds to CCR4 and which is capable of inhibiting the binding of MDC to CCR4 comprising a heavy chain CDR1 domain comprising the amino acid sequence of SEQ ID NO: 1, 7, 19, 101, 125, 126, 135 or 136 or a sequence substantially homologous to any one of these sequences, SEQ ID NOs: 101, 125, 126, 135 and 136 being especially preferred.

Alternatively or in addition, in an embodiment of the invention, the antibody that binds to CCR4 and which is capable of inhibiting the binding of MDC to CCR4 comprises a heavy chain CDR2 domain comprising the amino acid sequence of SEQ ID NO: 2, 8, 20, 127 or 128 or a sequence substantially homologous to any one of these sequences, SEQ ID NOs: 8, 127 and 128 being especially preferred.

Alternatively or in addition, in an embodiment of the invention, the antibody that binds to CCR4 and which is capable of inhibiting the binding of MDC to CCR4 comprises a heavy chain CDR3 domain comprising the amino acid sequence of SEQ ID NO: 3, 9, 15 or 21 or a sequence substantially homologous to any one of these sequences, SEQ ID NO: 9 being especially preferred.

Alternatively or in addition, in an embodiment of the invention, the antibody that binds to CCR4 and which is capable of inhibiting the binding of MDC to CCR4 comprises a light chain CDR1 domain comprising the amino acid sequence of SEQ ID NO: 4, 10, 16, 22, 108, 129 or 130 or a sequence substantially homologous to any one of these sequences, SEQ ID NOs: 10, 129 or 130 being especially preferred.

Alternatively or in addition, in an embodiment of the invention, the antibody that binds to CCR4 and which is capable of inhibiting the binding of MDC to CCR4 comprises a light chain CDR2 domain comprising the amino acid sequence of SEQ ID NO: 5, 11, 17, 23, 110, 131 or 132 or a sequence substantially homologous to any one of these sequences SEQ ID NOs: 11, 131 and 132 being especially preferred.

Alternatively or in addition, in an embodiment of the invention, the antibody that binds to CCR4 and which is capable of inhibiting the binding of MDC to CCR4 comprises a light chain CDR3 domain comprising the amino acid sequence of SEQ ID NO: 6, 12, 18, 24, 112, 133, 134, 137 or 138 or a sequence substantially homologous to any one of these sequences, SEQ ID NOs: 12, 133, 134, 137 and 138 being especially preferred.

SEQ ID NOs: 133 and 134 contain amino acid Y at position 11, but it is preferred that the amino acid at position 11 of these sequences is V. SEQ ID NOs: 137 and 138 correspond to SEQ ID NOs 133 and 134, except that the amino acid at position 11 is V. Thus, in any embodiments disclosed herein, any reference to SEQ ID NO: 133 should be understood to include a reference to SEQ ID NO: 137 and any reference to SEQ ID NO:134 should be understood to include a reference to SEQ ID NO: 138.

Thus, in certain embodiments, the invention provides an antibody that binds to CCR4 and which is capable of inhibiting the binding of MDC to CCR4 comprising one or more heavy chain CDR domains, wherein the heavy chain CDR domain is selected from the group consisting of:
(a) a heavy chain CDR1 domain comprising the amino acid sequence of SEQ ID NO: 1, 7, 19, 101, 125 or 126 or a sequence substantially homologous thereto;
(b) a heavy chain CDR2 domain comprising the amino acid sequence of SEQ ID NO: 2, 8, 20, 127 or 128 or a sequence substantially homologous thereto; and
(c) a heavy chain CDR3 domain comprising the amino acid sequence of SEQ ID NO: 3, 9, 15 or 21 or a sequence substantially homologous thereto.

The invention also provides, in certain embodiments an antibody that binds to binds to CCR4 and which is capable of inhibiting the binding of MDC to CCR4 comprising one or more light chain CDR domains, wherein the light chain CDR domain is selected from the group consisting of:
(a) a light chain CDR1 domain comprising the amino acid sequence of SEQ ID NO: 4, 10, 16, 22, 108, 129 or 130 or a sequence substantially homologous thereto;
(b) a light chain CDR2 domain comprising the amino acid sequence of SEQ ID NO: 5, 11, 17, 23, 110, 131 or 132 or a sequence substantially homologous thereto; and
(c) a light chain CDR3 domain comprising the amino acid sequence of SEQ ID NO: 6, 12, 18, 24, 112, 133, 134, 137 or 138 or a sequence substantially homologous thereto.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 3 or a sequence substantially homologous thereto and
(b) a light chain CDR3 comprising the amino acid sequence of SEQ ID NO: 6 or a sequence substantially homologous thereto.

More preferably, a CDR1 domain comprising the amino acid sequence of SEQ ID NO: 1 or a sequence substantially homologous thereto and/or SEQ ID NO: 4 or a sequence substantially homologous thereto, and/or a CDR2 domain comprising the amino acid sequence of SEQ ID NO: 2 or a sequence substantially homologous thereto and/or SEQ ID NO: 5 or a sequence substantially homologous thereto, are also present.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 9 or a sequence substantially homologous thereto and
(b) a light chain CDR3 comprising the amino acid sequence of SEQ ID NO: 12 or a sequence substantially homologous thereto.

More preferably, a CDR1 domain comprising the amino acid sequence of SEQ ID NO: 7 or a sequence substantially homologous thereto and/or SEQ ID NO: 10 or a sequence substantially homologous thereto, and/or SEQ ID NO: 101 or a sequence substantially homologous thereto, and/or a CDR2 domain comprising the amino acid sequence of SEQ ID NO: 8 or a sequence substantially homologous thereto and/or SEQ ID NO: 11 or a sequence substantially homologous thereto, are also present.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 15 or a sequence substantially homologous thereto and
(b) a light chain CDR3 comprising the amino acid sequence of SEQ ID NO: 18 or a sequence substantially homologous thereto.

More preferably, a CDR1 domain comprising the amino acid sequence of SEQ ID NO: 1 or a sequence substantially homologous thereto and/or SEQ ID NO: 16 or a sequence substantially homologous thereto, and/or a CDR2 domain comprising the amino acid sequence of SEQ ID NO: 2 or a sequence substantially homologous thereto and/or SEQ ID NO: 17 or a sequence substantially homologous thereto, are also present.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 21 or a sequence substantially homologous thereto and
(b) a light chain CDR3 comprising the amino acid sequence of SEQ ID NO: 24 or a sequence substantially homologous thereto.

More preferably, a CDR1 domain comprising the amino acid sequence of SEQ ID NO: 19 or a sequence substantially homologous thereto and/or SEQ ID NO: 22 or a sequence substantially homologous thereto, and/or a CDR2 domain comprising the amino acid sequence of SEQ ID NO: 20 or a sequence substantially homologous thereto and/or SEQ ID NO: 23 or a sequence substantially homologous thereto, are also present.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 9 or a sequence substantially homologous thereto and
(b) a light chain CDR3 comprising the amino acid sequence of SEQ ID NO: 112 or a sequence substantially homologous thereto.

More preferably, a CDR1 domain comprising the amino acid sequence of SEQ ID NO: 7 or a sequence substantially homologous thereto and/or SEQ ID NO: 108 or a sequence substantially homologous thereto, and/or a CDR2 domain comprising the amino acid sequence of SEQ ID NO: 8 or a sequence substantially homologous thereto and/or SEQ ID NO: 110 or a sequence substantially homologous thereto, are also present.

In certain preferred embodiments, the antibody that binds to binds to CCR4 and which is capable of inhibiting the binding of MDC to CCR4 comprises both
(a) a heavy chain CDR3 comprising the amino acid sequence of SEQ ID NO: 9 or a sequence substantially homologous thereto and
(b) a light chain CDR3 comprising the amino acid sequence of SEQ ID NO: 133, 134, 137 or 138, or a sequence substantially homologous thereto.

More preferably, a CDR1 domain comprising the amino acid sequence of SEQ ID NO: 125 or 126 or a sequence substantially homologous thereto and/or SEQ ID NO: 129 or 130 or a sequence substantially homologous thereto, and/or a CDR2 domain comprising the amino acid sequence of SEQ ID NO: 127 or 128 or a sequence substantially homologous thereto and/or SEQ ID NO: 131 or 132 or a sequence substantially homologous thereto, are also present.

In one preferred embodiment, the heavy chain CDR1 comprising the amino acid sequence of SEQ ID NO: 1 or a sequence substantially homologous thereto, CDR2 comprising the amino acid sequence of SEQ ID NO: 2 or a sequence substantially homologous thereto, and CDR3 comprising the amino acid sequence of SEQ ID NO: 3, or a sequence substantially homologous thereto, are present individually or in combination.

In yet another preferred embodiment, the light chain CDR1 comprising the amino acid sequence of SEQ ID NO: 4 or a sequence substantially homologous thereto, CDR2 comprising the amino acid sequence of SEQ ID NO: 5 or a sequence substantially homologous thereto, and CDR3 comprising the amino acid sequence of SEQ ID NO: 6 or a sequence substantially homologous thereto, are present individually or in combination.

In one preferred embodiment, the heavy chain CDR1 comprising the amino acid sequence of SEQ ID NO: 7 or a sequence substantially homologous thereto, CDR2 comprising the amino acid sequence of SEQ ID NO: 8 or a sequence substantially homologous thereto, and CDR3 comprising the amino acid sequence of SEQ ID NO: 9, or a sequence substantially homologous thereto, are present individually or in combination.

In one preferred embodiment, the heavy chain CDR1 comprising the amino acid sequence of SEQ ID NO: 101 or a sequence substantially homologous thereto, CDR2 comprising the amino acid sequence of SEQ ID NO: 8 or a sequence substantially homologous thereto, and CDR3 comprising the amino acid sequence of SEQ ID NO: 9, or a sequence substantially homologous thereto, are present individually or in combination.

In yet another preferred embodiment, the light chain CDR1 comprising the amino acid sequence of SEQ ID NO: 10 or a sequence substantially homologous thereto, CDR2 comprising the amino acid sequence of SEQ ID NO: 11 or a sequence substantially homologous thereto, and CDR3 comprising the amino acid sequence of SEQ ID NO: 12 or a sequence substantially homologous thereto, are present individually or in combination.

In yet another preferred embodiment, the light chain CDR1 comprising the amino acid sequence of SEQ ID NO: 108 or a sequence substantially homologous thereto, CDR2 comprising the amino acid sequence of SEQ ID NO: 110 or a sequence substantially homologous thereto, and CDR3 comprising the amino acid sequence of SEQ ID NO: 112 or a sequence substantially homologous thereto, are present individually or in combination.

In one preferred embodiment, the heavy chain CDR1 comprising the amino acid sequence of SEQ ID NO: 1 or a sequence substantially homologous thereto, CDR2 comprising the amino acid sequence of SEQ ID NO: 2 or a sequence substantially homologous thereto, and CDR3 comprising the amino acid sequence of SEQ ID NO: 15, or a sequence substantially homologous thereto, are present individually or in combination.

In yet another preferred embodiment, the light chain CDR1 comprising the amino acid sequence of SEQ ID NO: 16 or a sequence substantially homologous thereto, CDR2 comprising the amino acid sequence of SEQ ID NO: 17 or a sequence substantially homologous thereto, and CDR3 comprising the amino acid sequence of SEQ ID NO: 18 or a sequence substantially homologous thereto, are present individually or in combination.

In one preferred embodiment, the heavy chain CDR1 comprising the amino acid sequence of SEQ ID NO: 19 or a sequence substantially homologous thereto, CDR2 comprising the amino acid sequence of SEQ ID NO: 20 or a sequence substantially homologous thereto, and CDR3 comprising the amino acid sequence of SEQ ID NO: 21, or a sequence substantially homologous thereto, are present individually or in combination.

In yet another preferred embodiment, the light chain CDR1 comprising the amino acid sequence of SEQ ID NO: 22 or a sequence substantially homologous thereto, CDR2 comprising the amino acid sequence of SEQ ID NO: 23 or a sequence substantially homologous thereto, and CDR3 comprising the amino acid sequence of SEQ ID NO: 24 or a sequence substantially homologous thereto, are present individually or in combination.

In one preferred embodiment, the heavy chain CDR1 comprising the amino acid sequence of SEQ ID NO: 125 or 126 or a sequence substantially homologous thereto, CDR2 comprising the amino acid sequence of SEQ ID NO: 127 or 128 or a sequence substantially homologous thereto, and CDR3 comprising the amino acid sequence of SEQ ID NO: 9, or a sequence substantially homologous thereto, are present individually or in combination.

In yet another preferred embodiment, the light chain CDR1 comprising the amino acid sequence of SEQ ID NO: 129 or 130 or a sequence substantially homologous thereto, CDR2 comprising the amino acid sequence of SEQ ID NO: 131 or 132 or a sequence substantially homologous thereto, and CDR3 comprising the amino acid sequence of SEQ ID NO:

133, 134, 137 or 138 or a sequence substantially homologous thereto, are present individually or in combination.

Viewed alternatively, in certain embodiments, the present invention provides an antibody that binds to CCR4 and which is capable of inhibiting the binding of MDC to CCR4 comprising a heavy chain CDR3 domain comprising the amino acid sequence of SEQ ID NO: 3 or a sequence substantially homologous thereto and/or a light chain CDR3 domain comprising the amino acid sequence of SEQ ID NO: 6 or a sequence substantially homologous thereto.

Said antibody optionally further comprises a heavy chain CDR2 domain comprising the amino acid sequence of SEQ ID NO: 2 or a sequence substantially homologous thereto and/or a light chain CDR2 domain comprising the amino acid sequence of SEQ ID NO: 5 or a sequence substantially homologous thereto and/or further comprises a heavy chain CDR1 domain comprising the amino acid sequence of SEQ ID NO: 1 or a sequence substantially homologous thereto and/or a light chain CDR1 domain comprising the amino acid sequence of SEQ ID NO: 4 or a sequence substantially homologous thereto.

In certain embodiments, the present invention provides an antibody that binds to CCR4 and which is capable of inhibiting the binding of MDC to CCR4 comprising a heavy chain CDR3 domain comprising the amino acid sequence of SEQ ID NO: 9 or a sequence substantially homologous thereto and/or a light chain CDR3 domain comprising the amino acid sequence of SEQ ID NO: 12 or a sequence substantially homologous thereto.

Said antibody optionally further comprises a heavy chain CDR2 domain comprising the amino acid sequence of SEQ ID NO: 8 or a sequence substantially homologous thereto and/or a light chain CDR2 domain comprising the amino acid sequence of SEQ ID NO: 11 or a sequence substantially homologous thereto and/or further comprises a heavy chain CDR1 domain comprising the amino acid sequence of SEQ ID NO: 7 or a sequence substantially homologous thereto and/or a light chain CDR1 domain comprising the amino acid sequence of SEQ ID NO: 10 or a sequence substantially homologous thereto.

In certain embodiments, the present invention provides an antibody that binds to CCR4 and which is capable of inhibiting the binding of MDC to CCR4 comprising a heavy chain CDR3 domain comprising the amino acid sequence of SEQ ID NO: 9 or a sequence substantially homologous thereto and/or a light chain CDR3 domain comprising the amino acid sequence of SEQ ID NO: 112 or a sequence substantially homologous thereto.

Said antibody optionally further comprises a heavy chain CDR2 domain comprising the amino acid sequence of SEQ ID NO: 8 or a sequence substantially homologous thereto and/or a light chain CDR2 domain comprising the amino acid sequence of SEQ ID NO: 110 or a sequence substantially homologous thereto and/or further comprises a heavy chain CDR1 domain comprising the amino acid sequence of SEQ ID NO: 7 or 101 or a sequence substantially homologous thereto and/or a light chain CDR1 domain comprising the amino acid sequence of SEQ ID NO: 108 or a sequence substantially homologous thereto.

In certain embodiments, the present invention provides an antibody that binds to CCR4 and which is capable of inhibiting the binding of MDC to CCR4 comprising a heavy chain CDR3 domain comprising the amino acid sequence of SEQ ID NO: 15 or a sequence substantially homologous thereto and/or a light chain CDR3 domain comprising the amino acid sequence of SEQ ID NO: 18 or a sequence substantially homologous thereto.

Said antibody optionally further comprises a heavy chain CDR2 domain comprising the amino acid sequence of SEQ ID NO: 2 or a sequence substantially homologous thereto and/or a light chain CDR2 domain comprising the amino acid sequence of SEQ ID NO: 17 or a sequence substantially homologous thereto and/or further comprises a heavy chain CDR1 domain comprising the amino acid sequence of SEQ ID NO: 1 or a sequence substantially homologous thereto and/or a light chain CDR1 domain comprising the amino acid sequence of SEQ ID NO: 16 or a sequence substantially homologous thereto.

In certain embodiments, the present invention provides an antibody that binds to CCR4 and which is capable of inhibiting the binding of MDC to CCR4 comprising a heavy chain CDR3 domain comprising the amino acid sequence of SEQ ID NO: 21 or a sequence substantially homologous thereto and/or a light chain CDR3 domain comprising the amino acid sequence of SEQ ID NO: 24 or a sequence substantially homologous thereto.

Said antibody optionally further comprises a heavy chain CDR2 domain comprising the amino acid sequence of SEQ ID NO: 20 or a sequence substantially homologous thereto and/or a light chain CDR2 domain comprising the amino acid sequence of SEQ ID NO: 23 or a sequence substantially homologous thereto and/or further comprises a heavy chain CDR1 domain comprising the amino acid sequence of SEQ ID NO: 19 or a sequence substantially homologous thereto and/or a light chain CDR1 domain comprising the amino acid sequence of SEQ ID NO: 22 or a sequence substantially homologous thereto.

In certain embodiments, the present invention provides an antibody that binds to CCR4 and which is capable of inhibiting the binding of MDC to CCR4 comprising a heavy chain CDR3 domain comprising the amino acid sequence of SEQ ID NO: 9 or a sequence substantially homologous thereto and/or a light chain CDR3 domain comprising the amino acid sequence of SEQ ID NO: 133, 134, 137 or 138 or a sequence substantially homologous thereto.

Said antibody optionally further comprises a heavy chain CDR2 domain comprising the amino acid sequence of SEQ ID NO: 127 or 128 or a sequence substantially homologous thereto and/or a light chain CDR2 domain comprising the amino acid sequence of SEQ ID NO: 131 or 132 or a sequence substantially homologous thereto and/or further comprises a heavy chain CDR1 domain comprising the amino acid sequence of SEQ ID NO: 125 or 126 or a sequence substantially homologous thereto and/or a light chain CDR1 domain comprising the amino acid sequence of SEQ ID NO: 129 or 130 or a sequence substantially homologous thereto.

Viewed alternatively, in certain embodiments, the present invention provides an antibody that binds to binds to CCR4 and which is capable of inhibiting the binding of MDC to CCR4 comprising a heavy chain CDR2 domain comprising the amino acid sequence of SEQ ID NO: 2 or a sequence substantially homologous thereto and/or a light chain CDR2 domain comprising the amino acid sequence of SEQ ID NO: 5 or a sequence substantially homologous thereto.

Said antibody optionally further comprises a heavy chain CDR3 domain comprising the amino acid sequence of SEQ ID NO: 3 or a sequence substantially homologous thereto and/or a light chain CDR3 domain comprising the amino acid sequence of SEQ ID NO: 6 or a sequence substantially homologous thereto and/or further comprises a heavy chain CDR1 domain comprising the amino acid sequence of SEQ ID NO: 1 or a sequence substantially homologous thereto and/or a light chain CDR1 domain comprising the amino acid sequence of SEQ ID NO: 4 or a sequence substantially homologous thereto.

In certain embodiments, the present invention provides an antibody that binds to CCR4 and which is capable of inhibiting the binding of MDC to CCR4 comprising a heavy chain CDR2 domain comprising the amino acid sequence of SEQ ID NO: 8, 127 or 128 or a sequence substantially homologous thereto and/or a light chain CDR2 domain comprising the amino acid sequence of SEQ ID NO: 11, 131 or 132 or a sequence substantially homologous thereto.

Said antibody optionally further comprises a heavy chain CDR3 domain comprising the amino acid sequence of SEQ ID NO: 9 or a sequence substantially homologous thereto and/or a light chain CDR3 domain comprising the amino acid sequence of SEQ ID NO: 12, 133, 134, 137 or 138 or a sequence substantially homologous thereto and/or further comprises a heavy chain CDR1 domain comprising the amino acid sequence of SEQ ID NO: 7, 101, 125 or 126 or a sequence substantially homologous thereto and/or a light chain CDR1 domain comprising the amino acid sequence of SEQ ID NO: 10, 129 or 130 or a sequence substantially homologous thereto.

In certain embodiments, the present invention provides an antibody that binds to binds to CCR4 and which is capable of inhibiting the binding of MDC to CCR4 comprising a heavy chain CDR2 domain comprising the amino acid sequence of SEQ ID NO: 8 or a sequence substantially homologous thereto and/or a light chain CDR2 domain comprising the amino acid sequence of SEQ ID NO: 110 or a sequence substantially homologous thereto.

Said antibody optionally further comprises a heavy chain CDR3 domain comprising the amino acid sequence of SEQ ID NO: 9 or a sequence substantially homologous thereto and/or a light chain CDR3 domain comprising the amino acid sequence of SEQ ID NO: 112 or a sequence substantially homologous thereto and/or further comprises a heavy chain CDR1 domain comprising the amino acid sequence of SEQ ID NO: 7 or a sequence substantially homologous thereto and/or a light chain CDR1 domain comprising the amino acid sequence of SEQ ID NO: 108 or a sequence substantially homologous thereto.

In certain embodiments, the present invention provides an antibody that binds to binds to CCR4 and which is capable of inhibiting the binding of MDC to CCR4 comprising a heavy chain CDR2 domain comprising the amino acid sequence of SEQ ID NO: 2 or a sequence substantially homologous thereto and/or a light chain CDR2 domain comprising the amino acid sequence of SEQ ID NO: 17 or a sequence substantially homologous thereto.

Said antibody optionally further comprises a heavy chain CDR3 domain comprising the amino acid sequence of SEQ ID NO: 15 or a sequence substantially homologous thereto and/or a light chain CDR3 domain comprising the amino acid sequence of SEQ ID NO: 18 or a sequence substantially homologous thereto and/or further comprises a heavy chain CDR1 domain comprising the amino acid sequence of SEQ ID NO: 1 or a sequence substantially homologous thereto and/or a light chain CDR1 domain comprising the amino acid sequence of SEQ ID NO: 16 or a sequence substantially homologous thereto.

Viewed alternatively, in certain embodiments, the present invention provides an antibody that binds to binds to CCR4 and which is capable of inhibiting the binding of MDC to CCR4 comprising a heavy chain CDR2 domain comprising the amino acid sequence of SEQ ID NO: 20 or a sequence substantially homologous thereto and/or a light chain CDR2 domain comprising the amino acid sequence of SEQ ID NO: 23 or a sequence substantially homologous thereto.

Said antibody optionally further comprises a heavy chain CDR3 domain comprising the amino acid sequence of SEQ ID NO: 21 or a sequence substantially homologous thereto and/or a light chain CDR3 domain comprising the amino acid sequence of SEQ ID NO: 24 or a sequence substantially homologous thereto and/or further comprises a heavy chain CDR1 domain comprising the amino acid sequence of SEQ ID NO: 19 or a sequence substantially homologous thereto and/or a light chain CDR1 domain comprising the amino acid sequence of SEQ ID NO: 22 or a sequence substantially homologous thereto.

Viewed alternatively, in certain embodiments, the present invention provides an antibody that binds to CCR4 and which is capable of inhibiting the binding of MDC to CCR4 comprising a heavy chain CDR1 domain comprising the amino acid sequence of SEQ ID NO: 1 or a sequence substantially homologous thereto and/or a light chain CDR1 domain comprising the amino acid sequence of SEQ ID NO: 4 or a sequence substantially homologous thereto.

Said antibody optionally further comprises a heavy chain CDR3 domain comprising the amino acid sequence of SEQ ID NO: 3 or a sequence substantially homologous thereto and/or a light chain CDR3 domain comprising the amino acid sequence of SEQ ID NO: 6 or a sequence substantially homologous thereto and/or further comprises a heavy chain CDR2 domain comprising the amino acid sequence of SEQ ID NO: 2 or a sequence substantially homologous thereto and/or a light chain CDR2 domain comprising the amino acid sequence of SEQ ID NO: 5 or a sequence substantially homologous thereto.

In certain embodiments, the present invention provides an antibody that binds to CCR4 and which is capable of inhibiting the binding of MDC to CCR4 comprising a heavy chain CDR1 domain comprising the amino acid sequence of SEQ ID NO: 7, 125 or 126 or a sequence substantially homologous thereto and/or a light chain CDR1 domain comprising the amino acid sequence of SEQ ID NO: 10, 129 or 130 or a sequence substantially homologous thereto.

Said antibody optionally further comprises a heavy chain CDR3 domain comprising the amino acid sequence of SEQ ID NO: 9 or a sequence substantially homologous thereto and/or a light chain CDR3 domain comprising the amino acid sequence of SEQ ID NO: 12, 133, 134, 137 or 138 or a sequence substantially homologous thereto and/or further comprises a heavy chain CDR2 domain comprising the amino acid sequence of SEQ ID NO: 8, 127 or 128 or a sequence substantially homologous thereto and/or a light chain CDR2 domain comprising the amino acid sequence of SEQ ID NO: 11, 131 or 132 or a sequence substantially homologous thereto.

Viewed alternatively, in certain embodiments, the present invention provides an antibody that binds to CCR4 and which is capable of inhibiting the binding of MDC to CCR4 comprising a heavy chain CDR1 domain comprising the amino acid sequence of SEQ ID NO: 101 or a sequence substantially homologous thereto and/or a light chain CDR1 domain comprising the amino acid sequence of SEQ ID NO: 10 or a sequence substantially homologous thereto.

Said antibody optionally further comprises a heavy chain CDR3 domain comprising the amino acid sequence of SEQ ID NO: 9 or a sequence substantially homologous thereto and/or a light chain CDR3 domain comprising the amino acid sequence of SEQ ID NO: 12 or a sequence substantially homologous thereto and/or further comprises a heavy chain CDR2 domain comprising the amino acid sequence of SEQ ID NO: 8 or a sequence substantially homologous thereto and/or a light chain CDR2 domain comprising the amino acid sequence of SEQ ID NO: 11 or a sequence substantially homologous thereto.

In certain embodiments, the present invention provides an antibody that binds to CCR4 and which is capable of inhibiting the binding of MDC to CCR4 comprising a heavy chain CDR1 domain comprising the amino acid sequence of SEQ ID NO: 7 or a sequence substantially homologous thereto and/or a light chain CDR1 domain comprising the amino acid sequence of SEQ ID NO: 108 or a sequence substantially homologous thereto.

Said antibody optionally further comprises a heavy chain CDR3 domain comprising the amino acid sequence of SEQ ID NO: 9 or a sequence substantially homologous thereto and/or a light chain CDR3 domain comprising the amino acid sequence of SEQ ID NO: 112 or a sequence substantially homologous thereto and/or further comprises a heavy chain CDR2 domain comprising the amino acid sequence of SEQ ID NO: 8 or a sequence substantially homologous thereto and/or a light chain CDR2 domain comprising the amino acid sequence of SEQ ID NO: 110 or a sequence substantially homologous thereto.

In certain embodiments, the present invention provides an antibody that binds to CCR4 and which is capable of inhibiting the binding of MDC to CCR4 comprising a heavy chain CDR1 domain comprising the amino acid sequence of SEQ ID NO: 1 or a sequence substantially homologous thereto and/or a light chain CDR1 domain comprising the amino acid sequence of SEQ ID NO: 16 or a sequence substantially homologous thereto.

Said antibody optionally further comprises a heavy chain CDR3 domain comprising the amino acid sequence of SEQ ID NO: 15 or a sequence substantially homologous thereto and/or a light chain CDR3 domain comprising the amino acid sequence of SEQ ID NO: 18 or a sequence substantially homologous thereto and/or further comprises a heavy chain CDR2 domain comprising the amino acid sequence of SEQ ID NO: 2 or a sequence substantially homologous thereto and/or a light chain CDR2 domain comprising the amino acid sequence of SEQ ID NO: 17 or a sequence substantially homologous thereto.

In certain embodiments, the present invention provides an antibody that binds to CCR4 and which is capable of inhibiting the binding of MDC to CCR4 comprising a heavy chain CDR1 domain comprising the amino acid sequence of SEQ ID NO: 19 or a sequence substantially homologous thereto and/or a light chain CDR1 domain comprising the amino acid sequence of SEQ ID NO: 22 or a sequence substantially homologous thereto.

Said antibody optionally further comprises a heavy chain CDR3 domain comprising the amino acid sequence of SEQ ID NO: 21 or a sequence substantially homologous thereto and/or a light chain CDR3 domain comprising the amino acid sequence of SEQ ID NO: 24 or a sequence substantially homologous thereto and/or further comprises a heavy chain CDR2 domain comprising the amino acid sequence of SEQ ID NO: 20 or a sequence substantially homologous thereto and/or a light chain CDR2 domain comprising the amino acid sequence of SEQ ID NO: 23 or a sequence substantially homologous thereto.

Certain preferred antibodies of the invention comprise one or more of the CDRs selected from the group consisting of SEQ ID NOs: 1, 2, 3, 4, 5 and 6 or a sequence substantially homologous to any one of the foregoing SEQ ID NOs.

Certain preferred antibodies of the invention comprise one or more of the CDRs selected from the group consisting of SEQ ID NOs: 7, 8, 9, 10, 11 and 12 or a sequence substantially homologous to any one of the foregoing SEQ ID NOs.

Certain preferred antibodies of the invention comprise one or more of the CDRs selected from the group consisting of SEQ ID NOs: 101, 8, 9, 10, 11 and 12 or a sequence substantially homologous to any one of the foregoing SEQ ID NOs.

Certain preferred antibodies of the invention comprise one or more of the CDRs selected from the group consisting of SEQ ID NOs: 7, 8, 9, 108, 110 and 112 or a sequence substantially homologous to any one of the foregoing SEQ ID NOs.

Certain preferred antibodies of the invention comprise one or more of the CDRs selected from the group consisting of SEQ ID NOs: 1, 2, 15, 16, 17 and 18 or a sequence substantially homologous to any one of the foregoing SEQ ID NOs.

Certain preferred antibodies of the invention comprise one or more of the CDRs selected from the group consisting of SEQ ID NOs: 19, 20, 21, 22, 23 or 24 or
a sequence substantially homologous to any one of the foregoing SEQ ID NOs.

Certain preferred antibodies of the invention comprise one or more of the CDRs selected from the group consisting of SEQ ID NOs: 125, 127, 9, 129, 131 or 133 (137) or a sequence substantially homologous to any one of the foregoing SEQ ID NOs.

Certain preferred antibodies of the invention comprise one or more of the CDRs selected from the group consisting of SEQ ID NOs: 126, 128, 9, 130, 132 or 134 (138) or a sequence substantially homologous to any one of the foregoing SEQ ID NOs.

Certain preferred antibodies comprise two or more of the light chain CDRs of SEQ ID NOs: 4, 5 and 6, or 10, 11 and 12, or 16, 17 and 18, or 22, 23 and 24, or 108, 110 and 112, or 129, 131 and 133 (137), or 130, 132 and 134 (138); or sequences substantially homologous to any one of the foregoing SEQ ID NOs.

Especially preferred binding molecules comprise 3 of the light chain CDRs of SEQ ID NOs: 4, 5 and 6; or 10, 11 and 12; or 16, 17 and 18; or 22, 23 and 24; or 108, 110 and 112, or 129, 131 and 133 (137), or 130, 132 and 134 (138); or sequences substantially homologous to any one of the foregoing SEQ ID NOs (i.e. one of each of the aforementioned light chain CDR1 and CDR2 and CDR3 or sequences substantially homologous thereto).

Other certain preferred antibodies comprise two or more of the heavy chain CDRs of SEQ ID NOs: 1, 2 and 3; or 7, 8 and 9; or 1, 2 and 15; or 19, 20 and 21; or 101, 8 and 9, or 125 and 127 and 9, or 126 and 128 and 9; or sequences substantially homologous to any one of the foregoing SEQ ID NOs.

Especially preferred antibodies comprise 3 of the heavy chain CDRs of SEQ ID NOs: 1, 2 and 3; or 7, 8 and 9; or 1, 2 and 15; or 19, 20 and 21; or 101, 8 and 9, or 125 and 127 and 9, or 126 and 128 and 9; or sequences substantially homologous to any one of the foregoing SEQ ID NOs (i.e. one of each of the aforementioned heavy chain CDR1 and CDR2 and CDR3 or sequences substantially homologous thereto).

In some embodiments, the combination of a heavy chain CDR1 of SEQ ID NO: 1 with a heavy chain CDR2 of SEQ ID NO: 2 is particularly preferred.

In some embodiments, the combination of a heavy chain CDR3 of SEQ ID NO: 9 with a heavy chain CDR2 of SEQ ID NO: 8 and/or a heavy chain CDR1 of SEQ ID NO: 7 or 101 is particularly preferred.

Certain more especially preferred antibodies comprise 3 of the light chain CDRs of SEQ ID NOs: 4, 5 and 6 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 1, 2 and 3, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 10, 11 and 12 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 7, 8 and 9, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 10, 11 and 12 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 101, 8 and 9, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 108, 110 and 112 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 7, 8 and 9, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 16, 17 and 18 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 1, 2 and 15, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 22, 23 and 24 or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 19, 20 and 21, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 129, 131 and 133 (137) or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 125, 127 and 9, or sequences substantially homologous any one of these sequences (i.e. one of each of the aforementioned heavy chain CDR1 and CDR2 and CDR3 or sequences substantially homologous thereto).

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 3, or sequences substantially homologous to any one of the aforementioned sequences; and/or comprise a light chain CDR1 domain of SEQ ID NO: 4, a light chain CDR2 domain of SEQ ID NO: 5, and a light chain CDR 3 domain of SEQ ID NO: 6, or sequences substantially homologous to any one of the aforementioned sequences.

Certain especially preferred antibodies comprise a heavy chain CDR1 domain of SEQ ID NO: 7 or 101, a heavy chain CDR2 domain of SEQ ID NO: 8, and a heavy chain CDR3 domain of SEQ ID NO: 9, or sequences substantially homologous to any one of the aforementioned sequences; and/or comprise a light chain CDR1 domain of SEQ ID NO: 10, a light chain CDR2 domain of SEQ ID NO: 11, and a light chain CDR 3 domain of SEQ ID NO: 12, or sequences substantially homologous to any one of the aforementioned sequences.

Certain especially preferred antibodies comprise a heavy chain CDR1 domain of SEQ ID NO: 7, a heavy chain CDR2 domain of SEQ ID NO: 8, and a heavy chain CDR3 domain of SEQ ID NO: 9, or sequences substantially homologous to any one of the aforementioned sequences; and/or comprise a light chain CDR1 domain of SEQ ID NO: 108, a light chain CDR2 domain of SEQ ID NO: 110, and a light chain CDR 3 domain of SEQ ID NO: 112, or sequences substantially homologous to any one of the aforementioned sequences.

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 15, or sequences substantially homologous to any one of the aforementioned sequences; and/or comprise a light chain CDR1 domain of SEQ ID NO: 16, a light chain CDR2 domain of SEQ ID NO: 17, and a light chain CDR 3 domain of SEQ ID NO: 18, or sequences substantially homologous to any one of the aforementioned sequences.

Certain especially preferred antibodies comprise a heavy chain CDR1 domain of SEQ ID NO: 19, a heavy chain CDR2 domain of SEQ ID NO: 20, and a heavy chain CDR3 domain of SEQ ID NO: 21, or sequences substantially homologous to any one of the aforementioned sequences; and/or comprise a light chain CDR1 domain of SEQ ID NO: 22, a light chain CDR2 domain of SEQ ID NO: 23, and a light chain CDR 3 domain of SEQ ID NO: 24, or sequences substantially homologous to any one of the aforementioned sequences.

Certain especially preferred antibodies comprise a heavy chain CDR1 domain of SEQ ID NO: 125, 126, 135 or 136, a heavy chain CDR2 domain of SEQ ID NO: 127 or 128, and a heavy chain CDR3 domain of SEQ ID NO: 9, or sequences substantially homologous to any one of the aforementioned sequences; and/or comprise a light chain CDR1 domain of SEQ ID NO: 129 or 130, a light chain CDR2 domain of SEQ ID NO: 131 or 132, and a light chain CDR 3 domain of SEQ ID NO: 133 (137) or 134 (138), or sequences substantially homologous to any one of the aforementioned sequences.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 1,
(ii) a VH CDR2 that has the amino acid sequence of SEQ ID NO: 2, and
(iii) a VH CDR3 that has the amino acid sequence of SEQ ID NO: 3 or 15.

In a preferred aspect of this embodiment, one or more of said light chain variable region CDRs are selected from the group consisting of:
(i) a VL CDR1 that has the amino acid sequence of SEQ ID NO: 4 or 16,
(ii) a VL CDR2 that has the amino acid sequence of SEQ ID NO: 5 or 17, and
(iii) a VL CDR3 that has the amino acid sequence of SEQ ID NO: 6 or 18. Preferably, 2 or 3 of said light chain variable region CDRs are selected from the above group.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 7 or 101,
(ii) a VH CDR2 that has the amino acid sequence of SEQ ID NO: 8, and
(iii) a VH CDR3 that has the amino acid sequence of SEQ ID NO: 9.

In a preferred aspect of this embodiment, one or more of said light chain variable region CDRs are selected from the group consisting of:
(i) a VL CDR1 that has the amino acid sequence of SEQ ID NO: 10,
(ii) a VL CDR2 that has the amino acid sequence of SEQ ID NO: 11, and
(iii) a VL CDR3 that has the amino acid sequence of SEQ ID NO: 12. Preferably, 2 or 3 of said light chain variable region CDRs are selected from the above group.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 7,
(ii) a VH CDR2 that has the amino acid sequence of SEQ ID NO: 8, and
(iii) a VH CDR3 that has the amino acid sequence of SEQ ID NO: 9.

In a preferred aspect of this embodiment, one or more of said light chain variable region CDRs are selected from the group consisting of:
(i) a VL CDR1 that has the amino acid sequence of SEQ ID NO: 108,
(ii) a VL CDR2 that has the amino acid sequence of SEQ ID NO: 110, and
(iii) a VL CDR3 that has the amino acid sequence of SEQ ID NO: 112. Preferably, 2 or 3 of said light chain variable region CDRs are selected from the above group.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 19,
(ii) a VH CDR2 that has the amino acid sequence of SEQ ID NO: 20, and
(iii) a VH CDR3 that has the amino acid sequence of SEQ ID NO: 21.

In a preferred aspect of this embodiment, one or more of said light chain variable region CDRs are selected from the group consisting of:
(i) a VL CDR1 that has the amino acid sequence of SEQ ID NO: 22,
(ii) a VL CDR2 that has the amino acid sequence of SEQ ID NO: 23, and
(iii) a VL CDR3 that has the amino acid sequence of SEQ ID NO: 24. Preferably, 2 or 3 of said light chain variable region CDRs are selected from the above group.

In a further embodiment, the invention provides an antibody that binds to CCR4 and which is capable of inhibiting the binding of MDC to CCR4 and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 125, 126, 135 or 136,
(ii) a VH CDR2 that has the amino acid sequence of SEQ ID NO: 127 or 128, and
(iii) a VH CDR3 that has the amino acid sequence of SEQ ID NO: 9.

In a preferred aspect of this embodiment, one or more of said light chain variable region CDRs are selected from the group consisting of:
(i) a VL CDR1 that has the amino acid sequence of SEQ ID NO: 129 or 130,
(ii) a VL CDR2 that has the amino acid sequence of SEQ ID NO: 131 or 132, and
(iii) a VL CDR3 that has the amino acid sequence of SEQ ID NO: 133 (137) or 134 (138). Preferably, 2 or 3 of said light chain variable region CDRs are selected from the above group.

Certain further preferred embodiments of the invention provide an antibody that binds to CCR4 and which is capable of inhibiting the binding of MDC to CCR4 and that comprises:
a VH domain that comprises one, two or three of the heavy chain CDRs of SEQ ID NOs: 1, 2 or 3, or sequences substantially homologous to one or more of SEQ ID NOs: 1, 2 or 3, and/or a VL domain that comprises one, two or three of the light chain CDRs of SEQ ID NOs: 4, 5 or 6, or sequences substantially homologous to one or more of SEQ ID NOs: 4, 5 or 6.

Certain further preferred embodiments of the invention provide an antibody that binds to CCR4 and which is capable of inhibiting the binding of MDC to CCR4 and that comprises: a VH domain that comprises one, two or three of the heavy chain CDRs of SEQ ID NOs: 7, 8, 9 or 101, or sequences substantially homologous to one or more of SEQ ID NOs: 7, 8, 9 or 101, and/or a VL domain that comprises one, two or three of the light chain CDRs of SEQ ID NOs: 10, 11 or 12, or sequences substantially homologous to one or more of SEQ ID NOs: 10, 11 or 12.

Certain further preferred embodiments of the invention provide an antibody that binds to CCR4 and which is capable of inhibiting the binding of MDC to CCR4 and that comprises: a VH domain that comprises one, two or three of the heavy chain CDRs of SEQ ID NOs: 7, 8 or 9, or sequences substantially homologous to one or more of SEQ ID NOs: 7, 8 or 9, and/or a VL domain that comprises one, two or three of the light chain CDRs of SEQ ID NOs: 108, 110 or 112, or sequences substantially homologous to one or more of SEQ ID NOs: 108, 110 or 112.

Certain further preferred embodiments of the invention provide an antibody that binds to CCR4 and which is capable of inhibiting the binding of MDC to CCR4 and that comprises: a VH domain that comprises one, two or three of the heavy chain CDRs of SEQ ID NOs: 1, 2 or 15, or sequences substantially homologous to one or more of SEQ ID NOs: 1, 2 or 15, and/or a VL domain that comprises one, two or three of the light chain CDRs of SEQ ID NOs: 16, 17 or 18, or sequences substantially homologous to one or more of SEQ ID NOs: 16, 17 or 18.

Certain further preferred embodiments of the invention provide an antibody that binds to CCR4 and which is capable of inhibiting the binding of MDC to CCR4 and that comprises: a VH domain that comprises one, two or three of the heavy chain CDRs of SEQ ID NOs: 19, 20 or 21, or sequences substantially homologous to one or more of SEQ ID NOs: 19, 20 or 21, and/or a VL domain that comprises one, two or three of the light chain CDRs of SEQ ID NOs: 22, 23 or 24, or sequences substantially homologous to one or more of SEQ ID NOs: 22, 23 or 24.

Certain further preferred embodiments of the invention provide an antibody that binds to CCR4 and which is capable of inhibiting the binding of MDC to CCR4 and that comprises: a VH domain that comprises one, two or three of the heavy chain CDRs of SEQ ID NOs: 125, 127 or 9, or sequences substantially homologous to one or more of SEQ ID NOs: 125, 127 or 9, and/or a VL domain that comprises one, two or three of the light chain CDRs of SEQ ID NOs: 129, 131 or 133 (137), or sequences substantially homologous to one or more of SEQ ID NOs: 129, 131 or (137).

More especially preferred embodiments of the invention provide an antibody that binds to CCR4 and which is capable of inhibiting the binding of MDC to CCR4 and that comprises: a VL domain that comprises 3 light chain CDRs and a VH domain that comprises 3 heavy chain CDRs of SEQ ID NOs: 1, 2, and 3 or 15. In preferred embodiments one, two or three of the light chain CDRs are as defined in SEQ ID NOs: 4, 5 and 6, or 16, 17 and 18.

More especially preferred embodiments of the invention provide an antibody that binds to CCR4 and which is capable of inhibiting the binding of MDC to CCR4 and that comprises: a VL domain that comprises 3 light chain CDRs and a VH domain that comprises 3 heavy chain CDRs of SEQ ID NOs: 8, 9, and 7 or 101. In preferred embodiments one, two or three of the light chain CDRs are as defined in SEQ ID NOs: 10, 11 and 12, or 108, 110 and 112.

More especially preferred embodiments of the invention provide an antibody that binds to CCR4 and which is capable of inhibiting the binding of MDC to CCR4 and that comprises: a VL domain that comprises 3 light chain CDRs and a VH domain that comprises 3 heavy chain CDRs of SEQ ID NOs: 125, 127 and 9. In preferred embodiments one, two or three of the light chain CDRs are as defined in SEQ ID NOs: 129, 131 and 133 (137).

In all the embodiments of the present invention as described herein, X, where present in an amino acid sequence, represents a variable amino acid. Thus, where a sequence comprises more than one X, each X may be different, but one or more X may also be the same. Preferably, at position 1 of SEQ ID NO: 125, X=S or N; and/or at position 4 of SEQ ID NO: 125, X=I or M; and/or at position 1 of SEQ ID NO: 127, X=G or A; and/or at position 3 of SEQ ID NO: 127, X=I or S; and/or at position 5 of SEQ ID NO: 127, X=I or S; and/or at position 6 of SEQ ID NO: 127, X=F or G; and/or at position 8 of SEQ ID NO: 127, X=T or S; and/or at position 9 of SEQ ID NO: 127, X=A or T and/or at position 3 of SEQ ID NO: 129, X=S or G; and/or at position 4 of SEQ ID NO: 129, X=T or G; and/or at position 9 of SEQ ID NO: 129, X=S or R; and/or at position 10 of SEQ ID NO: 129, X=R or H; and/or at position 11 of SEQ ID NO: 129, X=Y or F; and/or at position 13 of SEQ ID NO: 129, X=Y or F; and/or at position 3 of SEQ ID NO: 131, X=H or N; and/or at position 2 of SEQ ID NO: 133 or 137, X=A or V; and/or at position 6 of SEQ ID NO: 133 or 137, X=S or T.

A preferred embodiment of SEQ ID NO: 125 is SEQ ID NO: 126, a preferred embodiment of SEQ ID NO: 127 is SEQ ID NO: 128, a preferred embodiment of SEQ ID NO: 129 is SEQ ID NO: 130, a preferred embodiment of SEQ ID NO:131 is SEQ ID NO: 132, and a preferred embodiment of SEQ ID NO:133 is SEQ ID NO: 134.

A preferred embodiment of SEQ ID NO:125 and/or SEQ ID NO: 126 is SEQ ID NO: 135, more preferably SEQ ID NO:136. A preferred embodiment of SEQ ID NO: 133 is SEQ ID NO: 137 or SEQ ID NO:138. A preferred embodiment of SEQ ID NO: 134 is SEQ ID NO:138.

Embodiments in which a heavy chain CDR1 of SEQ ID NO: 125 is present are preferred. Also preferred are embodiments in which a heavy chain CDR1 of SEQ ID NO: 101 is present. Thus, the heavy chain CDR1 preferably starts with the amino acid S (serine).

Certain preferred embodiments of the invention provide an antibody that binds to CCR4 and which is capable of inhibiting the binding of MDC to CCR4 comprising a VH domain that has the amino acid sequence of SEQ ID NO: 139, 69, 71, 73, 75 or 105 or a sequence substantially homologous thereto and/or a VL domain that has the amino acid sequence of SEQ ID NO: 140, 70, 72, 74, 76 or 115 or a sequence substantially homologous thereto. Preferably, said VH and/or VL domains have at least 1, 2, 3, 4, or 5, e.g. 6 of the CDR sequences disclosed herein.

Further preferred embodiments provide an antibody that binds to CCR4 and which is capable of inhibiting the binding of MDC to CCR4 comprising a VH domain that has the amino acid sequence of SEQ ID NO: 139, 69, 71, 73, 75 or 105 and a VL domain that comprises 3 light chain CDRs. Preferably said light chain CDRs have SEQ ID NOs 4, 5 and 6, or 10, 11 and 12, or 16, 17 and 18, or 22, 23 and 24, or 108, 110 and 112, or 129, 131 and 133 (137), or 130, 132 and 134 (138).

Further preferred embodiments provide an antibody that binds to CCR4 and which is capable of inhibiting the binding of MDC to CCR4 comprising a VH domain that has the amino acid sequence of SEQ ID NO: 69 or a sequence substantially homologous thereto and/or a VL domain that has the amino acid sequence of SEQ ID NO: 70 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 71 or a sequence substantially homologous thereto and/or a VL domain that has the amino acid sequence of SEQ ID NO: 72 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 71 or a sequence substantially homologous thereto and/or a VL domain that has the amino acid sequence of SEQ ID NO: 115 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 105 or a sequence substantially homologous thereto and/or a VL domain that has the amino acid sequence of SEQ ID NO: 72 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 73 or a sequence substantially homologous thereto and/or a VL domain that has the amino acid sequence of SEQ ID NO: 74 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 75 or a sequence substantially homologous thereto and/or a VL domain that has the amino acid sequence of SEQ ID NO: 76 or a sequence substantially homologous thereto.

Further preferred embodiments provide an antibody that binds to CCR4 and which is capable of inhibiting the binding of MDC to CCR4 comprising a VH domain that has the amino acid sequence of SEQ ID NO: 139 or a sequence substantially homologous thereto and/or a VL domain that has the amino acid sequence of SEQ ID NO: 140 or a sequence substantially homologous thereto.

In a yet further embodiment, the present invention provides an antibody that binds CCR4 and which is capable of inhibiting the binding of MDC to CCR4 comprising the amino acid sequence of SEQ ID NO: 35 (said antibody also being referred to herein as 17G scFv), SEQ ID NO: 46 (said antibody also being referred to herein as 9E scFv), SEQ ID NO: 104 (said antibody also being referred to herein as 9E10J scFv), SEQ ID NO: 114 (said antibody also being referred to herein as 9E1D scFv), SEQ ID NO: 57 (said antibody also being referred to herein as 1O scFv), or SEQ ID NO: 68 (said antibody also being referred to herein as 11F scFv), or comprising a fragment of any thereof that binds CCR4 and which is capable of inhibiting the binding of MDC to CCR4, or a sequence substantially homologous to any of the above sequence.

The invention is exemplified by monoclonal antibodies 17G, 9E, 1O, 11F, 9E10J and 9E1D, single chain forms of which are shown in Tables 1, 2, 3, 4, 11 and 12 (SEQ ID NOs: 35, 46, 57, 68, 103 and 114 respectively). Full length IgG forms of antibodies 17G, 9E, 1O and 11F have been made and their sequences are shown in Tables 5, 6, 7 and 8 respectively. The CDR domains, VH and VL domains of the 17G, 9E, 11F and 1O antibodies are shown in Tables 1 to 4 and FIGS. 1-4 and CDR domains, VH and VL domains of the 9E10J and 9E1D antibodies are shown in Tables 11 and 12. Full length IgG forms of antibodies 9E10J and 9E1D have been made and their sequences are shown in Tables 13 and 14. Table 23 lists consensus sequences. Antibodies comprising these CDR domains or VH and VL domains (or sequences substantially homologous thereto) are preferred aspects of the invention.

A preferred embodiment of the invention is a scFv form of the 17G antibody comprising or consisting of SEQ ID NO: 35, which is preferably encoded by SEQ ID NO: 34. More preferably, the antibody comprises or consists of the amino acid sequence shown in FIG. 1 and preferably this antibody is encoded by the nucleic acid sequence shown in FIG. 1.

Another preferred embodiment of the invention is a scFv form of the 9E antibody comprising or consisting of SEQ ID NO: 46, which is preferably encoded by SEQ ID NO: 45. More preferably, the antibody comprises or consists of the amino acid sequence shown in FIG. 2 and preferably this antibody is encoded by the nucleic acid sequence shown in FIG. 2.

Another preferred embodiment of the invention is a scFv form of the 9E10J antibody comprising or consisting of SEQ ID NO: 104, which is preferably encoded by SEQ ID NO: 103. More preferably, the antibody comprises or consists of the amino acid sequence shown in FIG. 27 and preferably this antibody is encoded by the nucleic acid sequence shown in FIG. 27.

Another preferred embodiment of the invention is a scFv form of the 9E1D antibody comprising or consisting of SEQ ID NO: 114, which is preferably encoded by SEQ ID NO: 113. More preferably, the antibody comprises or consists of the amino acid sequence shown in FIG. 28 and preferably this antibody is encoded by the nucleic acid sequence shown in FIG. 28.

Another preferred embodiment of the invention is a scFv form of the 10 antibody comprising or consisting of SEQ ID NO: 57, which is preferably encoded by SEQ ID NO: 56. More preferably, the antibody comprises or consists of the amino acid sequence shown in FIG. 3 and preferably this antibody is encoded by the nucleic acid sequence shown in FIG. 3.

Another preferred embodiment of the invention is a scFv form of the 11F antibody comprising or consisting of SEQ ID NO: 68, which is preferably encoded by SEQ ID NO: 67. More preferably, the antibody comprises or consists of the amino acid sequence shown in FIG. 4 and preferably this antibody is encoded by the nucleic acid sequence shown in FIG. 4.

Other preferred embodiments are IgG forms of the 17G, 9E, 1O, 11F, 9EJ10 and 9E1D antibodies, preferably full length IgG forms. The IgG1 form of any of these antibodies is most preferred.

Thus, another preferred embodiment of the invention is a full length IgG antibody which comprises a heavy chain of SEQ ID NO: 87 (amino acid) and/or a light chain of SEQ ID NO: 88 (amino acid). Also preferred is an IgG antibody which comprises a heavy chain encoded by SEQ ID NO:85 and/or a light chain encoded by SEQ ID NO:86. It is of course understood that full IgG antibodies will comprise two substantially identical heavy chains and two substantially identical light chains.

Another preferred embodiment of the invention is a full length IgG antibody which comprises a heavy chain of SEQ ID NO: 91 (amino acid) and/or a light chain of SEQ ID NO: 92 (amino acid). Also preferred is an IgG antibody which comprises a heavy chain encoded by SEQ ID NO: 89 and/or a light chain encoded by SEQ ID NO: 90.

Another preferred embodiment of the invention is a full length IgG antibody which comprises a heavy chain of SEQ ID NO: 95 (amino acid) and/or a light chain of SEQ ID NO: 96 (amino acid). Also preferred is an IgG antibody which comprises a heavy chain encoded by SEQ ID NO: 93 and/or a light chain encoded by SEQ ID NO: 94.

Another preferred embodiment of the invention is a full length IgG antibody which comprises a heavy chain of SEQ ID NO: 99 (amino acid) and/or a light chain of SEQ ID NO: 100 (amino acid). Also preferred is an IgG antibody which comprises a heavy chain encoded by SEQ ID NO: 97 and/or a light chain encoded by SEQ ID NO: 98.

Another preferred embodiment of the invention is a full length IgG antibody which comprises a heavy chain of SEQ ID NO: 119 (amino acid) and/or a light chain of SEQ ID NO: 120 (amino acid). Also preferred is an IgG antibody which comprises a heavy chain encoded by SEQ ID NO: 117 and/or a light chain encoded by SEQ ID NO: 118.

Another preferred embodiment of the invention is a full length IgG antibody which comprises a heavy chain of SEQ ID NO: 123 (amino acid) and/or a light chain of SEQ ID NO: 124 (amino acid). Also preferred is an IgG antibody which comprises a heavy chain encoded by SEQ ID NO: 121 and/or a light chain encoded by SEQ ID NO: 122.

It is believed that the antibodies of the invention may bind to a different epitope to the known anti-CCR4 antibody family which comprises KM2160, KM3060, KM2760 and KW-0761. Antibody KM2160 is a murine antibody which was raised against a peptide fragment of CCR4 and which recognises an epitope existing in a region of positions 2-29 from the N-terminal amino acid of human CCR4 (EP1270595). KM2760 is a chimeric version of the antibody having the same binding characteristics (EP1270595). Antibody KM3060 is identical to KM2760, except that it is highly fucosylated (Niwa et al. 2004, Cancer Research 64, 2127-2133). KW-0761 is a humanised version of KM2760 (Ishida et al. Annals of Oncology 2008, vol 19, supplement 4, 513).

KM2760 has been reported not to block the interaction between CCR4 and TARC or MDC (Ishida et al. 2006, Cancer Research 66 (11), pp 5716-5722), which is consistent with the inventors' findings using the equivalent antibody KM3060var (corresponding to KM3060, but potentially having a different sugar profile as it was expressed in a different host) shown in Example 3. By contrast, the antibodies of the present invention were found to block the interaction between CCR4 and MDC and the interaction between CCR4 and TARC (see Example 3). This strongly suggests that the antibodies of the invention bind to a different epitope than the prior art family which comprises KM2160, KM3060, KM2760 and KW-0761.

Moreover, antibodies 17G and 9E were found to compete with one another for binding to CCR4, indicating that they bind to the same, similar or at least overlapping epitopes. Neither of these antibodies competes with KM3060var for binding to CCR4, indicating that KM3060var binds to a different epitope.

It is also believed that the antibodies of the invention may bind to a different epitope to the commercially available anti-CCR4 antibody 1G1. BD Pharmingen make it clear on the technical data sheet for this antibody that this antibody is not a neutralising antibody. By contrast, the antibodies of the present invention are capable of blocking the binding of MDC and TARC to CCR4 and inhibiting the MDC or TARC-induced increase in intracellular calcium ions. This strongly suggests that the antibodies of the invention bind to a different epitope than the 1G1 antibody.

Thus, also provided are antibodies which can compete with any of the antibodies described herein for binding to CCR4.

The term "competing antibodies", as used herein, refers to antibodies that bind to about, substantially or essentially the same, or even the same, epitope as a "reference antibody". "Competing antibodies" include antibodies with overlapping epitope specificities. Competing antibodies are thus able to effectively compete with a reference antibody for binding to CCR4. Preferably, the competing antibody can bind to the same epitope as the reference antibody. Alternatively viewed, the competing antibody preferably has the same epitope specificity as the reference antibody.

"Reference antibodies" as used herein are antibodies which can bind to an epitope in the extracellular domain of human CCR4 and which have one or more of the CDR sequences are defined herein, preferably a VH and a VL domain as defined herein, more preferably a VH of SEQ ID NO: 130 and a VL of SEQ ID NO: 140, or a VH of SEQ ID NO: 69 and a VL of SEQ ID NO: 70, or a VH of SEQ ID NO: 71 and a VL of SEQ ID NO: 72, or a VH of SEQ ID NO: 105 and a VL of SEQ ID NO: 72, or a VH of SEQ ID NO: 71 and a VL of SEQ ID NO: 115, or a VH of SEQ ID NO: 73 and a VL of SEQ ID NO: 74, or a VH of SEQ ID NO: 75 and a VL of SEQ ID NO: 76. Most preferred reference antibodies are selected from 17G, 9E, 11F, 1O, 9E10J and 9E1D.

The identification of one or more competing antibodies is a straightforward technical matter now that reference antibodies such as 17G, 9E, 11F, 1O, 9E10J and 9E1D have been provided. As the identification of competing antibodies is determined in comparison to a reference antibody, it will be understood that actually determining the epitope to which either or both antibodies bind is not in any way required in order to identify a competing antibody. However, epitope mapping can be performed using standard techniques, if desired.

By way of example, the following methods for the identification and definition of epitopes are mentioned herein. The amino acid sequence of CCR4 is known, so synthetic peptides may be used for epitope mapping, e.g. using the Pepscan assay. Site directed mutagenesis is also a powerful tool in epitope mapping and can be used to evaluate the role of single amino acids in immune complex formation. Protein footprinting relies on the fact that the epitope is protected from cleavage when bound as an antibody-antigen complex. Enzyme linked immunosorbent assay (ELISA) and haemaglutination and slot-blotting may also be used in epitope mapping. Crystallisation of the antigen with the antibody may be used to map a non-linear epitope. Protocols for carrying out such methods are widely available and the skilled person will be aware of suitable alternative methods of epitope mapping.

The identification of competing antibodies can be readily determined using any one of variety of immunological screening assays in which antibody competition can be assessed. All such assays are routine in the art and are further described herein in detail. Each of U.S. Pat. Nos. 6,342,219, 6,524,583, 7,056,509, 6,887,468, 6,342,221, 6,676,941, 6,703,020 and 6,416,758 are specifically incorporated herein by reference for purposes including even further supplementing the present teaching concerning how to identify competing antibodies. Example 4 of the present specification discloses a suitable competition assay.

For example, where the test antibodies to be examined are obtained from different source animals, or are even of a different isotype, a simple competition assay may be employed in which the reference and test antibodies are admixed (or pre-adsorbed) and applied to CCR4-containing composition, preferably cells expressing CCR4, phage displaying CCR4, or biochips containing immobilised CCR4. Protocols based upon ELISAs are particularly suitable for use in such simple competition studies.

In certain embodiments, one would pre-mix the reference antibodies (e.g., 17G, 9E, 11F, 1O, 9E10J and 9E1D) with varying amounts of the test antibodies (e.g., 1:10, 1:100 or 1:1000) for a period of time prior to applying to an antigen composition. In other embodiments, the reference and varying amounts of test antibodies can simply be admixed during exposure to the antigen composition. In any event, by using species or isotype secondary antibodies one will be able to detect only the bound reference antibodies, the binding of which will be reduced by the presence of a test antibody that "competes" for binding.

In conducting an antibody competition study between a reference antibody and any test antibody (irrespective of species or isotype), one may first label the reference (e.g., 17G, 9E, 11F, 1O, 9E10J and 9E1D) with a detectable label, such as, e.g., biotin or an enzymatic or radioactive label to enable subsequent identification. In these cases, one would pre-mix or incubate the labeled reference antibodies with the test antibodies to be examined at various ratios (e.g., 1:10, 1:100 or 1:1000) and (optionally after a suitable period of time) then assay the reactivity of the labeled reference antibodies and compare this with a control value in which no potentially competing test antibody was included in the incubation.

The assay may be any one of a range of immunological assays based upon antibody binding, and the reference antibodies would be detected by means of detecting their label, e.g., using streptavidin in the case of biotinylated antibodies or by using a chromogenic substrate in connection with an enzymatic label (such as 3,3′5,5′-tetramethylbenzidine (TMB) substrate with peroxidase enzyme) or by simply detecting a radioactive label. An antibody that competes with the reference antibodies for binding to CCR4 will be able to effectively or significantly reduce reference antibody binding to CCR4, as evidenced by a reduction in bound label.

The reactivity of the (labeled) reference antibodies in the absence of a completely irrelevant antibody would be the control high value. The control low value would be obtained by incubating the labeled reference (e.g., 17G, 9E, 11F, 1O, 9E10J or 9E1D) antibodies with unlabelled antibodies of exactly the same type, when competition would occur and reduce binding of the labeled antibodies. In a test assay, a significant reduction in labeled antibody reactivity in the presence of a test antibody is indicative of a test antibody that "competes" with the labeled antibody for binding to CCR4.

A significant reduction is a "reproducible", i.e., consistently observed, reduction in binding. A "significant reduction" in terms of the present application is defined as a reproducible reduction (in binding of the reference antibody to CCR4 in an ELISA) of at least about 20%, more preferably at least about 25, 30, 35, 40, 45, 50, 55, 60 or 65%, even more preferably at least about 70%, about 75% or about 80% at any ratio between about 1:10 and about 1:100. Antibodies with even more stringent competing activities will exhibit a reproducible reduction (in binding of the reference antibody to CCR4 in an ELISA or other suitable assay) of at least about 82%, about 85%, about 88%, about 90%, about 92% or about 95% or so at any ratio between about 1:10 and about 1:100. Complete or near-complete competition, such as exhibiting a reproducible reduction in binding of the reference antibody to CCR4 of about 99%, about 98%, about 97% or about 96% or so, although by no means required to practice the invention, is certainly not excluded.

The method described above is only one example of a suitable competition assay. The skilled person will be aware of other suitable methods and variations. An alternative competition assay is described below.

Before the alternative competition assay is performed using flow cytometry, some quantities of the tested antibody should be labeled, e.g. by biotinylation. The functionality (retention of the cell-binding properties) of the biotinylated product and the minimal concentration of the biotinylated antibody of the invention (Ab1) that gives sub-maximal binding against a fixed number of CCR4+ cells is determined. A total of $10^6$ cells are harvested from exponentially growing cultures and incubated with various antibody concentrations for a suitable period of time at a suitable temperature, e.g. 1 hr at 4° C. The cells are washed and incubated with a suitable detection antibody for a suitable period of time at a suitable temperature, e.g. an additional hour at 4° C. After washing, the cells are analyzed by flow cytometry. For each test antibody, a saturation curve is generated from the data by plotting median fluorescence intensity (MFI) against the antibody concentration.

For the alternative competition assay, CCR4+ cells may be prepared as above and treated in duplicate with a mixture of fixed concentration of labeled (biotinylated) antibody (bio-Ab1) and increasing concentrations of non-labeled competitive antibody. The fixed concentration is the minimal concentration of antibody that generates reasonable fluorescence signal against a fixed number of tumor cells as determined above. Ideally, this fixed concentration in nM should be below the affinity of the treated antibody at equilibrium ($K_D$). In this case the described method can be used for estimation of affinities of competitive antibodies (Schodin and Kranz, 1993, J Biol Chem 268:25755-7). The antibody mixture is incubated with target cells for a suitable period of time at a suitable temperature, e.g. 1 hr at 4° C. The cells are washed and the cell binding of biotinylated antibody is revealed by incubation with FITC-labeled streptavidin. After subtracting the background fluorescence (PBS-5% FCS) from the median fluorescence reading for each test sample (bio-Ab1+Ab2), the percent of inhibition is calculated for each Ab2 concentration "c" according to the formula:

$$\% \text{ inhibition} = (1 - \text{MFI}^{bio\text{-}Ab1+Ab2"c"}/\text{MFI}^{bio\text{-}Ab1}) \times 100$$

is calculated.

Any antibodies which can bind to CCR4 and which are capable of inhibiting the binding of MDC to CCR4 and which can compete with any of the antibodies described herein are contemplated, but preferred antibodies are set out below. Accordingly, in some preferred embodiments there is provided the following.

An antibody which binds to an epitope in the extracellular domain of human CC chemokine receptor 4 (CCR4) and which is capable of inhibiting the binding of MDC to CCR4, wherein said antibody (a) comprises at least one heavy chain variable region that comprises three CDRs and at least one light chain variable region that comprises three CDRs, wherein said light chain variable region comprises:

(i) a variable light (VL) CDR1 that has the amino acid sequence of SEQ ID NO: 4;

(ii) a VL CDR2 that has the amino acid sequence of SEQ ID NO: 5; and/or (iii) a VL CDR3 that has the amino acid sequence of SEQ ID NO: 6; and/or wherein said heavy chain variable region comprises (iv) a variable heavy (VH) CDR1 that has the amino acid sequence of SEQ ID NO: 1;

(v) a VH CDR2 that has the amino acid sequence of SEQ ID NO: 2; and/or (vi) a VH CDR3 that has the amino acid sequence of SEQ ID NO: 3; or (b) is an antibody which can compete with antibody (a) for binding to CCR4.

An antibody which binds to an epitope in the extracellular domain of human CC chemokine receptor 4 (CCR4) and which is capable of inhibiting the binding of MDC to CCR4, wherein said antibody (a) comprises at least one heavy chain variable region that comprises three CDRs and at least one light chain variable region that comprises three CDRs, wherein said light chain variable region comprises:

(i) a variable light (VL) CDR1 that has the amino acid sequence of SEQ ID NO: 10;

(ii) a VL CDR2 that has the amino acid sequence of SEQ ID NO: 11; and/or (iii) a VL CDR3 that has the amino acid sequence of SEQ ID NO: 12; and/or wherein said heavy chain variable region comprises (iv) a variable heavy (VH) CDR1 that has the amino acid sequence of SEQ ID NO: 7 or 101, (v) a VH CDR2 that has the amino acid sequence of SEQ ID NO: 8; and/or (vi) a VH CDR3 that has the amino acid sequence of SEQ ID NO: 9; or
(b) is an antibody which can compete with antibody (a) for binding to CCR4.

An antibody which binds to an epitope in the extracellular domain of human CC chemokine receptor 4 (CCR4) and which is capable of inhibiting the binding of MDC to CCR4, wherein said antibody
(a) comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO: 108;
(ii) a VL CDR2 that has the amino acid sequence of SEQ ID NO: 110; and/or
(iii) a VL CDR3 that has the amino acid sequence of SEQ ID NO: 112; and/or wherein said heavy chain variable region comprises
(iv) a variable heavy (VH) CDR1 that has the amino acid sequence of SEQ ID NO: 7;
(v) a VH CDR2 that has the amino acid sequence of SEQ ID NO: 8; and/or
(vi) a VH CDR3 that has the amino acid sequence of SEQ ID NO: 9; or
b) is an antibody which can compete with antibody (a) for binding to CCR4.

An antibody which binds to an epitope in the extracellular domain of human CC chemokine receptor 4 (CCR4) and which is capable of inhibiting the binding of MDC to CCR4, wherein said antibody
(a) comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO: 16;
(ii) a VL CDR2 that has the amino acid sequence of SEQ ID NO: 17; and/or
(iii) a VL CDR3 that has the amino acid sequence of SEQ ID NO: 18; and/or wherein said heavy chain variable region comprises
(iv) a variable heavy (VH) CDR1 that has the amino acid sequence of SEQ ID NO: 1;
(v) a VH CDR2 that has the amino acid sequence of SEQ ID NO: 2; and/or
(vi) a VH CDR3 that has the amino acid sequence of SEQ ID NO: 15; or
b) is an antibody which can compete with antibody (a) for binding to CCR4.

An antibody which binds to an epitope in the extracellular domain of human CC chemokine receptor 4 (CCR4) and which is capable of inhibiting the binding of MDC to CCR4, wherein said antibody
(a) comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO: 22;
(ii) a VL CDR2 that has the amino acid sequence of SEQ ID NO: 23; and/or
(iii) a VL CDR3 that has the amino acid sequence of SEQ ID NO: 24; and/or wherein said heavy chain variable region comprises
(iv) a variable heavy (VH) CDR1 that has the amino acid sequence of SEQ ID NO: 19;
(v) a VH CDR2 that has the amino acid sequence of SEQ ID NO: 20; and/or
(vi) a VH CDR3 that has the amino acid sequence of SEQ ID NO: 21; or
(b) is an antibody which can compete with antibody (a) for binding to CCR4.

An antibody which binds to an epitope in the extracellular domain of human CC chemokine receptor 4 (CCR4) and which is capable of inhibiting the binding of MDC to CCR4, wherein said antibody
(a) comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO: 129 or 130;
(ii) a VL CDR2 that has the amino acid sequence of SEQ ID NO: 131 or 132; and/or
(iii) a VL CDR3 that has the amino acid sequence of SEQ ID NO: 133, 134, 137 or 138; and/or
wherein said heavy chain variable region comprises
(iv) a variable heavy (VH) CDR1 that has the amino acid sequence of SEQ ID NO: 125, 126, 135 or 136;
(v) a VH CDR2 that has the amino acid sequence of SEQ ID NO: 127 or 128; and/or
(vi) a VH CDR3 that has the amino acid sequence of SEQ ID NO: 9; or
(b) is an antibody which can compete with antibody (a) for binding to CCR4.

In one embodiment, the antibody
(a) has a VH domain of SEQ ID NO: 69 and a VL domain of SEQ ID NO: 70; or
(b) is an antibody which can compete with antibody (a) for binding to CCR4.

In one embodiment, the antibody
(a) has a VH domain of SEQ ID NO: 71 and a VL domain of SEQ ID NO: 72; or
(b) is an antibody which can compete with antibody (a) for binding to CCR4.

In one embodiment, the antibody
(a) has a VH domain of SEQ ID NO: 105 and a VL domain of SEQ ID NO: 72; or
(b) is an antibody which can compete with antibody (a) for binding to CCR4.

In one embodiment, the antibody
(a) has a VH domain of SEQ ID NO: 71 and a VL domain of SEQ ID NO: 115; or
(b) is an antibody which can compete with antibody (a) for binding to CCR4.

In one embodiment, the antibody
(a) has a VH domain of SEQ ID NO: 73 and a VL domain of SEQ ID NO: 74; or
(b) is an antibody which can compete with antibody (a) for binding to CCR4.

In one embodiment, the antibody
(a) has a VH domain of SEQ ID NO: 75 and a VL domain of SEQ ID NO: 76; or
(b) is an antibody which can compete with antibody (a) for binding to CCR4.

In one embodiment, the antibody
(a) has a VH domain of SEQ ID NO: 139 and a VL domain of SEQ ID NO: 140; or
(b) is an antibody which can compete with antibody (a) for binding to CCR4.

Preferably, antibody (b) has one or more of the CDR sequences, VH domains and/or VL domains described herein.

Preferably, antibody (b) can bind to the same epitope as antibody (a).

Certain examples of substantially homologous sequences are sequences that have at least 70% identity to the amino acid sequences disclosed. In certain embodiments, the antibodies of the invention that bind to CCR4 and which are capable of inhibiting the binding of MDC to CCR4 comprise at least one light chain variable region that includes an amino acid sequence region of at least about 75%, more preferably at least about 80%, more preferably at least about 85%, more preferably at least about 90% or 95% and most preferably at least about 97% amino acid sequence identity to the amino acid sequence of SEQ ID NO: 140, 70, 72, 74, 76 or 115; and/or at least one heavy chain variable region that includes an amino acid sequence region of at least about 75%, more preferably at least about 80%, more preferably at least about 85%, more preferably at least about 90% or 95% and most preferably at least about 97% amino acid sequence identity to the amino acid sequence of SEQ ID NO: 139, 69, 71, 73, 75 or 105.

Other preferred examples of substantially homologous sequences are sequences containing conservative amino acid substitutions of the amino acid sequences disclosed.

Other preferred examples of substantially homologous sequences are sequences containing up to 1, 2, 3 or 4 preferably up to 1 or 2, altered amino acids in one or more of the CDR regions disclosed. Such alterations might be conservative or non-conservative amino acid substitutions, or a mixture thereof.

In all such embodiments, preferred alterations are conservative amino acid substitutions.

In all embodiments, the antibodies containing substantially homologous sequences retain the ability to bind CCR4 and the ability to inhibit the binding of MDC to CCR4.

Other embodiments of the present invention provide binding proteins that bind to CCR4 and have the ability to inhibit the binding of MDC to CCR4 and that comprise an antibody of the invention, a VH or VL domain of the invention, or one or more of the CDRs of the invention. In a preferred embodiment, such binding proteins are antibodies.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "CCR4", unless otherwise specifically stated or made clear from the scientific terminology, means CC chemokine receptor 4 (also known as CD194).

CCR4 may be free CCR4, e.g. recombinant or purified CCR4, but preferably it is present in a native form, e.g. on the surface of a cell.

The antibodies or binding proteins of the invention can also bind to fragments of CCR4, in particular fragments comprising or consisting of the extracellular domain, or can bind to entities comprising CCR4 or fragments of CCR4. Indeed, the epitope of the antibodies of the invention is located in the extracellular domain of CCR4.

"CCR4" may also refer to any form of CCR4, particularly as CCR4 is conserved across mammalian species. The antibodies or antibody fragments of the invention may thus bind to human, monkey (e.g. cynomolgus monkey), cow (bovine), mouse, rat, hamster, ferret, guinea pig and/or rabbit CCR4, for example. Preferably, the antibodies or antibody fragments of the invention will bind at least to human CCR4. Thus, unless stated otherwise, any reference herein to "CCR4" may be read to mean "human CCR4". In certain preferred embodiments, the antibodies or antibody fragments of the invention will bind at least to human and monkey (e.g. cynomologus monkey) CCR4. In other preferred embodiments the antibodies or antibody fragments of the invention will bind at least to human and mouse CCR4. In other preferred embodiments the antibodies or antibody fragments of the invention will bind at least to human, monkey and mouse CCR4. In other preferred embodiments the antibodies or antibody fragments of the invention will bind at least to human, monkey, guinea pig and mouse CCR4. Antibodies 9E and 9E10J can bind to human and monkey CCR4, but not to murine CCR4 (Example 8), so in some preferred embodiments, the antibodies or antibody fragments of the invention will bind at least to human and monkey CCR4, but not to murine CCR4. In other preferred embodiments, the antibodies or antibody fragments of the invention will bind to human and monkey CCR4, but not to murine CCR4, e.g. only to human and monkey CCR4.

As used herein, the term "that binds to CCR4" or "anti-CCR4" in the context of antibodies or antibody fragments of the present invention, means antibodies or antibody fragments that are capable of one or more of the following; preferably, of more than one of the following; and most preferably, of all of the following:

(a) bind to CCR4 expressed on the surface of a cell, e.g. as assessed by flow cytometry or immunohistochemistry;

(b) bind to a conformationally dependent (e.g. non linear) CCR4 epitope, e.g. as assessed by binding to CCR4 in a Western blot under non-reducing conditions;

(c) bind to free CCR4; e.g. recombinantly expressed CCR4, on a solid support, e.g. as assessed by ELISA assay or BIAcore assay;

(d) bind at least to human CCR4, more preferably to human and monkey CCR4 or to human and mouse CCR4, most preferably to human, monkey and mouse CCR4 or to human and monkey CCR4 but not mouse CCR4;

(e) bind to human CCR4 with a binding affinity (Kd) of 10 nM or less, preferably 5 nM or less, more preferably 3 nM or less or 2 nM or less, most preferably 1 nM or less as also discussed elsewhere herein;

(f) bind to human and monkey CCR4 or to human and mouse CCR4, preferably to human and monkey CCR4 but not mouse CCR4, with similar affinities, e.g. with a Kd of 10 nM or less, preferably 5 nM or less, more preferably 3 nM or less or 2 nM or less, for example 1 nM or less as also discussed elsewhere herein;

Preferred antibodies or antibody fragments of the present invention are also capable of one or more of the following; preferably, of more than one of the following; and most preferably, of all of the following functional properties:

(g) induce ADCC of CCR4+ cells as described elsewhere herein;

(h) inhibit the binding of CCR4 to at least MDC and/or TARC, preferably MDC and TARC, or preferably at least MDC and/or TARC and one or more selected from RANTES, MCP-1 and MIP-1alpha (i) induce anti tumour effects in vivo;

(j) localize to tumours upon administration to an animal with a tumour;

(k) induce CDC of CCR4+ cells;

(l) inhibit CCR4-mediated cellular responses to a CCR4 ligand, preferably inhibit the increase in intracellular calcium ion concentration in response to a CCR4 ligand;

(m) inhibit chemotaxis of CCR4+ cells towards a CCR4 ligand such as MDC

In the context of binding to CCR4+ cells, it should be understood that the antibodies of the present invention bind to CCR4+ cells and do not significantly bind to CCR4⁻ cells (as shown in Example 2).

The term "do not significantly bind to CCR4⁻ cells" should be understood such that any binding of the antibody to CCR4⁻ cells does not prohibit the use of said antibody for therapeutic or diagnostic purposes. Thus, by "insignificant" binding to CCR4⁻ cells is meant that the binding of the antibody to CCR4⁻ cells is weaker than its binding to one or more CCR4+ cells. Some cross-reaction with normal cells may thus occur, but this level of binding can be considered to be "background" binding. For therapeutic or diagnostic purposes the main consideration is that the antibody must bind more strongly to one or more types of CCR4+ cells than to any CCR4⁻ with which the antibody may come into contact during the therapeutic or diagnostic application.

The antibody of the invention may be referred to as "CCR4-specific". The term "CCR-specific" should be interpreted such that the binding of the antibody to CCR4 expressing cells is specific enough to allow the use of said antibody for therapeutic or diagnostic purposes. The skilled person can easily determine if any given antibody is CCR4-specific by comparing the binding strength to the target CCR4⁺ cell with the binding strength to one or more types of CCR4⁻ cells, e.g. wild-type (i.e. not transformed with CCR4) HEK293T-cells or DT40-cells.

The skilled person will be aware that binding to CCR4+ cells compared to CCR4⁻ cells may be assessed, for example, using flow cytometry and a suitable example is described in Example 2.

Immunohistochemistry techniques, which are well known in the art, may be used to score the binding of antibodies to cells or samples. Such assays may be used to test the specificity of a particular antibody, or to detect CCR4 expression in tissue samples. Briefly, the antibody may tested for example on a high-density array of human tissues including a positive control (cells known to be CCR4-positive) and a negative contrail (cells known to be CCR4-negative). The membranous staining intensity may be estimated by visual inspection in a four step scale (0, 1, 2, 3). Preferred antibodies show weak or strong, preferably strong immunohistochemical scores for CCR4+ tissues.

Species cross-reactivity may be assayed using known methods and a suitable assay is described in Example 8.

The antibodies 17G, 9E, 1O and 11F have been shown to be capable of inhibiting the binding of CCR4 to its ligands TARC and MDC (Example 3). Thus, preferably the antibodies of the invention are capable of inhibiting the binding of CCR4 to one or more of its ligands. Preferably, the binding to at least MDC is inhibited. More preferably, the binding to MDC and TARC is inhibited. In some embodiments, the binding of CCR4 to TARC is inhibited. In embodiments of any of the aspects disclosed herein, the antibodies of the invention are capable of inhibiting the binding of MDC and/or TARC to CCR4. Thus, although reference is made throughout this text to the inhibition of the binding of MDC to CCR4, an embodiment of any of the aspects and embodiments disclosed herein is the inhibition of binding to MDC and/or TARC.

By the "inhibition of binding" of a ligand to CCR4 is meant that binding of the ligand to CCR4 is reduced by at least 20, 30, or 40%, more preferably at least 45, 50, 55, 60, 65, 70 or 75%, even more preferably at least 80% in the presence of the antibody compared to binding in the absence of the antibody. Embodiments in which the binding of ligand to CCR4 is reduced by at least 85, 90 or 95% are also contemplated.

Alternatively viewed, when the ligand is first contacted with CCR4 and the antibody is subsequently added, the ligand can inhibit the binding of the antibody to CCR4.

Assays for determining whether an antibody can inhibit the binding of a ligand to CCR4 are well known and a suitable assay is descried in Example 3. Briefly, CCR4+ cells were incubated with MDC or without MDC, then antibody was added and the antibody was then detected with labeled anti-human antibody. Pre-incubation in the presence of MDC resulted in a reduction in antibody binding to CCR4. Particularly, the binding of antibody to DT40 cells (ATCC CRL-2111) transfected with CCR4 and pre-incubated with MDC or TARC is inhibited.

Alternative assays for determining whether an antibody can block the binding of a ligand to CCR4 include the use of labeled ligand, e.g. radiolabelled ligand. A suitable assay is described in Example 9.

The antibodies 17G and 9E have been shown to be capable of inhibiting CCR4-mediated cellular responses to a CCR4 ligand, in particular by inhibiting the increase in intracellular calcium ion concentration in response to a CCR4 ligand (see Example 5). Dose-dependent inhibition of TARC-induced signalling was demonstrated for antibodies 9E and 9E10J (see Example 5). Thus, the antibodies of the invention are preferably capable of inhibiting CCR4-mediated cellular responses to a CCR4 ligand, in particular by inhibiting the increase in intracellular calcium ion concentration in response to a CCR4 ligand. In particular, the antibodies are preferably capable of inhibiting MDC-induced calcium flux and/or TARC-induced calcium flux in CCRF-CEM cells (ATCC CCL-119). Suitable assay methods are known and one assay is disclosed in Example 5.

Other preferred properties include the absence of significant toxicity in vivo when the antibodies of the invention are administered and the absence of significant other side effects in vivo.

In some embodiments, the antibodies may inhibit chemotaxis of CCR4+ cells towards a ligand of CCR4 such as MDC or TARC. Antibodies 9E and 9E10J were shown to be able to inhibit chemotaxis of CCR4+ cells towards a ligand of CCR4 (Example 13). Thus, the antibodies of the invention are preferably capable of inhibit chemotaxis of CCR4+ cells towards a ligand of CCR4, preferably MDC and/or TARC.

In some embodiments, the antibodies may induce complement-dependent cytotoxicity (CDC) of CCR4+ cells, but in other embodiments the antibodies are not capable of inducing CDC. In some embodiments, the antibodies may induce apoptosis of CCR4+ cells, but in other embodiments the antibodies are not capable of inducing apoptosis. Antibody 9E was shown not to induce apoptosis of Ramos cells (see Example 12), so the antibodies of the invention are in some embodiments not capable of inducing significant apoptosis of CCR4+ cells. In some embodiments, the antibodies may be internalised by CCR4+ cells upon binding to CCR4, but in other embodiments no significant internalisation takes place.

The induction of apoptosis may be assayed using well-known standard methods, for example methods which assay Annexin V staining. Briefly, cells may be incubated with an antibody for a suitable period of time, e.g. 24 hours and the effect, after cell harvesting and Annexin V staining may be measured by FACS analysis (e.g. using EasyCyte).

The induction of CDC may be assayed using well-known standard methods, for example methods which measure the relative number of viable cells based on the uptake and metabolism of a redox dye such as Alamar blue. A suitable assay is disclosed in H Gazzano-Santoro et al. J Immunol Methods. 1997, 28; 202(2):163-71.

The skilled person will be aware of suitable ways to assay internalisation, for example using temperature-differential fluorescence labeling on flow cytometry or confocal microscopy. An example of a suitable assay involves a secondary antibody labelled with a pH-sensitive dye (such as CypHer5E), which is minimally fluorescent at a basic pH (as found outside of cells) and maximally fluorescent at an acidic pH (as found inside of cells).

The inhibition of chemotaxis may be assayed using standard methods, for example using a transwell assay. Briefly, cells capable of chemotaxis and which express CCR4 are contacted with an antibody in one chamber and a ligand of CCR4 such as MDC is placed in another chamber separated from the first chamber by a membrane of filter having a suitable pore size. The effect of the antibody on cell migration towards the ligand (chemotaxis) is determined by comparing chemotaxis in the presence of the antibody to chemotaxis in the absence of the antibody.

The term "ligand" of CCR4 includes the natural ligands of CCR4 such as MDC, TARC, RANTES, MCP-1 and/or MIP-1alpha, which may be naturally produced, recombinantly expressed or synthesised in the laboratory.

By "CCR4$^+$ cells" is meant cells which express CCR4 on their surface, preferably at least substantially in its wild-type conformation. CCR4+ cells may be naturally positive for CCR4, or they may be transformants which express recombinant CCR4.

In light of this invention, therefore, a range of anti-CCR4 antibodies can be made and used in a variety of embodiments, including in the treatment of any of the disorders discussed elsewhere herein, particularly cancer, immune disorders, inflammatory disorders and infections.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Preferred embodiments of the invention are compositions comprising at least one anti-CCR4 antibody of the invention, or antigen binding fragment thereof.

Nucleic acid molecules comprising nucleotide sequences that encode the antibodies of the present invention as defined herein or parts or fragments thereof, or nucleic acid molecules substantially homologous thereto, form yet further aspects of the invention. Preferred nucleic acid molecules comprise sequences which encode the amino acid sequence set out in SEQ ID NO: 35 (which is preferably encoded by SEQ ID NO: 34), SEQ ID NO: 46 (which is preferably encoded by SEQ ID NO: 45), SEQ ID NO: 104 (which is preferably encoded by SEQ ID NO: 103), SEQ ID NO: 114 (which is preferably encoded by SEQ ID NO: 113), SEQ ID NO: 57 (which is preferably encoded by SEQ ID NO: 56) or SEQ ID NO: 68 (which is preferably encoded by SEQ ID NO: 67). Other preferred nucleic acid molecules comprise sequences which encode a heavy chain variable region (VH) that has the amino acid sequence of SEQ ID NO: 69, 71, 73, 75 or 105 (which is preferably encoded by SEQ ID NO: 77, 79, 81, 83 or 106 respectively) or 139, and/or comprise sequences which encode a light chain variable region (VL) which has the amino acid sequence of SEQ ID NO: 70, 72, 74, 76 or 115 (which is preferably encoded by SEQ ID NO: 78, 80, 82, 84 or 116 respectively) or 140. More preferred are nucleic acids which encode the following combinations: SEQ ID NOs: 139 and 140; or SEQ ID NOs: 69 and 70; or SEQ ID NOs: 71 and 72; or SEQ ID NOs 105 and 72; or SEQ ID NOs 71 and 115; or SEQ ID NOs 73 and 74; or SEQ ID NOs 75 and 76. Also preferred are nucleic acid molecules which comprise the following combinations: SEQ ID NOs: 77 and 78; or SEQ ID NOs: 79 and 80; or SEQ ID NOs: 106 and 80; or SEQ ID NOs: 79 and 116; or SEQ ID NOs: 81 and 82; or SEQ ID NOs: 83 and 84.

Other preferred nucleic acid molecules comprise sequences that encode IgG forms of the antibodies of the invention, for example those as described in Example 1, or murine chimeric forms.

As indicated above, other nucleic acid molecules encompassed by the present invention are those encoding parts or fragments of the human antibodies of the present invention, e.g., those encoding a heavy chain variable region (VH) of an antibody (e.g., those encoding SEQ ID NO: 69, 71, 73, 75 or 105, such as SEQ ID NOs: 77, 79, 81, 83 or 106 respectively) or those encoding a light chain variable region (VL) of an antibody (e.g., those encoding SEQ ID NO: 70, 72, 74, 76 or 115, such as SEQ ID NO: 78, 80, 82, 84 or 116 respectively). Other preferred nucleic acid molecules are those encoding a heavy chain of an antibody of the present invention (e.g., those encoding SEQ ID NO:87, 91, 95, 99, 119 or 123, such as SEQ ID NOs: 85, 89, 93, 97, 117 or 121 respectively) or those encoding a light chain of an antibody (e.g., those encoding SEQ ID NO: 88, 92, 96, 100, 120 or 124 such as SEQ ID NOs: 86, 90, 94, 98, 118 or 122 respectively).

Thus, fragments of the antibodies of the invention as defined herein, or sequences substantially homologous thereto, or nucleic acid molecules comprising sequences encoding such fragments form a yet further aspect of the invention.

Advantageously, the antibodies of the present invention, when in IgG format, have a high binding affinity for CCR4, i.e., have a Kd in the range of $1\times10^{-8}$ M or $1\times10^{-8}$ M or less. Importantly, antibodies with such an affinity are in the established range that has been shown to be useful for therapy. Preferably, the antibodies of the invention, when in IgG format, have a binding affinity for CCR4 that corresponds to a Kd of less than 30 nM, 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5 or 1 nM, most preferably less than 0.9, 0.8, 0.7, 0.6, 0.5, 0.4, 0.3, 0.2 or 0.1 nM.

Any appropriate method of determining Kd may be used. However, preferably the Kd is determined by testing various concentrations of the test antibody against various concentrations of antigen (CCR4) in vitro to establish a saturation curve, for example using the Lineweaver-Burk method, or by using commercially available binding model software, such as the 1:1 binding model in the BIAcore 1000 Evaluation software. A suitable assay in which Kd values were calculated from IgG titrations on CCR+ cells using "one site-specific binding" model f the software Prism (GraphPad, San Diego, Calif.) is used in Example 2.

With regard to determinations of Kd values, the skilled person will appreciate that apparent Kd values derived from binding experiments using cells expressing a target (e.g. CCR4) cannot be considered to be an absolute indication of affinity, because the experimental conditions will affect the apparent binding affinity. For example, the levels of expression of CCR4 may vary depending on the conditions under which the cells are cultured, as well as differing between different cell types. It is consequently best to compare apparent Kd values obtained within one set of experiments and it may not always be appropriate to compare Kd values obtained in one set of experiments with Kd values obtained in a different set of experiments, particularly if the experimental conditions varied significantly.

Alternatively, the off-rate and the antibody half-life on the surface of the CCR4-positive cell can be determined by performing the cell surface retention assay Adams et al., 1998, Prolonged in vivo tumour retention of a human diabody targeting the extracellular domain of human HER2/neu. Br J Cancer 77: 1405-12; Le Gall et al., 1999, Di-, tri- and tetrameric single chain Fv antibody fragments against human CD19: effect of valency on cell binding. FEBS Lett 453: 164-8. The latter method allows more appropriate mimicking the real situation in human patient under the treatment conditions.

In some embodiments, antibodies of the invention may bind to both human CCR4 and monkey CCR4. Such cross-reactivity between species and in particular between humans and species commonly used as pre-clinical animal models may be an advantage as it allows a more effective translation from pre-clinical studies to clinical use. For example, having an antibody which cross reacts with the native CCR4 present in the particular animal model used means that the results in this model are more likely to reflect the situation in a human patient, thereby allowing a more accurate assessment of for example dosing to be made and an increased likelihood of identifying any potentially relevant or problematic side effects. For example, the ability of an antibody of the invention to bind to both human CCR4 and monkey CCR4 means that such antibodies can be tested in preclinical toxicity studies to assess adverse side effects of the treatment and to find appropriate tolerated dosages.

In addition, the ability to bind both human CCR4 and mouse CCR4 means that the results shown by such antibodies of the invention in mouse models, e.g. mouse syngeneic models using immunocompetent mice, are more likely to be representative of the activity of the antibodies in human subjects. The reason for this is that antibodies which can bind to human CCR4 but not mouse CCR4 will bind to CCR4 expressed by the human tumor cells in the mouse model but will not be able to bind to endogenous murine CCR4. This is of course unlike the situation in a human patient, in which CCR4 expressed by the tumor and endogenous CCR4 would be present.

This is especially the case if the antibody has similar affinity to both murine and human CCR4.

The potential disadvantage with such a situation is that an antibody which binds to human CCR4 but not, or with significantly lower affinity, to mouse CCR4 might perform well in a human tumor xenograft model in immunocompromized mice (e.g. nude or SCID mice) but this might not be reflected by a similar performance in a human system where much more CCR4 was present. In other words, the anti-tumor effect seen in a mouse xenograft system with an antibody which can bind to human CCR4 but not mouse CCR4 might look better than the clinical reality. In contrast, when working with an antibody that can bind to both human and mouse CCR4 then this will bind to all forms of CCR4 present in the mouse model system and is likely to be more representative of the situation when the antibody is put into humans. This is especially the case if the antibody has similar affinity to both murine and human CCR4.

In preferred embodiments, antibodies of the invention bind to human and monkey CCR4 or to human and mouse CCR4 with similar affinities, e.g. with a Kd of 10 nM or less or 5 nM or less, more preferably 3 nM or less or 2 nM or less, most preferably 1 nM or less.

By "similar affinity" is also meant that the binding affinity of the antibody for human CCR4 and for one or more of the other species of interest (e.g. monkey or mouse) is comparable, e.g. is not more than a factor of 20 different. More preferably the difference between the binding affinities is less than a factor of 15, more preferably less than a factor of 10, most preferably less than a factor of 5, 4, 3 or 2.

However, in other embodiments the antibodies of the present invention may not bind to monkey CCR4 and/or they may not bind to mouse CCR4.

The antibodies of the invention bind to CCR4. Thus the antibodies or binding proteins of the invention can be used to detect CCR4 in vivo or in vitro, in particular to detect CCR4+ cells. For example, as CCR4 is expressed on certain tumour cells, the antibodies or binding proteins of the invention can be used to detect tumour cells in vivo or in vitro. In addition, the ability of the antibodies to localize to CCR4+ cells means that the antibodies of the invention can target body sites at which CCR4+ cells are present, whereupon the antibody can act at the target site. In particular, the ability of the antibodies to localize to CCR4+ tumour cells means that the antibodies of the invention can target body sites at which CCR4+ tumour cells are present, whereupon the antibody can act at the target site.

For example, the antibody may induce an anti-CCR4+ cell effect itself i.e. as a naked antibody, e.g. by activating or inducing ADCC. This ability to act as a naked Ab is advantageous. Alternatively, or in addition, the antibody can induce an anti-CCR4+ cell effect by virtue of being conjugated to an additional therapeutic molecule, e.g. a toxin or other anti-cancer molecule or an anti-inflammatory agent as described herein.

The antibodies of the invention preferably have the ability to induce antibody dependent cellular cytotoxicity (ADCC) of CCR4+ cells. ADCC may be assayed in vitro using methods well known in the art. A suitable method is described in Example 6. Alternatively, a Chromium-51 release assay may be used, for example. Thus, the antibodies of the invention may for example cause at least 10%, 15%, 20%, 22%, 25%, 30%, 40%, 50%, 60%, 70%, 80% or 90% killing of CCR4+ cells in vitro e.g., in the presence of human PBMCs. For example, the antibody 17G has been shown to cause at least 10%, 15%, 20% or 22% killing of the CCR4+ cell line CCRF-CEM in the presence of human PBMCs and the antibody 9E has been shown to cause at least 10%, 15%, 20%, 22%, 30%, 40%, 45%, 50%, 55% killing of the CCR4+ cell line CCRF-CEM in the presence of human PBMCs (see Example 6). Antibody 9E10J has been shown to cause at least 10%, 15%, 20%, 22%, 30%, 35%, 40%, 42% killing of the CCR4+ cell line CCRF-CEM in the presence of human PBMCs (see Example 6). ADCC is advantageous for some applications, particularly some therapeutic applications. Thus, in preferred embodiments the antibody can induce ADCC of CCR4+ cells, preferably of CCR4+ tumour cells and/or CCR4+ Th2 cells. In some embodiments the antibody-mediated ADCC is in the presence of PBMCs, but embodiments in which antibody-mediated ADCC is in the absence of PBMCs are also contemplated. In other embodiments, the antibodies induce little or no significant ADCC.

The antibodies of the invention are preferably also shown to be suitably potent in terms of the concentration of antibody required to achieve such ADCC levels. Again, a suitable in vitro test is described in Example 6. Thus, the antibody concentration required for half maximal cell lysis ($EC_{50}$) of CCR4+ cells, e.g. CCRF-CEM cells, in vitro is preferably less than 700 ng/ml, 650 ng/ml, 620 ng/ml, 600 ng/ml, 550 ng/ml, 500 ng/ml, 450 ng/ml, 400 ng/ml, 350 ng/ml, 300 ng/ml, 250 ng/ml, 200 ng/ml, 150 ng/ml, 100 ng/ml, 90 ng/ml, 80 ng/ml, 70 ng/ml, 60 ng/ml, 50 ng/ml, 46 ng/ml, 40 ng/ml, 35 ng/ml, 30 ng/ml, 25 ng/ml, 20 ng/ml, 15 ng/ml, 10 ng/ml, 9 ng/ml, 7 ng/ml, 5 ng/ml, 2 ng/ml, 1 ng/ml, 0.5 ng/ml or 0.25 ng/ml. For example, the 17G antibody of the invention has been shown to have an $EC_{50}$ of 619 ng/ml for CCRF-CEM cells, and antibody 9E of the invention has been shown to have an $EC_{50}$ of 46 ng/ml for CCRF-CEM cells and in a separate experiment antibody 9E10J of the invention has been shown to have an $EC_{50}$ of 25 ng/ml for CCRF-CEM cells (see Example 6).

Preferably, the above described abilities are observed at a measurable or significant level and more preferably at a statistically significant level, when compared to appropriate control levels.

It should be noted that PBMC (effector cells) prepared from different donors may exhibit a significant variation of ADCC with respect to the extent of non-specific and specific tumour cell lysis, as well as EC50 values. This phenomenon has been described by Naundorf et al, 2002 and it was also observed when assaying ADCC by the antibodies of the present invention (see Examples 6 and 11).

Human IgG1 is a glycoprotein bearing two N-linked oligosaccharide chains bound to the Fc region. The oligosaccharides are of the complex biantennary type, composed of a trimannosyl core structure with the presence or absence of core fucose, bisecting N-acetylglucosamine (GlcNAc), galactose, and terminal sialic acid, which gives rise to structural heterogeneity. Both human serum IgG and therapeutic antibodies are well known typically to be heavily fucosylated.

It has been reported that ADCC enhancement may in some instances be achieved by manipulating the state of oligosaccharides on human IgG1 subclass. In particular, defucosylation has been shown to cause an increase in ADCC activity of some antibodies (Niwa R et al, 2004). Thus, in preferred embodiments, antibodies according of the invention are modified during production/expression of the protein, and/or in vitro after production/expression, to generate a specific glycosylation pattern, particularly a glycosylation pattern which is beneficial for therapeutic application of the antibodies. Preferably, said specific glycosylation pattern is the reduction or absence of fucose-based glycosylation, which preferably increases the antibody's ability to induce ADCC. Thus, in preferred embodiments, the antibodies of the invention have a specific glycosylation pattern, preferably a specific glycosylation pattern which increases the ability of said antibody to induce ADCC. Preferable, the antibodies of the invention are defucosylated or non-fucosylated.

The skilled person is aware of suitable ways of preparing defucosylated or non-fucosylated antibodies. As described in Example 10, this can be achieved by producing the antibody in presence of Kifunensine (for example 100 ng/ml), a selective inhibitor of class I α-mannosidases, leading to a decrease in fucosylation of the molecule during production. Suitable host cells which lack one or more proteins required for fucosylation of oligosaccharide moieties can be used to produce defucosulated antibodies, e.g. fucosyltransferase-deficient host cells. Examples of suitable host cells are cells wherein the activity of an enzyme relating to the synthesis of an intracellular sugar nucleotide, GDP-fucose and/or the activity of an enzyme relating to the modification of a sugar chain in which 1-position of fucose is bound to 6-position of N-acetylglucosamine in the reducing end through an α-bond in the complex N-glycoside-linked sugar chain is decreased or deleted. Examples of such enzymes include enzymes relating to the synthesis of GDP-fucose include GMD (GDP-mannose 4,6-dehydratase), Fx (GDP-keto-6-deoxymannose 3,5-epimerase, 4-reductase), GFPP (GDP-beta-L-fucose pyrophosphorylase).

By "defucosulated" is meant that at least 10%, preferably at least 20, 30, 40 50, 60, 75, 80, 85, 90, 91, 92, 93, 94, 95, 96, 97, 98 or at least 99% of the total complex N-glycoside-linked sugar chains bound to the Fc region are sugar chains in which fucose is not bound to N-acetylglucosamine in the reducing end in the sugar chain.

By "non-fucosylated" is meant that no significant levels of fucose are present in the antibody.

Some antibodies are capable of being internalized into the cells to which they become bound. Thus, in some embodiments of the invention the antibodies are capable of being internalized. This property is particularly advantageous for use in immunoconjugates as any other agent attached to the antibody molecule should be internalized with the antibody molecule. In other embodiments no significant internalization is seen.

Particularly for medical applications, it is desirable that the andibody does not induce any significant platelet aggregation. Platelet aggregation may be assayed as described in Example 15. This Example shows that antibody 9E10J does not have any significant effect on platelet aggregation. Thus, in some embodiments of the invention the antibodies do not have any significant effect on platelet aggregation.

As discussed above, certain PBLs, including Tregs, express CCR4, so the ability of antibody 9E10J to PBLs was assayed in Example 16 and this Example shows that 9E10J can bind PBLs. Thus, in some embodiments of the invention the antibodies can bind to PBLs, preferably to Tregs and/or Th2 cells. This feature is advantageous, particularly in immunotherapy, as it may allow the depletion of Treg cells.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-CCR4 antibodies as well as to the specific 17G, 9E, 1O, 11F, 9E10J and 9E1D antibodies.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting. IgG1 antibodies are particularly preferred.

The "light chains" of mammalian antibodies are assigned to one of two clearly distinct types: kappa (κ) and lambda (λ), based on the amino acid sequences of their constant domains and some amino acids in the framework regions of their variable domains. There is essentially no preference to the use of κ or λ light chain constant regions in the antibodies of the present invention.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')$_2$, single domain antibodies (DABs), T and Abs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa (lamda) bodies (scFv-CL fusions); Bispecific T-cell Engager (BiTE) (scFv-scFv tandems to attract T cells); dual variable domain (DVD)-Ig (bispecific format); small immunoprotein (SIP) (kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004).

It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumours. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Preferred antibodies of the invention that bind to CCR4 comprise at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO: 1 or a sequence substantially homologous thereto, (b) a VH CDR2 that has the amino acid sequence of SEQ ID NO: 2 or a sequence substantially homologous thereto, and (c) a VH CDR3 that has the amino acid sequence of SEQ ID NO: 3 or 15 or a sequence substantially homologous thereto; or (d) a variable heavy (VH) CDR1 that has the amino acid sequence of SEQ ID NO: 7 or 101 or a sequence substantially homologous thereto, (e) a VH CDR2 that has the amino acid sequence of SEQ ID NO: 8 or a sequence substantially homologous thereto, and (f) a VH CDR3 that has the amino acid sequence of SEQ ID NO: 9 or a sequence substantially homologous thereto; or (g) a variable heavy (VH) CDR1 that has the amino acid sequence of SEQ ID NO: 19 or a sequence substantially homologous thereto,
(h) a VH CDR2 that has the amino acid sequence of SEQ ID NO: 20 or a sequence substantially homologous thereto, and
(i) a VH CDR3 that has the amino acid sequence of SEQ ID NO: 21 or a sequence substantially homologous thereto; or
(j) a variable heavy (VH) CDR1 that has the amino acid sequence of SEQ ID NO: 125 or 126 or a sequence substantially homologous thereto,
(k) a VH CDR2 that has the amino acid sequence of SEQ ID NO: 127 or 128 or a sequence substantially homologous thereto, and
(l) a VH CDR3 that has the amino acid sequence of SEQ ID NO: 9 or a sequence substantially homologous thereto.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds CCR4 can be readily identified by a person skilled in the art.

For example, a heavy chain variable region of the invention can be combined with a single light chain variable region or a repertoire of light chain variable regions and the resulting antibodies tested for binding to CCR4. It would be expected that a reasonable number of such combinations of heavy chain variable regions of the invention with different light chain variable regions would retain the ability to bind CCR4.

Similar methods could be used to identify alternative heavy chain variable regions for use in combination with preferred light chain variable regions of the invention.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies.

Antibodies containing an Fc region are preferred for certain uses, particularly therapeutic uses in vivo, where the Fc region mediates effector functions such as ADCC.

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain only up to 1, 2, 3, 4 or 5, preferably up to 1, 2 or 3, more preferably up to 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody (or the substantially homologous nucleic acid encoding it) should retain the ability to bind to CCR4 as described above. Preferably, any substantially homologous antibody should retain the functional capabilities of the antibody, e.g. as defined elsewhere herein. Preferably, any substantially homologous antibody should retain the ability to specifically bind to the same epitope of CCR4 as recognized by the antibody in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay. Retention of other functional properties can also readily be tested by methods well known and described in the art.

Thus, a person skilled in the art will appreciate that binding assays can be used to test whether "substantially homologous" antibodies have the same binding specificities as the antibodies and antibody fragments of the invention, for example, binding assays such as ELISA assays or BIAcore assays can readily be used to establish whether such "substantially homologous" antibodies can bind to CCR4. As outlined above, a competition binding assay can be used to test whether "substantially homologous" antibodies retain the ability to specifically bind to substantially the same epitope of CCR4 as recognized by the antibodies of the invention. The method described below is only one example of a suitable competition assay. The skilled person will be aware of other suitable methods and variations.

Substantially homologous sequences of proteins of the invention include, without limitation, conservative amino acid substitutions, or for example alterations that do not affect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

By "at least moderately stringent hybridization conditions" it is meant that conditions are selected that promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in Tm. For example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. By way of further example, sequences that "hybridize" are those sequences binding (hybridizing) under non-stringent conditions (e.g., 6×SSC, 50% formamide at room temperature) and washed under conditions of low stringency (e.g., 2×SSC, room temperature, more preferably 2×SSC, 42° C.) or conditions of higher stringency (e.g., 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Generally speaking, sequences that hybridize under conditions of high stringency are preferred, as are sequences which, but for the degeneracy of the code, would hybridize under high stringency conditions.

In other preferred embodiments, second generation antibodies are provided that have enhanced or superior properties in comparison to an original anti-CCR4 antibody, such as 17G, 9E, 1O, 11F, 9E10J or 9E1D. For example, the second generation antibodies may have a stronger binding affinity for CCR4, a superior cross reactivity profile, superior ability to target CCR4+ cells, particularly tumour cells, an improved ability to induce ADCC, an improved ability to induce CDC, an improved treatment of the disorders discussed elsewhere herein.

Comparisons to identify effective second generation antibodies are readily conducted and quantified, e.g., using one or more of the various assays described in detail herein or in the art. Second generation antibodies that have an enhanced biological property or activity of at least about 2-fold, 5-fold, 10-fold, 20-fold, and preferably, at least about 50-fold, in comparison to the anti-CCR4 antibodies of the present invention, as exemplified by the 17G, 9E, 1O, 11F, 9E10J or 9E1D antibody, are encompassed by the present invention.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In preferred embodiments the antibodies of the invention are human antibodies, more preferably fully human antibodies. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system, e.g., to destroy target cells more efficiently by complement-dependent cytotoxicity (CDC) or antibody-dependent cellular cytotoxicity (ADCC).

However, although human antibodies are generally recognized to display these advantages, it is known that the development of human antibodies that have high enough affinities and appropriate functional properties to make them candidates for successful human therapy is by no means straightforward. The art therefore still lacks anti-CCR4 for the safe and effective treatment of humans, and poses challenges to the development of such agents.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans, e.g., in the human germline or somatic cells. The 17G, 9E, 1O, 11F, 9E10J and 9E1D antibodies are examples of such a human antibody molecules wherein the variable regions have been isolated from a human repertoire.

The "human" antibodies and binding proteins of the invention further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in up to 5, 4, 3, 2 or 1 of the residues of the antibody or binding protein, preferably e.g., in up to 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of $V_H$, $V_L$ CDR or FR regions that are themselves found in combination in human antibody molecules. Thus, the human antibodies and binding proteins of the invention can include or correspond to combinations of such regions that do not necessarily exist naturally in humans.

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/ or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function of the CCR4 antigen. Certain preferred fragments comprise a heavy chain variable region ($V_H$ domain) and/or a light chain variable region ($V_L$ domain) of the antibodies of the invention. Other preferred fragments comprise one or more of the heavy chain CDRs of the antibodies of the invention (or of the $V_H$ domains of the invention), or one or more of the light chain CDRs of the antibodies of the invention (or of the $V_L$ domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences (for example comprise a fragment of SEQ ID NO:35, 46, 57, 68, 104 or 114), e.g., are antibodies comprising $V_H$ and/or $V_L$ domains of the invention, or are antibodies or binding proteins comprising one or more CDRs of the invention, then these regions/domains are generally separated within the antibody or binding protein so that each region/domain can perform its biological function and so that the contribution to antigen binding is retained. Thus, the $V_H$ and $V_L$ domains are preferably separated by appropriate scaffold sequences/linker sequences and the CDRs are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more (i.e. one, two, three or four) of the framework regions making up the $V_H$ and/or $V_L$ domains of the invention, i.e., one or more of the framework regions disclosed in Tables 1, 2, 3 or 4, or framework regions substantially homologous thereto, and in particular framework regions that allow the maintenance of antigen specificity, for example framework regions that result in substantially the same or the same 3D structure of the antibody.

In certain preferred embodiments, all four of the variable light chain (SEQ ID NOs:30, 31, 32 and 33) and/or variable heavy chain (SEQ ID NOs: 25, 26, 27 and 28), as appropriate, FR regions of SEQ ID NO: 35 (also shown in Table 1), or FR regions substantially homologous thereto, are found in the antibodies of the invention.

In certain preferred embodiments, all four of the variable light chain (SEQ ID NOs:41, 42, 43 and 44) and/or variable heavy chain (SEQ ID NOs: 36, 37, 38 and 39), as appropriate, FR regions of SEQ ID NO: 46 (also shown in Table 2), or FR regions substantially homologous thereto, are found in the antibodies of the invention.

In certain preferred embodiments, all four of the variable light chain (SEQ ID NOs:41, 42, 43 and 44) and/or variable heavy chain (SEQ ID NOs: 36, 37, 102 and 39), as appropriate, FR regions of SEQ ID NO: 103, or FR regions substantially homologous thereto, are found in the antibodies of the invention. Embodiments in which variable heavy chain FR region of SEQ ID NO: 102 or a sequence substantially homologous thereto is present are especially preferred.

In certain preferred embodiments, all four of the variable light chain (SEQ ID NOs: 107, 109, 111 and 44) and/or variable heavy chain (SEQ ID NOs: 36, 37, 38 and 39), as appropriate, FR regions of SEQ ID NO: 114, or FR regions substantially homologous thereto, are found in the antibodies of the invention.

In certain preferred embodiments, all four of the variable light chain (SEQ ID NOs:52, 53, 54 and 55) and/or variable heavy chain (SEQ ID NOs: 47, 48, 49 and 50), as appropriate, FR regions of SEQ ID NO: 57 (also shown in Table 3), or FR regions substantially homologous thereto, are found in the antibodies of the invention.

In certain preferred embodiments, all four of the variable light chain (SEQ ID NOs: 63, 64, 65 and 66) and/or variable heavy chain (SEQ ID NOs: 58, 59, 60 and 61), as appropriate, FR regions of SEQ ID NO: 68 (also shown in Table 4), or FR regions substantially homologous thereto, are found in the antibodies of the invention.

In addition, although preferred antibodies of the invention are made up of $V_H$, $V_L$ or CDRs of the invention, it should be noted that the antibodies of the invention also encompass one or more $V_H$, $V_L$ or CDRs of the invention in combination with other $V_H$, $V_L$ or CDRs not of the invention, provided that the CCR4 binding properties or anti-CCR4 properties of the antibodies of the invention as outlined herein are still present.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

It should be noted that the Kabat nomenclature is followed herein, where necessary, in order to define the positioning of the CDRs (Kabat et al., 1991, specifically incorporated herein by reference).

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally be sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (for example, see the regulatory sequences described in Goeddel, 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989, and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, 1990. In addition, the proteins of the invention may be expressed in prokaryotic cells, such as Escherichia coli (Zhang et al., 2004).

Yeast and fungi host cells suitable for carrying out the present invention include, but are not limited to Saccharomyces cerevisiae, the genera Pichia or Kluyveromyces and various species of the genus Aspergillus. Examples of vectors for expression in yeast *S. cerevisiae* include pYepSec1 (Baldari. et al., 1987), pMFa (Kurjan and Herskowitz, 1982), pJRY88 (Schultz et al., 1987), and pYES2 (Invitrogen Corporation, San Diego, Calif.). Protocols for the transformation of yeast and fungi are well known to those of ordinary skill in the art (see Hinnen et al., 1978; Ito et al., 1983, and Cullen et al. 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), NS-1 cells, NS0 (ATCC CRL-11177), and Per.C6® (Crucell, Leiden, Netherlands). Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., 1987) and pMT2PC (Kaufman et al., 1987).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., 1987, which reviews the use of *Agrobacterium rhizogenes* vectors; see also Zambryski et al., 1984, which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., 1983) and the pVL series (Luckow and Summers 1989). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. 1985; Palmiter et al. 1983; Brinster et al. 1985; Palmiter and Brinster 1985, and U.S. Pat. No. 4,736,866).

The proteins of the invention may also be prepared by chemical synthesis using techniques well known in the chemistry of proteins such as solid phase synthesis (Merrifield (1964); Frische et al., 1996) or synthesis in homogenous solution.

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of a first anti-CCR4 antibody nucleic acid segment, further suitable antibody nucleic acid segments may be readily prepared by standard molecular biological techniques. In order to confirm that any variant, mutant or second generation anti-CCR4 antibody nucleic acid segment is suitable for use in the present invention, the nucleic acid segment will be tested to confirm expression of an anti-CCR4 antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of antibodies may be readily prepared, the treatment methods of the invention may be executed by providing to the animal or patient at least a first nucleic acid segment or molecule that expresses a biologically effective amount of at least a first anti-CCR4 antibody of the invention in the patient. The "nucleic acid segment or molecule that expresses an anti-CCR4 antibody" will generally be in the form of at least an expression construct or vector, and may be in the form of an expression construct or vector comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

A yet further aspect provides an expression construct or expression vector comprising one or more of the nucleic acid segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

The antibodies of the invention may also be used to produce further antibodies that bind to CCR4. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to CCR4. Such methods can be used to form multiple new antibodies that can all be tested for their ability to bind CCR4. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding (Davies and Cohen, 1996). Subsequently, those residues can be mutated to enhance the interaction. Alternatively, one or more amino acid residues can simply be targeted for directed mutagenesis and the effect on binding to CCR4 assessed.

Random mutagenesis can be carried out in any appropriate way, e.g., by error-prone PCR, chain shuffling or mutator *E. coli* strains.

Thus, one or more of the $V_H$ domains of the invention can be combined with a single $V_L$ domain or a repertoire of $V_L$ domains from any appropriate source and the resulting new antibodies tested to identify antibodies specific for CCR4. Conversely, one or more of the $V_L$ domains of the invention can be combined with a single $V_H$ domain or repertoire of $V_H$ domains from any appropriate source and the resulting new antibodies tested to identify antibodies that bind to CCR4.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antibodies tested to identify antibodies that bind to CCR4.

The targeted mutations of the CDRs, especially CDR3 of the light and/or heavy chains, have been shown to be an effective technique for increasing antibody affinity and are preferred. Preferably, blocks of 3 to 4 amino acids of the CDR3 or specific regions called "hot-spots" are targeted for mutagenesis.

"Hot spots" are the sequences where somatic hypermutation takes place in vivo (and below Neuberger and Milstein, 1995). The hotspot sequences can be defined as consensus nucleotide sequences in certain codons. The consensus sequence is the tetranucleotide, RGYW, in which R can be either A or G, Y can be C or T and W can be either A or T (Neuberger and Milstein, 1995). In addition, the serine residues encoded by the nucleotides AGY are predominantly present in the CDRs regions of the variable domain over those encoded by TCN corresponding to a potential hot-spot sequences (Wagner et al., 1995).

Thus, the nucleotide sequence of the CDRs of the heavy and light chains of each antibody of the invention can be scanned for the presence of the hot-spot sequences and AGY codons. The identified hot-spots of the CDR regions of the light and heavy chain can then optionally be compared to the germinal sequences of the heavy and light chains using the International ImMunoGenTics database (IMGT, http://imgt-.cines.fr/textes/vquest/) (Davies et al., 1990). A sequence, identical to the germ line, suggest that somatic mutation has not occurred; therefore random mutations can be introduced mimicking the somatic events occurring in vivo or alternatively, site directed mutagenesis can be carried out, e.g., at the hot spots and/or AGY codons. In contrast, a different sequence shows that some somatic mutations have already occurred. It will remain to be determined if the in vivo somatic mutation was optimal.

Preferred hot-spots for mutation are those that code for exposed amino acids and preferably those that encode amino acids that form part of the antigen binding sites. Other preferred hot-spots for mutation are those that code for non-conserved amino acids. The hot-spots that code for buried or conserved amino acids within the CDRs are preferably not mutagenized. These residues are usually critical for the overall structure and are unlikely to interact with the antigen since they are buried.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

Testing the ability of one or more antibodies to specifically bind to CCR4 can be carried out by any appropriate method, which are well known and described in the art. CCR4+ cell lines may be obtained from culture collections, or they may be prepared by transforming CCR4-negative cells with a construct that allows expression of recombinant CCR4. Such cells, or immobilised CCR4 can readily be used to assay binding, for example by conventional methods such as ELISA, BiaCon, etc.

The new antibodies produced by these methods will preferably have improved functional properties, e.g. a higher or enhanced affinity (or at least an equivalent affinity) for CCR4 as the parent antibodies, and can be treated and used in the same way as the antibodies of the invention as described elsewhere herein (e.g., for therapy, diagnosis, in compositions etc). Alternatively, or additionally, the new antibodies will have one or more other improved functional properties as described elsewhere herein.

New antibodies produced, obtained or obtainable by these methods form a yet further aspect of the invention.

This invention further provides compositions comprising at least one human antibody or antibody fragment of the invention, optionally including a diluent. Such compositions may be pharmaceutically acceptable compositions or compositions for use in laboratory studies. In terms of the pharmaceutical compositions, they may preferably be formulated for parenteral, intravenous or even subcutaneous administration.

The present invention provides a number of methods and uses of the human antibodies and antibody fragments of the invention. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-CCR4 therapeutic antibody.

Various useful in vitro methods and uses of the antibodies or immunoconjugates of the invention are provided that have important biological implications. First provided are methods of, and uses in, binding CCR4, which generally comprise effectively contacting a composition comprising CCR4 with at least a first anti-CCR4 antibody of the invention, or antigen-binding fragment thereof. The antibodies of the invention, or immunoconjugates thereof, can thus be used in binding assays. Suitably useful binding assays include those commonly employed in the art, such as in immunoblots, Western blots, dot blots, RIAs, ELISAs, immunohistochemistry, fluorescent activated cell sorting (FACS), immunoprecipitation, affinity chromatography, and the like.

Methods of, and uses in, detecting CCR4 are provided, which generally comprise contacting a composition suspected of containing CCR4 with at least a first antibody or immunoconjugate of the invention, or antigen-binding fragment thereof, under conditions effective to allow the formation of CCR4/antibody complexes and detecting the complexes so formed. The detection methods and uses may be used in connection with biological samples, e.g., in diagnostics for tumours, and diagnostic kits based thereon are also provided.

The methods and uses of the present invention are particularly intended for use in animals and patients that have, or are at risk for developing, any disease or condition associated with CCR4 expression or activity or in which CCR4 plays a biological role. Such diseases and disorders include diseases which are mediated by CCR4 positive cells, typically CCR4+ Th2 or Th17 cells, which, upon binding of a ligand to CCR4, may take part in a signaling pathway which will cause or contribute to a disorder or disease. They also include diseases caused by aberrant proliferation of cells expressing CCR4. Such aberrantly proliferating cells may naturally be CCR4+, or they may have mutated/been transformed to express CCR4 As mentioned above, expression of CCR4 may help cancer cells expressing this antigen to evade the immune system. Thus, there is provided a method of treating a disease or disorder mediated by CCR4 and/or characterised by aberrant proliferation of CCR4-positive cells.

Alternatively viewed, there is provided the treatment of a condition which can benefit from one or more of the following (i) the selective elimination of CCR4+ cells
(ii) the inhibition of CCR4 binding to one or more of its ligands
(iii) the inhibition of CCR4-mediated cellular responses to a CCR4 ligand, particularly the inhibition of chemotaxis or increased intracellular calcium ion concentration (cell activation).

Preferably, the CCR4 ligand is MDC and/or TARC.

It is well known to those of ordinary skill in the art that as CCR4 is involved in a wide range of diseases and disorders, a given anti-CCR4 therapy, once shown to be effective in any acceptable model system, can be used to treat the entire range of diseases and disorders connected with CCR4 expression.

In one embodiment, the CCR4-mediated condition is a T-helper cell type 2-mediated immune disease. By "T-helper cell type 2-mediated immune disease" is meant a disease involving immunoglobulin E (IgE) and mast cells due to the development and activation of allergen-specific Th2 cells.

The CCR4-mediated disease or disorder may be a disease or condition associated with inflammation, infection and/or cancer. Such diseases or disorders can be treated or prevented with the present antibodies and compositions. Preferred diseases or conditions include: (1) allergic diseases such as systemic anaphylaxis or hypersensitivity responses, drug allergies, allergic bronchopulmonary aspergillosis (ABPA), insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, chronic obstructive pulmonary disease, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, T-cell mediated neurodegenerative diseases, multiple sclerosis, encephalitis, meningitis, hepatitis, nephritis, sepsis, sarcoidosis, allergic conjunctivitis, otitis, Castleman's disease, sinusitis, LPS-induced endotoxic shock, Behcet's syndrome and gout, (12) cancers, both hematological and non-hematological cancers, preferably Breast cancer, Colorectal cancer, Esophageal cancer, Gastric cancer, Hepatocellular carcinoma, Lung cancer, Melanoma, Ovarian cancer, Pancreatic cancer, Adult T-cell leukemia/lymphoma (ATL), Peripheral T-cell lymphoma, unspecified Diffuse large B-cell lymphoma, Hodgkin's lymphoma, B-cell chronic lymphocytic leukemia, CTCL, particularly Mycosis fungoides, Sezary syndrome, cervical cancer, kidney cancer, brain cancer, prostate cancer, stomach cancer (13) infections such as Epstein-Barr virus (EBV) infection, HIV infection and other viral infections.

The binding of the antibody of the present invention to CCR4 may also impair the ability of CCR4-positive aberrant cells such as cancer cells to evade the host immune system. The antibodies of the present invention may be used to block the suppression of DCs by Treg cells, so there is provided the use of an anti-CCR4 antibody of the present invention as an adjuvant in a vaccine. The vaccine is preferably a vaccine for cancer or an infectious disease. The vaccine may be a preventative vaccine or a curative vaccine. By "adjuvant" is meant an agent which enhances the immune response of a host to an antigen. When used as vaccine adjuvants, the antibodies of the present invention are therefore typically administered in conjunction or combined with an antigen against which it is desired to elicit an immune response.

As used herein, the term "aberrant proliferation" means cell proliferation that deviates from the normal, proper, or expected course. For example, aberrant cell proliferation may include inappropriate proliferation of cells whose DNA or other cellular components have become damaged or defective.

Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue (s), cancerous or non-cancerous, benign or malignant.

Any reference to "tumour(s)" herein also refers to "cancer(s)" or "carcinoma(s)". Metastatic cancers can also be treated, as can the reduction of metastases from a primary tumour. So-called minimal residual disease (MRD), which is left in post-surgery patients, may be amenable for immunotherapy with anti-CCR4 antibodies.

The present invention thus further provides methods of, and uses in, treating a disease as defined above, comprising administering to an animal or patient with such a disease, a therapeutically effective amount of an anti-CCR4 antibody of the invention, or an antigen-binding fragment or immunoconjugate of such an anti-CCR4 antibody.

A yet further aspect of the invention provides the use of the antibodies of the invention or an antigen-binding fragment or immunoconjugate of such an antibody in the manufacture of a composition or medicament for use in therapy, imaging or diagnosis.

A yet further aspect provides the antibodies of the invention or an antigen-binding fragment or immunoconjugate of such an antibody for use in therapy, diagnosis or imaging.

In addition, the invention provides compositions comprising the antibodies of the invention or an antigen-binding fragment or immunoconjugate of such an antibody with one or more pharmaceutically acceptable excipient, carrier, diluent, buffer or stabilizer.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkey. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkey. Preferably, however, the animal or patient is a human subject.

This invention links both methods of treating disorders as defined above using unconjugated or naked antibodies and fragments thereof, and CCR4+ cell, preferably CCR4+ tumour cell, targeting methods using immunoconjugates in which an antibody of the invention or antigen-binding fragment thereof, is operatively attached to a therapeutic agent. Unless otherwise specifically stated or made clear in scientific terms, the terms "antibody and fragment thereof", as used herein, therefore mean an "unconjugated or naked" antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The treatment methods and uses of the invention also encompass the use of both unconjugated or naked antibodies and immunoconjugates. In the immunoconjugate-based treatment methods, an antibody of the invention, or antigen-binding fragment thereof, is preferably operatively attached to a second therapeutic agent (the anti-CCR4 antibody itself, being the first therapeutic agent). The therapeutic agent may for example be an anti-cancer agent or an anti-inflammatory agent, including corticosteroids and non-steroidal anti-inflammatory drugs (NSAIDs).

The foregoing treatment methods and uses will generally involve the administration of the pharmaceutically effective composition to the animal or patient systemically, such as by transdermal, intramuscular, intravenous injection and the like. However, any route of administration that allows the therapeutic agent to localize to the tumour site or sites, will be acceptable. Therefore, other suitable routes of delivery include oral, nasal or respiratory and topical.

"Administration", as used herein, means provision or delivery of anti-CCR4 antibody therapeutics in an amount(s) and for a period of time(s) effective to exert therapeutic, e.g. anti-tumour effects. The passive administration of proteinaceous therapeutics is generally preferred, in part, for its simplicity and reproducibility.

However, the term "administration" is herein used to refer to any and all means by which anti-CCR4 antibodies of the invention are delivered or otherwise provided to the target site. "Administration" therefore includes the provision of cells that produce the anti-CCR4 antibody of the invention in a manner effective to result in delivery to the target site. In such embodiments, it may be desirable to formulate or package the cells in a selectively permeable membrane, structure or implantable device, generally one that can be removed to cease therapy. Exogenous anti-CCR4 antibody of the invention will still generally be preferred, as this represents a non-invasive method that allows the dose to be closely monitored and controlled.

The therapeutic methods and uses of the invention also extend to the provision of nucleic acids that encode an anti-CCR4 antibody of the invention in a manner effective to result in their expression in the vicinity of the tumour or their localization to the target site. Any gene therapy technique may be employed, such as naked DNA delivery, recombinant genes and vectors, cell-based delivery, including ex vivo manipulation of patients' cells, and the like.

The anti-CCR4 antibodies of the invention can also be used to deliver other therapeutic or diagnostic agents to the target site. In such embodiments, the other therapeutic or diagnostic agents are generally operatively attached to the anti-CCR4 antibodies of the invention.

The "therapeutically effective amounts" for use in the invention are amounts of anti-CCR4 antibody of the invention, or immunoconjugates thereof, effective to specifically kill at least a portion of target CCR4+ cells; to specifically induce apoptosis in at least a portion of target CCR4+ cells; to specifically induce necrosis in at least a portion of target CCR4+ cells; to inhibit the binding of a CCR4 ligand to CCR4; to inhibit CCR4-mediated cellular responses to a CCR4 ligand, preferably inhibit the increase in intracellular calcium ion concentration in response to a CCR4 ligand; to reduce inflammation; and/or to induce tumour regression or remission upon administration to animals or patients having a CCR4+ tumour. Such effects are preferably achieved while exhibiting little or no binding to, or little or no killing of cells in normal, healthy tissues; and exerting negligible or manageable adverse side effects on normal, healthy tissues of the animal or patient.

By "target site" is meant the location of CCR4+ cells which mediate a disorder or which proliferate in an aberrant manner causing or exacerbating a disorder. The target site may thus for example be a tumour or the site of CCR4-mediated inflammation. "Target cells" are CCR4+ cells which mediate a disorder or which proliferate in an aberrant manner causing or exacerbating a disorder. Thus, target cells may for example include CCR4+ tumour cells, CCR4+ Treg cells and/or CCR4+Th2 cells.

The terms "preferentially" and "specifically", as used herein in the context of killing or inducing apoptosis or of inducing necrosis of CCR4+ cells such as CCR4+ tumour cells or of reducing inflammation or of inducing tumour regression or remission, thus mean that the anti-CCR4 antibody of the invention or immunoconjugates thereof, function to achieve CCR4+ target cell destruction, e.g. tumour cell destruction and/or tumour necrosis, that is substantially confined to the target site, and does not substantially extend to causing destruction and/or tissue necrosis in normal, healthy tissues of the animal or subject.

Anti-CCR4 antibodies of the invention or therapeutic conjugates are preferably linked to one or more radiotherapeutic agents, chemotherapeutic agents, anti-angiogenic agents, apoptosis-inducing agents, anti-tubulin drugs, anti-cellular or cytotoxic agents, cytokine or chemokine antagonists, inhibitors of cytokine or chemokine expression, ATPase inhibitors, anti-inflammatory agents, other antibodies (e.g. as bispecific antibodies) or coagulants (coagulation factors) or anti-inflammatory agents such as corticosteroids, preferably glucocorticoids, or non-steroidal anti-inflammatory drugs (NSAIDs).

The invention thus provides a range of conjugated antibodies and fragments thereof in which the anti-CCR4 antibody is operatively attached to at least one other therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr where X is any amino acid except Pro) into the primary sequence of the antibody.

Currently preferred agents for use in anti-CCR4 antibody or therapeutic conjugates of the invention and related methods and uses are those that complement or enhance the effects of the antibody and/or those selected for a particular type of disorder (e.g. tumour type) or patient.

"Therapeutic agents that complement or enhance the effects of the antibody" include radiotherapeutic agents, chemotherapeutic agents, anti-angiogenic agents, apoptosis-inducing agents, anti-tubulin drugs, anti-cellular or cytotoxic agents, coagulants, cytokine or chemokine antagonists, inhibitors of cytokine or chemokine expression, ATPase inhibitors, anti-inflammatory agents such as corticosteroids, preferably glucocorticoids, or non-steroidal anti-inflammatory drugs (NSAIDs), other antibodies, (e.g. as bispecific antibodies), any one or more of which are preferred for use herewith.

Currently preferred anti-cancer, particularly anti-leukaemia agents include Anthracycline drugs such as daunorubicin, Doxorubicin, Cytarabine, 6-thioguanine, Mitoxantrone, busulfan (Myleran®), dasatinib (Sprycel™), prednisone, vincristine sulfate (Oncovin®), Chlorambucil, Fludarabine, Pentostatin and Cladribine.

Currently preferred agents for the treatment of ATL include zidovudine (azidothymidine) and the CHOP regimen. CHOP stands for Cyclophosphamide, Hydroxydaunorubicin (Adriamycin), Oncovin (Vincristine), Prednisone/Prednisolone.

Currently preferred anti-angiogenic agents include angiostatin, endostatin, any one of the angiopoietins, vasculostatin, canstatin and maspin.

"Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization. Currently preferred anti-tubulin drugs include colchicine, taxol, vinblastine, vincristine, vindescine and one or more of the combretastatins.

Currently preferred NSAIDs include COX-2 inhibitors, sulphonanilides, licofelone and omega-3 fatty acids The attachment or association of the preferred agents with anti-CCR4 antibodies of the invention gives "immunoconjugates", wherein such immunoconjugates often have enhanced and even synergistic therapeutic properties, e.g. anti-tumour or anti-inflammatory properties.

The use of anti-cellular and cytotoxic agents results in anti-CCR4 antibody "immunotoxins" of the invention, whereas the use of coagulation factors results in anti-CCR4 antibody "coaguligands" of the invention.

The use of at least two therapeutic agents is also contemplated, such as combinations of one or more radiotherapeutic agents, chemotherapeutic agents, anti-angiogenic agents, apoptosis-inducing agents, anti-tubulin drugs, anti-cellular and cytotoxic agents, cytokine or chemokine antagonists, inhibitors of cytokine or chemokine expression, ATPase inhibitors, anti-inflammatory agents such as corticosteroids, preferably glucocorticoids, or non-steroidal anti-inflammatory drugs (NSAIDs), other antibodies, (e.g. as bispecific antibodies) and coagulation factors.

In certain applications, the anti-CCR4 antibody therapeutics of the invention will be operatively attached to cytotoxic, cytostatic or otherwise anti-cellular agents that have the ability to kill or suppress the growth or cell division of cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: hormones, such as steroids; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Certain preferred anti-cellular agents are DNA synthesis inhibitors, such as daunorubicin, doxorubicin/adriamycin, and the like. Overall, taxol/paclitaxel, docetaxel, cisplatin, gemcitabine, a combretastatin and doxorubicin/adriamycin are currently preferred anti-cancer agents.

V-type ATPase inhibitors are also currently preferred, such as salicylihalamide, concanamycin or bafilomycin, as are protein synthesis inhibitors, such as psymberin, pederin, irciniastatin A.

In certain therapeutic applications, toxin moieties will be preferred, due to the much greater ability of most toxins to deliver a cell killing effect, as compared to other potential agents. Therefore, certain preferred anti-cellular agents for anti-CCR4 antibody constructs of the invention are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin. Currently preferred examples are ricin, gelonin, abrin, diphtheria, pseudomonas and pertussis toxins.

Certain preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

The anti-CCR4 antibody therapeutics of the invention may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/Vila, Factor IX/IXa and Factor X/Xa; vitamin K-dependent coagulation factors that lack the Gla modification; Russell's viper venom Factor X activator; platelet-activating compounds, such as thromboxane $A_2$ and thromboxane $A_2$ synthase; and inhibitors of fibrinolysis, such as α2-antiplasmin. Overall, truncated Tissue Factor (tTF) is currently preferred.

The preparation of immunoconjugates and immunotoxins is generally well known in the art (see, e.g., U.S. Pat. No. 4,340,535). Each of the following patents are further incorporated herein by reference for the purposes of even further supplementing the present teachings regarding immunotoxin generation, purification and use: U.S. Pat. Nos. 6,004,554; 5,855,866; 5,965,132; 5,776,427; 5,863,538; 5,660,827 and 6,051,230.

A variety of chemotherapeutic and other pharmacological agents can also be successfully conjugated to anti-CCR4 antibody therapeutics of the invention. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,660,827; 5,855,866; and 5,965,132; each incorporated herein.)

The preparation of coaguligands is also easily practiced. The operable association of one or more coagulation factors with an anti-CCR4 antibody of the invention may be a direct linkage, such as those described above for the immunotoxins. Alternatively, the operative association may be an indirect attachment, such as where the antibody is operatively attached to a second binding region, preferably an antibody or antigen binding region of an antibody, which binds to the coagulation factor. The coagulation factor should be attached to the anti-CCR4 antibody of the invention at a site distinct from its functional coagulating site, particularly where a covalent linkage is used to join the molecules.

Bispecific or trispecific antibodies may also be employed in the methods of the invention. In such antibodies one arm binds to CCR4 and is an antibody of the present invention. Methods for preparing bispecific antibodies are well known and described in the art.

In the preparation of immunoconjugates, immunotoxins and coaguligands, recombinant expression may be employed. The nucleic acid sequences encoding the chosen anti-CCR4 antibody of the invention, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the anti-CCR4 antibody of the invention.

The compositions and methods of the present invention may be used in combination with other therapeutics and diagnostics. In terms of biological agents, preferably diagnostic or therapeutic agents, for use "in combination" with an anti-CCR4 antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the anti-CCR4 of the invention is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the target disease site. The use of such targeted forms of biological agents, both diagnostics and therapeutics, is also quite standard in the art.

In other "combined" embodiments of the invention, the anti-CCR4 antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of an anti-CCR4 antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the anti-CCR4 antibodies of the present invention.

In certain preferred embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antibody of the invention is operatively attached to a component capable of converting the prodrug to the active drug, not that the antibody is attached to the prodrug itself. However, there is no requirement that the prodrug embodiments of the invention need to be used as prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include anti-CCR4 antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the anti-CCR4 antibodies of the invention. It will therefore be understood that such antibodies themselves have anti-CCR4 properties and that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first anti-CCR4 antibody of the invention, or an antigen-binding fragment or immunoconjugate of such an anti-CCR4 antibody; and a biologically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with the treatment or diagnosis of one or more of the disorders defined above.

Thus, in certain embodiments "at least a second therapeutic agent" will be included in the therapeutic kit or cocktail. The term "at least a second therapeutic agent" is chosen in reference to the anti-CCR4 antibody of the invention being the first therapeutic agent. The antibodies of the invention may thus be combined with chemotherapeutic agents, radiotherapeutic agents, cytokine or chemokine antagonists, inhibitors of cytokine or chemokine expression, anti-angiogenic agents, apoptosis-inducing agents or anti-cancer immunotoxins or coaguligands, or anti-inflammatory agents including corticosteroids and NSAIDs, some examples of which are discussed elsewhere herein.

Other exemplary anti-cancer agent include, e.g., neomycin, podophyllotoxin(s), TNF-$\alpha$, $\alpha_v\beta_3$ antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second therapeutic agent may be administered to the animal or patient substantially simultaneously with the anti-CCR4 antibody of the invention; such as from a single pharmaceutical composition or from two pharmaceutical compositions administered closely together.

Alternatively, the at least a second therapeutic agent may be administered to the animal or patient at a time sequential to the administration of the anti-CCR4 antibody of the invention. "At a time sequential", as used herein, means "staggered", such that the at least a second anti-cancer agent is administered to the animal or patient at a time distinct to the administration of the anti-CCR4 antibody of the invention. Generally, the two agents are administered at times effectively spaced apart to allow the two agents to exert their respective therapeutic effects, i.e., they are administered at "biologically effective time intervals". The at least a second therapeutic agent may be administered to the animal or patient at a biologically effective time prior to the anti-CCR4 antibody of the invention, or at a biologically effective time subsequent to that therapeutic.

Accordingly, the present invention provides methods for treating an animal or patient with a tumor, comprising:
(a) subjecting the animal or patient to a first treatment that substantially reduces the tumor burden; and
(b) subsequently administering at least a first anti-CCR4 antibody of the invention, or antigen-binding fragment thereof; optionally wherein the antibody or fragment is operatively associated with a second therapeutic agent.

Preferred first treatments include surgical resection and chemotherapeutic intervention.

In other embodiments, the present invention provides methods for treating an animal or patient with a CCR4-mediated disorder, comprising:
(a) subjecting the animal or patient to a first treatment that substantially reduces the CCR4-mediated burden such as inflammation; and
(b) subsequently administering at least a first anti-CCR4 antibody of the invention, or antigen-binding fragment thereof; optionally wherein the antibody or fragment is operatively associated with a second therapeutic agent.

In certain other embodiments, the antibodies and immunoconjugates of the invention may be combined with one or more diagnostic agents, typically diagnostic agents for use in connection with the diagnosis of a disorder as defined above. A range of diagnostic compositions, kits and methods are thus included within the invention.

Yet further aspects are methods of diagnosis or imaging of a subject comprising the administration of an appropriate amount of an antibody or other protein of the invention as defined herein to the subject and detecting the presence and/or amount and/or the location of the antibody or other protein of the invention in the subject.

In one embodiment, the invention provides a method of reducing immunosuppression associated with CCR4 expression in an animal, comprising administering to said animal the antibody of the invention, or an immunoconjugate thereof, in an amount effective to form complexes between said antibody and CCR4 in said animal, thereby reducing immunosuppression associated with CCR4 expression in an animal.

Appropriate diseases to be imaged or diagnosed in accordance with the above described uses and methods include any disease and preferably any cancer as described elsewhere herein.

In one embodiment, the invention provides a method of diagnosing disease or monitoring the progress of disease in an animal comprising the step of:
(a) contacting a test sample taken from said animal with an antibody of the invention or an immunoconjugate thereof.

In a further embodiment, the invention provides a method of diagnosing disease or monitoring the progress of disease in an animal comprising the steps of:
(a) contacting a test sample taken from said animal with an antibody of the invention or an immunoconjugate thereof;
(b) measuring or detecting the presence and/or amount and/or location of antibody-antigen complex in the test sample; and, optionally
(c) comparing the presence and/or amount of antibody-antigen complex in the test sample to a control.

In the above methods, said contacting step is carried out under conditions that permit the formation of an antibody-antigen complex. Appropriate conditions can readily be determined by a person skilled in the art.

In the above methods any appropriate test sample may be used, for example biopsy cells, tissues or organs suspected of being affected by disease or histological sections.

In certain of the above methods, the presence of any amount of antibody-antigen complex in the test sample would be indicative of the presence of disease. Preferably, for a positive diagnosis to be made, the amount of antibody-antigen complex in the test sample is greater than, preferably significantly greater than, the amount found in an appropriate control sample. More preferably, the significantly greater levels are statistically significant, preferably with a probability value of <0.05. Appropriate methods of determining statistical significance are well known and documented in the art and any of these may be used.

Monitoring the progress of a disease may also involve monitoring the presence and/or amount of antibody-antigen complex in test samples over time. Thus, monitoring may involve (d) comparing the presence and/or amount of antibody-antigen complex in a first test sample to the presence and/or amount of antibody-antigen complex in a second test sample taken from said animal. By "first test sample" is meant a sample that was taken prior to taking the "second test sample", for example 1, 2, 3, 4, 5, 6, 7, 8, 9, 10, 11 or 12 days, weeks, months or years prior to taking the second test sample. A decrease in the amount of antibody-antigen complex in the second test sample compared to the first test sample is indicative of the disease regressing, whereas an increase is indicative of the disease progressing.

Appropriate control samples could be readily chosen by a person skilled in the art, for example, in the case of diagnosis of a particular disease, an appropriate control would be a sample from a subject that did not have that disease. Appropriate control "values" could also be readily determined without running a control "sample" in every test, e.g., by reference to the range for normal subjects known in the art.

For use in the diagnostic or imaging applications, the antibodies of the invention may be labeled with a detectable marker such as a radio-opaque or radioisotope, such as $^3$H, $^{14}$C, $^{32}$P, $^{35}$S, $^{123}$I, $^{125}$I, $^{131}$I; a radioactive emitter (e.g., α, β or γ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g., labelled avidin/streptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antibodies of the invention attached to a label that produces a detectable signal, directly or indirectly. Appropriate labels are described elsewhere herein.

The invention further includes kits comprising one or more of the antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immunoconjugate. Preferably said kits comprise instructions for use of the kit components, for example in diagnosis. Preferably said kits are for diagnosing or treating diseases as described elsewhere herein and optionally comprise instructions for use of the kit components to diagnose or treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

Cancer treatment may also be carried out by:
(a) forming an image of a tumor by administering to an animal or patient having a tumor a diagnostic amount of at least a first detectably-labeled anti-CCR4 antibody of the invention, comprising a diagnostic agent operatively attached to the anti-CCR4 antibody of the invention, thereby forming a detectable image of the tumor; and
(b) subsequently administering to the same animal or patient a therapeutically optimized amount of at least a first naked anti-CCR4 antibody of the invention or therapeutic agent-antibody construct using such an antibody, thereby causing an anti-tumor effect.

The invention will now be described in more detail in the following non-limited examples with reference to the Tables and Figures in which:

Table 1 lists some of the sequences disclosed herein relating to antibody 17G

Table 2 lists some of the sequences disclosed herein relating to antibody 9E

Table 3 lists some of the sequences disclosed herein relating to antibody 1O

Table 4 lists some of the sequences disclosed herein relating to antibody 11F

Table 5 lists some of the sequences disclosed herein relating to the IgG form of antibody 17 G. The variable regions are underlined.

Table 6 lists some of the sequences disclosed herein relating to IgG form of antibody 9E. The variable regions are underlined.

Table 7 lists some of the sequences disclosed herein relating to IgG form of antibody 10. The variable regions are underlined.

Table 8 lists some of the sequences disclosed herein relating to IgG form of antibody 11F. The variable regions are underlined.

Table 9 shows the calculated affinities ($K_D$ values) from IgG titrations on CCR4$^+$ cells using "One site—Specific binding" model of the software Prism (GraphPad, San Diego, Calif.). The IgG forms of antibodies 17G, 9E and KM3060var using various CCR4+ cell types were used (see Example 2).

Table 10 shows the sequences of antibody KM3060var.

Table 11 lists some of the sequences disclosed herein relating to antibody 9E10J.

Table 12 lists some of the sequences disclosed herein relating to antibody 9E1D.

Table 13 lists some of the sequences disclosed herein relating to IgG form of antibody 9E10J. The variable regions are underlined.

Table 14 lists some of the sequences disclosed herein relating to IgG form of antibody 9E1D. The variable regions are underlined.

Table 15 shows apparent affinities ($IC_{50}$ and $K_D$) determined from results obtained in Example 4.

Table 16 shows $IC_{50}$ values determined in $Ca^{++}$ flux assays (Example 5).

Table 17 shows a comparison of ADCC activity of anti-CCR4 antibodies (Example 6).

Table 18 shows a comparison of ADCC activity of anti-CCR4 antibodies including defucosylated 9E10J (Example 11).

Table 19 shows some of the results of Example 14. Apparent affinities ($K_D$) as determined by saturated antibody titration on cells in flow cytometry.

Table 20 shows some of the results of Example 9. $IC_{50}$ values and calculated affinities ($K_D$) for cell-binding inhibition of biotinylated MDC, as determined from competition binding experiments on DT-40-CCR4+ and CCRF-CEM cells.

Table 21 shows some of the results of Example 9. $IC_{50}$ values for cell-binding inhibition of biotinylated TARC, as determined from competition binding experiments on DT-40-CCR4+ and CCRF-CEM cells.

Table 22 shows an overview of determined $IC_{50}$-values from competition experiments of Example 9.

Table 23 shows CDR consensus sequences based on the antibodies discloses herein.

Table 24 shows some results of Example 15 concerning the determination of the effect of 9E10J on platelet aggregation. Platelets were isolated from fresh donor-blood and incubated in presence of either 9E10J-IgG (10 µg/ml) or native ligands MDC and TARC (0.25 µg/ml). ADP (3 µM) was used as control to demonstrate that platelets behave as expected. Anti-GFP (10 µg/ml) was included into the measurements as well to demonstrate specificity of the assay. Aggregation was determined and expressed in % by measuring the absorbance in the sample chambers which were compared to a platelet-depleted plasma (=0% aggregation) in parallel. Preincubation=IgG-samples were first incubated with the platelets for 10 min, followed by addition of the ligands; mixture=IgG-samples were mixed with the ligands and followed by incubation with the platelets.

FIG. 1 shows the nucleotide and amino acid sequence of inter alia the heavy and light chain of clone 17G. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 2 shows the nucleotide and amino acid sequence of inter alia the heavy and light chain of clone 9E. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 3 shows the nucleotide and amino acid sequence of inter alia the heavy and light chain of clone 10. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 4 shows the nucleotide and amino acid sequence of inter alia the heavy and light chain of clone 11F ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

Figure 6:
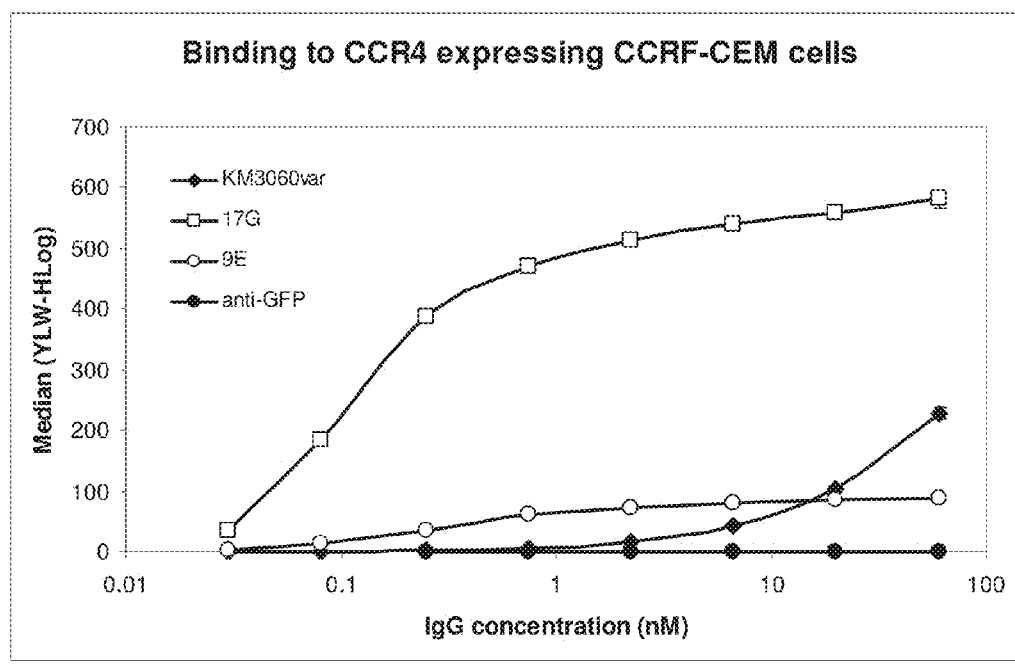

FIG. 5 illustrates some of the results of the flow cytometry of Example 2. The CCR4-specificity of the antibodies 17G IgG and 9E IgG was confirmed by staining CCR4 transfected and untransfected DT40 cells. The anti-CCR4 antibody KM3060var IgG served as a positive control and anti-GFP IgG was used as a negative control in this experiment FIG. 6 illustrates some of the results of the flow cytometry of Example 2. The binding of anti-CCR4 antibodies KM3060var, 17G and 9E to CCR4 expressing cell line CCRF-CEM was analyzed using flow cytometry. Staining of the cells was performed in triplicate and error-bars indicate the standard deviations which are too small to be seen. The negative control antibody anti-GFP did not give any staining signals.

Figure 7:
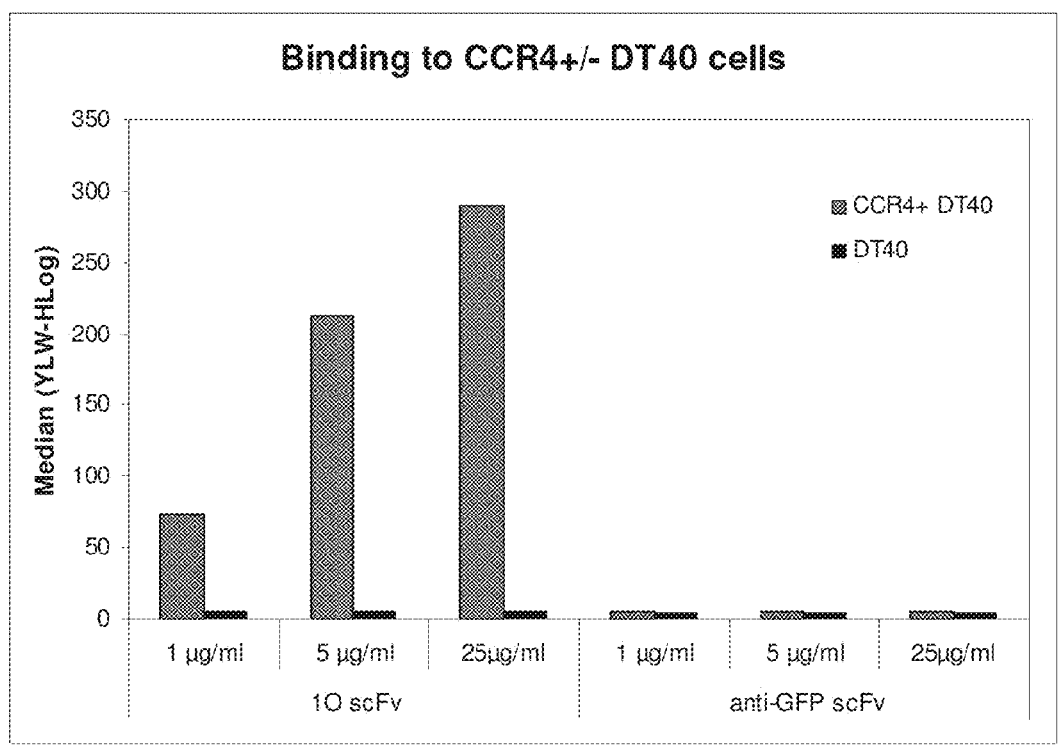

FIG. 7 illustrates some of the results of the flow cytometry of Example 2. The CCR4-specificity of the 10 antibody was confirmed by staining CCR4 transfected and untransfected DT40-cells. The anti-GFP scFv served as a negative control in this experiment.

Figure 8:
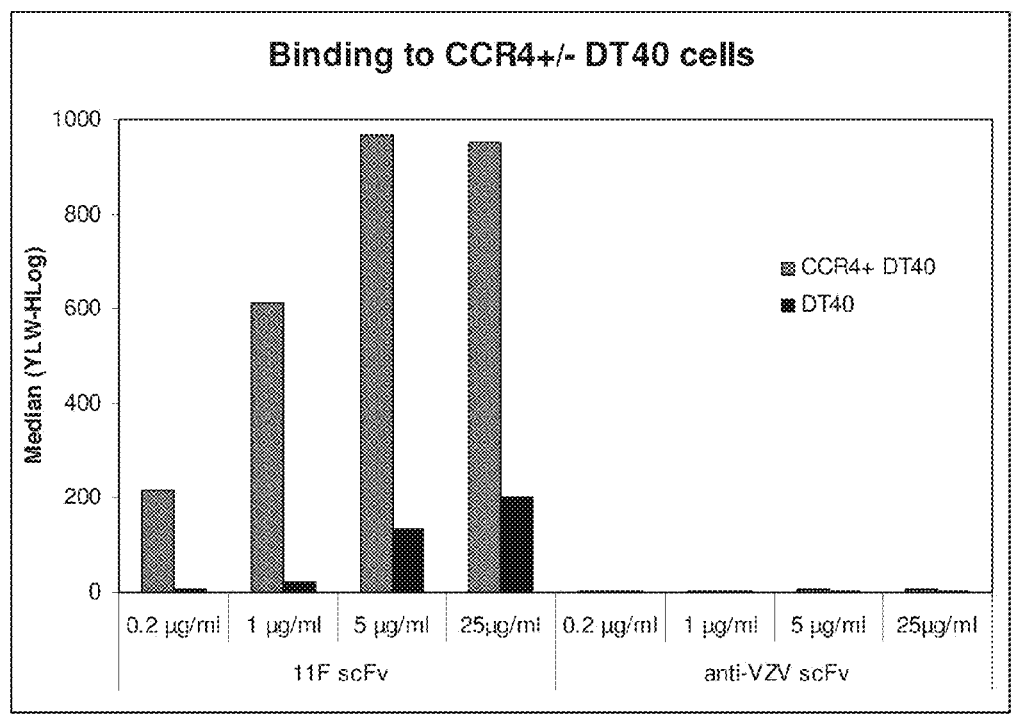

FIG. 8 illustrates some of the results of the flow cytometry of Example 2. The CCR4-specificity of the 11F antibody was confirmed by staining CCR4 transfected and untransfected DT40-cells. The anti-VZV scFv served as a negative control in this experiment.

Figure 9:
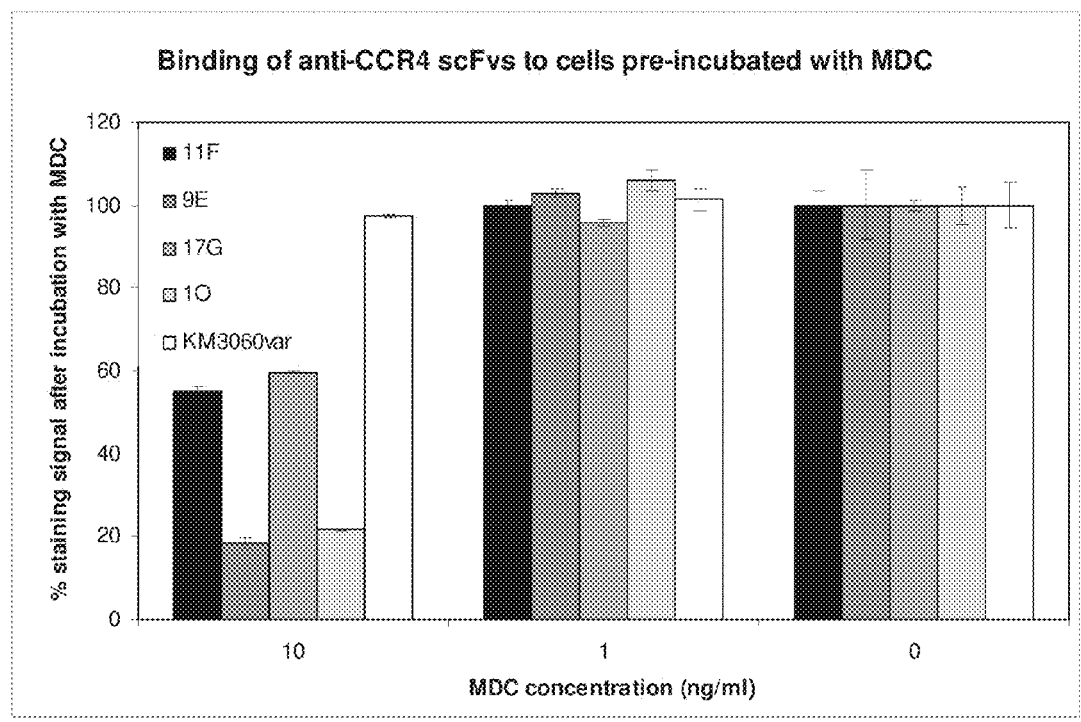

FIG. 9 is a graph which shows some of the results of Example 3. The anti-CCR4 antibodies 11F, 9E, 17G and 10 interfere with the ligand MDC binding to CCR4 transfected DT40 cells as determined by flow cytometry by staining cells with the scFvs after pre-incubation with different concentrations of MDC. In accordance with previous reports, the antibody KM3060var did not interfere the MDC binding to the CCR4 receptor.

Figure 10:
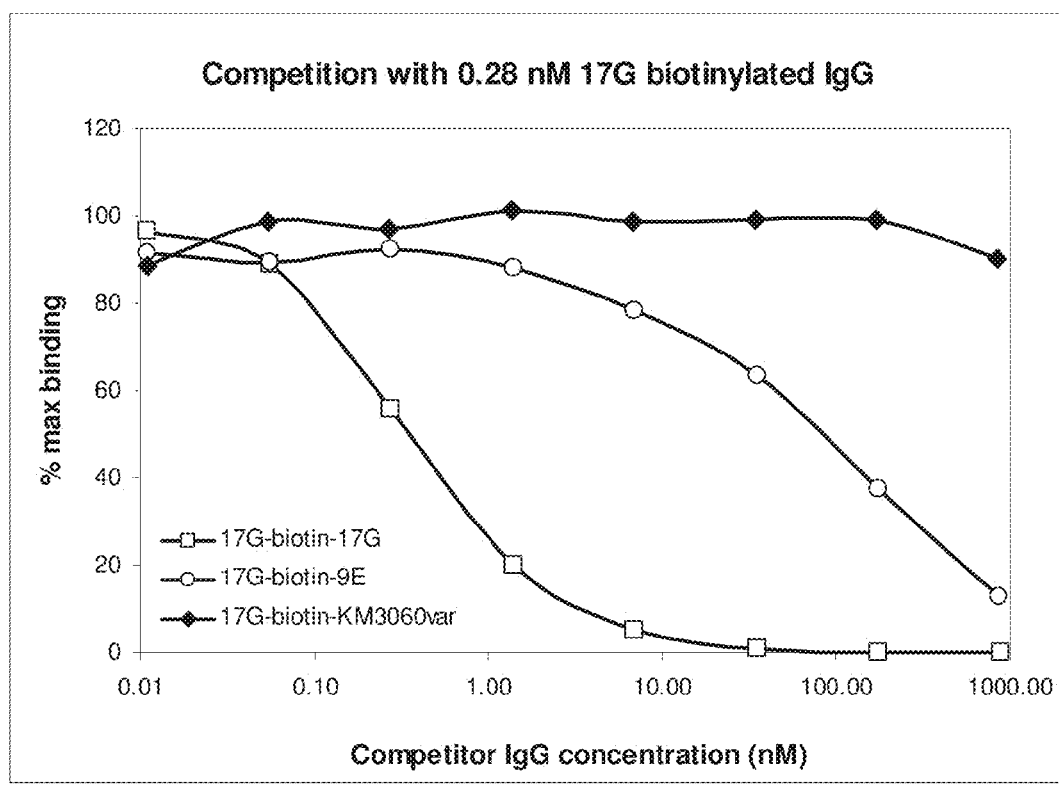
Figure 10:
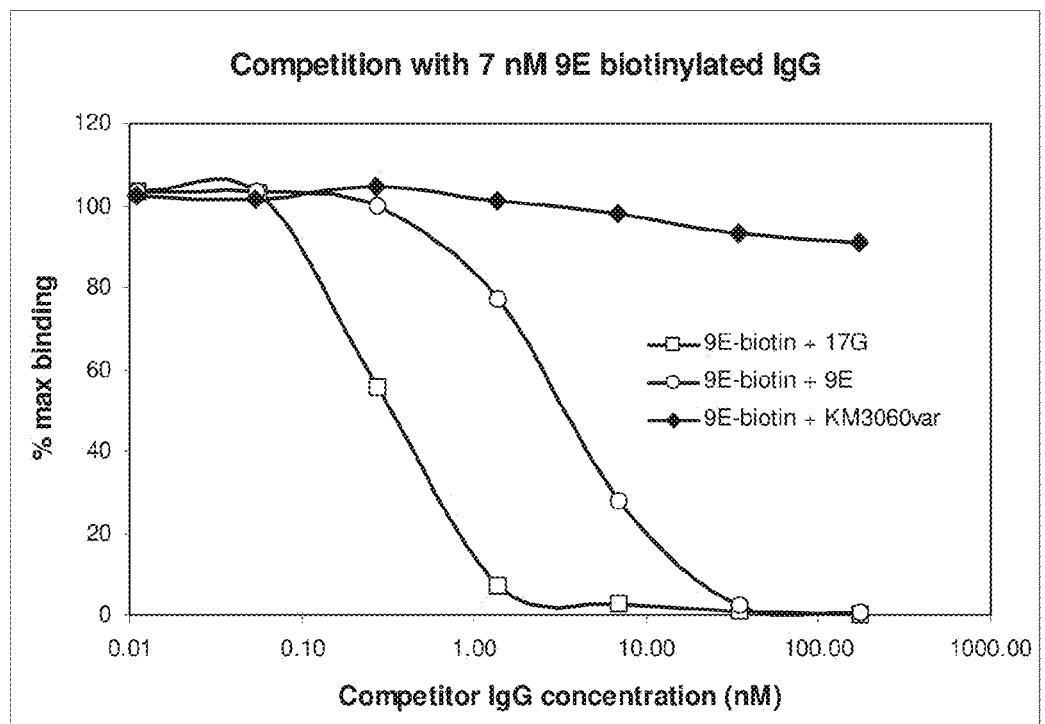
Figure 10:
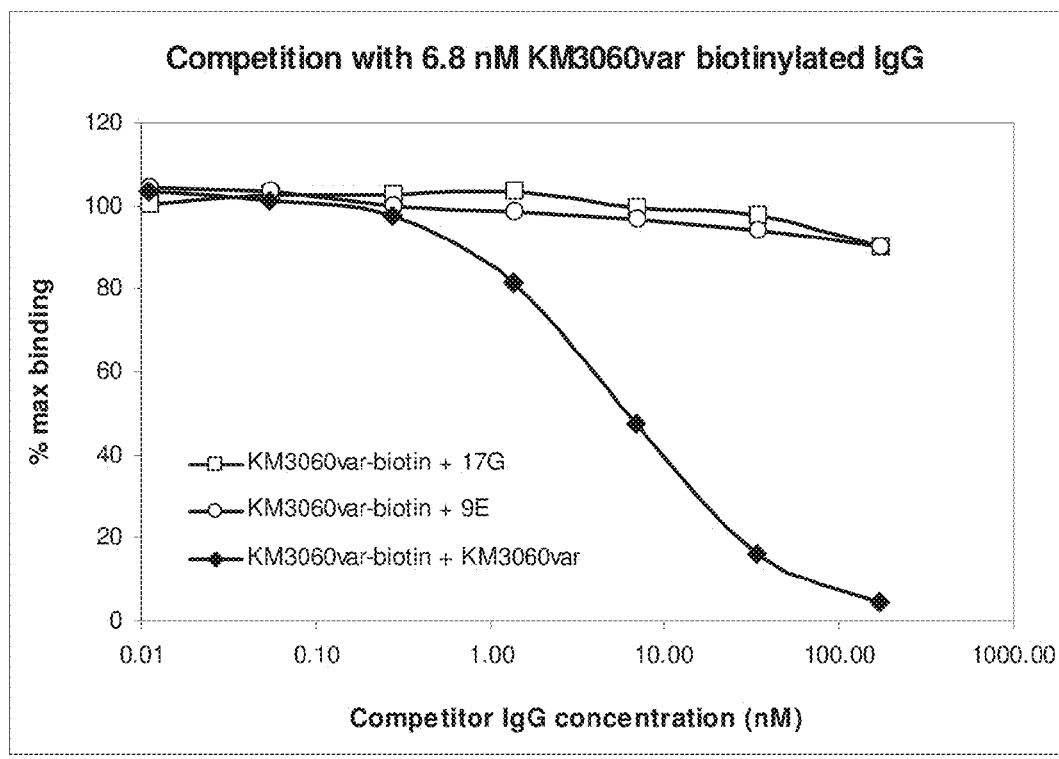

FIG. 10 FIGS. 10A, B and C are graphs showing the results of the competition assay of Example 4. The binding of antibody to CCR4 is shown as the percentage of maximum binding (i.e. binding in the absence of any competitor) plotted against increasing concentrations of the test antibodies (i.e. the putative competitors).

FIG. 10A shows binding of 0.28 nM biotinylated 17G IgG to CCR4 transfected DT40-cells in presence of non-biotinylated 17G, 9E and KM3060var IgGs. KM3060var does not have any appreciable effect on the binding of 17G to CCR4, whereas the presence of antibody 9E causes a reduction in the amount of 17G that binds to CCR4, indicating that 17G and 9E compete with one another for binding to CCR4.

FIG. 10B shows binding of 7 nM biotinylated 9E IgG to CCR4 transfected DT40-cells in presence of non-biotinylated 17G, 9E and KM3060var. KM3060var does not have any appreciable effect on the binding of 9E to CCR4, whereas the presence of antibody 17G causes a reduction in the amount of 9E that binds to CCR4, confirming the results of FIG. 10A that 17G and 9E compete with one another for binding to CCR4.

FIG. 10C shows binding of 6.8 nM biotinylated KM3060var IgG to CCR4 transfected DT40-cells in presence of non-biotinylated 17G, 9E and KM3060var. It can be seen that neither 17G nor 9E compete with KM3060var for binding to CCR4.

Figure 11:
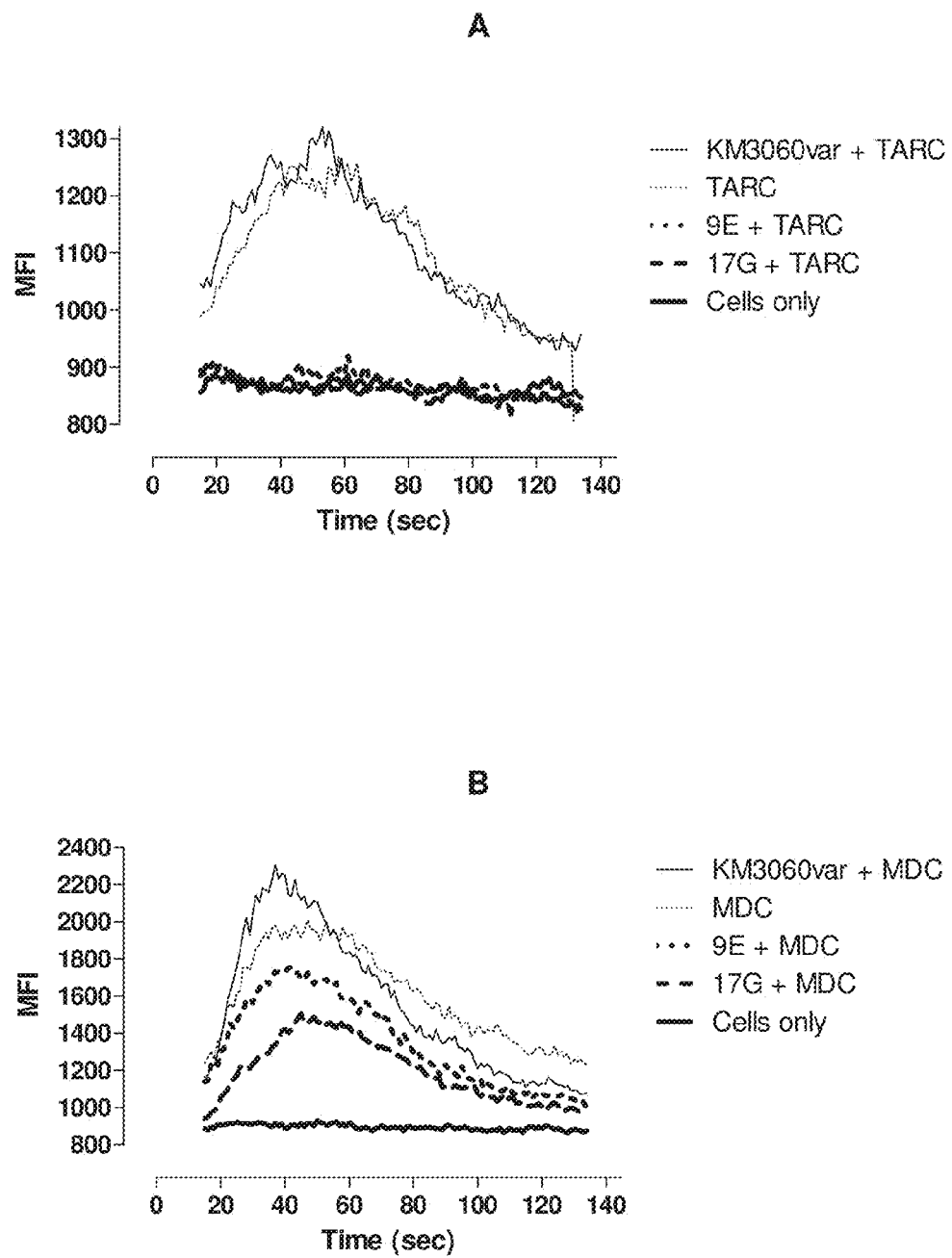

FIG. 11 shows the results of Example 5 in which calcium flux inhibition by 9E, 17G and KM3060var IgG was assayed. The natural CCR4$^+$ CCRF-CEM cell line, labeled with Fluo-4, was preincubated with antibodies followed by stimulation with TARC (A) or MDC (B) ligands. The recording of the cells started about 15 sec after the ligand addition. TARC and MDC both cause calcium flux, seen as a high peak in the Figures. TARC-induced calcium flux is almost completely inhibited by 17G and 9E respectively, but not by KM3060var. MDC-induced calcium flux is also strongly inhibited by 17G and 9E respectively, but not by KM3060var.

FIGS. 12 A and B shows antibody-dependent cell cytotoxicity (ADCC) results of Example 6. The figure shows that 17G (FIG. 12B) and 9E (FIG. 12A) are able to induce ADCC of CCRF-CEM cells in the presence of human PBMCs.

Figure 13:
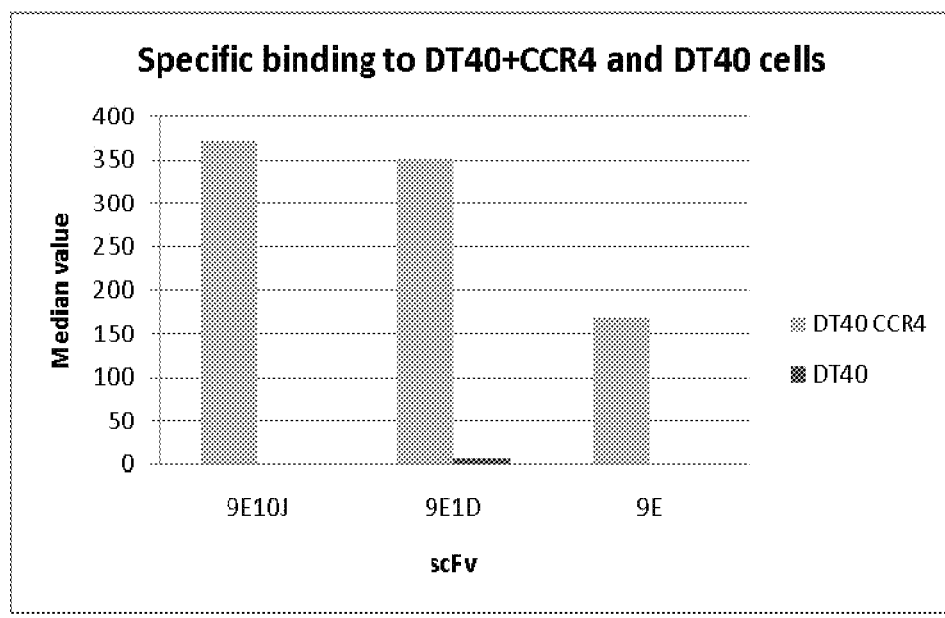

FIG. 13 is a graph which shows some of the results from Example 2. The CCR4-specificity of the antibodies 9E10J and 9E1D was confirmed by staining CCR4 transfected and untransfected DT40 cells. 9E served as a positive control in this experiment. Binding to CCR4+ cells is shown using light grey bars. Binding to CCR4− cells is shown using dark grey bars, the absence of a dark grey bar meaning that no significant binding could be detected.

Figure 14:
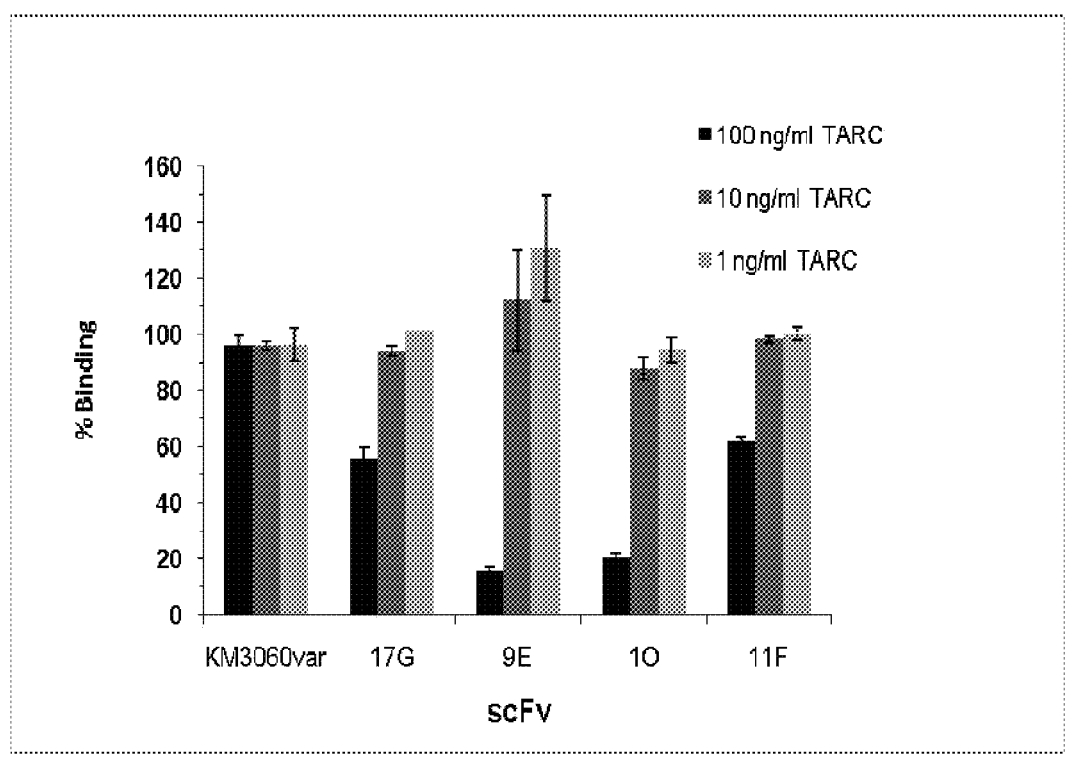

FIG. 14 is a graph which shows some of the results from Example 3. Binding of anti-CCR4 scFv antibodies 17G, 9E, 1O, 11F and KM3060var to CCR4-transfected DT-40 cells was assayed in the presence or absence of the CCR4 ligand TARC, as determined by flow cytometry.

Figure 16:
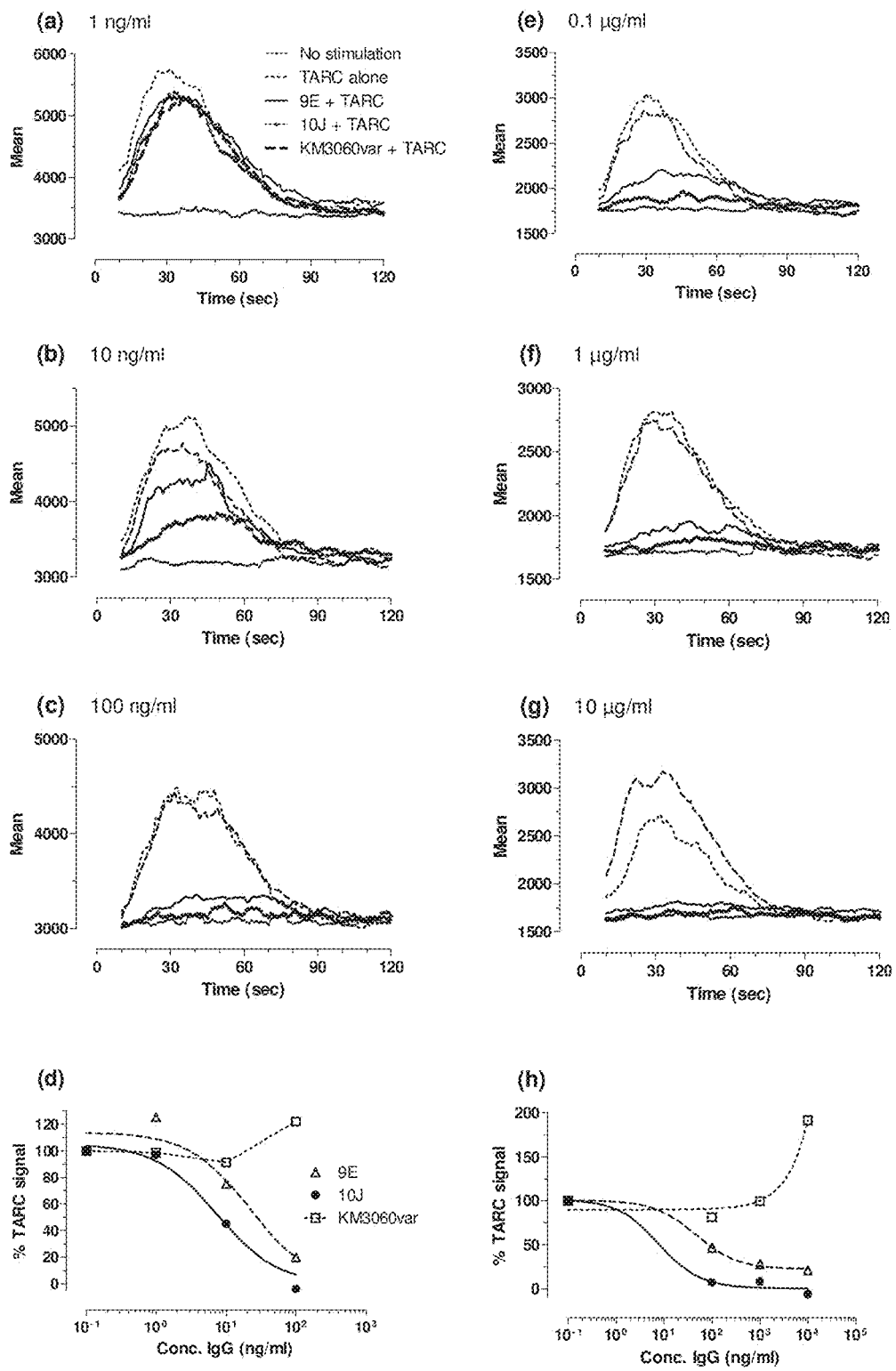

FIG. 15 shows some of the results from Example 4. Competition titration of fixed amounts of biotinylated IgG1 9E at concentration of either 0.7 (a, c) or 3.3 nM (b) in presence of increasing concentrations of unlabelled IgGs 9E, 9E10J or KM3060var on DT-40-CCR4$^+$ (a-b) or CCRF-CEM cells (c). Detection of bound biotinylated IgG was performed by Strep-PE. MFI=median fluorescence intensity FIG. 16 shows some of the results from Example 5. Ca$^{++}$-flux assays were carried out on CCRF-CEM cells labelled with Fluo-4 using overlapping concentration intervals. Cells were pre-incubated with 9E, 9E10J, or KM3060var IgGs for 15 min before adding the CCR4-specific ligand TARC. The IgG concentrations were 0.001 µg/ml (a), 0.01 µg/ml (b), 0.1 µg/ml (c), 0.1 µg/ml (e), 1.0 µg/ml (f) and 10 µg/ml (g). The areas under the curves (AUC) were integrated using software Prism (GraphPad) and plotted as percentage of AUC for maximal stimulation with TARC alone, as shown in panels (d) and (h) for the left and right columns, respectively.

Figure 17:
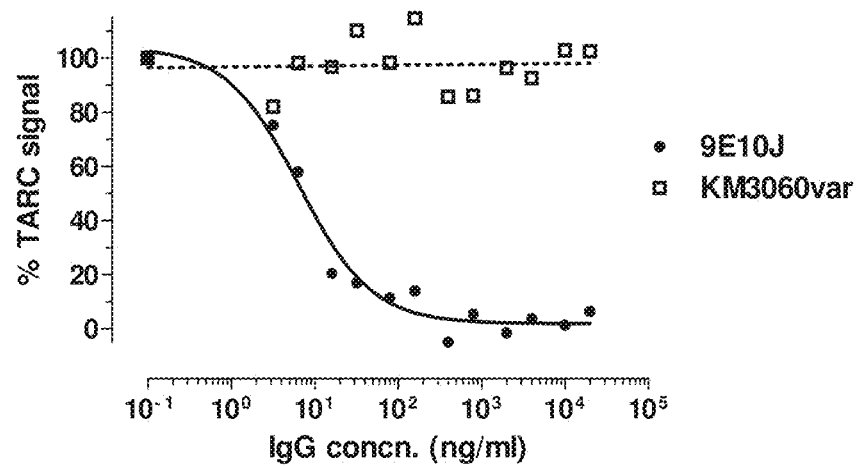

FIG. 17 shows some of the results from Example 5. Ca$^{++}$-flux assays were carried out on CCRF-CEM cells labelled with Fluo-4 using overlapping concentration intervals. Cells were pre-incubated with 9E10J or KM3060var IgGs for 15 min before adding the CCR4-specific ligand TARC. A broad range of IgG concentrations was used. Signals were recorded and the areas under the curves (AUC) were integrated using software Prism (GraphPad) and plotted as percentage of AUC for maximal stimulation with TARC alone.

Figure 18:
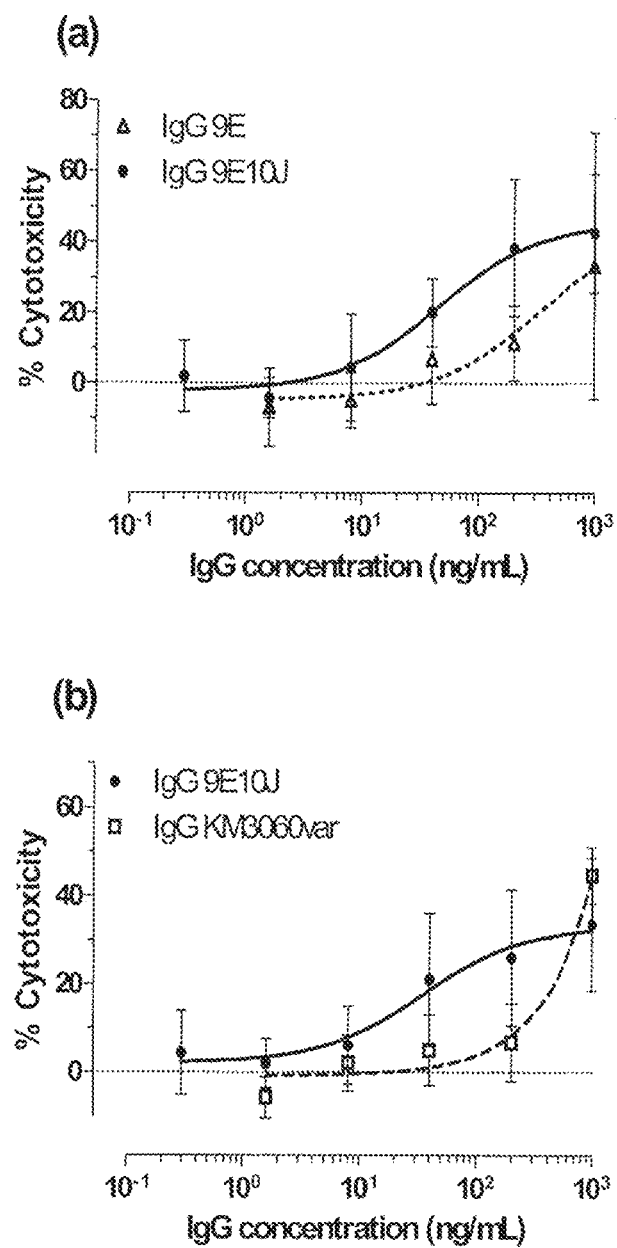

FIG. 18 shows some of the results from Example 6, concerning ADCC of CCRF-CEM cells mediated by anti-CCR4 antibodies. FIG. 18 (*a*) comparison of IgG 9E to IgG 9E10J, FIG. 18 (*b*) comparison of 9E10J to KM3060var.

Figure 19:
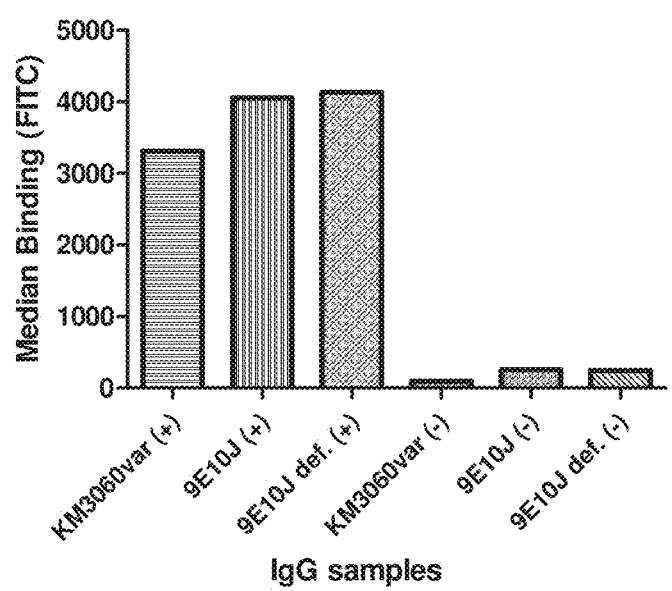

FIG. 19 shows some of the results from Example 10. Binding of defucosylated 9E10J (9E10Jdef), unmodified 9E10J and KM3060var to DT40 cells, stably transfected with CCR4 (+) or untransfected, i.e. CCR4-negative (−). Presented is the binding signal at a concentration of 20 µg/ml. Binding was detected using anti-human-FITC (fluorescein isothiocyanate) (goat) conjugated-IgG.

Figure 20:
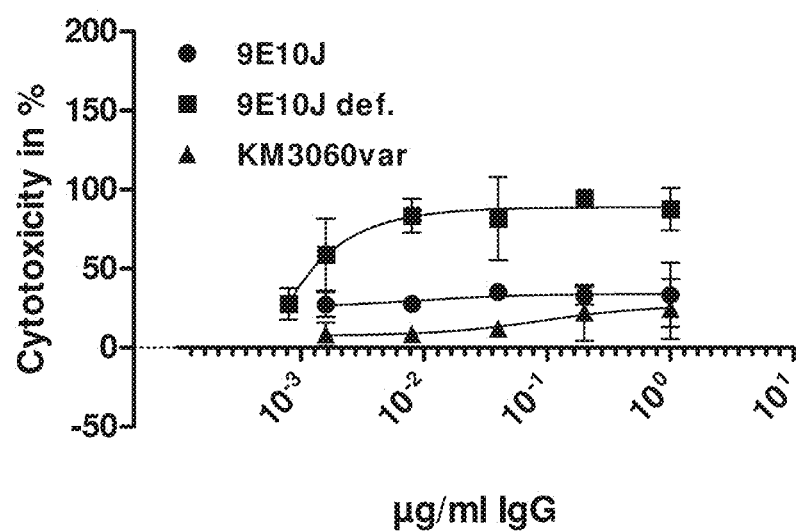

FIG. 20 shows some of the results from Example 11. ADCC of CCRF-CEM cells mediated by anti-CCR4 antibodies, comparing defucosylated 9E10J (9E10Jdef) to unmodified 9E10J and KM3060var.

Figure 21:
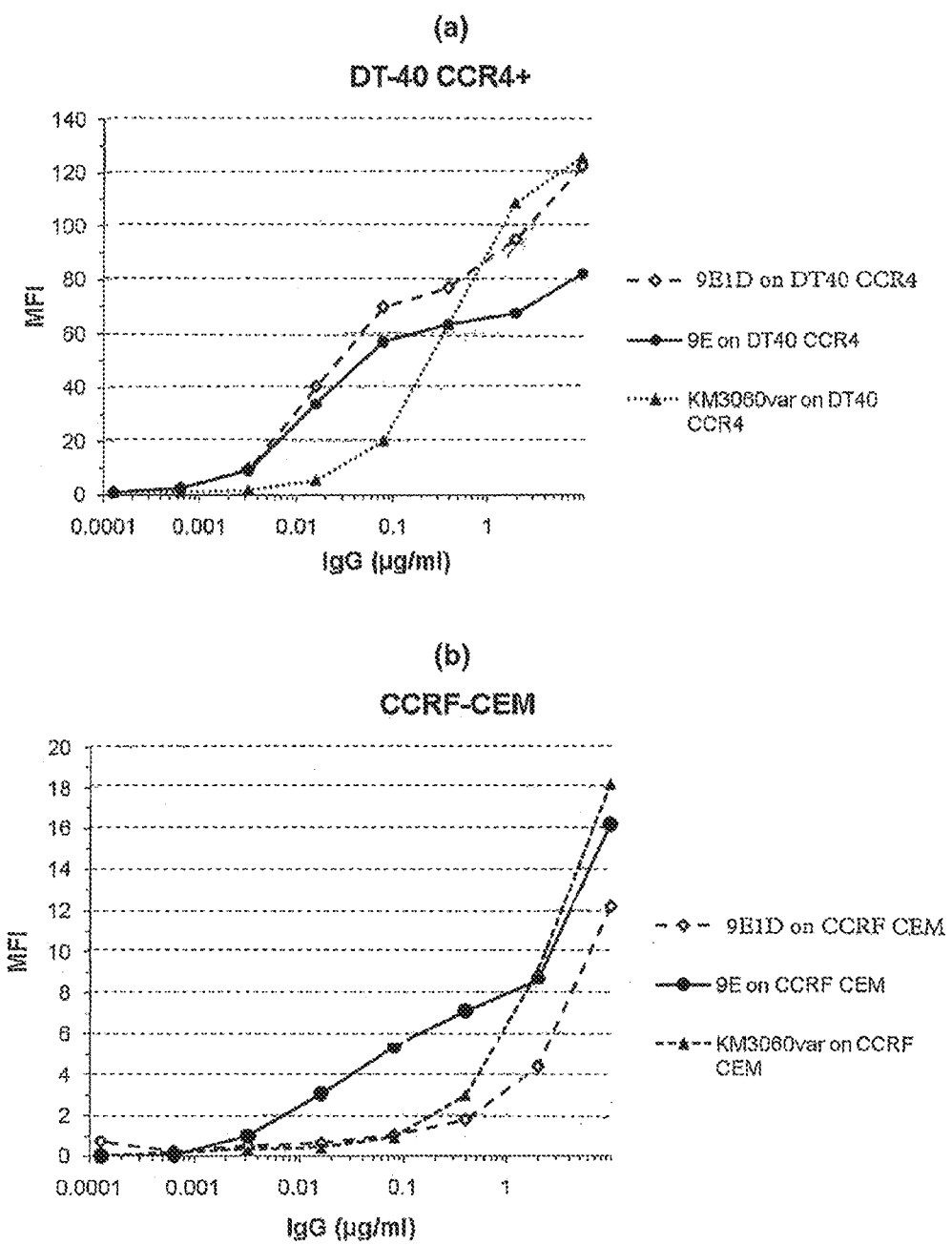
Figure 22:
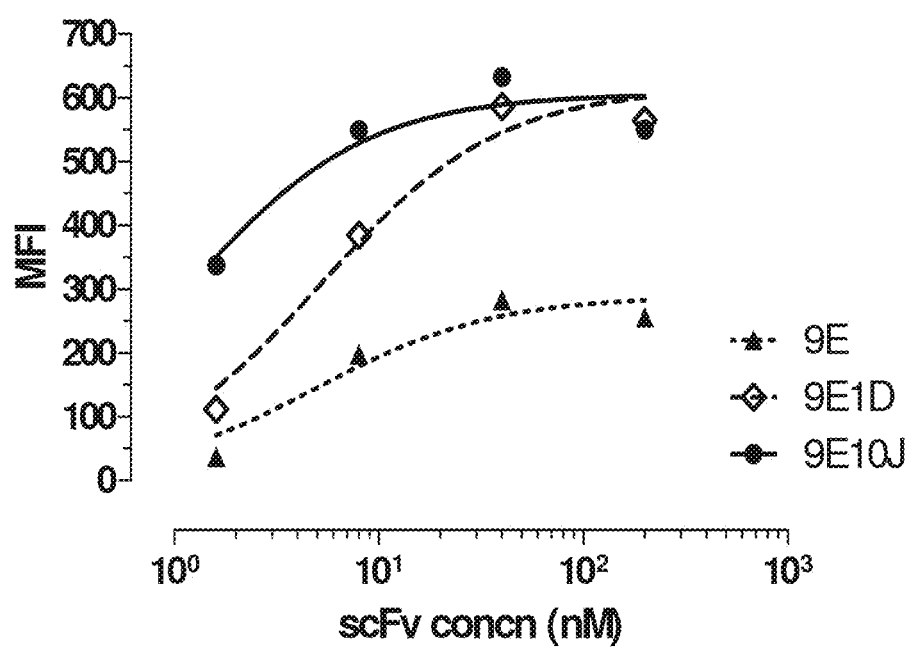
Figure 23:
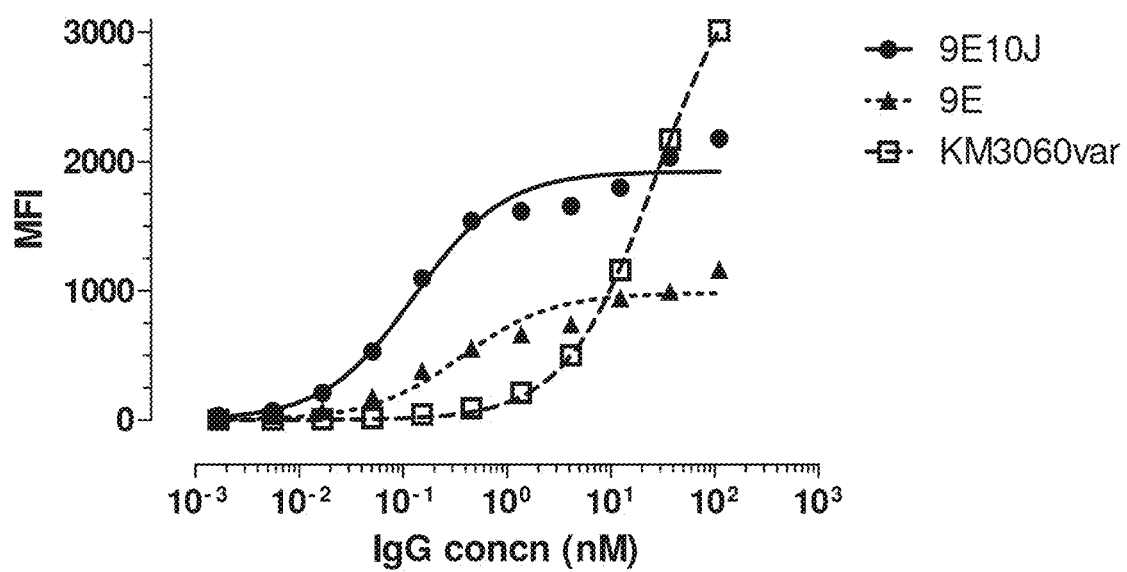
Figure 24:
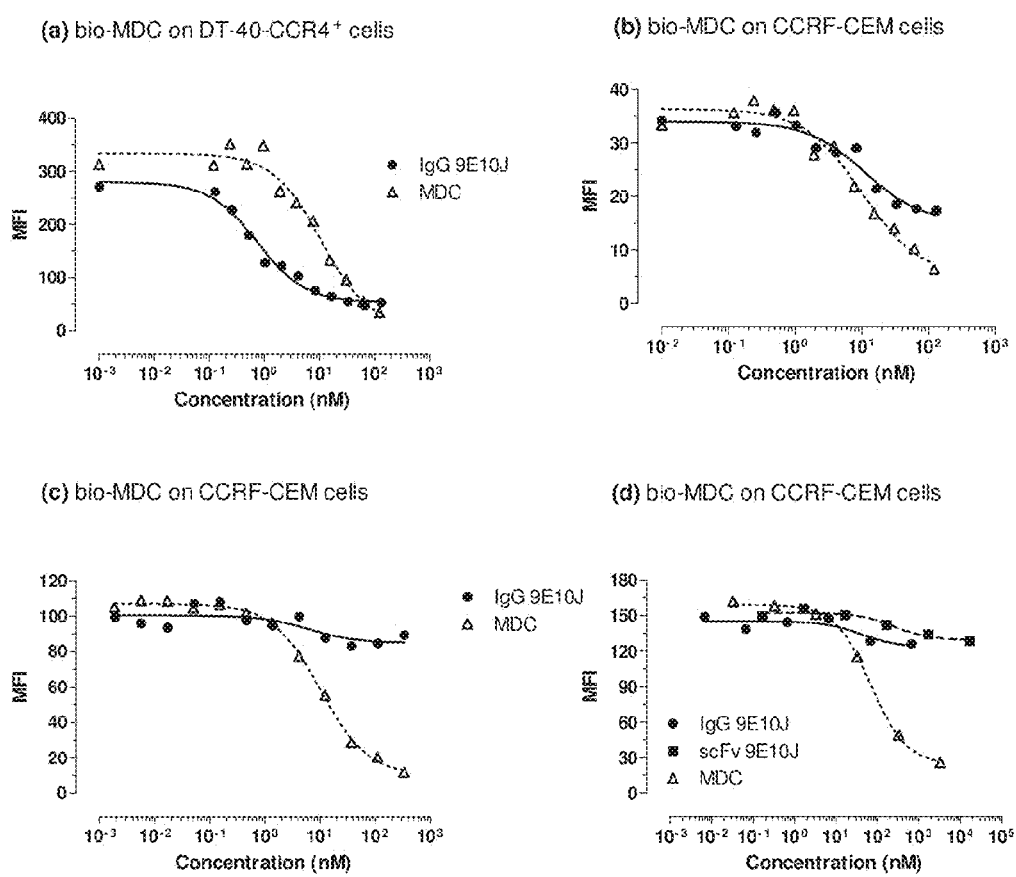

FIG. 21 shows some of the results from Example 14. Binding titration of IgGs 9E, 9E1D and KM3060var on DT-40 CCR4+ cells (a) and on human T-cell leukaemia cells CCRF-CEM (b). Detection was performed with anti-human-FITC. MFI, median fluorescence intensity FIG. 22 shows some of the results from Example 14. Binding titration of scFv 9E, 9E1D and 9E10J on DT-40 CCR4$^+$ cells. The scFvs were cross-linked via myc-tag in order to simulate a dimeric IgG-alike situation. Detection was performed with anti-human-PE. MFI, median fluorescence intensity FIG. 23 shows some of the results from Example 14. Binding titration of IgGs 9E, 9E10J and KM3060var on human T-cell leukaemia cells CCRF-CEM. Detection was performed with anti-human-PE. MFI, median fluorescence intensity FIG. 24 shows some of the results from Example 9. Competition titration of fixed amounts of biotinylated MDC (ca. 10 nM in a, b and ca. 20 nM in c, d) in presence of increasing concentrations of either unlabelled antibody (scFv or IgG 9E10J) or CCR4 ligand (MDC) on DT-40-CCR4$^+$ (a) or CCRF-CEM cells (b-d). Detection of bound biotinylated MDC was performed by Strep-PE. MFI, median fluorescence intensity.

Figure 25:
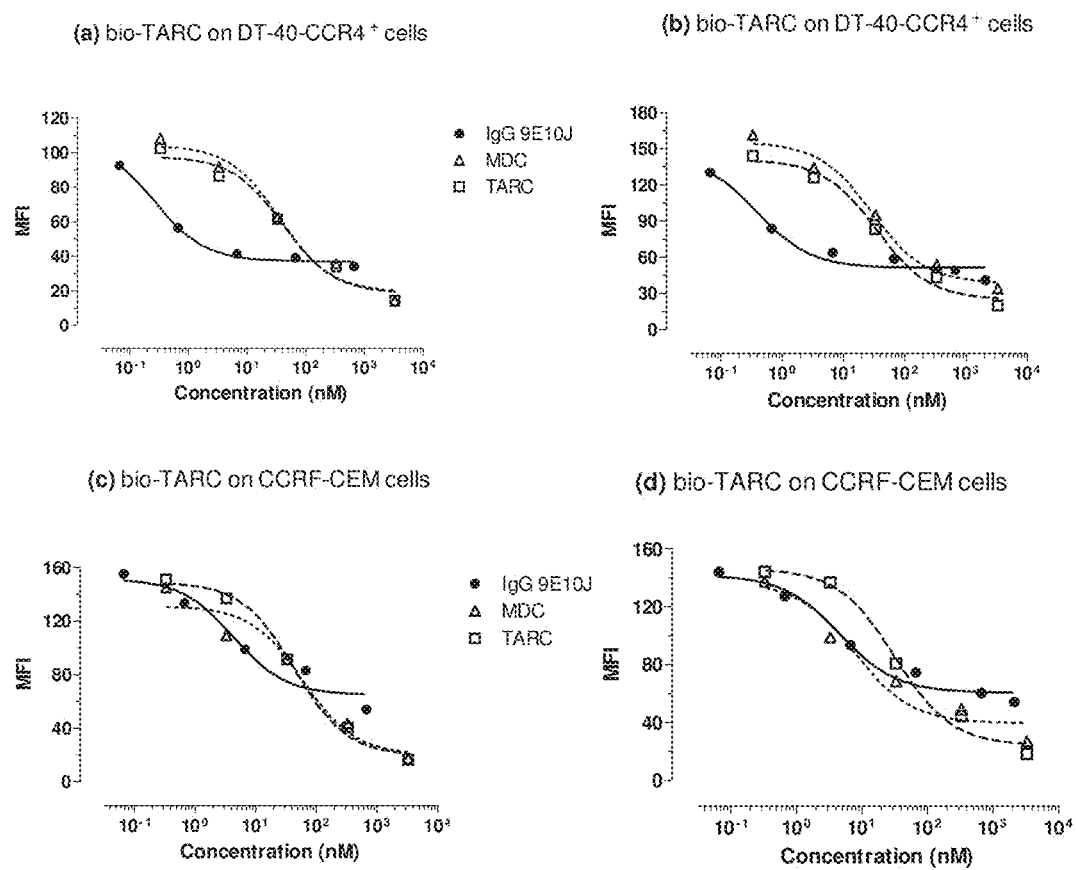
Figure 26:
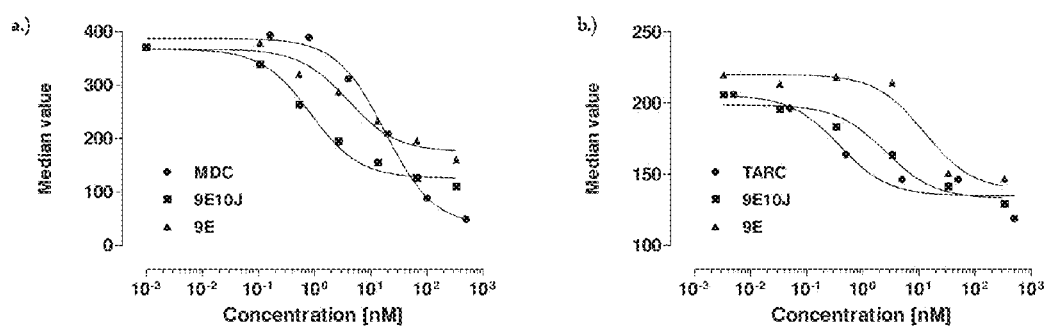

FIG. 25 shows some of the results from Example 9. Competition titration of fixed amounts of biotinylated TARC (ca. 20 nM) in presence of increasing concentrations of either unlabelled antibody (IgG 9E10J) or CCR4 ligands, MDC or TARC on DT-40-CCR4$^+$ (a,b) or CCRF-CEM cells (c,d). Detection of bound biotinylated TARC was performed using Strep-PE. In (b) and (d), incubation of proteins with cells was performed in presence of 1% BSA. MFI, median fluorescence intensity FIG. 26 shows some of the results from Example 9. Competition titration of fixed amounts of biotinylated MDC (a) and TARC (b) in presence of increasing amounts of unlabelled antibodies 9E, 9E10J or unlabelled ligands.

FIG. 27 shows the nucleotide and amino acid sequence of inter alia the heavy and light chain of clone 9E10J. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 28 shows the nucleotide and amino acid sequence of inter alia the heavy and light chain of clone 9E1D. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

Figure 29:
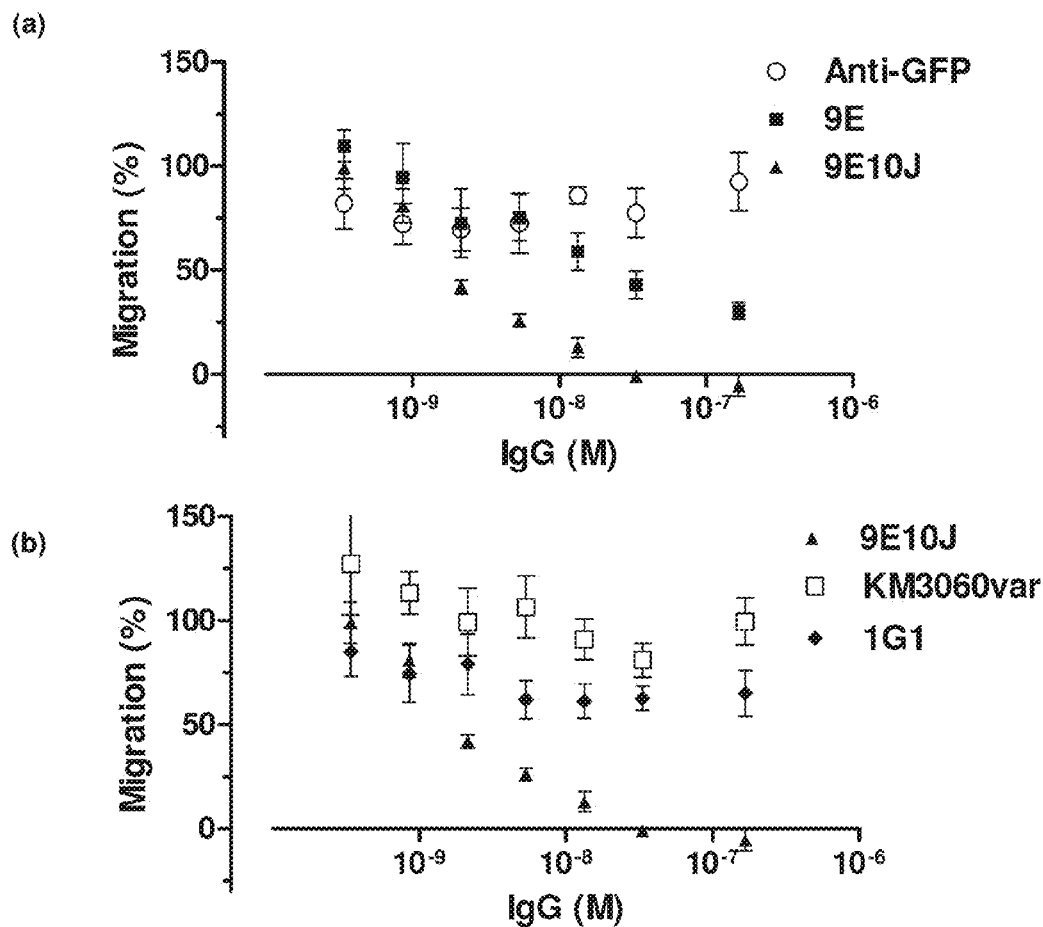

FIG. 29 shows some results of Example 13. Inhibition of ligand (TARC; 3.5 nM) induced cell migration by anti-CCR4 antibodies and controls. Human T-cell leukaemia CCRF-CEM cells were induced to migrate in Multiscreen-MIC chambers, where the ligand TARC was placed in the lower chamber and the cells were co-incubated with antibodies or medium only as a control in the upper chambers. Migrated cells to the lower chamber were detected and counted. Mean and SD values of triplicates are plotted. (a) Inhibition of TARC-induced migration of 9E10J in comparison to 9E and anti-GFP. (b) Inhibition of TARC-induced migration of 9E10J in comparison to 1G1 and KM3060var.

Figure 30:
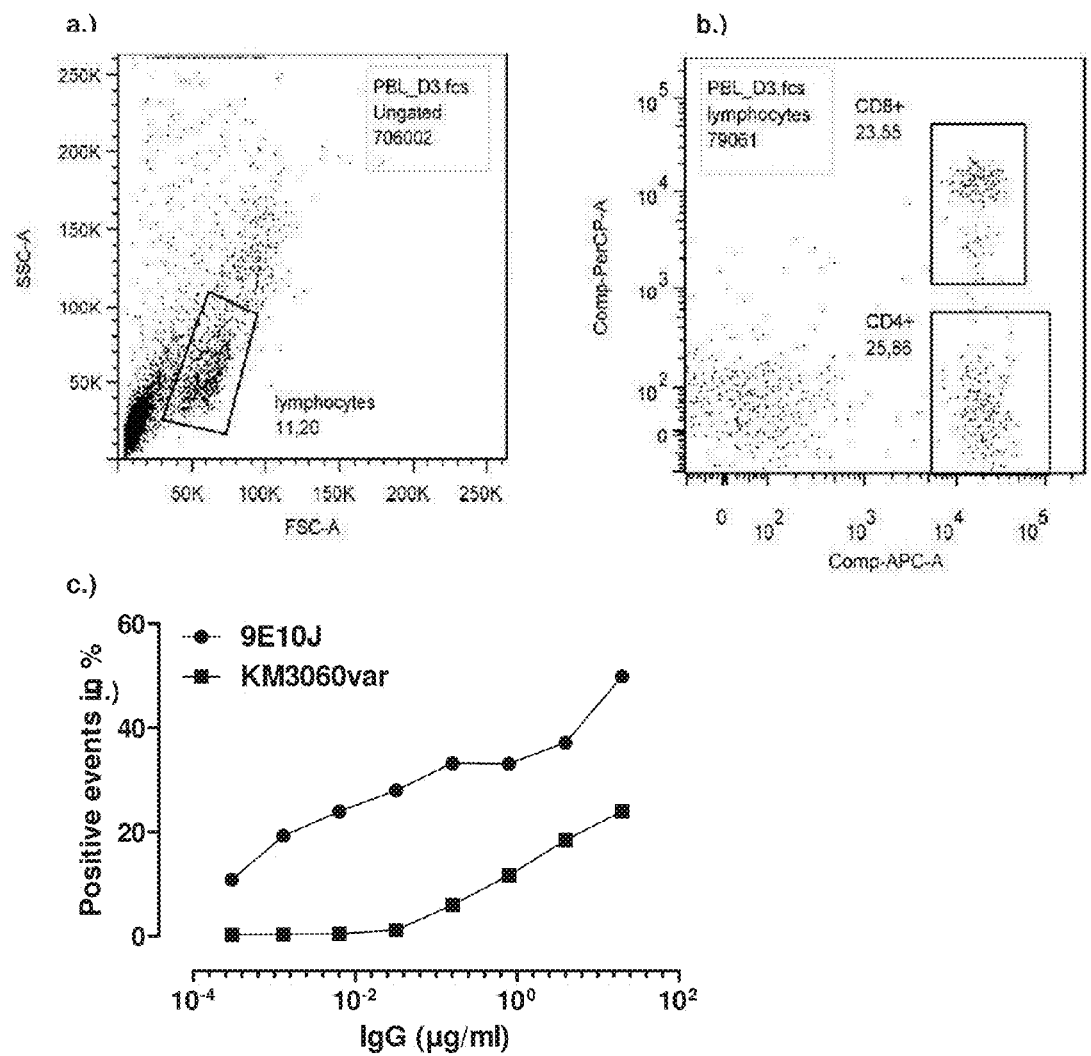

FIG. 30 shows some results from Example 16. Staining of peripheral blood lymphocytes (PBL). Lymphoctyes were gated out of the total cell population. T-cells were gated upon incubation with anti-CD3-APC-IgGs (human) and anti-CD8-PE-Cy5-IgGs (human). Biotinylated 9E10J and biotinylated comparator KM3060var were titrated from 20 µg/ml down to 0.3 ng/ml and detected with PE-conjugated Streptavidin were used PBLs were a.) Gating of lymphocyte population. b.) Gating of CD3-positive cells and sub-dividing into CD8-positive (CD4-negative) and CD8-negative (CD4-positive) cells. c.) Titration curves of 9E10J and KM3060var *on* gated CD8-negative (CD4-positve) cells, expressed in % of positive events.

The following non-limiting examples are illustrative of the present invention:

EXAMPLES

Example 1

Novel Antibodies

Four human antibodies have been identified which can specifically bind to CCR4. Single chain forms of the antibodies were cloned in the pHOG21 plasmid which contains a c-myc and 6×His tag epitopes. TG1 bacteria were transformed, and the scFv was expressed upon IPTG induction. The binding of the purified scFv was confirmed by EasyCyte.

The nucleotide sequences of the heavy and light chain of the antibody producing clones were sequenced. The antibodies are designated as 17G, 9E, 11F, 1O, 9E10J and 9E1D. The nucleotide sequence and amino acid sequence of the light and heavy chain of 17G are shown in FIG. 1. The CDR regions of the light and heavy chains of 17G are shown in Table 1. The nucleotide sequence and amino acid sequence of the light and heavy chain of 9E are shown in FIG. 2. The CDR regions of the light and heavy chains of 9E are shown in Table 2. The nucleotide sequence and amino acid sequence of the light and heavy chain of 1O are shown in FIG. 3. The CDR regions of the light and heavy chains of 1O are shown in Table 3. The nucleotide sequence and amino acid sequence of the light and heavy chain of 11F are shown in FIG. 4. The CDR regions of the light and heavy chains of 11F are shown in Table 4.

Two further antibodies have been identified which can specifically bind to CCR4. Single chain forms of the antibodies were prepared as described above. The nucleotide sequence and amino acid sequence of the light and heavy chain of 9E10J are shown in FIG. 27. The CDR regions of the light and heavy chains of 9E10J are shown in Table 11. The nucleotide sequence and amino acid sequence of the light and heavy chain of 9E1D are shown in FIG. 28. The CDR regions of the light and heavy chains of 9E1D are shown in Table 12.

The IgG form of antibodies 17G, 9E, 1O, 11F, 9E10J and 9E1D has also been made. IgGs were prepared using standard protocols. Briefly, the genes encoding the corresponding variable domains were cloned into the mammalian expression vector pLNO comprising the genes for human constant domains (Norderhaug et al, 1997). The antibodies were expressed in a cell factory, and the first harvest was purified on a protein A column and fractionated into monomer by size exclusion chromatography. The IgGs retained their ability to specifically bind to CCR4.

The IgG form is of the IgG1 isotype and it comprises two heavy chains and two light chains. Each heavy chain comprises a VH domain of SEQ ID NO: 69 (for 17G), SEQ ID NO: 71 (for 9E or 9E1D), SEQ ID NO:73 (for 1O), SEQ ID NO:75 (for 11F), or SEQ ID NO: 105 (for 9E10J), and a human IgG1 constant region. Each light chain comprises a VL domain of SEQ ID NO: 70 (for 17G), SEQ ID NO: 72 (for 9E or 9E10J), SEQ ID NO: 74 (for 1O) SEQ ID NO: 76 (for 11F), or SEQ ID NO: 115 (for 9E1D), and a human lambda light constant region, except for the IgG form of 11F, which has a human kappa light chain. The full IgG sequences of 17G, 9E, 1O, 11F, 9E10J and 9E1D are shown in Tables 5, 6, 7, 8, 13 and 14 respectively.

A further antibody, 9E1 Dv, has been identified. This antibody has a point mutation at position 88 in FR3 (numbering according to Kabat et al., Sequences of proteins of immunological interest; Fifth edition, 1991), where 9E1 Dv has an Alanine (A) instead of the Valine (V) found in 9E1D. The properties of 9E1 Dv, insofar as they have been tested, appear to correspond to those of antibody 9E1D.

Example 2

Binding of Anti-CCR4 Antibodies to Tartlet Expressing Cells

To demonstrate the CCR4-specificity of the antibodies disclosed in Example 1 and to estimate their binding affinities, in-house CCR4 transfected and untransfected HEK293T-cells, DT40-cells and the natural CCR4+ CCRF-CEM cell line were used in flow cytometry for staining with IgGs 17G and 9E as well as with scFvs 1O and 11F. As a positive control, in-house cloned and expressed KM3060var IgG which is specific for an epitope present in positions 2-29 in N-terminal part of human CCR4 (EP1270595) was used. An anti-GFP antibody (raised against the green fluorescent protein) or the anti-VZV antibody (raised against Varicella zoster virus) were used as negative controls (anti-GFP both as scFv and IgG, while anti-VZV only as scFv).

CCRF-CEM (acute lymphoblastic leukemia, ATCC number CCL-119), HEK293T/17 (human kidney, ATCC number CRL-11268), and DT40 (chicken lymphoma, ATCC number CRL-2111) cell lines were obtained from the American Type Culture Collection (ATCC, Rockville, Md.). The CCRF-CEM and DT40 cells were maintained in RPMI-1640 culture medium and the HEK293T cells were maintained in Dulbecco's Modified Eagle Medium (DMEM) culture medium. All cells were maintained with fetal calf serum, the concentration was 10% for DT40 and HEK293T cells and 20% for CCRF-CEM cells. All media were supplemented with Penicillin and Streptomycin.

For the flow cytometry experiments, the cells were harvested from the culture flasks, washed 2 times with PBS, re-suspended in PBS with 0.2% BSA and 0.09% $NaN_3$ and finally aliquoted $1 \times 10^5$ cells per well into V-shaped 96-well plates (Greiner Bio-One, Frickenhausen, Germany). Cells were centrifuged at 400×g for 5 min and then incubated at 4° C. for 45 min with different antibody dilutions.

For staining with scFvs, the scFv preparations were pre-incubated with a chimeric (mouse variable/human constant domains) anti-c-myc antibody prior adding to the cells.

After washing with PBS with 0.2% BSA and 0.09% $NaN_3$, the cells were stained with 10 µg/ml of RPE-conjugated goat anti-human IgG (AbDSerotec, Düsseldorf, Germany) for 30 minutes at 4° C. The stained cells were washed, re-suspended in 200 µl PBS with 0.2% BSA and 0.09% NaN$_3$ and transferred to a U-shaped 96-well plate (Corning, Schiphol-Rijk, The Netherlands) for acquisition on EasyCyte flow cytometer (Guava Technologies, Hayward, Calif., USA).

The results obtained clearly indicate that the antibodies 17G, 9E, 1O and 11F are specific for CCR4. Binding of antibodies 17G and 9E to CCR4-positive DT40 cells compared to CCR4-negative DT40 cells is illustrated in FIG. 5. Binding of 17G and 9E to CCR4-expressing CCRF-CEM cells is illustrated in FIG. 6. Selective binding of 17G and 9E to CCR+HEK293T cells compared to CCR-HEK293T cells was also found.

The affinity values (K$_D$) deduced from these IgG titration experiments were estimated to be in low nanomolar range (see Table 9).

The specificity of antibody 1O scFv for CCR4 is illustrated in FIG. 7 and the specificity of antibody 11F scFv for CCR4 is illustrated in FIG. 8.

The binding specificity of 9E10J and 9E1D was also tested against untransfected and CCR4-transfected DT40 cells under conditions corresponding essentially to those described above. For this experiment, 9E10J and 9E1D were expressed as scFvs having a c-myc tag at the 3' end, which was used to create dimers to mimic the IgG format. The antibodies were pre-incubated with an anti-c-myc antibody prior to adding to cells. Staining was carried out essentially as describe above. The results show that 9E10J and 9E1D bind selectively to CCR4-positive cells (FIG. 13).

Example 3

Anti-CCR4 Antibodies Interference with Ligand Binding

To determine whether the anti-CCR4 antibodies interfere with the binding of CCR4 ligands to the receptor, MDC (obtained from PeproTech EC Ltd., London, UK) was pre-incubated with CCR4-transfected DT40-cells prior to staining with the scFvs. As a negative control, the KM3060var scFv (see Table 10 for sequence) was used which is specific for the N-terminal part of human CCR4. It was shown previously that the antibody KM3060 does not interfere with ligand binding to the receptor (T Ishida et al (2006) Specific Recruitment of CC Chemokine Receptor 4-Positive Regulatory T Cells in Hodgkin Lymphoma Fosters Immune Privilege, *Cancer Res* 66: (11): 5716-5722). KM3060var corresponds to KM3060, but it has been expressed in a different host cell, which may have led to differences in the sugar chains attached to this antibody.

The CCR4+ DT40-cells were harvested from culture flasks, washed 2 times with RPMI-1640 culture medium and aliquoted 1×105 cells per well into V-shaped 96-well plates (Greiner Bio-One, Frickenhausen, Germany). Cells were centrifuged at 500×g for 5 minutes and then incubated for 30 minutes at 37° C. with 0, 1 or 10 ng/ml of MDC (PeproTech EC, London, UK) in RPMI-1640 culture medium. The supernatants were aspirated after a centrifugation step at 500×g for 5 minutes and cells were incubated for 1 hour at 4° C. with 0.5 µg/ml of scFv and 2.5 µg/ml of an in-house produced anti-cMyc with human Fc. After washing three times with PBS containing 0.2% BSA and 0.09% NaN3, the cells were stained with 2.5 µg/ml of RPE-conjugated goat anti-human IgG (AbDSerotec, Düsseldorf, Germany) for 1 hour at 4° C. Cells were washed, re-suspended in 200 µl PBS with 0.2% BSA and 0.09% NaN3 and transferred to a U-shaped 96-well plate (Corning, Schiphol-Rijk, The Netherlands) for flow cytometry using an EasyCyte device (Guava Technologies, Hayward, Calif., USA). The results showed a clear decrease in staining signals, apart from staining with KM3060var antibody, after pre-incubation of CCR4 transfected DT40 cells with 10 ng/ml of MDC (FIG. 9). This indicates that the antibodies 17G, 9E, 1O and 11F interfere with the ligand binding and thus have a CCR4-blocking activity.

A similar experiment showed that all four antibodies 17G, 9E, 1O and 11F also interfere with the binding of TARC to CCR4. The results are shown in FIG. 14.

Example 4

Competition Between Anti-CCR4 Antibodies

To analyze the epitope binding of anti-CCR4 antibodies 17G, 9E and KM3060var, competition experiments were performed using flow cytometry. The binding of biotinylated antibodies to CCR4 transfected DT40-cells was challenged in the presence of different concentrations of non-biotinylated anti-CCR4 antibodies. The CCR4$^+$ DT40 cells were harvested from culture flasks, washed 2 times with PBS, re-suspended in PBS with 0.2% BSA and 0.09% NaN$_3$ and finally aliquoted 1×10$^5$ cells per well into V-shaped 96-well plates (Greiner Bio-One, Frickenhausen, Germany). Cells were centrifuged at 400×g for 5 min and then incubated at 4° C. for 3-4 hours with fixed amounts of biotinylated IgG and different concentrations of non-biotinylated antibodies. After washing with PBS with 0.2% BSA and 0.09% NaN$_3$, the cells were stained with 2.5 µg/ml of Streptavidin—RPE (BD Pharmingen, San Diego, Calif., USA) for 30 minutes at 4° C. The stained cells were washed, re-suspended in 250 µl PBS with 0.2% BSA and 0.09% NaN$_3$ and transferred to a U-shaped 96-well plate (Corning, Schiphol-Rijk, The Netherlands) for acquisition on EasyCyte flow cytometer (Guava Technologies, Hayward, Calif., USA). The results shown in FIGS. 10 A, B and C illustrate that the 17G and 9E antibodies have epitopes that are identical or at least overlapping. There was no competition between KM3060var *antibody* binding to the cells and the other two antibodies indicating that 17G and 9E do not bind to the same epitope as KM3060var.

Further competition experiments were carried out to assess whether or not the test antibodies recognise the same or overlapping epitopes, and to determine their relative affinities for CCR4. Antibodies 9E10J, 9E and KM3060var were tested using labelled 9E as a competitor.

DT40 and CCRF-CEM cells were cultivated as described in Example 2. The cells were harvested from culture flasks, washed 2 times with PBS (400×g, 5 min, 4° C.) and resuspended in PBS containing 0.2% BSA and 0.09% NaN3. 1×105 cells per well were aliquoted into V-shaped 96-well plates (Griner Bio-One, Frikenhausen, Germany). Cells were centrifuged (400×g, 5 min, 4° C.) and resuspended in 50 µl IgG 9E10J or KM3060var (dilution series starting at 5 µg/ml) mixed with biotinylated competitor antibody 9E (0.1 or 0.5 µg/ml). The cells were incubated for 2 hours at 4° C., mixing with a pipette every 45 min. The cells were washed three times with 150 µl PBS with 0.2% BSA and 0.09% NaN3 and stained with 3 µg/ml streptavidin PE (BD Biosciences) for 45 minutes at 4° C. Cells were washed, resuspended in 200 µl PBS with 0.2% BSA and 0.09% NaN3, and transferred to a U-shaped 96 well Costar (Corning, Schiphol-Rijik, The Netherlands) plate for flow cytometry using an FACS Canto II flow cytometer (BD Biosciences, Heidelberg, Germany).

The results shown in FIG. 15 demonstrate that both 9E and 9E10J effectively inhibited cell binding of biotinylated IgG 9E in a dose-dependent manner. In contrast, nearly no decrease of binding signals was observed when KM3060var was titrated with biotinylated 9E, thus confirming that epitopes recognized by these antibodies do not overlap.

To determine IC50 values (antibody concentrations leading to 50% inhibition of biotinylated IgG binding), the experimental data were fitted by non-linear regression curve fit using a model "log (inhibitor) vs. response" of software Prism (GraphPad). Apparent binding affinities ($K_D$) were calculated according to the following equation derived from previously described methods (Kipriyanov et al, 1997b; Schodin & Kranz, 1993):

$$K_D^{(I)}=IC_{50}/(1+[\text{bio-IgG}^{(9E)}]/K_D^{(9E)}),$$

where I is the unlabelled inhibitor (IgG), [bio-IgG$^{(9E)}$] is fixed concentration of biotinylated IgG 9E, and $K_D^{(9E)}$ is the binding affinity of IgG 9E derived from saturation titration experiments (4.95 nM). Results are shown in Table 15.

Example 5

Antagonistic Activity

The ability of 9E and 17G to reduce ligand induced calcium flux in the natural CCR4$^+$ CCRF-CEM cell line was assessed. The antibody KM3060var was used as a negative control. The sequence-identical defucosylated clone KM2760 has been reported to be not inhibiting CCR4 signaling. The CCRF-CEM target cells, cultivated under regular conditions, were sedimented by centrifugation and resuspended twice in RPMI-1640 culture medium. One ml with 2.5×10$^6$ cells was mixed with Fluo-4-AM (Invitrogen, Carlsbad, Calif.), Pluronic F-127 (Invitrogen, Carlsbad, Calif.) and Probenecid to final concentrations of 1 µM, 0.02% and 1 mM respectively. The cells were incubated at 37° C. for 30 min on a vertical rotating wheel (7 rpm). All subsequent steps were done in the presence of 1 mM Probenecid. The cells were washed twice in RPMI-1640 with 10% FCS, once in assay buffer (145 mM NaCl, 4 mM KCl, 1 mM NaH$_2$PO$_4$, 0.8 mM MgCl$_2$, 25 mM Hepes, 22 mM glucose) and then resuspended to a final density of 1.2×10$^6$ cells/ml. Equal volumes of cells, assay buffer with or without antibodies and ligand (MDC or TARC) were mixed. The first two components (cells and antibodies) were pre-incubated for 15 min prior to addition of the ligand. The final concentrations of the IgGs, TARC and MDC were 10 µg/ml, 10 ng/ml and 2.5 ng/ml, respectively. The samples were immediately analyzed using the 515-545 nm band pass filter on a FACSCanto II flow cytometer (BD Biosciences, Heidelberg, Germany).

The results shown in FIG. 11 clearly demonstrated that both 9E and 17G act as inhibitors of TARC and MDC. Cells preincubated with 9E, 17G and KM3060var IgGs at concentration 10 µg/mL showed signal responses to TARC stimulation of 3%, −1% and 104% assuming the signal to TARC alone as 100% (FIG. 11A). Accordingly, the cells preincubated with 9E, 17G and KM3060var IgGs showed signal responses to MDC stimulation of 64%, 42% and 92%, respectively of the signal to MDC in the absence of IgGs (FIG. 11B). No signal was detected when either 9E or 17G IgGs were added to the cells instead of TARC or MDC ligands (data not shown). The 9E or 17G IgGs also did not show any inhibition of the CXCR4 specific SDF-1 ligand (data not shown).

The experiment was also carried out under similar conditions using antibody 9E10J in the human IgG1 format, except that incubation of the cells with Fluo4-AM was carried out for 40 min at 37° C. without rotating wheel. Antibody KM3060var was included as a negative control and antibody 9E was also included (both also in human IgG1 format). The results shown in FIG. 16 demonstrate dose-dependent inhibition of TARC-induced signalling by both 9E and 9E10J antibodies.

Detailed analysis of Ca$^{++}$ flux inhibition was performed using the broad range of IgG concentrations for 9E10J (FIG. 17). IC$_{50}$ (ng/ml) values were calculated as explained in Example 4. Complete signal inhibition was reached at concentrations 100-300 ng/ml (0.7-2.0 nM) with the calculated IC$_{50}$ value of 43.3 pM (Table 16).

Example 6

Antibody-Dependent Cell-Mediated Cytotoxicity (ADCC)

The ability of 9E and 17G to induce ADCC was assessed on the natural CCR4$^+$ CCRF-CEM cell line. The CCRF-CEM target cells, cultivated under regular conditions, were sedimented by centrifugation and resuspended in RPMI-1640 culture medium. This step was repeated once. One ml with 2.5×10$^6$ cells was mixed with calcein-AM (Invitrogen, Carlsbad, Calif.) to a final concentration of 10 µM and then incubated at 37° C. for 30 min on a vertical rotating wheel (7 rpm). The cells were washed three times in RPMI-1640 with 10% FCS and the cell density was adjusted to 3×10$^5$/ml. Separately, peripheral blood mononuclear cells (PBMC) were prepared following conventional procedures (enriched by Ficoll-Hypaque gradient centrifugation), washed in RPMI-1640 with 10% FCS and resuspended at 6×10$^6$ per milliliter. Fifty µl of each target and effector cells were added to the same wells in a 96-well microtiter plate giving a ratio of effector to target cells (E:T) of 20:1. The antibodies (all in IgG format) were added to the same wells in a volume of 20 µl giving a final concentration range of 10 to 10 000 ng/mL, and with each concentration in quadruplicate samples. The microtiter plate was then incubated four hours at 37° C., and 20 µl 0.9% Triton-X100 was added to some of the wells after 3 hrs and 45 minutes to achieve complete lysis of the target cells. One hundred µl supernatant of each sample was then transferred to a black microtiter plate and the fluorescence (excitation: 488 nm, emission: 518 nm) was analyzed in a TECAN M200 plate reader. The fluorescence intensity in the samples with no antibodies was subtracted from the intensity of all other samples. The percentage of lysis in samples with antibodies was estimated based on fluorescence intensity of the samples with 100% cell lysis after treatment with TritonX-100. The dose-response curves were computed by nonlinear regression analysis and a three-parameter fit model using software Prism (GraphPad, San Diego, Calif., USA).

The results shown in FIGS. 12A and 12B clearly demonstrated that both 9E and 17G were able to induce ADCC in the presence of human PBMCs with EC$_{50}$ values of 619 ng/ml and 46 ng/ml and maximum killing of 55% and 22% respectively.

The ability of antibody 9E10J to induce ADCC of CCRF-CEM cells was also tested and compared to antibody 9E and antibody KM3060var under conditions similar to those described above, except that a rotating wheel was not used. The results, shown in FIG. 18 and Table 17, show that 9E and 9E10J can induce ADCC and that ADCC-induction by 9E10J is superior to ADCC induction by KM3060var.

Example 7

Preparation of Anti-cMyc Hybrid/Human IgG1 Antibody

Anti-cMyc hybrid/human IgG1 antibody: 9E10 H-chain (AJ000488) and light-chain 9E10 L-chain (AJ000489) variable DNA sequences were ordered from GeneArt and converted into a hybrid Human IgG1/Kappa protein. Cloning of the variable VH and VL regions by PCR with specific primers on the scFv template, digested and ligated into heavy- and light-chain vectors, respectively according to the method of Norderhaug et al, JIM 204:77-87. HEK293/T cells were transiently transfected and after 5-6 days, the IgG was purified via Protein-A followed by size exclusion to isolate the monomeric IgG fraction.

Example 8

Species Cross-Reactivity

Antibodies 9E and 9E10J were tested for their ability to cross-react with CCR4 from species other than human.

Hek293T/17 were cultured in DMEM (from PAA, cat# E15-810) with 10% FBS (from PAA cat# A15-252) and 1× penicillin/streptomycin (from PAA cat#P11-010). They were split 2-3× per week. Hek293T/17 were seeded to 32000 cells/cm2 for 48 h and 27000 cells/cm2 over the week end.

For transient transfection, Hek293T/17 cells were seeded as 2×106 cells in a T75 (NUNC) flask. 48 h after seeding, the cells were transfected with Fugene (ROCHE). 40 µl Fugene and 16 µg DNA are used per T75. The cells were used for assays 48 h after transfection.

HEK-293T/17 cells, were transiently transfected either with pcDNA3.1 plasmid encoding human CCR4 or with pLNO plasmids (Norderhaug et al, 1997) encoding either mouse (GeneBank CAA62372) or monkey (*Macaca mulatta*) CCR4 (PubMed access number XP_001098807) using Fugene (Roche) as a transfection reagent. Non-transfected (CCR4 negative) cells served as a negative control. The cells were cultivated further for 48 hours under regular conditions described above. The cells were washed twice with PBS, detached from the culture flasks by incubating with Accutase (PAA laboratories, Linz, Austria) for 3 minutes at room temperature. The cells were then washed 2 times with PBS (400× g, 5 min, 4° C.) and resuspended in PBS containing 0.2% BSA and 0.09% NaN$_3$. 1×10$^5$ cells per well were aliquoted into V-shaped 96-well plates (Griner Bio-One, Frikenhausen, Germany). Cells were centrifuged (400×g, 5 min, 4° C.) and resuspended in 50 µl of 10 µg/ml 9E or 9E10J, in PBS containing 0.2% BSA and 0.09% NaN3. The cells were incubated further at 4° C. for 60 min. The samples were then washed twice by centrifugation and re-suspension in 100 µl FACS buffer. The cell pellets were finally re-suspended in 50 µl with 3 µg/ml anti-human-IgG-PE (BD Biosciences) and incubated at 4° C. for 45 min. The samples were washed twice as described above and re-suspended in 250 µl FACS buffer followed by transfer into a U-shaped 96-well plate (Corning, Schiphol-Rijk, Netherlands) for flow cytometry on FACS-CantoII (BD Biosciences, San Jose, Calif.).

9E and 9E10J both strongly bound to human and monkey CCR4; no binding to murine CCR4 was detected.

Example 9

Inhibition of Ligand Binding

Antibodies 9E and 9E10J were tested for their ability to inhibit binding of MDC and TARC to CCR4+ cells in a competition experiment using biotinylated ligands. The experiment is designed to give an indication of the affinity of the antibodies for CCR4 compared to affinity of the ligands for CCR4.

The competition binding assays were performed with biotinylated MDC or biotinylated TARC on DT-40-CCR4+ and CCRF-CEM cells. DT40 and CCRF-CEM cells were cultured as described in Example 2. TARC and MDC were biotinylated using standard procedures. The biotinylation process causes some losses, so the concentrations of biotinylated MDC and TARC recited herein are approximate.

The cells were harvested from culture flasks, washed 2 times with PBS (400×g, 5 min, 4° C.) and resuspended in PBS containing 0.2% BSA and 0.09% NaN3. 1×10$^5$ cells per well were aliquoted into V-shaped 96-well plates (Greiner Bio-One, Frikenhausen, Germany). Cells were centrifuged (400× g, 5 min, 4° C.) and resuspended in 50 µl IgG, single chain or unlabeled ligand (1:10 dilution series starting on 100/500/26.4 µg/ml) mixed with a fixed concentration of biotinylated ligand (10 or 20 nM, see legend to FIG. 24). The cells were incubated for 2 hours at 4° C. and mixed with a pipette every 45 min. The cells were washed three times with 150 µl PBS with 0.2% BSA and 0.09% NaN3 and stained with 3 µg/ml streptavidin PE (BD Biosciences) for 45 minutes at 4° C. Cells were washed, resuspended in 200 µl PBS with 0.2% BSA and 0.09% NaN3, and transferred to a U-shaped 96 well Costar (Corning, Schiphol-Rijik, The Netherlands) plate for flow cytometry using an FACS Canto II flow cytometer (BD Biosciences, Heidelberg, Germany). To determine IC50 values (concentration of inhibitor leading to 50% decrease of signal), the experimental data were fitted by non-linear regression curve fit using a model "log(inhibitor) vs. response" of software Prism (GraphPad). Apparent binding affinities (KD) were calculated according to the following equation derived from previously described methods (Kipriyanov et al, 1997b; Schodin & Kranz, 1993):

$KD(I)=IC50/(1+[bio-MDC]/KD(MDC))$, where I is the unlabelled inhibitor (antibody or ligand), [bio-MDC] is fixed concentration of biotinylated MDC, and KD(MDC) is the binding affinity of MDC, 0.18 nM (Imai et al, 1998).

The results of competition binding experiments shown in FIG. 24 and Table 20 demonstrate that CCR4-binding of high-affinity ligand MDC can effectively be inhibited in a dose-dependent manner by IgG 9E10J. CCR4-transfected DT-40 cells express a much higher density of CCR4 than CCRF-CEM cells which have 15-fold fewer CCR4 receptors on their surface.

It should be noted that unlabelled MDC was able to completely inhibit binding of biotinylated MDC to CCRF-CEM cells while antibody 9E10J was not (FIG. 24). This observation indicates possible binding of MDC to another receptor on CCRF-CEM cells. Most probably, this is an atypical scavenger (decoy) GPCR receptor D6 which is able to bind MDC with high affinity (Graham, 2009; Locati et al, 2005). This also explains the higher apparent IC50.

Similar binding inhibition experiments were performed using biotinylated TARC. As expected, TARC, antibody 9E10J and MDC all competed effectively with labelled TARC (FIG. 25). To avoid non-specific cell-binding of the labelled ligand, half of the experiments were performed in the presence of 1% BSA as a blocking agent. The presence or absence of BSA did not seem to have any significant effect (BSA present in FIGS. 25 *b* and *d*, absent in FIGS. 25 *a* and *c*).

Example 10

Generation of Defucosylated 9E10J

It has been reported that ADCC enhancement can be achieved by manipulating the state of oligosaccharides on human IgG1 subclass (Niwa R et al, CanRes, Vol. 64, 2004). Modifying the amount of fucose was demonstrated to have a beneficial effect on enhancement of ADCC. Therefore, antibody 9E10J was produced in the presence of Kifunensine, a selective inhibitor of class I α-mannosidases, causing a stop in fucosylation of the IgG during production in cell culture. For quality control, the defucosylated 9E10J IgG was first tested for binding specificity on DT40 cells, stably transfected with CCR4 and compared to unmodified 9E10J and KM3060var.

IgGs were produced in the presence of Kifunensine (100 ng/ml; Sigma). After harvesting the cell medium, IgGs were isolated first upon affinity purification using a ProteinA column (HiTrap, 5 ml, ProteinA; GE). IgGs were eluted using citrate buffer (pH 3) and transferred into 1M Tris-buffer (pH 9). Prior a second purification, IgG samples were up-concentrated and loaded on to a size exclusion chromatography (HiLoad Sephadex 200, GE; running buffer PBS pH 7.4). Monomeric fractions were collected and IgGs were up-concentrated a second time. For binding experiments, IgGs were serial diluted 2-fold, starting at a concentration from 20 µg/ml down to 0.15625 µg/ml. IgGs were incubated on DT40 cells (1.5*106/ml), stably transfected with human CCR4. Untransfected DT-40 cells were used as a negative control. Bound IgGs were detected via anti-human-FITC (goat) conjugated antibodies.

The results presented in the FIG. 19 demonstrate that the modification of the fucosylation pattern has no influence on the CCR4 binding capabilities of 9E10J.

Example 11

Induction of Antibody Dependent Cellular Cytotoxicity (ADCC) of Defucosylated IgG1-Variant Defucosylated 9E10J prepared as described in Example 10 was compared to unmodified 9E10J and unmodified KM3060var. The IgGs were tested using CCRF-CEM cells which constitutively express CCR4. ADCC induction was assayed as described in Example 6.

The results shown in FIG. 20 and Table 18 demonstrate that the defucosyalted variant of candidate 9E10J has increased killing properties of CCR4-positive CCRF-CEM cells by human PBMCs and possesses much higher cytolytic activity in comparison to the unmodified version of 9E10J (4 to 5-fold lower EC50)

Example 12

Inhibition of Growth and Induction of Apoptosis

The ability of antibody 9E to induce apoptosis in Ramos cells (a B-lymphoblastoid cell line derived from a Burkitt lymphoma). was assayed using Annexin V staining and FACS analysis. No significant induction of apoptosis was observed.

A growth inhibition test was carried out using 9E, 9E10J and KM3060var (all in IgG format) on CCRF-CEM cells and Ramos cells (a B-lymphoblastoid cell line derived from a Burkitt lymphoma). No growth inhibition was observed.

Example 13

Inhibition of Chemotaxis i) The inhibition of chemotaxis by antibodies 9E and 9E10J was assayed by contacting CCR4+ cells capable of chemotaxis with antibody 9E or 9E10J in one chamber, and a ligand of CCR4 (MDC or TARC) was placed in another chamber separated from the first chamber by a membrane or filter having a suitable pore size. The effect of the antibody on cell migration towards the ligand (chemotaxis) was determined by comparing chemotaxis in the presence of the antibody to chemotaxis in the absence of the antibody. Both 9E and 9E10J were found to inhibit chemotaxis of CCR4-positive cells towards MDC and TARC.

ii) The ability of 9E10J to reduce ligand induced migration of the natural CCR4+ CCRF-CEM cells was assessed and compared with 9E, KM3060var and 1G1 antibodies. All antibodies were tested in IgG1 format.

CCRF-CEM target cells, cultivated as described in example 2, were sedimented by centrifugation and re-suspended twice in RPMI-1640 culture medium without FCS. In a third centrifugation step, cells were re-suspended in RPMI-1640 culture medium supplemented with 1% FCS and adjusted to a final density of 1.6×107 cells/ml. In parallel, 150 µl of RPMI supplemented with 1% FCS containing TARC at 3.5 nM was added into each of the lower chamber of a Multiscreen-MIC plate 96 well (8 µm pores, Millipore, Billerica, Mass., USA, MAMIC5S10). 50 µl of the cells with IgGs (serial diluted from 167 nM down to 0.3 nM) were added to the upper compartment of the Multiscreen-MIC 96 chamber plate and incubated at 37° C. for 3 hr. The filter was removed and 100 µl of cells (from the lower chamber) were transferred after re-suspending into a 96-well COASTAR plate (Greiner Bio-One, Frikenhausen, Germany); an additional volume of 100 µl of PBS (supplemented with 0.2% BSA and 0.09% NaN3) was added to the samples. Migration was evaluated by counting of gated cells.

The data presented in FIG. 29 demonstrate inhibition of TARC induced chemotaxis of CCRF-CEM cells by 9E and 9E10J. No significant inhibition of chemotaxis was observed for a antibodies KM3060var and 1G1 or for the control IgG (anti-GFP).

Example 14

Binding Specificity and Affinity for CCR4

The quality of the specific binding to DT40+ cells was tested for 9E1D and 9E10J in scFv or IgG format in a titration experiment.

DT 40 and CCRF-CEM cells were cultured as described in Example 2. The DT40 CCR4+ and DT40 (CCR4−) cells were harvested from culture flasks, washed 2 times with PBS (400×g, 5 min, 4° C.) and resuspended in PBS containing 0.2% BSA and 0.09% $NaN_3$. 1×10$^5$ cells per well were aliquoted into V-shaped 96-well plates (Greiner Bio-One, Frikenhausen, Germany). The cells were centrifuged (400×g, 5 min, 4° C.) and resuspended in 50 µl ScFvs (5 µg/ml) in PBS containing 0.2% BSA and 0.09% $NaN_3$, and an in-house produced anti-cMyc antibody with a human Fc (25 µg/ml). After 1 hour incubation (4° C.), the cells were washed three times with 150 µl PBS with 0.2% BSA and 0.09% $NaN_3$ and stained with 2.5 µg/ml RPE conjugated goat anti-human IgG (AbDSerotec, Düsseldorf, Germany) for 45 minutes at 4° C. Cells were washed, resuspended in 200 µl PBS with 0.2% BSA and 0.09% $NaN_3$, and transferred to a U-shaped 96 well Costar (Corning, Schiphol-Rijik, The Netherlands) plate for flow cytometry using an Easy Cyte device (Guava Technologies, Hayward, Calif., USA).

Alternatively, 9E1D and 9E10J were converted into the full-length human IgG1 and tested for cell binding. The DT40+CCR4 and DT40 cells were harvested from culture flasks, washed 2 times with PBS (400×g, 5 min, 4° C.) and resuspended in PBS containing 0.2% BSA and 0.09% NaN$_3$. 1×10$^5$ cells per well were aliquoted into V-shaped 96-well plates (Greiner Bio-One, Frikenhausen, Germany). Cells were centrifuged (400×g, 5 min, 4° C.) and resuspended in a 1:5 dilution series of IgG starting on 10 µg/ml (50 µl/well). After 1 hour incubation at 4° C., the cells were washed three times with 150 µl PBS with 0.2% BSA and 0.09% NaN$_3$ and stained with 2.5 µg/ml RPE conjugated goat anti-human IgG (AbDSerotec, Düsseldorf, Germany) or 2.5 µg/ml anti human IgG Fc (goat polyclonal aff. pur) FITC (Sigma Aldrich) for 45 minutes at 4° C. Cells were washed, resuspended in 200 µl PBS with 0.2% BSA and 0.09% NaN$_3$, and transferred to a U-shaped 96 well Costar (Corning, Schiphol-Rijik, The Netherlands) plate for flow cytometry using an Easy Cyte device (Guava Technologies, Hayward, Calif., USA) or FACS Canto II flow cytometer (BD Biosciences, Heidelberg, Germany).

The apparent affinity values ($K_D$) were deduced from non-linear fit of the experimental data curves using "One site—Specific binding" model of software Prism (GraphPad, San Diego, Calif.). KM3060var was included as positive control, as it is known to bind to CCR4. Results are shown in FIGS. 21, 22 and 23 and in Table 19.

Example 15

Appreciation Measurements on Platelets

CCR4 is known to be expressed on platelets, and its ligands MDC and TARC are known to induce platelet aggregation. This could potentially be problematic, as IgG molecules have two ligand binding sites, so there is a possibility that an IgG capable of recognizing CCR4 may be able to cross link platelets if both arms are able to bind to CCR4 on different platelets. This might result in blot clotting in vivo. Therefore, the effect of 9E10J-IgG on platelet aggregation was examined. 9E10J-IgG was incubated with isolated platelets alone or in combination with the ligands MDC or TARC. ADP, a well-described inducer of aggregation (Varon and Spectre "Anti-platelet agents" Hematology Am Soc Hematol Educ Program. 267-72, 2009), was included as positive control during each measurement.

A total of 30 ml of fresh donor blood was collected into sodium citrate containing tubes. Platelet rich plasma was obtained by centrifuging at room temperature (RT) for 15 min at 185 g. The platelet containing plasma was transferred into a fresh tube. To define the baseline, platelet depleted plasma was prepared by centrifugation of 1 ml of the platelet rich plasma for 5 min at 1200 g at RT, the supernatant transferred into a new tube and treated in the following the same way as the platelet rich sample. Aggregation measurements are performed at 37° C. under stirring using a Packs-4 aggregometer (Helena Biosciences, USA). IgGs (9E10J and anti-GFP as negative control) were incubated with platelets at a concentration of 10 µg/ml in FACS buffer (PBS, pH 7.4, 0.2% BSA, 0.09% NaN$_3$). ADP served as a positive control for aggregation and was used at a final concentration of 3 µM. Ligands (MDC and TARC) were tested 0.25 µg/ml. The signal obtained with ADP was set as 100%, the baseline 0 was defined by the platelet depleted serum, which was measured in parallel in all experimental settings To check that the tested IgGs bind to the isolated platelets, FACS staining of platelets were performed in parallel. Platelets were transferred into V-shaped 96 well plates (Greiner Bio-One, Frikenhausen, Germany) and washed once by adding 100 µl of FACS-buffer (1×PBS, pH 7.4, supplemented with 0.02% BSA and 0.09% NaN$_3$). Platelets were then incubated for 1 h at 4° C. in presence of 9E10J-IgG (at 10 µg/ml) and washed afterwards twice in presence of 100 µl of FACS-buffer (1×PBS, pH 7.4, supplemented with 0.02% BSA and 0.09% NaN$_3$). Bound IgG was detected using anti-human-PE (1:400 dilutions) after incubation on the IgG-stained cells for 1 h at 4° C. Stained platelets were analyzed in FACS measurements.

Binding of 9E10J-IgG to platelets was observed (data not shown). The results are of the aggregation measurements are summarized in Table 24. It is concluded that although 9E10J-IgG binds to platelets, it has no effect on platelet aggregation: it does not induce aggregation by itself, nor does it inhibit ligand-induced platelet aggregation.

Example 16

Binding of IgG 9E10J to Peripheral Blood Lymphocytes (PBL)

As CCR4 is known to be expressed on lymphocytes (e.g. Th2-cells and Treg-cells) titration curves of 9E10J and KM3060var on isolated PBLs from buffy coats were performed.

The antibodies 9E10J and KM3060var were biotinylated following the manual of the EZ-link Maleimide-PEO Solid Phase Biotinylation Kit (Pierce, Thermo Fisher, P.O. Box 117 Rockford, Ill. 61105 U.S.A). The biotinylation did not significantly affect the antibodies' ability to recognize their targets, as judged by assessing the binding of the biotinylated and non-biotinylated antibodies to CCRF-CEM cells following the protocols given in example 2 (data not shown).

Human PBLs were prepared from fresh donor blood by Ficoll-(Hypaque) gradient centrifugation, washed in RPMI-1640/10% FCS. Leucosep tubes (50 ml; Greiner Bio-One, Frikenhausen, Germany) were filled with 15 ml of lymphoprep (Fresenius Kabi Norge, Oslo, Norway) and centrifuged for 30 sec at 1000 g at room temperature.

The buffy coat was diluted with 280 ml of 1× Dulbeccos PBS (pH 7.4) and 35 ml of the diluted blood were transferred into each Leucosep tube (50 ml; Greiner; Bio-One, Frikenhausen). Upon centrifugation for 10 min at room temperature at 1000 g (no break, no acceleration), the target cells were transferred into 50 ml tubes (50 ml Falcon, Greiner Bio-One, Frikenhausen, Germany), in a total volume of 50 ml of RPMI-medium. PBLs were pelleted for 15 min at 200 g at room temperature, resuspended in 50 ml of RPMI-medium and filtered through a 70 µm cell strainer before counting cells. PBLs were diluted to a final cell number of 1.5×106 cells/ml in 1×PBS (pH 7.4), supplemented with 0.2% BSA and 0.09% NaN3.

Biotinylated IgGs 9E10J and KM3060var were diluted from 20 µg/ml down to 0.3 ng/ml in 1×PBS Dulbeccos (pH 7.4), supplemented with 0.2% BSA and 0.09% NaN3 and incubated for 2 h on a total of 1.5×105 PBLs. Unbound IgG was removed after washing cells twice with 150 µl of PBS (pH 7.4), supplemented with 0.2% BSA and 0.09% NaN3. Detection of bound IgG was after incubation with PE-labeled streptavidin (BD-Biosciences Norge; dilution of 1:100 in PBS (pH 7.4), supplemented with 0.2% BSA and 0.09% NaN3).

Cells were double stained with an anti-CD3-APC-conjugated antibody and with an anti-CD8-PE-Cy5-conjugated antibody (BD-Biosciences Norge; dilution of 1:10 for both in PBS (pH 7.4), supplemented with 0.2% BSA and 0.09% NaN3). To compensate signal overlapping of the fluorochromes, an anti-CD4-PE-conjugated IgG (BD-Biosciences Norge) was added in a separate well. Samples were analyzed on a FACS-cantoll (BD-Biosciences Norge).

To assess binding to PBLs of 9E10J and KM3060var IgGs, lymphocytes were first gated out of the total events. Next, CD3-positive cells were gated form lymphocyte population. The CD3-positive population was next divided into CD8-positive (=CD4-negative) and CD8-negative (=CD4-positive) cells, which include the Treg fraction. The signal intensity in the PE-channel indicates the binding of the 9E10J and KM3060var IgGs to CD8-negative (=CD4-positive) cells.

Binding was expressed in % (positive events) after comparison to the negative control (=PE-conjugated streptavidin).

As presented in FIG. 30, 9E10J binds to gated CD4-positive cells (determined by CD8-negative staining). Binding is still detectable at a concentration as low as 32 ng/ml (corresponding to ~210 pM of IgG). At this concentration, no binding signal for comparator KM3060var was detectable. In this sense, 9E10J could be useful in immunotherapy for the depletion of Treg-cells.

TABLE 1

| SEQ ID NO: | scFv 17G | |
|---|---|---|
| 25 | Heavy chain FR1: | QVQLVESGGGLVQPGGSLRLSCAASGFTFS |
| 1 | CDR 1: | SYAMS |
| 26 | FR 2 | WVRQAPGKGLEWVS |
| 2 | CDR 2: | AISGSGGSTYYADSVKG |
| 27 | FR 3: | RFTISRDNSKNTLYLQMNSLRAEDTAVYYCAN |
| 3 | CDR 3: | IRYSAGY |
| 28 | FR 4: | WGQGTLVTVSS |
| 29 | Linker: | KLSGSASAPKLEEGEFSEARV |
| 30 | Light chain FR1: | SYVLTQPPSASGTPGQRVTISC |
| 4 | CDR 1: | SGSSSNIGSNYVY |
| 31 | FR 2 | WYQQLPGTAPKLLIY |
| 5 | CDR 2: | RNNQRPS |
| 32 | FR 3: | GVPDRFSGSKSGTSASLAISGLRSEDEADYYC |
| 6 | CDR 3: | AAWDDRLSGWV |
| 33 | FR 4: | FGGGTKLTVL |
| 34 | scFv 17G n.a. | caggtgcagctggtggagtctgggggaggcttggtacagcct gggggtccctgagactctcctgtgcagcctctggattcacc tttagcagctatgccatgagctgggtccgccaggctccaggg aaggggctggagtgggtctcagctattagtggtagtggtggt agcacatactacgcagactccgtgaagggccggttcaccatc tccagagacaattccaagaacacgctgtatctgcaaatgaac agcctgagagccgaggacacggccgtatattactgtgcgaat attaggtatagtgcaggctactggggccagggaaccctggtc accgtctcctcaaagctttcagggagtgcatccgccccaaaa cttgaagaaggtgaattttcagaagcacgcgtatcctatgtg ctgacacagccaccctcagcgtctgggaccccgggcagagg gtcaccatctcttgttctggaagcagctccaacatcggaagt aattatgtatactggtaccagcagctcccaggaacggccccc aaactcctcatctataggaataatcagcggccctcagggtc cctgaccgattctctggctccaagtctggcacctcagcctcc ctggccatcagtgggctccggtccgaggatgaggctgattat tactgtgcagcatgggatgaccgcctgagtggttgggtgttc ggcggagggaccaagctgaccgtccta |
| 35 | scFv 17G a.a. | QVQLVESGGGLVQPGGSLRLSCAASGFTFSSYAMSWVRQAPG KGLEWVSAISGSGGSTYYADSVKGRFTISRDNSKNTLYLQMN SLRAEDTAVYYCANIRYSAGYWGQGTLVTVSSKLSGSASAPK LEEGEFSEARVSYVLTQPPSASGTPGQRVTISCSGSSSNIGS NYVYWYQQLPGTAPKLLIYRNNQRPSGVPDRFSGSKSGTSAS LAISGLRSEDEADYYCAAWDDRLSGWVFGGGTKLTVL |
| 69 | $V_H$ (aa) | QVQLVESGGGLVQPGGSLRLSCAASGFTFSSYAMSWVRQAPG KGLEWVSAISGSGGSTYYADSVKGRFTISRDNSKNTLYLQMN SLRAEDTAVYYCANIRYSAGYWGQGTLVTVSS |

TABLE 1-continued

| SEQ ID NO: | scFv 17G | |
|---|---|---|
| 70 | V_L (aa) | SYVLTQPPSASGTPGQRVTISCSGSSSNIGSNYVYWYQQLPG TAPKLLIYRNNQRPSGVPDRFSGSKSGTSASLAISGLRSEDE ADYYCAAWDDRLSGWVFGGGTKLTVL |
| 77 | VH domain (nt) | CAGGTGCAGCTGGTGGAGTCTGGGGGAGGCTTGGTACAGCCT GGGGGGTCCCTGAGACTCTCCTGTGCAGCCTCTGGATTCACC TTTAGCAGCTATGCCATGAGCTGGGTCCGCCAGGCTCCAGGG AAGGGGCTGGAGTGGGTCTCAGCTATTAGTGGTAGTGGTGGT AGCACATACTACGCAGACTCCGTGAAGGGCCGGTTCACCATC TCCAGAGACAATTCCAAGAACACGCTGTATCTGCAAATGAAC AGCCTGAGAGCCGAGGACACGGCCGTATATTACTGTGCGAAT ATTAGGTATAGTGCAGGCTACTGGGGCCAGGGAACCCTGGTC ACCGTCTCCTCA |
| 78 | VL domain (nt) | TCCTATGTGCTGACACAGCCACCCTCAGCGTCTGGGACCCCC GGGCAGAGGGTCACCATCTCTTGTTCTGGAAGCAGCTCCAAC ATCGGAAGTAATTATGTATACTGGTACCAGCAGCTCCCAGGA ACGGCCCCCAAACTCCTCATCTATAGGAATAATCAGCGGCCC TCAGGGGTCCCTGACCGATTCTCTGGCTCCAAGTCTGGCCTC TCAGCCTCCCTGGCCATCAGTGGGCTCCGGTCCGAGGATGAG GCTGATTATTACTGTGCAGCATGGGATGACCGCCTGAGTGGT GGGTGTTCGGCGGAGGGACCAAGCTGACCGTCCTA |

TABLE 2

| SEQ ID NO: | scFv 9E | |
|---|---|---|
| 36 | Heavy chain FR1: | QVQLVQSGAEVKKPGSSVKVSCKASGGTFS |
| 7 | CDR 1: | NYAIS |
| 37 | FR 2 | WVRQAPGQGLEWMG |
| 8 | CDR 2: | GIIPIFGTANYAQKFQG |
| 38 | FR 3: | RVTITADESTSTAYMELSSLRSEDTAVYYCAR |
| 9 | CDR 3: | RGGSYFDY |
| 39 | FR 4: | WGQGTLVTVSS |
| 40 | Linker: | KLSGSASAPKLEEGEFSEARV |
| 41 | Light chain FR1: | SYVLTQPPSASGTPGQSVTISC |
| 10 | CDR 1: | SGSTSNIGSHYVF |
| 42 | FR 2 | WYQQLPGTAPRLLIY |
| 11 | CDR 2: | RNHQRPS |
| 43 | FR 3: | GVPDRLSGSKSGTSASLAISGLRSEDEADYYC |
| 12 | CDR 3: | AVWDDTLSGWV |
| 44 | FR 4: | FGGGTKLTVL |
| 45 | scFv 9E n.a. | caggtccagcttgtacagtctggggctgaggtgaagaagcct gggtcctcggtgaaggtctcctgcaaggcttctggaggcacc ttcagcaactatgctatcagctgggtgcgacaggcccctgga caagggcttgagtggatgggagggatcatccctatctttggt acagcaaactacgcacagaagttccagggcagagtcacgatt accgcggacgaatccacgagcacagcctacatggagctgagc agcctgagatctgaggacacggccgtgtattactgtgcgaga cgcggtgggagctactttgactactggggcagggaaccctg gtcaccgtctcttcaaagcttcagggagtgcatccgcccca aaacttgaagaaggtgaattttcagaagcacgcgtatcctat gtgctgactcagccacccctcagcgtctgggacccccgggcag agcgtcaccatctcttgttctggaagcacctccaacatcgga agtcattatgtgttctggtaccagcagctcccaggaacggcc |

TABLE 2-continued

| SEQ ID NO: | scFv 9E | |
|---|---|---|
| | | cccagactcctcatctataggaatcatcagcggccctcaggg gtccctgaccgactctctggctccaagtctggcacctcagcc tccctggccatcagtgggctccggtccgaggatgaggctgat tattactgtgcagtgtgggatgacaccctgagtggctgggtg ttcggcggagggaccaagctgaccgtcctagcggccgctgga tccgaacaaaagctgatctcagaagaagacctaaactcacat caccatcaccatcac |
| 46 | scFv 9E a.a. | QVQLVQSGAEVKKPGSSVKVSCKASGGTFSNYAISWVRQAPG QGLEWMGGIIPIFGTANYAQKFQGRVTITADESTSTAYMELS SLRSEDTAVYYCARRGGSYFDYWGQGTLVTVSSKLSGSASAP KLEEGEFSEARVSYVLTQPPSASGTPGQSVTISCSGSTSNIG SHYVFWYQQLPGTAPRLLIYRNHQRPSGVPDRLSGSKSGTSA SLAISGLRSEDEADYYCAVWDDTLSGWVFGGGTKLTVLAAAG SEQKLISEEDLNSHHHHHH |
| 71 | V$_H$ (aa) | QVQLVQSGAEVKKPGSSVKVSCKASGGTFSNYAISWVRQAPG QGLEWMGGIIPIFGTANYAQKFQGRVTITADESTSTAYMELS SLRSEDTAVYYCARRGGSYFDYWGQGTLVTVSS |
| 72 | V$_L$ (aa) | SYVLTQPPSASGTPGQSVTISCSGSTSNIGSHYVFWYQQLPG TAPRLLIYRNHQRPSGVPDRLSGSKSGTSASLAISGLRSEDE ADYYCAVWDDTLSGWVFGGGTKLTVL |
| 79 | VH domain (nt) | CAGGTCCAGCTTGTACAGTCTGGGGCTGAGGTGAAGAAGCCT GGGTCCTCGGTGAAGGTCTCCTGCAAGGCTTCTGGAGGCACC TTCAGCAACTATGCTATCAGCTGGGTGCGACAGGCCCCTGGA CAAGGGCTTGAGTGGATGGGAGGGATCATCCCTATCTTTGGT ACAGCAAACTACGCACAGAAGTTCCAGGGCAGAGTCACGATT ACCGCGGACGAATCCACGAGCACAGCCTACATGGAGCTGAGC AGCCTGAGATCTGAGGACACGGCCGTGTATTACTGTGCGAGA CGCGGTGGGAGCTACTTTGACTACTGGGGCCAGGGAACCCTG GTCACCGTCTCTTCA |
| 80 | VL domain (nt) | TCCTATGTGCTGACTCAGCCACCCTCAGCGTCTGGGACCCCC GGGCAGAGCGTCACCATCTCTTGTTCTGGAAGCACCTCCAAC ATCGGAAGTCATTATGTGTTCTGGTACCAGCAGCTCCCAGGA ACGGCCCCCAGACTCCTCATCTATAGGAATCATCAGCGGCCC TCAGGGGTCCCTGACCGACTCTCTGGCTCCAAGTCTGGCACC TCAGCCTCCCTGGCCATCAGTGGGCTCCGGTCCGAGGATGAG GCTGATTATTACTGTGCAGTGTGGGATGACACCCTGAGTGGC TGGGTGTTCGGCGGAGGGACCAAGCTGACCGTCCTA |

TABLE 3

| SEQ ID NO: | scFv 10 | |
|---|---|---|
| 47 | Heavy chain FR1: | QVQLVESGGGLVQPGRSLRLSCAASGFTFS |
| 1 or 13* | CDR 1: | SYAMS |
| 48 | FR 2 | WVRQAPGKGLEWVS |
| 2 or 14** | CDR 2: | AISGSGGSTYYADSVKG |
| 49 | FR 3: | RFTISRDNSKNTLYLQMNSLRAEDTAVYYCAK |
| 15 | CDR 3: | GAGEGRGLGVV |
| 50 | FR 4: | MGQGTLVTVSS |
| 51 | Linker: | KLSGSASAPKLEEGEFSEARV |
| 52 | Light chain FR1: | QAVVTQEPSLTVSPGGTVTLTC |
| 16 | CDR 1: | ASSTGAVTSGYFPN |
| 53 | FR 2 | WFQQKPGQAPRALIY |

TABLE 3-continued

| SEQ ID NO: | scFv 10 | |
|---|---|---|
| 17 | CDR 2: | STTNKHS |
| 54 | FR 3: | WTPARFSGSLLGGKAALTLSGVQPEDEAEYYC |
| 18 | CDR 3: | LLYYGGARV |
| 55 | FR 4: | FGGGTKLTVL |
| 56 | scFV 10 n.a. | caggtgcagctggtggaatctgggggaggcttggtacagcct ggcaggtccctgagactctcctgtgcagcctctggattcacc tttagcagctatgccatgagctgggtccgccaggctccaggg aaggggctggagtgggtctcagctattagtggtagtggtggt agcacatactacgcagactccgtgaagggccggttcaccatc tccagagacaattccaagaacacgctgtatctgcaaatgaac agcctgagagccgaggacacggccgtatattactgtgcgaag ggggccggcgagggtcgagggcttggagtggttatgggccag ggaaccctggtcaccgtctcctcaaagctttcagggagtgca tccgccccaaaacttgaagaaggtgaattttcagaagcacgc gtacaggctgtggtgacccaggagccctcactgactgtgtcc ccaggagggacagtcactctcacctgtgcttccagcactgga gcagtcaccagtggttactttccaaactggttccagcagaaa cctggacaagcacccagggcactcatttatagtacaaccaac aaacactcctggacccctgcccggttctcaggctccctcctt gggggcaaagctgccctgacactgtcaggtgtgcagcctgag gacgaggctgagtattactgctgctctactatggtggtgct cgggtgttcggcggagggaccaagctcaccgtcctagcggcc gctggatccgaacaaaagctgatctcagaagaagacctaaac tcacatcaccatcaccatcac |
| 57 | scFv 10 a.a. | QVQLVESGGGLVQPGRSLRLSCAASGFTFSSYAMSWVRQAPG KGLEWVSAISGSGGSTYYADSVKGRFTISRDNSKNTLYLQMN SLRAEDTAVYYCAKGAGEGRGLGVVMGQGTLVTVSSKLSGSA SAPKLEEGEFSEARVQAVVTQEPSLTVSPGGTVTLTCASSTG AVTSGYFPNWFQQKPGQAPRALIYSTTNKHSWTPARFSGSLL GGKAALTLSGVQPEDEAEYYCLLYYGGARVFGGGTKLTVLAA AGSEQKLISEEDLNSHHHHHH |
| 73 | V_H (aa) | QVQLVESGGGLVQPGRSLRLSCAASGFTFSSYAMSWVRQAPG KGLEWVSAISGSGGSTYYADSVKGRFTISRDNSKNTLYLQMN SLRAEDTAVYYCAKGAGEGRGLGVVMGQGTLVTVSS |
| 74 | V_L (aa) | QAVVTQEPSLTVSPGGTVTLTCASSTGAVTSGYFPNWFQQKP GQAPRALIYSTTNKHSWTPARFSGSLLGGKAALTLSGVQPED EAEYYCLLYYGGARVFGGGTKLTVL |
| 81 | VH domain (nt) | CAGGTGCAGCTGGTGGAATCTGGGGGAGGCTTGGTACAGCCT GGCAGGTCCCTGAGACTCTCCTGTGCAGCCTCTGGATTCACC TTTAGCAGCTATGCCATGAGCTGGGTCCGCCAGGCTCCAGGG AAGGGGCTGGAGTGGGTCTCAGCTATTAGTGGTAGTGGTGGT AGCACATACTACGCAGACTCCGTGAAGGGCCGGTTCACCATC TCCAGAGACAATTCCAAGAACACGCTGTATCTGCAAATGAAC AGCCTGAGAGCCGAGGACACGGCCGTATATTACTGTGCGAAG GGGGCCGGCGAGGGTCGAGGGCTTGGAGTGGTTATGGGCCAG GGAACCCTGGTCACCGTCTCCTCA |
| 82 | VL domain (nt) | CAGGCTGTGGTGACCCAGGAGCCCTCACTGACTGTGTCCCCA GGAGGGACAGTCACTCTCACCTGTGCTTCCAGCACTGGAGCA GTCACCAGTGGTTACTTTCCAAACTGGTTCCAGCAGAAACCT GGACAAGCACCCAGGGCACTCATTTATAGTACAACCAACAAA CACTCCTGGACCCCTGCCCGGTTCTCAGGCTCCCTCCTTGGG GGCAAAGCTGCCCTGACACTGTCAGGTGTGCAGCCTGAGGAC GAGGCTGAGTATTACTGCTGCTCTACTATGGTGGTGCTCGG GTGTTCGGCGGAGGGACCAAGCTCACCGTCCTA |

*SEQ ID NO: 1 is identical to SEQ ID NO: 13
**SEQ ID NO: 2 is identical to SEQ ID NO: 14

TABLE 4

| SEQ ID NO: | scFv 11F | |
|---|---|---|
| 58 | Heavy chain FR1: | QVQLVQSGAEVKKPGASVKVSCKASGYTFT |
| 19 | CDR 1: | GYYMH |
| 59 | FR 2 | WVRQAPGQGLEWMG |
| 20 | CDR 2: | WINPNSGGTNYAQKFQG |
| 60 | FR 3: | RVTMTRDTSISTAYMELSRLRSDDTAVYYCAR |
| 21 | CDR 3: | GTVTRIQGRSLYGMDV |
| 61 | FR 4: | WGQGTTVTVSS |
| 62 | Linker: | KLSGSASAPKLEEGEFSEARV |
| 63 | Light chain FR1: | ETTLTQSPGTLSLSPGEGVTLSC |
| 22 | CDR 1: | RASQSVNRRYLA |
| 64 | FR 2 | WYQQKPGQAPRLLIY |
| 23 | CDR 2: | GASSRAT |
| 65 | FR 3: | GIPDRFSGSGSGTDFTLTISRLEPEDFAVYYC |
| 24 | CDR 3: | QQYGSSPLT |
| 66 | FR 4: | FGGGTKVEIK |
| 67 | scFv 11F n.a. | caggtccagcttgtgcagtctggggctgaggtgaagaagc ctggggcctcagtgaaggtctcctgcaaggcttctggata caccttcaccggctactatatgcactgggtgcgacaggcc cctggacaagggcttgagtggatgggatggatcaaccta acagtggtggcacaaactatgcacagaagtttcagggcag ggtcaccatgaccagggacacgtccatcagcacagcctac atggagctgagcaggctgagatctgacgacacggccgtgt attactgtgcgagaggtacggtgactaggattcagggccg ctctctctacggtatggacgtctggggccaagggaccacg gtcaccgtctcttcaaagctttcagggagtgcatccgcc caaaacttgaagaaggtgaattttcagaagcacgcgtaga aacgacactcacgcagtctccaggcaccctgtctttgtct ccaggggaaggagtcaccctctcctgcagggccagtcaga gtgttaacaggaggtacttagcctggtaccagcagaaacc tggccaggctcccaggctcctcatctatggggcatccagc agggccactggcatcccgacaggttcagtggcagtgggt ctgggacagacttcactctcaccatcagcagactggagcc tgaagattttgcagtgtattactgtcagcagtatggtagc tcaccccctcactttcggcggagggaccaaggtggaaatca aagcggccgctggatccgaacaaaaagctgatctcagaaga agacctaaactcacatcaccatcaccatcac |
| 68 | scFv 11F a.a | QVQLVQSGAEVKKPGASVKVSCKASGYTFTGYYMHWVRQAP GQGLEWMGWINPNSGGTNYAQKFQGRVTMTRDTSISTAYME LSRLRSDDTAVYYCARGTVTRIQGRSLYGMDVWGQGTTVTV SSKLSGSASAPKLEEGEFSEARVETTLTQSPGTLSLSPGEG VTLSCRASQSVNRRYLAWYQQKPGQAPRLLIYGASSRATGI PDRFSGSGSGTDFTLTISRLEPEDFAVYYCQQYGSSPLTFG GGTKVEIKAAAGSEQKLISEEDLNSHHHHHH |
| 75 | $V_H$ (aa) | QVQLVQSGAEVKKPGASVKVSCKASGYTFTGYYMHWVRQA PGQGLEWMGWINPNSGGTNYAQKFQGRVTMTRDTSISTAY MELSRLRSDDTAVYYCARGTVTRIQGRSLYGMDVWGQGTT VTVSS |
| 76 | $V_L$ (aa) | ETTLTQSPGTLSLSPGEGVTLSCRASQSVNRRYLAWYQQK PGQAPRLLIYGASSRATGIPDRFSGSGSGTDFTLTISRLE PEDFAVYYCQQYGSSPLTFGGGTKVEIK |
| 83 | VH domain (nt) | CAGGTCCAGCTTGTGCAGTCTGGGGCTGAGGTGAAGAAGC CTGGGGCCTCAGTGAAGGTCTCCTGCAAGGCTTCTGGATA CACCTTCACCGGCTACTATATGCACTGGGTGCGACAGGCC CCTGGACAAGGGCTTGAGTGGATGGGATGGATCAACCCTA ACAGTGGTGGCACAAACTATGCACAGAAGTTTCAGGGCAG GGTCACCATGACCAGGGACACGTCCATCAGCACAGCCTAC |

TABLE 4-continued

| SEQ ID NO: | scFv 11F | |
|---|---|---|
| | | ATGGAGCTGAGCAGGCTGAGATCTGACGACACGGCCGTGT<br>ATTACTGTGCGAGAGGTACGGTGACTAGGATTCAGGGCCG<br>CTCTCTCTACGGTATGGACGTCTGGGGCCAAGGGACCACG<br>GTCACCGTCTCTTCA |
| 84 | VL domain (nt) | GAAACGACACTCACGCAGTCTCCAGGCACCCTGTCTTTGT<br>CTCCAGGGGAAGGAGTCACCCTCTCCTGCAGGGCCAGTCA<br>GAGTGTTAACAGGAGGTACTTAGCCTGGTACCAGCAGAAA<br>CCTGGCCAGGCTCCCAGGCTCCTCATCTATGGGGCATCCA<br>GCAGGGCCACTGGCATCCCTGACAGGTTCAGTGGCAGTGG<br>GTCTGGGACAGACTTCACTCTCACCATCAGCAGACTGGAG<br>CCTGAAGATTTTGCAGTGTATTACTGTCAGCAGTATGGTA<br>GCTCACCCCTCACTTTCGGCGGAGGGACCAAGGTGGAAAT<br>CAAA |

TABLE 5

| IgG sequences of 17G | | |
|---|---|---|
| SEQ ID NO: 85 | IgG1 heavy chain (nt) | caggtgcagctggtggagtctgggggaggcttggtacagcctg<br>gggggtccctgagactctcctgtgcagcctctggattcacctt<br>tagcagctatgccatgagctgggtccgccaggctccagggaag<br>gggctggagtgggtctcagctattagtggtagtggtggtagca<br>catactacgcagactccgtgaagggccggttcaccatctccag<br>agacaattccaagaacacgctgtatctgcaaatgaacagcctg<br>agagccgaggacacggccgtatattactgtgcgaatattggt<br>atagtgcaggctactggggccagggaaccctggtcaccgtctc<br>ctcagcctccaccaagggcccatcggtcttccccctggcacc<br>tcctccaagagcacctctgggggcacagcggccctgggctgcc<br>tggtcaaggactacttccccgaaccggtgacggtgtcgtggaa<br>ctcaggcgccctgaccagcggcgtgcacaccttcccggctgtc<br>ctacagtcctcaggactctactccctcagcagcgtggtgaccg<br>tgccctccagcagcttgggcacccagacctacatctgcaacgt<br>gaatcacaagcccagcaacaccaaggtggacaagaaagttgag<br>cccaaatcttgtgacaaaactcacacatgcccaccgtgcccag<br>cacctgaactcctggggggaccgtcagtcttcctcttccccc<br>aaaacccaaggacaccctcatgatctcccggacccctgaggtc<br>acatgcgtggtggtggacgtgagccacgaagaccctgaggtca<br>agttcaactggtacgtggacggcgtggaggtgcataatgccaa<br>gacaaagccgcgggaggagcagtacaacagcacgtaccgtgtg<br>gtcagcgtcctcaccgtcctgcaccaggactggctgaatggca<br>aggagtacaagtgcaaggtctccaacaaagcccctcccagccc<br>catcgagaaaaccatctccaaagccaaagggcagccccgagaa<br>ccacaggtgtacaccctgcccccatcccgggatgagctgacca<br>agaaccaggtcagcctgacctgcctggtcaaaggcttctatcc<br>cagcgacatcgccgtggagtgggagagcaatgggcagccggag<br>aacaactacaagaccacgcctcccgtgctggactccgacggct<br>ccttcttcctctacagcaagctcaccgtggacaagagcaggtg<br>gcagcaggggaacgtcttctcatgctccgtgatgcatgaggct<br>ctgcacaaccactacacgcagaagagcctctccctgtctccgg<br>gtaaa |
| SEQ ID NO: 86 | Lambda light chain (nt) | <u>tcctatgtgctgacacagccaccctcagcgtctgggacccc<br>gggcagagggtcaccatctcttgttctggaagcagctccaac<br>atcggaagtaattatgtatactggtaccagcagctcccagga<br>acggccccaaactcctcatctataggaataatcagcggccc<br>tcaggggtccctgaccgattctctggctccaagtctggcacc<br>tcagcctccctggccatcagtgggctccggtccgaggatgag<br>gctgattattactgtgcagcatgggatgaccgcctgagtggt<br>tgggtgttcggcggagggaccaagctgaccgtcctaggtcag</u><br>cccaaggctgcccccctcggtcactctgttcccgccctcctct<br>gaggagcttcaagccaacaaggccacactggtgtgtctcata<br>agtgacttctacccgggagccgtgacagtggcctggaaggca<br>gatagcagccccgtcaaggcgggagtggagaccaccacaccc<br>tccaaacaaagcaacaacaagtacgcggccagcagctatctg<br>agcctgacgcctgagcagtggaagtcccacagaagctacagc<br>tgccaggtcacgcatgaagggagcaccgtggagaagacagtg<br>gcccctacagaatgttca |
| SEQ ID NO: 87 | IgG1 heavy chain (aa) | <u>qvqlvesgggvlvqpggslrlscaasgftfssyamswvrqapq<br>kglewvsaisgsggstyyadsvkgrftisrdnskntlylqmn<br>slraedtavyycaniryysagywgqgtlvtvss</u>astkgpsvfp<br>lapsskstsggtaalgclvkdyfpepvtvswnsgaltsgvht<br>fpavlqssglyslssvvtvpssslgtqtyicnvnhkpsntkv |

TABLE 5-continued

IgG sequences of 17G

| | | |
|---|---|---|
| | | dkkvepkscdkthtcppcpapellggpsvflfppkpkdtlmi srtpevtcvvvdvshedpevkfnwyvdgvevhnaktkpreeq ynstyrvvsvltvlhqdwlngkeykckvsnkalpapiektis kakgqprepqvytlppsrdeltknqvsltclvkgfypsdiav ewesngqpennyktttppvldsdgsfflyskltvdksrwqqgn vfscsvmhealhnhytqkslslspgk |
| SEQ ID NO: 88 | Lambda light chain (aa) | syvltqppsasgtpgqrvtiscsgsssnigsnyvywyqqlpg tapklliyrnnqrpsqvpdrfsqsksqtsaslaisqlrsede adyycaawddrlsqwvfgqgtkltvlgqpkaapsvtlfppss eelqankativclisdfypgavtvawkadsspvkagvetttp skqsnnkyaassylsltpeqwkshrsyscqvthegstvektv aptecs |

TABLE 6

IgG sequences of 9E

| | | |
|---|---|---|
| SEQ ID NO: 89 | IgG1 heavy chain (nt) | caggtccagcttgtacagtctggggctgaggtgaagaagcct ggggtcctcggtgaaggtctcctgcaaggcttctggaggcacc ttcagcaactatgctatcagctgggtgcgacaggcccctgga caagggcttgagtggatgggagggatcatccctatctttggt acagcaaactacgcacagaagttccagggcagagtcacgatt accgcggacgaatccacgagcacagcctacatggagctgagc agcctgagatctgaggacacggccgtgtattactgtgcgaga cgcggtgggagctactttgactactggggccagggaaccctg gtcaccgtctcttcagcctccaccaagggcccatcggtcttc cccctggcaccctcctccaagagcacctctgggggcacagcg gccctgggctgcctggtcaaggactacttccccgaaccggtg acggtgtcgtggaactcaggcgccctgaccagcggcgtgcac accttcccggctgtcctacagtcctcaggactctactccctc agcagcgtggtgaccgtgccctccagcagcttgggcacccag acctacatctgcaacgtgaatcacaagcccagcaacaccaag gtggacaagaaagttgagcccaaatcttgtgacaaaactcac acatgcccaccgtgcccagcacctgaactcctggggggaccg tcagtcttcctcttccccccaaaacccaaggacaccctcatg atctcccggacccctgaggtcacatgcgtggtggtggacgtg agccacgaagaccctgaggtcaagttcaactggtacgtggac ggcgtggaggtgcataatgccaagacaaagccgcgggaggag cagtacaacagcacgtaccgtgtggtcagcgtcctcaccgtc ctgcaccaggactggctgaatggcaaggagtacaagtgcaag gtctccaacaaagcccctcccagccccatcgagaaaaccatc tccaaagccaaagggcagccccgagaaccacaggtgtacacc ctgcccccatcccgggatgagctgaccaagaaccaggtcagc ctgacctgcctggtcaaaggcttctatcccagcgacatcgcc gtggagtgggagagcaatgggcagccggagaacaactacaag accacgcctcccgtgctggactccgacggctccttcttcctc tacagcaagctcaccgtggacaagagcaggtggcagcagggg aacgtcttctcatgctccgtgatgcatgaggctctgcacaac cactacacgcagaagagcctctccctgtctccgggtaaa |
| SEQ ID NO: 90 | Lambda light chain (nt) | tcctatgtgctgactcagccaccctcagcgtctgggacccc gggcagagcgtcaccatctcttgttctggaagcacctccaac atcggaagtcattatgtgttctggtaccagcagctcccagga acggcccccagactcctcatctataggaatcatcagcggccc tcagggqtccctgaccgactctctggctccaagtctggcacc tcagcctccctggccatcagtgggctccggtccgaggatgag gctgattattactgtgcagtgtgggatgacaccctgagtggc tgggtgttcggcggagggaccaagctgaccgtcctaggtcag cccaaggctgcccctcggtcactctgttcccgccctcctct gaggagcttcaagccaacaaggccacactggtgtgtctcata agtgacttctacccgggagccgtgacagtggcctggaaggca gatagcagccccgtcaaggcgggagtggagaccaccacaccc tccaaacaaagcaacaacaagtacgcggccagcagctatctg agcctgacgcctgagcagtggaagtcccacagaagctacagc tgccaggtcacgcatgaagggagcaccgtggagaagacagtg gcccctacagaatgttca |
| SEQ ID NO: 91 | IgG1 heavy chain (aa) | qvqlvqsqaevkkpqssvkvsckasqqtfsnyaiswvrqapq qglewmqgiipifgtanyaqkfqgrvtitadeststaymels slrsedtavyycarrqgsyfdywgqgtivtvssastkgpsvf plapssksstsggtaalgclvkdyfpepvtvswnsgaltsgvh tfpavlqssglyslssvvtvpssslgtqtyicnvnhkpsntk vdkkvepkscdkthtcppcpapellggpsvflfppkpkdtlm isrtpevtcvvvdvshedpevkfnwyvdgvevhnaktkpree |

TABLE 6-continued

IgG sequences of 9E

|  |  |  |
|---|---|---|
|  |  | qynstyrvvsvltvlhqdwlngkeykckvsnkalpapiekti skakgqprepqvytlppsrdeltknqvsltclvkgfypsdia vewesngqpennykttppvldsdgsfflyskltvdksrwqqg nvfscsvmhealhnhytqkslslspgk |
| SEQ ID NO: 92 | Lambda light chain (aa) | syvltqppsasqtpqqsvtiscsqstsniqshyvfwyqqlpq taprlliyrnhqrpsgvpdrlsgsksgtsaslaisglrsede adyycavwddtlsqwvfgqgtkltvlgqpkaapsvtlfppss eelqankativclisdfypgavtvawkadsspvkagvetttp skqsnnkyaassylsltpeqwkshrsyscqvthegstvektv aptecs |

TABLE 7

IgG sequences of 10

| SEQ ID NO: 93 | IgG1 heavy chain (nt) | caggtgcagctggtggaatctgggggaggcttggtacagcct ggcaggtccctgagactctcctgtgcagcctctggattcacc tttagcagctatgccatgagctgggtccgccaggctccaggg aaggggctggagtgggtctcagctattagtggtagtggtggt agcacatactacgcagactccgtgaaggcccggttcaccatc tccagagacaattccaagaacacgctgtatctgcaaatgaac agcctgagagccgaggacacggccgtatattactgtgcaaag gggggccggcgagggtcgagggcttggagtggttatgggccag ggaaccctggtcaccgtctcctcagcctccaccaagggccca tcggtcttccccctggcaccctcctccaagagcacctctggg ggcacagcggccctgggctgcctggtcaaggactacttcccc gaaccggtgacggtgtcgtggaactcaggcgccctgaccagc ggcgtgcacaccttcccggctgtcctacagtcctcaggactc tactccctcagcagcgtggtgaccgtgccctccagcagcttg ggcacccagacctacatctgcaacgtgaatcacaagcccagc aacaccaaggtggacaagaaagttgagcccaaatcttgtgac aaaactcacacatgcccaccgtgcccagcacctgaactcctg ggggggaccgtcagtcttcctcttccccccaaaacccaaggac accctcatgatctcccggacccctgaggtcacatgcgtggtg gtggacgtgagccacgaagaccctgaggtcaagttcaactgg tacgtggacggcgtggaggtgcataatgccaagacaaagccg cgggaggagcagtacaacagcacgtaccgtgtggtcagcgtc ctcaccgtcctgcaccaggactggctgaatggcaaggagtac aagtgcaaggtctccaacaaagcccctcccagccccatcgag aaaaccatctccaaagccaaagggcagccccgagaaccacag gtgtacaccctgcccccatcccgggatgagctgaccaagaac caggtcagcctgacctgcctggtcaaaggcttctatcccagc gacatcgccgtggagtgggagagcaatgggcagccggagaac aactacaagaccacgcctcccgtgctggactccgacggctcc ttcttcctctacagcaagctcaccgtggacaagagcaggtgg cagcaggggaacgtcttctcatgctccgtgatgcatgaggct ctgcacaaccactacacgcagaagagcctctccctgtctccg ggtaaa |
| SEQ ID NO: 94 | Lambda light chain (nt) | caggctgtggtgacccaggagccctcactgactgtgtcccca ggagggacagtcactctcacctgtgcttccagcactggagca gtcaccagtggttactttccaaactggttccagcagaaacct ggacaagcacccagggcactcatttatagtacaaccaacaaa cactcctggacccctgcccggttctcaggctccctccttggg ggcaaagctgccctgacactgtcaggtgtgcagcctgaggac gaggctgagtattactgcctgctctactatggtggtgctcgg gtgttcggcggagggaccaagctcaccgtcctaggtcagccc aaggctgcccctcggtcactctgttcccgccctcctctgag gagcttcaagccaacaaggccacactggtgtgtctcataagt gacttctacccgggagccgtgacagtggcctggaaggcagat agcagccccgtcaaggcgggagtggagaccaccacaccctcc aaacaaagcaacaacaagtacgcggccagcagctatctgagc ctgacgcctgagcagtggaagtcccacagaagctacagctgc caggtcacgcatgaagggagcaccgtggagaagacagtggcc cctacagaatgttca |
| SEQ ID NO: 95 | IgG1 heavy chain (aa) | qvqlvesgggvlqpgrslrlscaasgftfssyamswvrqapg kglewvsaisgsgqstyyadsvkgrftisrdnskntlylqmn slraedtavyycakgagegrqlgvvmgqgtlvtvssastkgp svfplapsskstsggtaalgclvkdyfpepvtvswnsgaits gvhtfpavlqssglyslssvvtvpssslgtqtyicnvnhkps ntkvdkkvepkscdkthtcppcpapellggpsvflfppkpkd tlmisrtpevtcvvvdvshedpevkfnwyvdgvevhnaktkp reeqynstyrvvsvltvlhqdwlngkeykckvsnkalpapie |

TABLE 7-continued

IgG sequences of 10

| | | |
|---|---|---|
| | | ktiskakgqprepqvytlppsrdeltknqvsltclvkgfyps<br>diavewesngqpennykttppvldsdgsfflyskitvdksrw<br>qqgnvfscsvmhealhnhytqkslslspgk |
| SEQ ID<br>NO: 96 | Lambda light<br>chain (aa) | qavvtqepsltvspqgtvtltcasstqavtsqyfpnwfqqkp<br>gqapraliysttnkhswtparfsqsllqgkaaltlsgvqped<br>eaeyycllyyggarvfgggtkltvlgqpkaapsvtlfppsse<br>elqankatlvclisdfypgavtvawkadsspvkagvetttps<br>kqsnnkyaassylsltpeqwkshrsyscqvthegstvektva<br>ptecs |

TABLE 8

IgG sequences of 11F

| | | |
|---|---|---|
| SEQ ID<br>NO: 97 | IgG1 heavy<br>chain (nt) | caggtccagcttgtgcagtctggggctgaggtgaagaagcctg<br>gggcctcagtgaaggtctcctgcaaggcttctggatacacctt<br>caccggctactatatgcactgggtgcgacaggcccctggacaa<br>gggcttgagtggatgggatggatcaaccctaacagtggtggca<br>caaactatgcacagaagtttcagggcagggtcaccatgaccag<br>ggacacgtccatcagcacagcctacatggagctgagcaggctg<br>agatctgacgacacggccgtgtattactgtgcgagaggtacgg<br>tgactaggattcagggccgctctctctacggtatggacgtctg<br>gggccaagggaccacggtcaccgtctcttcagcctccaccaag<br>ggcccatcggtcttccccctggcaccctcctccaagagcacct<br>ctgggggcacagcggccctgggctgcctggtcaaggactactt<br>ccccgaaccggtgacggtgtcgtggaactcaggcgccctgacc<br>agcggcgtgcacaccttcccggctgtcctacagtcctcaggac<br>tctactccctcagcagcgtggtgaccgtgccctccagcagctt<br>gggcacccagacctacatctgcaacgtgaatcacaagcccagc<br>aacaccaaggtggacaagaaagttgagcccaaatcttgtgaca<br>aaactcacacatgcccaccgtgcccagcacctgaactcctggg<br>gggaccgtcagtcttcctcttccccccaaaacccaaggacacc<br>ctcatgatctcccggacccctgaggtcacatgcgtggtggtgg<br>acgtgagccacgaagaccctgaggtcaagttcaactggtacgt<br>ggacggcgtggaggtgcataatgccaagacaaagccgcgggag<br>gagcagtacaacagcacgtaccgtgtggtcagcgtcctcaccg<br>tcctgcaccaggactggctgaatggcaaggagtacaagtgcaa<br>ggtctccaacaaagcccttccagcccccatcgagaaaaccatc<br>tccaaagccaaagggcagccccgagaaccacaggtgtacaccc<br>tgcccccatcccgggatgagctgaccaagaaccaggtcagcct<br>gacctgcctggtcaaaggcttctatcccagcgacatcgccgtg<br>gagtgggagagcaatgggcagccggagaacaactacaagacca<br>cgcctcccgtgctggactccgacggctccttcttcctctacag<br>caagctcaccgtggacaagagcaggtggcagcaggggaacgtc<br>ttctcatgctccgtgatgcatgaggctctgcacaaccactaca<br>cgcagaagagcctctccctgtctccgggtaaa |
| SEQ ID<br>NO: 98 | Kappa light<br>chain (nt) | gaaacgacactcacgcagtctccaggcaccctgtctttgtctc<br>cagggggaaggagtcaccctctcctgcagggccagtcagagtgt<br>taacaggaggtacttagcctggtaccagcagaaacctggccag<br>gctcccaggctcctcatctatggggcatccagcagggccactg<br>gcatcccagacaggttcagtggcagtgggtctgggacagactt<br>cactctcaccatcagcagactggagcctgaagattttgcagtg<br>tattactgtcagcagtatggtagctcacccctcactttcggcg<br>gagggaccaaggtggaaatcaaacgaactgtggctgcaccatc<br>tgtcttcatcttcccgccatctgatgagcagttgaaatctgga<br>actgcctctgttgtgtgcctgctgaataacttctatcccagag<br>aggccaaagtacagtggaaggtggataacgccctccaatcggg<br>taactcccaggagagtgtcacagagcaggacagcaaggacagc<br>acctacgcctcagcagcaccctgacgctgagcaaagcagact<br>acgagaaacacaaagtctacgcctgcgaagtcacccatcaggg<br>cctgagctcgcccgtcacaaagagcttcaacaggggagagtgt |
| SEQ ID<br>NO: 99 | IgG1 heavy<br>chain (aa) | qvqlvqsqaevkkpqasvkvsckasqytftqyymhwvrqapqq<br>glewmqwinpnsggtnyaqkfqgrvtmtrdtsistaymelsrl<br>rsddtavyycargtvtriqqrslyqmdvwqqgttvtvssastk<br>gpsvfplapsskstsggtaalgclvkdyfpepvtvswnsgalt<br>sgvhtfpavlqssglyslssvvtvpssslgtqtyicnvnhkps<br>ntkvdkkvepkscdkthtcppcpapellggpsvflfppkpkdt<br>lmisrtpevtcvvvdvshedpevkfnwyvdgvevhnaktkpre<br>eqynstyrvvsvltvlhqdwlngkeykckvsnkalpapiekti<br>skakgqprepqvytlppsrdeltknqvsltclvkgfypsdiav<br>ewesngqpennykttppvldsdgsfflysklTvdksrwqqgnv<br>fscsvmhealhnhytqkslslspgk |

TABLE 8-continued

IgG sequences of 11F

| SEQ ID NO: 100 | Kappa light chain (aa) | ettltqspqtlslspgegvtlscrasqsvnrrylawyqqkpgq aprlliygassratgipdrfsgsgsgtdftltisrlepedfav yycqqyqsspltfgqgtkveikrtvaapsvfifppsdeqlksg tasvvcllnnfypreakvqwkvdnalqsgnsqesvteqdskds tyslsstltlskadyekhkvyacevthqglsspvtksfnrgec |
|---|---|---|

TABLE 9

| IgG | CCR4+ DT40 | CCR4+ DT40 (2) | CCR4+ HEK293T | CCRF-CEM |
|---|---|---|---|---|
| 17G | 0.42 ± 0.07 nM | 0.42 ± 0.03 nM | 0.62 ± 0.22 nM | 0.16 ± 0.02 nM |
| 9E | 0.72 ± 0.28 nM | 0.17 ± 0.03 nM | 0.36 ± 0.19 nM | 0.39 ± 0.02 nM |
| KM3060var | 3.67 ± 0.29 nM | 4.82 ± 0.16 nM | 11.40 ± 1.74 nM | 79.83 ± 6.59 nM |

TABLE 10

| SEQ ID NOS | scFv KM3060var | |
|---|---|---|
| 141 | Heavy chain FR1: | EVQLVESGGDLMKPGGSLKISCAASGFIFS |
| 142 | CDR 1: | NYGMS |
| 143 | FR 2: | WVRQTPDMRLEWVA |
| 144 | CDR 2: | TISSASTYSYYPDSVKG |
| 145 | FR 3: | RFTISRDNAENSLYLQMNSLRSEDTGIYYC |
| 146 | CDR 3: | GRHSDGNFAFGY |
| 147 | FR 4: | WGRGTLVTVSS |
| 148 | Linker: | *KLSGSASAPKLEEGEFSEARV* |
| 149 | Light chain FR1: | DVLMTQTPLSLPVSLGDQASISC |
| 150 | CDR 1: | RSSRNIVHINGDTYLE |
| 151 | FR 2: | WYLQRPGQSPKLLIY |
| 152 | CDR 2: | KVSNRFS |
| 153 | FR 3: | GVPDRFSGSGSGTDFTLKISRVEAEDLGVYYC |
| 154 | CDR 3: | FQGSLLPWT |
| 155 | FR 4: | FGGGTRLEIK |
| 156 | scFv KM3060var n.a. | gaggtgcagctggtcgagagcggaggcgacctgatgaagcctggcgg cagcctgaagatcagctgcgccgccagcggcttcatcttcagcaact acggcatgagctgggtgcgccagacccccgacatgcggctggaatgg gtggcaaccatcagcagcgccagcacctacagctactaccccgacag cgtgaagggccggttcaccatcagccgggacaacgccgagaacagcc tgtatctgcagatgaacagcctgcggagcgaggacaccggcatctac tactgcggcagacacagcgacggcaacttcgccttcggctactgggg cagaggcaccctggtgaccgtgtccagcaagctttccggcagcgcct ccgcccccaagctggaagagggcgagttcagcgaggcacgcgtggac gtgctgatgacccagacccctctgagcctgcccgtgtccctgggcga ccaggccagcatcagctgcagaagcagccggaacatcgtccacatca acggcgacacctacctggaatggtatctgcagcggcctggacagagc cccaagctgctgatctacaaggtgtccaaccggttcagcggcgtgcc cgacagattcagcggaagcggctccggcaccgacttcacactgaaga tctcccgggtggaggccgaggacctgggcgtgtactactgctttcaa ggcagcctgctgccctggaccttcggcggaggcacacggctggaaat caaagcggccgctggatccgaacaaaagctgatctcagaagaagacc taaactca*catcaccatcaccatcac* |
| 157 | scFv KM060var a.a. | EVQLVESGGDLMKPGGSLKISCAASGFIFSNYGMSWVRQTPDMRLEW VATISSASTYSYYPDSVKGRFTISRDNAENSLYLQMNSLRSEDTGIY YCGRHSDGNFAFGYWGRGTLVTVSS*KLSGSASAPKLEEGEFSEARV*D VLMTQTPLSLPVSLGDQASISCRSSRNIVHINGDTYLEWYLQRPGQS PKLLIYKVSNRFSGVPDRFSGSGSGTDFTLKISRVEAEDLGVYYCFQ GSLLPWTFGGGTRLEIKAAAGSEQKLISEEDLNSHHHHHH |

TABLE 11

| SEQ ID NO: | scFv 9E10J | |
|---|---|---|
| 36 | Heavy chain FR1: | QVQLVQSGAEVKKPGSSVKVSCKASGGTFS |
| 101 | CDR 1: | SYAIS |
| 37 | FR 2 | WVRQAPGQGLEWMG |
| 8 | CDR 2: | GIIPIFGTANYAQKFQG |
| 102 | FR 3: | RVTMTRDTSTSTVYMELSSLRSEDTAVYYCAR |
| 9 | CDR 3: | RGGSYFDY |
| 39 | FR 4: | WGQGTLVTVSS |
| 40 | Linker: | KLSGSASAPKLEEGEFSEARV |
| 41 | Light chain FR1: | SYVLTQPPSASGTPGQSVTISC |
| 10 | CDR 1: | SGSTSNIGSHYVF |
| 42 | FR 2 | WYQQLPGTAPRLLIY |
| 11 | CDR 2: | RNHQRPS |
| 43 | FR 3: | GVPDRLSGSKSGTSASLAISGLRSEDEADYYC |
| 12 | CDR 3: | AVWDDTLSGWV |
| 44 | FR 4: | FGGGTKLTVL |
| 103 | scFv 9E10J | CAGGTCCAGCTTGTACAGTCTGGGGCTGAGGTGAAGAAGC CTGGGTCCTCGGTGAAGGTCTCCTGCAAGGCTTCTGGAGG CACCTTCAGCAGCTATGCTATCAGCTGGGTGCGACAGGCC CCTGGACAAGGGCTTGAGTGGATGGGAGGGATCATCCCTA TCTTTGGTACAGCAAACTACGCACAGAAGTTCCAGGGCAG AGTCACCATGACCAGGGACACGTCCACGAGCACAGTCTAC ATGGAGCTGAGCAGCCTGAGATCTGAGGACACGGCCGTGT ATTACTGTGCGAGACGCGGTGGGAGCTACTTTGACTACTG GGGCCAAGGGACCCTGGTCACCGTCTCCTCAAAGCTTTCA GGGAGTGCATCCGCCCCAAAACTTGAAGAAGGTGAATTTT CAGAAGCACGCGTATCCTATGTGCTGACTCAGCCACCCTC AGCGTCTGGGACCCCCGGGCAGAGCGTCACCATCTCTTGT TCTGGAAGCACCTCCAACATCGGAAGTCATTATGTGTTCT GGTACCAGCAGCTCCCAGGAACGGCCCCCAGACTCCTCAT CTATAGGAATCATCAGCGGCCCTCAGGGGTCCCTGACCGA CTCTCTGGCTCCAAGTCTGGCACCTCAGCCTCCCTGGCCA TCAGTGGGCTCCGGTCCGAGGATGAGGCTGATTATTACTG TGCAGTGTGGGATGACACCCTGAGTGGCTGGGTGTTCGGC GGAGGGACCAAGCTGACCGTCCTA |
| 104 | scFv-9E10J a.a. | QVQLVQSGAEVKKPGSSVKVSCKASGGTFSSYAISWVRQA PGQGLEWMGGIIPIFGTANYAQKFQGRVTMTRDTSTSTVY MELSSLRSEDTAVYYCARRGGSYFDYWGQGTLVTVSSKLS GSASAPKLEEGEFSEARVSYVLTQPPSASGTPGQSVTISC SGSTSNIGSHYVFWYQQLPGTAPRLLIYRNHQRPSGVPDR LSGSKSGTSASLAISGLRSEDEADYYCAVWDDTLSGWVFG GGTKLTVL |
| 105 | $V_{H(aa)}$ | QVQLVQSGAEVKKPGSSVKVSCKASGGTFSSYAISWVRQA PGQGLEWMGGIIPIFGTANYAQKFQGRVTMTRDTSTSTVY MELSSLRSEDTAVYYCARRGGSYFDYWGQGTLVTVSS |
| 72 | $V_{L(aa)}$ | SYVLTQPPSASGTPGQSVTISCSGSTSNIGSHYVFWYQQL PGTAPRLLIYRNHQRPSGVPDRLSGSKSGTSASLAISGLR SEDEADYYCAVWDDTLSGWVFGGGTKLTVL |
| 106 | $V_H$ Domain (nt) | CAGGTCCAGCTTGTACAGTCTGGGGCTGAGGTGAAGAAGC CTGGGTCCTCGGTGAAGGTCTCCTGCAAGGCTTCTGGAGG CACCTTCAGCAGCTATGCTATCAGCTGGGTGCGACAGGCC CCTGGACAAGGGCTTGAGTGGATGGGAGGGATCATCCCTA TCTTTGGTACAGCAAACTACGCACAGAAGTTCCAGGGCAG AGTCACCATGACCAGGGACACGTCCACGAGCACAGTCTAC ATGGAGCTGAGCAGCCTGAGATCTGAGGACACGGCCGTGT ATTACTGTGCGAGACGCGGTGGGAGCTACTTTGACTACTG GGGCCAAGGGACCCTGGTCACCGTCTCCTCA |

TABLE 11-continued

| SEQ ID NO: | scFv 9E10J | |
|---|---|---|
| 80 | V_L Domain (nt) | TCCTATGTGCTGACTCAGCCACCCTCAGCGTCTGGGACCC CCGGGCAGAGCGTCACCATCTCTTGTTCTGGAAGCACCTC CAACATCGGAAGTCATTATGTGTTCTGGTACCAGCAGCTC CCAGGAACGGCCCCAGACTCCTCATCTATAGGAATCATC AGCGGCCCTCAGGGGTCCCTGACCGACTCTCTGGCTCCAA GTCTGGCACCTCAGCCTCCCTGGCCATCAGTGGGCTCCGG TCCGAGGATGAGGCTGATTATTACTGTGCAGTGTGGGATG ACACCCTGAGTGGCTGGGTGTTCGGCGGAGGGACCAAGCT GACCGTCCTA |

TABLE 12

| SEQ ID NO: | scFv 9E1D | |
|---|---|---|
| 36 | Heavy chain FR1: | QVQLVQSGAEVKKPGSSVKVSCKASGGTFS |
| 7 | CDR1: | NYAIS |
| 37 | FR2 | WVRQAPGQGLEWMG |
| 8 | CDR2: | GIIPIFGTANYAQKFQG |
| 38 | FR3: | RVTITADESTSTAYMELSSLRSEDTAVYYCAR |
| 9 | CDR3: | RGGSYFDY |
| 39 | FR4: | WGQGTLVTVSS |
| 40 | Linker: | KLSGSASAPKLEEGEFSEARV |
| 107 | Light chainFR1: | QPVLTQPPSASGTPGQRVTISC |
| 108 | CDR1: | SGGGSNIGRRFVN |
| 109 | FR2 | WYQQLPGTAPKLLIY |
| 110 | CDR2: | RNNQRPS |
| 111 | FR3: | GVPDRFSGSKSGTSASLVISGLRSEDEADYYC |
| 112 | CDR3: | AAWDDSLSGWV |
| 44 | FR4: | FGGGTKLTVL |
| 113 | scFv9E1D | CAGGTCCAGCTTGTACAGTCTGGGGCTGAGGTGAAGAAG CCTGGGTCCTCGGTGAAGGTCTCCTGCAAGGCTTCTGGA GGCACCTTCAGCAACTATGCTATCAGCTGGGTGCGACAG GCCCCTGGACAAGGGCTTGAGTGGATGGGAGGGATCATC CCTATCTTTGGTACAGCAAACTACGCACAGAAGTTCCAG GGCAGAGTCACGATTACCGCGGACGAATCCACGAGCACA GCCTACATGGAGCTGAGCAGCCTGAGATCTGAGGACACG GCCGTGTATTACTGTGCGAGACGCGGTGGGAGCTACTTT GACTACTGGGGCCAGGGAACCCTGGTCACCGTCTCTTCA AAGCTTTCAGGGAGTGCATCCGCCCCAAAACTTGAAGAA GGTGAATTTTCAGAAGCACGCGTACAGCCTGTGCTGACT CAGCCCCCCTCAGCGTCTGGGACCCCCGGGCAGAGGGTC ACCATCTCTTGTTCTGGAGGCGGATCCAACATCGGAAGA AGGTTTGTAAACTGGTACCAGCAGCTCCCAGGAACGGCC CCCAAACTCCTCATCTATAGGAATAATCAGCGGCCCTCA GGGGTCCCTGACCGATTCTCTGGCTCCAAGTCTGGCACC TCAGCCTCCCTGGTCATCAGTGGGCTCCGGTCCGAGGAT GAGGCTGATTATTACTGTGCAGCATGGGATGACAGCCTG AGTGGTTGGGTGTTCGGCGGAGGGACCAAGCTGACCGTC CTA |
| 114 | scFv9E1D a.a. | QVQLVQSGAEVKKPGSSVKVSCKASGGTFSNYAISWVRQ APGQGLEWMGGIIPIFGTANYAQKFQGRVTITADESTST AYMELSSLRSEDTAVYYCARRGGSYFDYWGQGTLVTVSS KLSGSASAPKLEEGEFSEARVQPVLTQPPSASGTPGQRV TISCSGGGSNIGRRFVNWYQQLPGTAPKLLIYRNNQRPS |

TABLE 12-continued

| SEQ ID NO: | | scFv 9E1D |
|---|---|---|
| | | GVPDRFSGSKSGTSASLVISGLRSEDEADYYCAAWDDSL<br>SGWVFGGGTKLTVL |
| 71 | V$_H$ (aa) | QVQLVQSGAEVKKPGSSVKVSCKASGGTFSNYAISWVRQ<br>APGQGLEWMGGIIPIFGTANYAQKFQGRVTITADESTST<br>AYMELSSLRSEDTAVYYCARRGGSYFDYWGQGTLVTVSS |
| 115 | V$_L$ (aa) | QPVLTQPPSASGTPGQRVTISCSGGGSNIGRRFVNWYQQ<br>LPGTAPKLLIYRNNQRPSGVPDRFSGSKSGTSASLVISG<br>LRSEDEADYYCAAWDDSLSGWVFGGGTKLTVL |
| 79 | V$_H$ domain (nt) | CAGGTCCAGCTTGTACAGTCTGGGGCTGAGGTGAAGAAG<br>CCTGGGTCCTCGGTGAAGGTCTCCTGCAAGGCTTCTGGA<br>GGCACCTTCAGCAACTATGCTATCAGCTGGGTGCGACAG<br>GCCCCTGGACAAGGGCTTGAGTGGATGGGAGGGATCATC<br>CCTATCTTTGGTACAGCAAACTACGCACAGAAGTTCCAG<br>GGCAGAGTCACGATTACCGCGGACGAATCCACGAGCACA<br>GCCTACATGGAGCTGAGCAGCCTGAGATCTGAGGACACG<br>GCCGTGTATTACTGTGCGAGACGCGGTGGGAGCTACTTT<br>GACTACTGGGGCCAGGGAACCCTGGTCACCGTCTCTTCA |
| 116 | V$_L$ domain (nt) | CAGCCCCCCTCAGCGTCTGGGACCCCCGGGCAGAGGGTC<br>ACCATCTCTTGTTCTGGAGGCGGATCCAACATCGGAAGA<br>AGGTTTGTAAACTGGTACCAGCAGCTCCCAGGAACGGCC<br>CCCAAACTCCTCATCTATAGGAATAATCAGCGGCCCTCA<br>GGGGTCCCTGACCGATTCTCTGGCTCCAAGTCTGGCACC<br>TCAGCCTCCCTGGTCATCAGTGGGCTCCGGTCCGAGGAT<br>GAGGCTGATTATTACTGTGCAGCATGGGATGACAGCCTG<br>AGTGGTTGGGTGTTCGGCGAGGGACCAAGCTGACCGTC<br>CTA |

TABLE 13

| Sequence of 9E10J IgG. | | |
|---|---|---|
| SEQ. ID NO: 117 | IgG1 heavy chain (nt) | caggtccagcttgtacagtctggggctgaggtgaagaagcct<br>gggtcctcggtgaaggtctcctgcaaggcttctggaggcacc<br>ttcagcagctatgctatcagctgggtgcgacaggcccctgga<br>caagggcttgagtggatgggagggatcatccctatctttggt<br>acagcaaactacgcacagaagttccagggcagagtcaccatg<br>accagggacacgtccacgagcacagtctacatggagctgagc<br>agcctgagatctgaggacacggccgtgtattactgtgcgaga<br>cgcggtgggagctactttgactactggggccaagggaccctg<br>gtcaccgtctcctcagcctccaccaagggcccatcggtcttc<br>cccctggcaccctcctccaagagcacctctgggggcacagcg<br>gccctgggctgcctggtcaaggactacttccccgaaccggtg<br>acggtgtcgtggaactcaggcgccctgaccagcggcgtgcac<br>accttcccggctgtcctacagtcctcaggactctactccctc<br>agcagcgtggtgaccgtgccctccagcagcttgggcacccag<br>acctacatctgcaacgtaatcacaagcccagcaacaccaag<br>gtggacaagaaagttgagcccaaatcttgtgacaaaactcac<br>acatgcccaccgtgcccagcacctgaactcctggggggaccg<br>tcagtcttcctcttccccccaaaacccaaggacaccctcatg<br>atctcccggacccctgaggtcacatgcgtggtggtggacgtg<br>agccacgaagaccctgaggtcaagttcaactggtacgtggac<br>ggcgtggaggtgcataatgccaagacaaagccgcgggaggag<br>cagtacaacagcacgtaccgtgtggtcagcgtcctcaccgtc<br>ctgcaccaggactggctgaatggcaaggagtacaagtgcaag<br>gtctccaacaaagccctcccagcccccatcgagaaaaccatc<br>tccaaagccaaagggcagccccgagaaccacaggtgtacacc<br>ctgcccccatcccgggatgagctgaccaagaaccaggtcagc<br>ctgacctgcctggtcaaaggcttctatcccagcgacatcgcc<br>gtggagtgggagagcaatgggcagccggagaacaactacaag<br>accacgcctcccgtgctggactccgacggctccttcttcctc<br>tacagcaagctcaccgtggacaagagcaggtggcagcagggg<br>aacgtcttctcatgctccgtgatgcatgaggctctgcacaac<br>cactacacgcagaagagcctctccctgtctccgggtaaa |
| SEQ. ID NO: 118 | Lambda Light chain (nt) | tcctatgtgctgactcagccaccctcagcgtctgggacccc<br>gggcagagcgtcaccatctcttgttctggaagcacctccaac<br>atcggaagtcattatgtgttctggtaccagcagctcccagga<br>acgccccagactcctcatctataggaatcatcagcggccc<br>tcagggtccctgaccgactctctggctccaagtctggcacc<br>tcagcctccctggccatcagtgggctccggtccgaggatgag |

TABLE 13-continued

Sequence of 9E10J IgG.

gctgattattactgtgcagtgtgggatgacaccctgagtggc
tgggtgttcggcggagggaccaagctgaccgtcctaggtcag
cccaaggctgcccctcggtcactctgttcccgccctcctct
gaggagcttcaagccaacaaggccacactggtgtgtctcata
agtgacttctacccgggagccgtgacagtggcctggaaggca
gatagcagccccgtcaaggcgggagtggagaccaccacaccc
tccaaacaaagcaacaacaagtacgcggccagcagctatctg
agcctgacgcctgagcagtggaagtcccacagaagctacagc
tgccaggtcacgcatgaagggagcaccgtggagaagacagtg
gcccctacagaatgttca

| SEQ. ID NO: 119 | IgG-heavy chain (aa) | qvqlvqsgaevkkpgssvkvsckasgqtfssyaiswvrqapq qglewmggiipifgtanyaqkfqgrvtmtrdtststvymels slrsedtavyycarrqqsyfdywgqgtivtvssastkgpsvf plapsskstsggtaalgclvkdyfpepvtvswnsgaltsgvh tfpavlqssglyslssvvtvpssslgtqtyicnvnhkpsntk vdkkvepkscdkthtcppcpapellggpsvflfppkpkdtlm isrtpevtcvvvdvshedpevkfnwyvdgvevhnaktkpree qynstyrvvsvltvlhqdwlngkeykckvsnkalpapiekti skakgqprepqvytlppsrdeltknqvsltclvkgfypsdia vewesngqpennykttppvldsdgsfflysklvdksrwqqg nvfscsvmhealhnhytqkslslspgk |
| --- | --- | --- |
| SEQ. ID NO: 120 | Lambda Light-chain (aa) | syvltqppsasgtpgqsvtiscsgstsnigshyvfwyqqlpg taprlliyrnhqrpsgvpdrlsgsksgtsaslaisglrsede adyycavwddtlsqwvfgggtkltvlgqpkaapsvtlfppss eelqankativclisdfypgavtvawkadsspvkagvetttp skqsnnkyaassylsltpeqwkshrsyscqvthegstvektv aptecs |

TABLE 14

Sequences of 9E1D IgG.

| SEQ. ID NO: 121 | IgG1 heavy chain (nt) | caggtccagcttgtacagtctggggctgaggtgaagaagcct ggggcctcggtgaaggtctcctgcaaggcttctggaggcacc ttcagcaactatgctatcagctgggtgcgacaggcccctgga caagggcttgagtggatgggagggatcatccctatctttggt acagcaaactacgcacagaagttccagggcagagtcacgatt accgcggacgaatccacgagcacagcctacatggagctgagc agcctgagatctgaggacacggccgtgtattactgtgcgaga cgcggtgggagctactttgactactggggccaggggaaccctg gtcaccgtctcttcagcctccaccaagggcccatcggtcttc cccctggcaccctcctccaagagcacctctgggggcacagcg gccctgggctgcctggtcaaggactacttccccgaaccggtg acggtgtcgtggaactcaggcgccctgaccagcggcgtgcac accttcccggctgtcctacagtcctcaggactctactccctc agcagcgtggtgaccgtgccctccagcagcttgggcacccag acctacatctgcaacgtgaatcacaagcccagcaacaccaag gtggacaagaaagttgagcccaaatcttgtgacaaaactcac acatgcccaccgtgcccagcacctgaactcctggggggaccg tcagtcttcctcttccccccaaaacccaaggacaccctcatg atctcccggacccctgaggtcacatgcgtggtggtggacgtg agccacgaagaccctgaggtcaagttcaactggtacgtggac ggcgtggaggtgcataatgccaagacaaagccgcgggaggag cagtacaacagcacgtaccgtgtggtcagcgtcctcaccgtc ctgcaccaggactggctgaatggcaaggagtacaagtgcaag gtctccaacaaagccctcccagcccccatcgagaaaaccatc tccaaagccaaagggcagccccgagaaccacaggtgtacacc ctgcccccatcccgggatgagctgaccaagaaccaggtcagc ctgacctgcctggtcaaaggcttctatcccagcgacatcgcc gtggagtgggagagcaatgggcagccggagaacaactacaag accacgcctcccgtgctggactccgacggctccttcttcctc tacagcaagctcaccgtggacaagagcaggtggcagcagggg aacgtcttctcatgctccgtgatgcatgaggctctgcacaac cactacacgcagaagagcctctccctgtctccgggtaaa |

TABLE 14-continued

Sequences of 9E1D IgG.

| SEQ. ID NO: 122 | Lambda Light-chain (nt) | cagcctgtgctgactcagccccctcagcgtctgggaccccgggcagagggtcaccatctcttgttctggaggcggatccaacatcggaagaaggtttgtaaactggtaccagcagctcccaggaacggcccccaaactcctcatctataggaataatcagcggccctcaggggtccctgaccgattctctggctccaagtctggcacctcagcctcccggtcatcagtgggctccggtccgaggatgaggctgattattactgtgcagcatgggatgacagcctgagtggttgggtgttcggcggagggaccaagctgaccgtcctaggtcagcccaaggctgcccctcggtcactctgttccgcctcctctgaggagcttcaagccaacaaggccacactggtgtgtctcatagtgacttctacccgggagccgtgacagtggcctggaaggcagatagcagccccgtcaaggcgggagtggagaccaccacacctccaaacaaagcaacaacaagtacgcggccagcagctatctgagcctgacgcctgagcagtggaagtcccacagaagctacagctgccaggtcacgcatgaagggagcaccgtggagaagacagtgccccctacagaatgttca |
| --- | --- | --- |
| SEQ. ID NO: 123 | IgG-heavy chain (aa) | qvqlvqsgaevkkpgssvkvsckasqgtfsnyaiswvrqapgqglewmqgiipifgtanyaqkfqgrvtitadeststaymelsslrsedtavyycarrggsyfdywgqgtlvtvssastkgpsvfplapssksts ggtaalgclvkdyfpepvtvswnsgaltsgvhtfpavlqssglyslssvvtvpssslgtqtyicnvnhkpsntkvdkkvepkscdkthtcppcpapellggpsvflfppkpkdtlmisrtpevtcvvvdvshedpevkfnwyvdgvevhnaktkpreeqynstyrvvsvltvlhqdwlngkeykckvsnkalpapiektiskakgqprepqvytlppsrdeltknqvsltclvkgfypsdiavewesngqpennykttppvldsdgsfflyskltvdksrwqqgnvfscsvmhealhnhytqkslslspgk |
| SEQ. ID NO: 124 | Lambda Light-chain (aa) | qpvltqppsasgtpgqrvtiscsgggsnigrrfvnwyqqlpgtapkllyrnnqrpsqvpdrfsqsksqtsaslvisqlrsedeadyycaawddslsgwvfgggtkltvlgqpkaapsvtlfppsseelqankatlvclisdfypgavtvawkadsspvkagvetttpskqsnnkyaassylsltpeqwkshrsyscqvthegstvektvaptecs |

TABLE 15

Apparent affinities (IC$_{50}$ and K$_D$) as determined from binding inhibition experiments

| | DT-40-CCR4$^+$ (bio-IgG 9E 3.3 nM) | | DT-40-CCR4$^+$ (bio-IgG 9E 0.7 nM) | | CCRF-CEM (bio-IgG 9E 0.7 nM) | |
| --- | --- | --- | --- | --- | --- | --- |
| IgG | IC$_{50}$ (nM) | K$_D$ (nM) | IC$_{50}$ (nM) | K$_D$ (nM) | IC$_{50}$ (nM) | K$_D$ (nM) |
| 9E | 3.50 | 2.1 | 0.44 | 0.39 | 0.38 | 0.33 |
| 9E10J | 0.15 | 0.09 | 0.06 | 0.05 | 0.07 | 0.06 |

TABLE 16

Calculated antibody concentrations leading to 50% TARC-induced CCR4 signalling (IC$_{50}$), as determined in Ca$^{++}$ flux assays

| | IC$_{50}$ (ng/ml) | | |
| --- | --- | --- | --- |
| Antibody (IgG1) | Conc. range: 1-100 ng/ml | Conc. range: 0.1-10 µg/ml | Conc. range: 3.2 ng/ml-10 µg/ml |
| 9E | 21.36 ng/ml (142.4 pM) | 46.15 ng/ml (307.7 pM) | ND |
| 9E10J | 7.24 ng/ml (48.3 pM) | 7.88 ng/ml (52.5 pM) | 6.48 ng/ml (43.3 pM) |

TABLE 17

Comparative ADCC activity of anti-CCR4 antibodies.

| | 9E | | 9E10J | | KM3060var | |
| --- | --- | --- | --- | --- | --- | --- |
| | EC$_{50}$ (ng/mL) | Max killing (%) | EC$_{50}$ (ng/mL) | Max killing (%) | EC$_{50}$ (ng/mL) | Max killing (%) |
| Mean | 185.6 | 31.8 | 24.7 | 42.4 | 367.0 | 38.8 |
| SD | 199.4 | 2.3 | 15.9 | 15.6 | 549.2 | 9.9 |
| N | 2 | 2 | 5 | 5 | 3 | 3 |

TABLE 18

Comparative ADCC activity of defucosylated 9E10J-anti-CCR4 antibody in comparison to unmodified 9E10J and comparator KM3060var.

| | 9E10J | | 9E10J-defucosylated | | KM3060var | |
| --- | --- | --- | --- | --- | --- | --- |
| | EC$_{50}$ (ng/mL) | Max killing (%) | EC$_{50}$ (ng/mL) | Max killing (%) | EC$_{50}$ (ng/mL) | Max killing (%) |
| Mean | 8.7 | 21.4 | 2.1 | 78.3 | 405 | 40.4 |
| SD | 0.4 | 16.9 | 0.83 | 13.5 | 466 | 17.5 |
| N | 2 | 2 | 4 | 4 | 3 | 3 |

TABLE 19

Apparent affinities ($K_D$) as determined by saturated antibody titration on cells in flow cytometry.

| scFv | DT-40 CCR4+ | IgG | CCRF-CEM |
|---|---|---|---|
| 9E | 4.95 ± 2.67 nM | 9E | 0.37 ± 0.11 nM |
| 9E1D | 5.22 ± 1.61 nM | 9E1D | ND |
| 9E10J | 1.17 ± 0.45 nM | 9E10J | 0.13 ± 0.03 nM |

ND, not determined;

TABLE 20

$IC_{50}$ values and calculated affinities ($K_D$) for cell-binding inhibition of biotinylated MDC, as determined from competition binding experiments on DT-40-CCR4+ and CCRF-CEM cells.

| | DT-40-CCR4+ cells | | CCRF-CEM cells | |
|---|---|---|---|---|
| Inhibitor | $IC_{50}$ (nM) | $K_D$ (nM) | $IC_{50}$ (nM) | $K_D$ (nM) |
| IgG 9E10J | 0.76 | 0.01 | 11.21 | 0.20 |
| | | | 6.28 | |
| | | | 39.97 | |
| MDC | 10.76 | 0.19 | 10.10 | 0.18 |
| | | | 10.12 | |
| | | | 69.36 | |

TABLE 21

$IC_{50}$ values for cell-binding inhibition of biotinylated TARC, as determined from competition binding experiments on DT-40-CCR4+ and CCRF-CEM cells.

| | $IC_{50}$ (nM) | |
|---|---|---|
| Inhibitor | DT-40-CCR4+ cells | CCRF-CEM cells |
| IgG 9E10J | 0.26 | 4.26 |
| | 0.40 | 4.57 |
| TARC | 40.93 | 43.44 |
| | 34.58 | 31.79 |

TABLE 22

Overview of determined $IC_{50}$-values from competition experiments.

| | $IC_{50}$ (nM) | |
|---|---|---|
| | 9E10J | 9E |
| MDC | 0.85 | 3.9 |
| TARC | 2.5 | 12.5 |

TABLE 23

| Consensus sequences<br>X = any amino acid | CDR/variable chain | SEQ ID NO: |
|---|---|---|
| XYAXS ($X_1YAX_2S$) | Heavy CDR1 | 125 |
| S/N Y A I/M S | Heavy CDR1 | 126 |
| XIXPXXGXXNYAQKFQG | Heavy CDR2 | 127 |
| G/A I I/S P I/S F/G G T/S A/T NYAQKFQG | Heavy CDR2 | 128 |
| SGXXSNIGXXXVX | Light CDR1 | 129 |
| SG S/G T/G SNIG S/R R/H Y/F V Y/F | Light CDR1 | 130 |
| RNXQRPS | Light CDR2 | 131 |
| RN H/N QRPS | Light CDR2 | 132 |
| AXWDDXLSGWY | Light CDR3 | 133 |
| A A/V WDD S/T LSGWY | Light CDR3 | 134 |
| XYAIS | heavy CDR1 | 135 |
| S/N YAIS | heavy CDR1 | 136 |
| AXWDDXLSGWV | Light CDR3* | 137 |
| A A/V WDD S/T LSGWV | Light CDR3* | 138 |
| QVQLVQSGAEVKKPGSSVKVSCKASGGTFSXYAISWVRQAPGQGLEWMGGIIPIFGTANYAQKFQGRVTXTXDXSTSTXYMELSSLRSEDTAVYYCARRGGSYFDYWGQGTLVTVSS | VH | 139 |

TABLE 23-continued

| Consensus sequences<br>X = any amino acid | CDR/variable<br>chain | SEQ<br>ID NO: |
|---|---|---|
| XXVLTQPPSASGTPGQXVTISCSGXXSNIGXXXVXWYQQ<br>LPGTAPXLLIYRNXQRPSGVPDRXSGSKSGTSASLXISGL<br>RSEDEADYYCAXWDDXLSGWVFGGGTKLTVL | VL | 140 |

*corrected sequence

TABLE 24

|  | % aggregation |
|---|---|
| IgGs alone |  |
| 9E10J | Non detectable |
| Anti-GFP ligands alone | Non detectable |
| TARC | 98% |
| MDC | 97% |
| Preincubation IgGs/ligands |  |
| anti-GFP/TARC | 88% |
| anti-GFP/MDC | 100% |
| 9E10J/TARC | 82% |
| 9E10J/MDC | 93% |
| Mixture IgG/ligands |  |
| 9E10J/TARC | 100% |
| 9E10J/MDC | 78% |

REFERENCES

The following references, to the extent that they provide exemplary procedural or other details supplementary to those set forth herein, are specifically incorporated herein by reference.

Altschul, Madden, Schaffer, Zhang, Zhang, Miller, Lipman, "Gapped BLAST and PSI-BLAST: a new generation of protein database search programs", Nucleic Acids Res., 25:3389-3402, 1997.

Arbabi-Ghahroudi, Desmyter, Wyns, Hamers, Muyldermans, "Selection and identification of single domain antibody fragments from camel heavy-chain antibodies", FEBS Lett., 414:521-526, 1997.

Baatar, Olkhanud, Newton, Sumitom, Biragyn. CCR4 expressing T cell tumors can be specifically controlled via delivery of toxins to chemokine receptors. J Immunol 179: 1996-2004 (2007a)

Baatar, Olkhanud, Sumitomo, Taub, Gress, Biragyn. Human peripheral blood T regulatory cells (Tregs), functionally primed CCR4$^+$ Tregs and unprimed CCR4$^-$ Tregs, regulate effector T cells using FasL. J Immunol 178: 4891-900 (2007b)

Baeverle and Gires, B J C, 96: 417-423, 2007.

Baldari, Murray, Ghiara, Cesareni, Galeotti, "A Novel Leader Peptide Which Allows Efficient Secretion of a Fragment of Human Interleukin 1 Beta in Saccharomyces Cerevisiae", EMBO J., 6:229-234, 1987

Bayry, Tchilian, Davies, Forbes, Draper, Kaveri, Hill, Kazatchkine, Beverley, Flower, Tough. In silico identified CCR4 antagonists target regulatory T cells and exert adjuvant activity in vaccination. Proc Natl Acad Sci USA 105: 10221-6 (2008)

Beckman, Weiner and Davis, "Antibody Constructs in Cancer Therapy", Cancer, 109(2):170-179, 2006.

Brinster, Chen, Trumbauer, Yagle, Palmiter, "Factors Affecting the Efficiency of introducing Foreign DNA into Mice by Microinjecting Eggs", Proc. Natl. Acad. Sci. USA, 82(13):4438-4442, 1985.

Burdi, Chi, Mattia, Harrington, Shi, Chen, Jacutin-Porte, Bennett, Carson, Yin, Kansra, Gonzalo, Coyle, Jaffee, Ocain, Hodge, LaRosa, Harriman. Small molecule antagonists of the CC chemokine receptor 4 (CCR4). Bioorg Med Chem Lett 17: 3141-5 (2007)

Carillo and Lipton, "The Multiple Sequence Alignment Problem in Biology", SIAM J. Applied Math., 48:1073, 1988.

Cullen, Gray, Wilson, Hayenga, Lamsa, Rey, Norton, Berka, "Controlled Expression and Secretion of Bovine Chymosin in Aspergillus Nidulans", BioTechnology, 5:369, 1987.

Church: Clinical advances in therapies targeting the interleukin-2 receptor. QJM 96: 91-102 (2003)

Chvatchko, Hoogewerf, Meyer, Alouani, Juillard, Buser, Conquet, Proudfoot, Wells, Power A key role for CC chemokine receptor 4 in lipopolysaccharide-induced endotoxic shock. J Exp Med 191: 1755-64 (2000)

Curiel: (2008) Regulatory T cells and treatment of cancer. Curr Opin Immunol 20: 241-6

Dannull, Su, Rizzieri, Yang, Coleman, Yancey, Zhang, Dahm, Chao, Gilboa, Vieweg Enhancement of vaccine-mediated antitumor immunity in cancer patients after depletion of regulatory T cells. J Clin Invest 115: 3623-33 (2005)

Davies, Bayry, Tchilian, Vani, Shaila, Forbes, Draper, Beverley, Tough, Flower. Toward the discovery of vaccine adjuvants: coupling in silico screening and in vitro analysis of antagonist binding to human and mouse CCR4 receptors. PLoS One 4: e8084 (2009)

Davies and Cohen, "Interactions of protein antigens with antibodies," Proc Natl. Acad. Sci. U.S.A. 93:7-12, 1996.

Davies, Padlan, Sheriff, "Antibody-antigen complexes," Annu. Rev. Biochem. 59:439-473, 1990.

Davies and Riechmann, "Antibody VH domains as small recognition units", Biotechnology (NY), 13:475-479, 1995.

Devereux, Haeberli, Smithies, "A Comprehensive Set of Sequence Analysis Programs for the VAX", Nucleic Acids Res., 12:387, 1984.

Di Paolo et al., "A recombinant immunotoxin derived from a humanized epithelial cell adhesion molecule-specific single-chain antibody fragment has potent and selective antitumor activity", Clin Cancer Res 9: 2837-48, 2003.

Frische, Meldal, Werdelin, Mouritsen, Jensen, Galli-Stampino, Bock, "Multiple Column Synthesis of a Library of T-Cell Stimulating Tri-Antigenic Glycopeptide Analogues for the Molecular Characterization of T-Cell-Glycan Specificity", J. Pept. Sci., 2(4): 212-22, 1996.

Goeddel, "Gene Expression Technology: Methods in Enzymology 185, Academic Press, San Diego, Calif., 1990.

Graham: D6 and the atypical chemokine receptor family: novel regulators of immune and inflammatory processes. Eur J Immunol 39: 342-51 (2009)

Hamers-Casterman and Atarhouch, "Naturally Occurring antibodies Devoid of Light Chains", *Nature*, 363(6428): 446-448, 1993.

Hammer, Pursel, Rexroad, Wall, Bolt, Ebert, Palmiter, Brinster, "Production of Transgenic Rabbits, Sheep and Pigs by Microinjection", *Nature*, 315:680-683, 1985.

Henikoff and Henikoff, "Amino acid Substitution Matrices from Protein Blocks", *Proc. Natl. Acad. Sci. USA*, 89:10915-10919, 1992.

Hinnen, Hicks, Fink, "Transformation of Yeast", *Proc. Natl. Acad. Sci. USA*, 75:1929, 1978.

Holliger and Hudson, "Engineered Antibody Fragments and the Rise of Single Domains", *Nature Biotechnology*, 23(9): 1126-1136, 2005.

Holm, "Dali: a Network Tool for Protein Structure Comparison", *Trends in Biochemical Sciences*, 20:478-480, 1995.

Holm, "Protein Structure Comparison by Alignment of Distance Matrices", *J. Mol. Biol.*, 233:123-38, 1993

Holm, "Touring Protein Fold Space With Dali/FSSP", *Nucleic Acid Res.*, 26:316-9, 1998.

Hoogenboom, Lutgerink, Pelsers, Rousch, Coote, Van Neer, De Bruïne, Van Nieuwenhoven, Glatz, Arends. Selection-dominant and nonaccessible epitopes on cell-surface receptors revealed by cell-panning with a large phage antibody library. Eur. J. Biochem 260, 774-784 (1999)

Ishida, Ishii, Inagaki, Yano, Komatsu, Iida, Inagaki, Ueda. Specific recruitment of CC chemokine receptor 4-positive regulatory T cells in Hodgkin lymphoma fosters immune privilege. Cancer Research, 66:11, pages 5716-5722, 2006

Ito, Fukuda, Murata, Kimura, "Transformation of Intact Yeast Cells Treated with Alkali Cations", *J. Bacteriol.*, 153:163-168, 1983.

Kabat, Wu, Perry, Gottesman, Foeller, "Sequences of Proteins of Immunological Interest", 5th Ed. *Public Health Service, National Institutes of Health*, Bethesda, Md., 647-669, 1991.

Kawasaki, Takizawa, Yoneyama, Nakayama, Fujisawa, Izumizaki, Imai, Yoshie, Homma, Yamamoto, Matsushima. Intervention of thymus and activation-regulated chemokine attenuates the development of allergic airway inflammation and hyperresponsiveness in mice. *J Immunol* 166: 2055-62 (2001)

Kaufman, Murtha, Davies, "Translational Efficiency of Polycistronic Mrnas and Their Utilization to Express Heterologous Genes in Mammalian Cells", *EMBO J.*, 6:187-195, 1987.

Kipriyanov, Moldenhauer, Martin, Kupriyanova, Little. Two amino acid mutations in an anti-human CD3 single chain Fv antibody fragment that affect the yield on bacterial secretion but not the affinity. *Protein Eng* 10: 445-53 (1997)

Kiss, Fisher, Pesavento, Dai, Valero, Ovecka, Nolan, Phipps, Velappan, Chasteen, Martinez, Waldo, Pavlik, Bradbury, "Antibody binding loop insertions as diversity elements", Nucleic Acids Research, 34(19):e132, 2006.

Kurjan and Herskowitz, "Structure of a Yeast Pheromone Gene (MFα): a Putative α-Factor Precursor Contains Four Tandem Copies of mature α-Factor", *Cell*, 30:933-943, 1982.

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection*, 17(4):357-366, 2004.

Levings, Sangregorio, Sartirana, Moschin, Battaglia, Orban, Roncarolo. Human $CD25^+CD4^+$ T suppressor cell clones produce transforming growth factor beta, but not interleukin 10, and are distinct from type 1 T regulatory cells. *J Exp Med* 196: 1335-46 (2002)

Locati, Torre, Galliera, Bonecchi, Bodduluri, Vago, Vecchi, Mantovani. Silent chemoattractant receptors: D6 as a decoy and scavenger receptor for inflammatory CC chemokines. *Cytokine Growth Factor Rev* 16: 679-86 (2005)

Luckow and Summers, "High Level Expression of Nonfused Foreign Genes with *Autographa Californica* Nuclear Polyhedrosis Virus Expression Vectors", *Virology*, 170:31-39, 1989.

Mahnke, Schonfeld, Fondel, Ring, Karakhanova, Wiedemeyer, Bedke, Johnson, Storn, Schallenberg, Enk. Depletion of $CD4^+CD25^+$ human regulatory T cells in vivo: kinetics of Treg depletion and alterations in immune functions in vivo and in vitro. *Int J Cancer* 120: 2723-33 (2007)

Marhaba et al., "CD44 and EpCAM: cancer-initiating cell markers", Curr Mol Med 8: 784-804, 2008.

Merrifield, "Solid Phase Peptide Synthesis 1. Synthesis of a Tetrapeptide", *J. Am. Chem. Assoc.*, 85:2149-2154, 1964.

Munz et al., "The carcinoma-associated antigen EpCAM upregulates c-myc and induces cell proliferation", Oncogene 23: 5748-58, 2004.

Myers and Miller, "Optimal Alignments in Linear Space", *CABIOS*, 4:11-17, 1988.

Naundorf, Preithner, Mayer, Lippold, Wolf, Hanakam, Fichtner, Kufer, Raum, Riethmuller, Baeuerle, Dreier. In vitro and in vivo activity of MT201, a fully human monoclonal antibody for pancarcinoma treatment. *Int J Cancer* 100: 101-10 (2002)

Needleman and Wunsch, "A General Method Applicable to the Search For Similarities in the Amino Acid Sequence of Two Proteins", *J. Mol. Biol.*, 48:443, 1970.

Neuberger and Milstein, "Somatic hypermutation," *Curr. Opin. Immunol.*, 7:248-254, 1995.

Nicaise, Valerio-Lepiniec, Minard, Desmadril, "Affinity transfer by CDR grafting on a nonimmunoglobulin scaffold", *Protein Sci.*, 13: 1882-1891, 2004.

Niwa, Shoji-Hosaka, Sakurada, Shinkawa, Uchida, Nakamura, Matsushima, Ueda, Hanai, Shitara. Defucosylated chimeric anti-CC chemokine receptor 4 IgG1 with enhanced antibody-dependent cellular cytotoxicity shows potent therapeutic activity to T-cell leukemia and lymphoma. *Cancer Res* 64: 2127-33 (2004)

Norderhaug, Olafsen, Michaelsen, Sandlie Versatile vectors for transient and stable expression of recombinant antibody molecules in mammalian cells. *J Immunol Methods* 204: 77-87 (1997)

O'Brien et al., "A human colon cancer cell capable of initiating tumour growth in immunodeficient mice", Nature 445: 106-10, 2007.

Olsen, Duvic, Frankel, Kim, Martin, Vonderheid, Jegasothy, Wood, Gordon, Heald, Oseroff, Pinter-Brown, Bowen, Kuzel, Fivenson, Foss, Glode, Molina, Knobler, Stewar, Cooper, Stevens, Craig, Reuben, Bacha, Nichols. Pivotal phase III trial of two dose levels of denileukin diftitox for the treatment of cutaneous T-cell lymphoma. *J Clin Oncol* 19: 376-88 (2001)

Palmiter and Brinster, "Transgenic Mice", *Cell*, 41:343-345, 1985.

Palmiter, Norstedt, Gelinas, Hammer, Brinster, "Metallothionein-Human GH Fusion Genes Stimulate Growth of Mice", *Science,* 222:809-814, 1983.

Panina-Bordignon, Papi, Mariani, Di Lucia, Casoni, Bellettato, Buonsanti, Miotto, Mapp, Villa, Arrigoni, Fabbri, Sinigaglia. The C—C chemokine receptors CCR4 and CCR8 identify airway T cells of allergen-challenged atopic asthmatics. *J Clin Invest* 107: 1357-64 (2001)

Pearson and Lipman, "Improved tools for biological sequence analysis", *Proc. Natl. Acad. Sci. USA,* 85:2444-2448, 1988.

Pearson, "Rapid and sensitive sequence comparison with FASTP and FASTA", *Methods in Enzymology,* 183:63-98, 1990.

Perros, Hoogsteden, Coyle, Lambrecht, Hammad. Blockade of CCR4 in a humanized model of asthma reveals a critical role for DC-derived CCL17 and CCL22 in attracting Th2 cells and inducing airway inflammation. *Allergy* 64: 995-1002 (2009)

Prang, Preithner, Brischwein, Göster, Wöppel, Müller, Steiger, Peters, Baeuerle, da Silva, "Cellular and complement-dependent cytotoxicity of Ep-CAM-specific monoclonal antibody MT201 against breast cancer cell lines", Br J Cancer, 92(2):342-349, 2005.

Purandare, Wan, Somerville, Burke, Vaccaro, Yang, McIntyre, Poss. Core exploration in optimization of chemokine receptor CCR4 antagonists. *Bioorg Med Chem Lett* 17: 679-82 (2007)

Qiu, Wang, Cai, Wang, Yue, "Small antibody mimetics comprising two complementarity-determining regions and a framework region for tumor targeting|, *Nature Biotechnology,* 25(8): 921-929, 2007.

Reff and Heard, "A Review of Modifications to Recombinant Antibodies: Attempt to Increase Efficacy in Oncology Applications", *Critical Reviews in Oncology Hematology,* 40:25-35, 2001.

Reiter, Ulrich Brinkmann, Lee and Pastan, "Engineering Antibody Fv Fragments for Cancer Detection and Therapy: Disulfide-Stabilized Fv Fragments", *Nature Biotechnology,* 14:1239-1245, 1996.

Ruter, Barnett, Krycze, Brumlik, Daniel, Coukos, Zou, Curiel. Altering regulatory T cell function in cancer immunotherapy: a novel means to boost the efficacy of cancer vaccines. *Front Biosci* 14: 1761-70 (2009)

Schodin, Kranz. Binding affinity and inhibitory properties of a single-chain anti-T cell receptor antibody. *J Biol Chem* 268: 25722-7 (1993)

Schultz, Tanner, Hofmann, Emini, Condra, Jones, Kieff, Ellis, "Expression and Secretion in Yeast of a 400-Kda Envelope Glycoprotein Derived from Epstein-Barr Virus", *Gene,* 54:113-123, 1987.

Seed, "an LFA-3 Cdna Encodes a Phospholipid-Linked Membrane Protein Homologous to its Receptor CD2", *Nature,* 329:840, 1987.

Sinkar, White, Gordon, "Molecular Biology of Ri-Plasmid a Review", *J. Biosci (Bangalore),* 11:47-58, 1987.

Smith and Waterman, "Comparison of Biosequences", *Adv. Appl. Math.,* 2:482, 1981.

Smith, Summers, Fraser, "Production of Human Beta Interferon in Insect Cells Infected With Baculovirus Expression Vector", *Mol. Cell. Biol.,* 3:2156-2165, 1983.

Spizzo et al., "High Ep-CAM expression is associated with poor prognosis in node-positive breast cancer", Breast Cancer Res Treat 86: 207-13, 2004.

Spizzo et al., "Overexpression of epithelial cell adhesion molecule (Ep-CAM) is an independent prognostic marker for reduced survival of patients with epithelial ovarian cancer", Gynecol Oncol 103: 483-8, 2006.

Sui, Bai, St Clair Tallarico, Xu, Marasco. Identification of CD4 and transferrin receptor antibodies by CXCR4 antibody-guided Pathfinder selection. Eur. J. Biochem 270, 4497-4506 (2003)

Thompson, Higgins, Gibson, "CLUSTAL W: Improving the sensitivity of progressive multiple sequence alignment through sequence weighting, position-specific gap penalties and weight matrix choice", *Nucleic Acids Res.,* 22:4673-4680, 1994.

van den Beucken, Neer, Sablon, Desmet, Celis, Hoogenboom, Hufton, "Building novel binding ligands to B7.1 and B7.2 based on human antibody single variable light chain domains", *J. Mol. Biol.,* 310:591-601, 2001.

Varga et al., "Overexpression of epithelial cell adhesion molecule antigen in gallbladder carcinoma is an independent marker for poor survival", Clin Cancer Res 10: 3131-6, 2004.

Wagner, Milstein, Neuberger, "Codon bias targets mutation," *Nature,* 376:732, 1995.

Ward, Güssow, Griffiths, Jones, Winter, "Binding Activities of a Repertoire of Single Immunoglobulin Variable Domains Secreted from *Escherichia Coli*", *Nature,* 341 (6242):544-546, 1989.

Went et al., "Frequent high-level expression of the immunotherapeutic target Ep-CAM in colon, stomach, prostate and lung cancers", Br J Cancer 94: 128-35, 2006.

Yang, Huang, Huang, Pardoll. Persistent Toll-like receptor signals are required for reversal of regulatory T cell-mediated CD8 tolerance. *Nat Immunol* 5: 508-15 (2004)

Yokoyama, Ishikawa, Igarashi, Kawano, Masuda, Hamaguchi, Yamasaki, Koganemaru, Hattori, Miyazaki, Ogino, Matsumoto, Takeuchi, Ohta. (2009) Potent and orally bioavailable CCR4 antagonists: Synthesis and structure-activity relationship study of 2-aminoquinazolines. *Bioorg Med Chem* 17: 64-73 (2009)

Yokoyama, Ishikawa, Igarashi, Kawano, Masuda, Hattori, Miyazaki, Ogino, Orita, Matsumoto, Takeuchi, Ohta M. Potent CCR4 antagonists: synthesis, evaluation, and docking study of 2,4-diaminoquinazolines. *Bioorg Med Chem* 16: 7968-74 (2008)

Young, MacKenzie, Narang, Oomen and Baenziger, "Thermal Stabilization of a Single-Chain Fv Antibody Fragment by Introduction of a Disulphide Bond", *FEBS Letters,* 16396(377):135-139, 1995.

Zambryski, Herrera-Estreila, DeBlock, Van Montagu, Schell "Genetic Engineering, Principles and Methods", *Hollaender and Setlow* (eds.), Vol. VI, pp. 253-278, Plenum Press, New York, 1984.

Zapata, Ridgway, Mordenti, Osaka, Wong, Bennett, Carter, "Engineering Linear F(Ab')$_2$ Fragments For Efficient Production in *Escherichia Coli* and Enhanced Antiproliferative Activity", *Protein Eng.,* 8(10):1057-1062, 1995.

Zhang, Gildersleeve, Yang, Xu, Loo, Uryu, Wong, Schultz, "A New Strategy for the Synthesis of Glycoproteins", *Science,* 303(5656): 371-373, 2004.

The invention claimed is:

1. A human antibody which binds to an epitope in the extracellular domain of human CC chemokine receptor 4 (CCR4) and which is capable of inhibiting the binding of macrophage-derived chemokine (MDC) and/or *thymus and activation regulated chemokine* (TARC) to CCR4, wherein said human antibody comprises:
   (i) VH CDR1 of $X_1YAX_2S$ (SEQ ID NO: 126), wherein $X_1$ is S or N, and $X_2$ is I or M;
   (ii) VH CDR2 of $X_1IX_2PX_3X_4GX_5X_6NYAQKFQG$ (SEQ ID NO: 128), wherein $X_1$ is G or A, $X_2$ is I or S, $X_3$ is I or S, $X_4$ is F or G, $X_5$ is T or S and $X_6$ is A or T;
   (iii) VH CDR3 of SEQ ID NO: 9;
   (iv) VL CDR1 of $SGX_1X_2SNIGX_3X_4X_5VX_6$ (SEQ ID NO: 130), wherein $X_1$ is S or G, $X_2$ is T or G, $X_3$ is S or R, $X_4$ is R or H, $X_5$ is Y or F and $X_6$ is Y or F;
   (v) VL CDR2 of RNXQRPS (SEQ ID NO: 132), wherein X is H or N; and
   (vi) VL CDR3 of $AX_1WDDX_2LSGWV$ (SEQ ID NO: 138), wherein $X_1$ is A or V and $X_2$ is S or T.

2. The human antibody of claim 1, wherein said human antibody comprises a VH domain of SEQ ID NO: 105 and/or a VL domain of SEQ ID NO: 72.

3. The human antibody of claim 1, wherein said antibody is a fully human antibody.

4. The human antibody of claim 1, wherein said human antibody comprises all or a portion of an antibody heavy chain constant region and/or an antibody light chain constant region.

5. The human antibody of claim 1, wherein said human antibody is an IgG antibody.

6. The human antibody of claim 1, wherein at least 10, 20, 30, 40 50, 60, 75, 80, 85, 90, 91, 92, 93, 94, 95, 96, 97, 98 or at least 99% of the total complex N-glycoside-linked sugar chains bound to the Fc region of said human antibody are sugar chains in which fucose is not bound to N-acetylglucosamine in the reducing end in the sugar chain.

7. The human antibody of claim 1, wherein said human antibody is an antigen binding fragment of an antibody.

8. The human antibody of claim 1, wherein said human antibody is an antigen binding fragment of an antibody and wherein said antigen binding fragment is a Fab', Fab, F(ab')$_2$, single domain antibody, TandAbs dimer, Fv, scFv, dsFv, ds-scFv, Fd, linear antibody, minibody, diabody, bispecific antibody fragment, bibody, tribody, sc-diabody, kappa(lamda) body, bispecific T-cell engager (BiTE), dual variable domain immunoglobulin (DVD-Ig), small immunoprotein (SIP), small modular immunopharmaceutical (SMIP), dual affinity retargeting construct (DART) or a small antibody mimetic comprising the CDRs.

9. An immunoconjugate comprising the human antibody of claim 1 attached to at least a therapeutic or diagnostic agent.

10. An immunoconjugate comprising the human antibody of claim 1 attached to at least a therapeutic or diagnostic agent selected from a radiotherapeutic agent, chemotherapeutic agent, anti-angiogenic agent, apoptosis-inducing agent, anti-tubulin drug, anti-cellular or cytotoxic agent, steroid, cytokine antagonist, cytokine expression inhibitor, chemokine antagonist, chemokine expression inhibitor, anti-inflammatory corticosteroid or NSAIDs, coagulant or anti-viral agent, wherein said anti-viral agent is preferably selected from the group consisting of a nucleoside, a nucleoside reverse transcriptase inhibitor, a non-nucleoside reverse transcriptase inhibitor and a protease inhibitor.

11. An immunoconjugate comprising the human antibody of claim 1 attached to daunorubicin, Doxorubicin, Cytarabine, 6-thioguanine, Mitoxantrone, busulfan (Myleran®), dasatinib (Sprycel™), prednisone, vincristine sulfate (Oncovin®), Chlorambucil, Fludarabine, Pentostatin or Cladribine.

12. A composition comprising at least the human antibody according any claim 1, wherein said composition is a pharmaceutically acceptable composition, a liposome, a nanoparticle composition, and/or further comprises at least a further therapeutic agent.

* * * * *

SEQUENCE LISTING

<160> NUMBER OF SEQ ID NOS: 157

<210> SEQ ID NO 1
<211> LENGTH: 5
<212> TYPE: PRT
<213> ORGANISM: Homo sapiens

<400> SEQUENCE: 1

Ser Tyr Ala Met Ser
1               5

<210> SEQ ID NO 2
<211> LENGTH: 17
<212> TYPE: PRT
<213> ORGANISM: Homo sapiens

<400> SEQUENCE: 2

Ala Ile Ser Gly Ser Gly Gly Ser Thr Tyr Tyr Ala Asp Ser Val Lys Gly
1               5                   10                  15

<210> SEQ ID NO 3
<211> LENGTH: 7
<212> TYPE: PRT
<213> ORGANISM: Homo sapiens

<400> SEQUENCE: 3

Ile Arg Tyr Ser Ala Gly Tyr
1               5

<210> SEQ ID NO 4
<211> LENGTH: 13
<212> TYPE: PRT
<213> ORGANISM: Homo sapiens

<400> SEQUENCE: 4

Ser Gly Ser Ser Ser Asn Ile Gly Ser Asn Tyr Val Tyr
1               5                   10

<210> SEQ ID NO 5
<211> LENGTH: 7
<212> TYPE: PRT
<213> ORGANISM: Homo sapiens

<400> SEQUENCE: 5

Arg Asn Asn Gln Arg Pro Ser
1               5

<210> SEQ ID NO 6
<211> LENGTH: 11
<212> TYPE: PRT
<213> ORGANISM: Homo sapiens

<400> SEQUENCE: 6

Ala Ala Trp Asp Asp Arg Leu Ser Gly Trp Val
1               5                   10

<210> SEQ ID NO 7
<211> LENGTH: 5
<212> TYPE: PRT
<213> ORGANISM: Homo sapiens

<400> SEQUENCE: 7

Asn Tyr Ala Ile Ser
1               5

```
<210> SEQ ID NO 8
<211> LENGTH: 17
<212> TYPE: PRT
<213> ORGANISM: Homo sapiens

<400> SEQUENCE: 8

Gly Ile Ile Pro Ile Phe Gly Thr Ala Asn Tyr Ala Gln Lys Phe Gln Gly
1               5                   10                  15

<210> SEQ ID NO 9
<211> LENGTH: 8
<212> TYPE: PRT
<213> ORGANISM: Homo sapiens

<400> SEQUENCE: 9

Arg Gly Gly Ser Tyr Phe Asp Tyr
1               5

<210> SEQ ID NO 10
<211> LENGTH: 13
<212> TYPE: PRT
<213> ORGANISM: Homo sapiens

<400> SEQUENCE: 10

Ser Gly Ser Thr Ser Asn Ile Gly Ser His Tyr Val Phe
1               5                   10

<210> SEQ ID NO 11
<211> LENGTH: 7
<212> TYPE: PRT
<213> ORGANISM: Homo sapiens

<400> SEQUENCE: 11

Arg Asn His Gln Arg Pro Ser
1               5

<210> SEQ ID NO 12
<211> LENGTH: 11
<212> TYPE: PRT
<213> ORGANISM: Homo sapiens

<400> SEQUENCE: 12

Ala Val Trp Asp Asp Thr Leu Ser Gly Trp Val
1               5                   10

<210> SEQ ID NO 13
<211> LENGTH: 5
<212> TYPE: PRT
<213> ORGANISM: Homo sapiens

<400> SEQUENCE: 13

Ser Tyr Ala Met Ser
1               5

<210> SEQ ID NO 14
<211> LENGTH: 17
<212> TYPE: PRT
<213> ORGANISM: Homo sapiens

<400> SEQUENCE: 14

Ala Ile Ser Gly Ser Gly Gly Ser Thr Tyr Tyr Ala Asp Ser Val Lys Gly
1               5                   10                  15

<210> SEQ ID NO 15
```

```
<211> LENGTH: 11
<212> TYPE: PRT
<213> ORGANISM: Homo sapiens

<400> SEQUENCE: 15

Gly Ala Gly Glu Gly Arg Gly Leu Gly Val Val
1               5                   10

<210> SEQ ID NO 16
<211> LENGTH: 14
<212> TYPE: PRT
<213> ORGANISM: Homo sapiens

<400> SEQUENCE: 16

Ala Ser Ser Thr Gly Ala Val Thr Ser Gly Tyr Phe Pro Asn
1               5                   10

<210> SEQ ID NO 17
<211> LENGTH: 7
<212> TYPE: PRT
<213> ORGANISM: Homo sapiens

<400> SEQUENCE: 17

Ser Thr Thr Asn Lys His Ser
1               5

<210> SEQ ID NO 18
<211> LENGTH: 9
<212> TYPE: PRT
<213> ORGANISM: Homo sapiens

<400> SEQUENCE: 18

Leu Leu Tyr Tyr Gly Gly Ala Arg Val
1               5

<210> SEQ ID NO 19
<211> LENGTH: 5
<212> TYPE: PRT
<213> ORGANISM: Homo sapiens

<400> SEQUENCE: 19

Gly Tyr Tyr Met His
1               5

<210> SEQ ID NO 20
<211> LENGTH: 17
<212> TYPE: PRT
<213> ORGANISM: Homo sapiens

<400> SEQUENCE: 20

Trp Ile Asn Pro Asn Ser Gly Gly Thr Asn Tyr Ala Gln Lys Phe Gln Gly
1               5                   10                  15

<210> SEQ ID NO 21
<211> LENGTH: 16
<212> TYPE: PRT
<213> ORGANISM: Homo sapiens

<400> SEQUENCE: 21

Gly Thr Val Thr Arg Ile Gln Gly Arg Ser Leu Tyr Gly Met Asp Val
1               5                   10                  15

<210> SEQ ID NO 22
<211> LENGTH: 12
<212> TYPE: PRT
```

<213> ORGANISM: Homo sapiens

<400> SEQUENCE: 22

Arg Ala Ser Gln Ser Val Asn Arg Arg Tyr Leu Ala
1               5                   10

<210> SEQ ID NO 23
<211> LENGTH: 7
<212> TYPE: PRT
<213> ORGANISM: Homo sapiens

<400> SEQUENCE: 23

Gly Ala Ser Ser Arg Ala Thr
1               5

<210> SEQ ID NO 24
<211> LENGTH: 9
<212> TYPE: PRT
<213> ORGANISM: Homo sapiens

<400> SEQUENCE: 24

Gln Gln Tyr Gly Ser Ser Pro Leu Thr
1               5

<210> SEQ ID NO 25
<211> LENGTH: 30
<212> TYPE: PRT
<213> ORGANISM: Homo sapiens

<400> SEQUENCE: 25

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 26
<211> LENGTH: 14
<212> TYPE: PRT
<213> ORGANISM: Homo sapiens

<400> SEQUENCE: 26

Trp Val Arg Gln Ala Pro Gly Lys Gly Leu Glu Trp Val Ser
1               5                   10

<210> SEQ ID NO 27
<211> LENGTH: 32
<212> TYPE: PRT
<213> ORGANISM: Homo sapiens

<400> SEQUENCE: 27

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Asn
            20                  25                  30

<210> SEQ ID NO 28
<211> LENGTH: 11
<212> TYPE: PRT
<213> ORGANISM: Homo sapiens

<400> SEQUENCE: 28

Trp Gly Gln Gly Thr Leu Val Thr Val Ser Ser
1               5                   10

<210> SEQ ID NO 29
<211> LENGTH: 21
<212> TYPE: PRT
<213> ORGANISM: Homo sapiens

<400> SEQUENCE: 29

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 30
<211> LENGTH: 22
<212> TYPE: PRT
<213> ORGANISM: Homo sapiens

<400> SEQUENCE: 30

Ser Tyr Val Leu Thr Gln Pro Pro Ser Ala Ser Gly Thr Pro Gly Gln
1               5                   10                  15

Arg Val Thr Ile Ser Cys
            20

<210> SEQ ID NO 31
<211> LENGTH: 15
<212> TYPE: PRT
<213> ORGANISM: Homo sapiens

<400> SEQUENCE: 31

Trp Tyr Gln Gln Leu Pro Gly Thr Ala Pro Lys Leu Leu Ile Tyr
1               5                   10                  15

<210> SEQ ID NO 32
<211> LENGTH: 32
<212> TYPE: PRT
<213> ORGANISM: Homo sapiens

<400> SEQUENCE: 32

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 33
<211> LENGTH: 10
<212> TYPE: PRT
<213> ORGANISM: Homo sapiens

<400> SEQUENCE: 33

Phe Gly Gly Gly Thr Lys Leu Thr Val Leu
1               5                   10

<210> SEQ ID NO 34
<211> LENGTH: 741
<212> TYPE: DNA
<213> ORGANISM: Homo sapiens

<400> SEQUENCE: 34
caggtgcagc tggtggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240

```
ctgcaaatga acagcctgag agccgaggac acggccgtat attactgtgc gaatattagg    300
tatagtgcag gctactgggg ccagggaacc ctggtcaccg tctcctcaaa gctttcaggg    360
agtgcatccg ccccaaaact gaagaaggt gaattttcag aagcacgcgt atcctatgtg     420
ctgacacagc caccctcagc gtctggggacc cccgggcaga gggtcaccat ctcttgttct   480
ggaagcagct ccaacatcgg aagtaattat gtatactggt accagcagct cccaggaacg    540
gccccaaaac tcctcatcta taggaataat cagcggccct caggggtccc tgaccgattc    600
tctggctcca agtctggcac ctcagcctcc ctggccatca gtgggctccg gtccgaggat    660
gaggctgatt attactgtgc agcatgggat gaccgcctga gtggttgggt gttcggcgga    720
gggaccaagc tgaccgtcct a                                              741
```

<210> SEQ ID NO 35
<211> LENGTH: 247
<212> TYPE: PRT
<213> ORGANISM: Homo sapiens

<400> SEQUENCE: 35

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Arg Tyr Ser Ala Gly Tyr Trp Gly Gln Gly Thr Leu Val
            100                 105                 110

Thr Val Ser Ser Lys Leu Ser Gly Ser Ala Ser Ala Pro Lys Leu Glu
        115                 120                 125

Glu Gly Glu Phe Ser Glu Ala Arg Val Ser Tyr Val Leu Thr Gln Pro
    130                 135                 140

Pro Ser Ala Ser Gly Thr Pro Gly Gln Arg Val Thr Ile Ser Cys Ser
145                 150                 155                 160

Gly Ser Ser Asn Ile Gly Ser Asn Tyr Val Tyr Trp Tyr Gln Gln
                165                 170                 175

Leu Pro Gly Thr Ala Pro Lys Leu Leu Ile Tyr Arg Asn Asn Gln Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Arg Ser Glu Asp Glu Ala Asp Tyr
    210                 215                 220

Tyr Cys Ala Ala Trp Asp Asp Arg Leu Ser Gly Trp Val Phe Gly Gly
225                 230                 235                 240

Gly Thr Lys Leu Thr Val Leu
                245
```

<210> SEQ ID NO 36
<211> LENGTH: 30
<212> TYPE: PRT

```
<213> ORGANISM: Homo sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 37
<211> LENGTH: 14
<212> TYPE: PRT
<213> ORGANISM: Homo sapiens

<400> SEQUENCE: 37

Trp Val Arg Gln Ala Pro Gly Gln Gly Leu Glu Trp Met Gly
1               5                   10

<210> SEQ ID NO 38
<211> LENGTH: 32
<212> TYPE: PRT
<213> ORGANISM: Homo sapiens

<400> SEQUENCE: 38

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 39
<211> LENGTH: 11
<212> TYPE: PRT
<213> ORGANISM: Homo sapiens

<400> SEQUENCE: 39

Trp Gly Gln Gly Thr Leu Val Thr Val Ser Ser
1               5                   10

<210> SEQ ID NO 40
<211> LENGTH: 21
<212> TYPE: PRT
<213> ORGANISM: Homo sapiens

<400> SEQUENCE: 40

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 41
<211> LENGTH: 22
<212> TYPE: PRT
<213> ORGANISM: Homo sapiens

<400> SEQUENCE: 41

Ser Tyr Val Leu Thr Gln Pro Pro Ser Ala Ser Gly Thr Pro Gly Gln
1               5                   10                  15

Ser Val Thr Ile Ser Cys
            20

<210> SEQ ID NO 42
<211> LENGTH: 15
<212> TYPE: PRT
<213> ORGANISM: Homo sapiens
```

<400> SEQUENCE: 42

Trp Tyr Gln Gln Leu Pro Gly Thr Ala Pro Arg Leu Leu Ile Tyr
1               5                   10                  15

<210> SEQ ID NO 43
<211> LENGTH: 32
<212> TYPE: PRT
<213> ORGANISM: Homo sapiens

<400> SEQUENCE: 43

Gly Val Pro Asp Arg Leu Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
                20                  25                  30

<210> SEQ ID NO 44
<211> LENGTH: 10
<212> TYPE: PRT
<213> ORGANISM: Homo sapiens

<400> SEQUENCE: 44

Phe Gly Gly Gly Thr Lys Leu Thr Val Leu
1               5                   10

<210> SEQ ID NO 45
<211> LENGTH: 813
<212> TYPE: DNA
<213> ORGANISM: Homo sapiens

<400> SEQUENCE: 45
caggtccagc ttgtacagtc tggggctgag gtgaagaagc ctgggtcctc ggtgaaggtc      60
tcctgcaagg cttctggagg caccttcagc aactatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagacgcggt     300
gggagctact ttgactactg gggccaggga acccctggtca ccgtctcttc aaagctttca     360
gggagtgcat ccgccccaaa acttgaagaa ggtgaatttt cagaagcacg cgtatcctat     420
gtgctgactc agccaccctc agcgtctggg accccgggc agagcgtcac catctcttgt     480
tctggaagca cctccaacat cggaagtcat tatgtgttct ggtaccagca gctcccagga     540
acggccccca gactcctcat ctataggaat catcagcggc cctcagggt ccctgaccga     600
ctctctggct ccaagtctgg cacctcagcc tccctggcca tcagtgggct ccggtccgag     660
gatgaggctg attattactg tgcagtgtgg atgacaccc tgagtggctg ggtgttcggc     720
ggagggacca agctgaccgt cctagcggcc gctggatccg aacaaaagct gatctcagaa     780
gaagacctaa actcacatca ccatcaccat cac                                 813

<210> SEQ ID NO 46
<211> LENGTH: 271
<212> TYPE: PRT
<213> ORGANISM: Homo sapiens

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr

```
            20                  25                  30
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Phe Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Val Trp Asp Asp Thr Leu Ser Gly Trp Val Phe Gly
225                 230                 235                 240

Gly Gly Thr Lys Leu Thr Val Leu Ala Ala Gly Ser Glu Gln Lys
                245                 250                 255

Leu Ile Ser Glu Glu Asp Leu Asn Ser His His His His His His
            260                 265                 270

<210> SEQ ID NO 47
<211> LENGTH: 30
<212> TYPE: PRT
<213> ORGANISM: Homo sapiens

<400> SEQUENCE: 47

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser
            20                  25                  30

<210> SEQ ID NO 48
<211> LENGTH: 14
<212> TYPE: PRT
<213> ORGANISM: Homo sapiens

<400> SEQUENCE: 48

Trp Val Arg Gln Ala Pro Gly Lys Gly Leu Glu Trp Val Ser
1               5                   10

<210> SEQ ID NO 49
<211> LENGTH: 32
<212> TYPE: PRT
<213> ORGANISM: Homo sapiens

<400> SEQUENCE: 49
```

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30
```

<210> SEQ ID NO 50
<211> LENGTH: 11
<212> TYPE: PRT
<213> ORGANISM: Homo sapiens

<400> SEQUENCE: 50

```
Met Gly Gln Gly Thr Leu Val Thr Val Ser Ser
1               5                   10
```

<210> SEQ ID NO 51
<211> LENGTH: 21
<212> TYPE: PRT
<213> ORGANISM: Homo sapiens

<400> SEQUENCE: 51

```
Lys Leu Ser Gly Ser Ala Ser Ala Pro Lys Leu Glu Glu Gly Glu Phe
1               5                   10                  15

Ser Glu Ala Arg Val
            20
```

<210> SEQ ID NO 52
<211> LENGTH: 22
<212> TYPE: PRT
<213> ORGANISM: Homo sapiens

<400> SEQUENCE: 52

```
Gln Ala Val Val Thr Gln Glu Pro Ser Leu Thr Val Ser Pro Gly Gly
1               5                   10                  15

Thr Val Thr Leu Thr Cys
            20
```

<210> SEQ ID NO 53
<211> LENGTH: 15
<212> TYPE: PRT
<213> ORGANISM: Homo sapiens

<400> SEQUENCE: 53

```
Trp Phe Gln Gln Lys Pro Gly Gln Ala Pro Arg Ala Leu Ile Tyr
1               5                   10                  15
```

<210> SEQ ID NO 54
<211> LENGTH: 32
<212> TYPE: PRT
<213> ORGANISM: Homo sapiens

<400> SEQUENCE: 54

```
Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30
```

<210> SEQ ID NO 55
<211> LENGTH: 10
<212> TYPE: PRT
<213> ORGANISM: Homo sapiens

<400> SEQUENCE: 55

Phe Gly Gly Gly Thr Lys Leu Thr Val Leu
1               5                   10

<210> SEQ ID NO 56
<211> LENGTH: 819
<212> TYPE: DNA
<213> ORGANISM: Homo sapiens

<400> SEQUENCE: 56

| | | | | |
|---|---|---|---|---|
| caggtgcagc | tggtggaatc | tgggggaggc | ttggtacagc | ctggcaggtc cctgagactc | 60 |
| tcctgtgcag | cctctggatt | cacctttagc | agctatgcca | tgagctgggt ccgccaggct | 120 |
| ccagggaagg | ggctggagtg | gtctcagct | attagtggta | gtggtggtag cacatactac | 180 |
| gcagactccg | tgaagggccg | gttcaccatc | tccagagaca | attccaagaa cacgctgtat | 240 |
| ctgcaaatga | acagcctgag | agccgaggac | acggccgtat | attactgtgc gaaggggggcc | 300 |
| ggcgagggtc | gagggcttgg | agtggttatg | gccagggaa | ccctggtcac cgtctcctca | 360 |
| aagctttcag | ggagtgcatc | cgccccaaaa | cttgaagaag | gtgaatttc agaagcacgc | 420 |
| gtacaggctg | tggtgaccca | ggagccctca | ctgactgtgt | ccccaggagg acagtcact | 480 |
| ctcacctgtg | cttccagcac | tggagcagtc | accagtggtt | actttccaaa ctggttccag | 540 |
| cagaaacctg | gacaagcacc | cagggcactc | atttatagta | caaccaacaa acactcctgg | 600 |
| accctgccc | ggttctcagg | ctccctcctt | ggggcaaag | ctgccctgac actgtcaggt | 660 |
| gtgcagcctg | aggacgaggc | tgagtattac | tgcctgctct | actatggtgg tgctcgggtg | 720 |
| ttcggcggag | ggaccaagct | caccgtccta | gcggccgctg | gatccgaaca aaagctgatc | 780 |
| tcagaagaag | acctaaactc | acatcaccat | caccatcac | | 819 |

<210> SEQ ID NO 57
<211> LENGTH: 273
<212> TYPE: PRT
<213> ORGANISM: Homo sapiens

<400> SEQUENCE: 57

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly Glu Gly Arg Gly Leu Gly Val Val Met Gly Gln
            100                 105                 110

Gly Thr Leu Val Thr Val Ser Ser Lys Leu Ser Gly Ser Ala Ser Ala
        115                 120                 125

Pro Lys Leu Glu Glu Gly Glu Phe Ser Glu Ala Arg Val Gln Ala Val
    130                 135                 140

Val Thr Gln Glu Pro Ser Leu Thr Val Ser Pro Gly Gly Thr Val Thr
145                 150                 155                 160

Leu Thr Cys Ala Ser Ser Thr Gly Ala Val Thr Ser Gly Tyr Phe Pro
                165                 170                 175

```
Asn Trp Phe Gln Gln Lys Pro Gly Gln Ala Pro Arg Ala Leu Ile Tyr
            180                 185                 190

Ser Thr Thr Asn Lys His Ser Trp Thr Pro Ala Arg Phe Ser Gly Ser
        195                 200                 205

Leu Leu Gly Gly Lys Ala Ala Leu Thr Leu Ser Gly Val Gln Pro Glu
    210                 215                 220

Asp Glu Ala Glu Tyr Tyr Cys Leu Leu Tyr Tyr Gly Gly Ala Arg Val
225                 230                 235                 240

Phe Gly Gly Gly Thr Lys Leu Thr Val Leu Ala Ala Ala Gly Ser Glu
                245                 250                 255

Gln Lys Leu Ile Ser Glu Glu Asp Leu Asn Ser His His His His His His
            260                 265                 270

<210> SEQ ID NO 58
<211> LENGTH: 30
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 59
<211> LENGTH: 14
<212> TYPE: PRT
<213> ORGANISM: Homo sapiens

<400> SEQUENCE: 59

Trp Val Arg Gln Ala Pro Gly Gln Gly Leu Glu Trp Met Gly
1               5                   10

<210> SEQ ID NO 60
<211> LENGTH: 32
<212> TYPE: PRT
<213> ORGANISM: Homo sapiens

<400> SEQUENCE: 60

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 61
<211> LENGTH: 11
<212> TYPE: PRT
<213> ORGANISM: Homo sapiens

<400> SEQUENCE: 61

Trp Gly Gln Gly Thr Thr Val Thr Val Ser Ser
1               5                   10

<210> SEQ ID NO 62
<211> LENGTH: 21
<212> TYPE: PRT
<213> ORGANISM: Homo sapiens

<400> SEQUENCE: 62

Lys Leu Ser Gly Ser Ala Ser Ala Pro Lys Leu Glu Glu Gly Glu Phe
1               5                   10                  15
```

```
Ser Glu Ala Arg Val
        20

<210> SEQ ID NO 63
<211> LENGTH: 23
<212> TYPE: PRT
<213> ORGANISM: Homo sapiens

<400> SEQUENCE: 63

Glu Thr Thr Leu Thr Gln Ser Pro Gly Thr Leu Ser Leu Ser Pro Gly
1               5                   10                  15

Glu Gly Val Thr Leu Ser Cys
        20

<210> SEQ ID NO 64
<211> LENGTH: 15
<212> TYPE: PRT
<213> ORGANISM: Homo sapiens

<400> SEQUENCE: 64

Trp Tyr Gln Gln Lys Pro Gly Gln Ala Pro Arg Leu Leu Ile Tyr
1               5                   10                  15

<210> SEQ ID NO 65
<211> LENGTH: 32
<212> TYPE: PRT
<213> ORGANISM: Homo sapiens

<400> SEQUENCE: 65

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
        20                  25                  30

<210> SEQ ID NO 66
<211> LENGTH: 10
<212> TYPE: PRT
<213> ORGANISM: Homo sapiens

<400> SEQUENCE: 66

Phe Gly Gly Gly Thr Lys Val Glu Ile Lys
1               5                   10

<210> SEQ ID NO 67
<211> LENGTH: 831
<212> TYPE: DNA
<213> ORGANISM: Homo sapiens

<400> SEQUENCE: 67
caggtccagc ttgtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaaccctc acagtggtgg cacaaactat     180
gcacagaagt ttcagggcag ggtcaccatg accagggaca cgtccatcag cacagcctac     240
atggagctga gcaggctgag atctgacgac acggccgtgt attactgtgc gagaggtacg     300
gtgactagga ttcagggccg ctctctctac ggtatggacg tctggggcca agggaccacg     360
gtcaccgtct cttcaaaagct tcagggagt gcatccgccc caaaacttga agaaggtgaa     420
ttttcagaag cacgcgtaga acgacactc acgcagtctc caggcaccct gtctttgtct     480
ccaggggaag gagtcaccct ctcctgcagg gccagtcaga gtgttaacag gaggtactta     540
```

```
gcctggtacc agcagaaacc tggccaggct cccaggctcc tcatctatgg ggcatccagc    600
agggccactg gcatccctga caggttcagt ggcagtgggt ctgggacaga cttcactctc    660
accatcagca gactggagcc tgaagatttt gcagtgtatt actgtcagca gtatggtagc    720
tcacccctca ctttcggcgg agggaccaag gtggaaatca agcggccgc tggatccgaa    780 caaaagctga tctcagaaga agacctaaac tcacatcacc atcaccatca c            831
```

```
<210> SEQ ID NO 68
<211> LENGTH: 277
<212> TYPE: PRT
<213> ORGANISM: Homo sapiens

<400> SEQUENCE: 68
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Val Thr Arg Ile Gln Gly Arg Ser Leu Tyr Gly Met
            100                 105                 110

Asp Val Trp Gly Gln Gly Thr Thr Val Thr Val Ser Ser Lys Leu Ser
        115                 120                 125

Gly Ser Ala Ser Ala Pro Lys Leu Glu Glu Gly Glu Phe Ser Glu Ala
    130                 135                 140

Arg Val Glu Thr Thr Leu Thr Gln Ser Pro Gly Thr Leu Ser Leu Ser
145                 150                 155                 160

Pro Gly Glu Gly Val Thr Leu Ser Cys Arg Ala Ser Gln Ser Val Asn
                165                 170                 175

Arg Arg Tyr Leu Ala Trp Tyr Gln Gln Lys Pro Gly Gln Ala Pro Arg
            180                 185                 190

Leu Leu Ile Tyr Gly Ala Ser Ser Arg Ala Thr Gly Ile Pro Asp Arg
        195                 200                 205

Phe Ser Gly Ser Gly Ser Gly Thr Asp Phe Thr Leu Thr Ile Ser Arg
    210                 215                 220

Leu Glu Pro Glu Asp Phe Ala Val Tyr Tyr Cys Gln Gln Tyr Gly Ser
225                 230                 235                 240

Ser Pro Leu Thr Phe Gly Gly Gly Thr Lys Val Glu Ile Lys Ala Ala
                245                 250                 255

Ala Gly Ser Glu Gln Lys Leu Ile Ser Glu Glu Asp Leu Asn Ser His
            260                 265                 270

His His His His His
        275

```
<210> SEQ ID NO 69
<211> LENGTH: 116
<212> TYPE: PRT
<213> ORGANISM: Homo sapiens
```

```
<400> SEQUENCE: 69

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Arg Tyr Ser Ala Gly Tyr Trp Gly Gln Gly Thr Leu Val
            100                 105                 110

Thr Val Ser Ser
            115

<210> SEQ ID NO 70
<211> LENGTH: 110
<212> TYPE: PRT
<213> ORGANISM: Homo sapiens

<400> SEQUENCE: 70

Ser Tyr Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Arg Leu
                85                  90                  95

Ser Gly Trp Val Phe Gly Gly Gly Thr Lys Leu Thr Val Leu
            100                 105                 110

<210> SEQ ID NO 71
<211> LENGTH: 117
<212> TYPE: PRT
<213> ORGANISM: Homo sapiens

<400> SEQUENCE: 71

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95

Ala Arg Arg Gly Gly Ser Tyr Phe Asp Tyr Trp Gly Gln Gly Thr Leu
                100                 105                 110

Val Thr Val Ser Ser
            115

<210> SEQ ID NO 72
<211> LENGTH: 110
<212> TYPE: PRT
<213> ORGANISM: Homo sapiens

<400> SEQUENCE: 72

Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Phe Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu
                100                 105                 110

<210> SEQ ID NO 73
<211> LENGTH: 120
<212> TYPE: PRT
<213> ORGANISM: Homo sapiens

<400> SEQUENCE: 73

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Gly Glu Gly Arg Gly Leu Gly Val Val Met Gly Gln
                100                 105                 110

Gly Thr Leu Val Thr Val Ser Ser
            115                 120

<210> SEQ ID NO 74
<211> LENGTH: 109
<212> TYPE: PRT
<213> ORGANISM: Homo sapiens

<400> SEQUENCE: 74

Gln Ala Val Val Thr Gln Glu Pro Ser Leu Thr Val Ser Pro Gly Gly
1               5                   10                  15
```

Thr Val Thr Leu Thr Cys Ala Ser Ser Thr Gly Ala Val Thr Ser Gly
            20                  25                  30

Tyr Phe Pro Asn Trp Phe Gln Gln Lys Pro Gly Gln Ala Pro Arg Ala
        35                  40                  45

Leu Ile Tyr Ser Thr Thr Asn Lys His Ser Trp Thr Pro Ala Arg Phe
    50                  55                  60

Ser Gly Ser Leu Leu Gly Gly Lys Ala Ala Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Arg Val Phe Gly Gly Gly Thr Lys Leu Thr Val Leu
            100                 105

<210> SEQ ID NO 75
<211> LENGTH: 125
<212> TYPE: PRT
<213> ORGANISM: Homo sapiens

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Val Arg Ile Gln Gly Arg Ser Leu Tyr Gly Met
            100                 105                 110

Asp Val Trp Gly Gln Gly Thr Thr Val Thr Val Ser Ser
        115                 120                 125

<210> SEQ ID NO 76
<211> LENGTH: 108
<212> TYPE: PRT
<213> ORGANISM: Homo sapiens

<400> SEQUENCE: 76

Glu Thr Thr Leu Thr Gln Ser Pro Gly Thr Leu Ser Leu Ser Pro Gly
1               5                   10                  15

Glu Gly Val Thr Leu Ser Cys Arg Ala Ser Gln Ser Val Asn Arg Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 77
<211> LENGTH: 348
<212> TYPE: DNA
<213> ORGANISM: Homo sapiens

<400> SEQUENCE: 77

| caggtgcagc tggtggagtc tgggggaggc ttggtacagc ctggggggtc cctgagactc | 60 |
| tcctgtgcag cctctggatt cacctttagc agctatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtat attactgtgc gaatattagg | 300 |
| tatagtgcag ctactgggg ccagggaacc ctggtcaccg tctcctca | 348 |

<210> SEQ ID NO 78
<211> LENGTH: 330
<212> TYPE: DNA
<213> ORGANISM: Homo sapiens

<400> SEQUENCE: 78

| tcctatgtgc tgacacagcc accctcagcg tctgggaccc ccgggcagag ggtcaccatc | 60 |
| tcttgttctg gaagcagctc caacatcgga agtaattatg tatactggta ccagcagctc | 120 |
| ccaggaacgg cccccaaact cctcatctat aggaataatc agcggccctc aggggtccct | 180 |
| gaccgattct ctggctccaa gtctggcacc tcagcctccc tggccatcag tgggctccgg | 240 |
| tccgaggatg aggctgatta ttactgtgca gcatgggatg accgcctgag tggttgggtg | 300 |
| ttcggcggag ggaccaagct gaccgtccta | 330 |

<210> SEQ ID NO 79
<211> LENGTH: 351
<212> TYPE: DNA
<213> ORGANISM: Homo sapiens

<400> SEQUENCE: 79

| caggtccagc ttgtacagtc tggggctgag gtgaagaagc ctgggtcctc ggtgaaggtc | 60 |
| tcctgcaagg cttctggagg caccttcagc aactatgcta tcagctgggt gcgacaggcc | 120 |
| cctggacaag ggcttgagtg gatgggaggg atcatcccta tctttggtac agcaaactac | 180 |
| gcacagaagt tccagggcag agtcacgatt accgcggacg aatccacgag cacagcctac | 240 |
| atggagctga gcagcctgag atctgaggac acggccgtgt attactgtgc gagacgcggt | 300 |
| gggagctact ttgactactg ggccaggga accctggtca ccgtctcttc a | 351 |

<210> SEQ ID NO 80
<211> LENGTH: 330
<212> TYPE: DNA
<213> ORGANISM: Homo sapiens

<400> SEQUENCE: 80

| tcctatgtgc tgactcagcc accctcagcg tctgggaccc ccgggcagag cgtcaccatc | 60 |
| tcttgttctg gaagcaccte caacatcgga agtcattatg tgttctggta ccagcagctc | 120 |
| ccaggaacgg cccccagact cctcatctat aggaatcatc agcggccctc aggggtccct | 180 |
| gaccgactct ctggctccaa gtctggcacc tcagcctccc tggccatcag tgggctccgg | 240 |
| tccgaggatg aggctgatta ttactgtgca gtgtgggatg acaccctgag tggctgggtg | 300 |

```
ttcggcggag ggaccaagct gaccgtccta                                    330
```

<210> SEQ ID NO 81
<211> LENGTH: 360
<212> TYPE: DNA
<213> ORGANISM: Homo sapiens

<400> SEQUENCE: 81

```
caggtgcagc tggtggaatc tgggggaggc ttggtacagc ctggcaggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc aaggggggcc   300
ggcgagggtc gagggcttgg agtggttatg ggccagggaa ccctggtcac cgtctcctca   360
```

<210> SEQ ID NO 82
<211> LENGTH: 327
<212> TYPE: DNA
<213> ORGANISM: Homo sapiens

<400> SEQUENCE: 82

```
caggctgtgg tgacccagga gccctcactg actgtgtccc caggagggac agtcactctc    60
acctgtgctt ccagcactgg agcagtcacc agtggttact ttccaaactg gttccagcag   120
aaacctggac aagcacccag ggcactcatt tatagtacaa ccaacaaaca ctcctggacc   180
cctgcccggt tctcaggctc cctccttggg ggcaaagctg ccctgacact gtcaggtgtg   240
cagcctgagg acgaggctga gtattactgc ctgctctact atggtggtgc tcgggtgttc   300
ggcggaggga ccaagctcac cgtccta                                       327
```

<210> SEQ ID NO 83
<211> LENGTH: 375
<212> TYPE: DNA
<213> ORGANISM: Homo sapiens

<400> SEQUENCE: 83

```
caggtccagc ttgtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccctaacagtggtgg cacaaactat     180
gcacagaagt tcagggcag gtcaccatg accaggaca cgtccatcag cacagcctac      240
atggagctga gcaggctgag atctgacgac acggccgtgt attactgtgc gagaggtacg   300
gtgactagga ttcagggccg ctctctctac ggtatggacg tctggggcca agggaccacg   360
gtcaccgtct cttca                                                   375
```

<210> SEQ ID NO 84
<211> LENGTH: 324
<212> TYPE: DNA
<213> ORGANISM: Homo sapiens

<400> SEQUENCE: 84

```
gaaacgacac tcacgcagtc tccaggcacc ctgtctttgt ctccagggga aggagtcacc    60
ctctcctgca gggccagtca gagtgttaac aggaggtact tagcctggta ccagcagaaa   120
cctggccagg ctcccaggct cctcatctat ggggcatcca gcagggccac tggcatccct   180
gacaggttca gtggcagtgg gtctgggaca gacttcactc tcaccatcag cagactggag   240
```
cctgaagatt ttgcagtgta ttactgtcag cagtatggta gctcacccct cactttcggc    300
ggagggacca aggtggaaat caaa    324

<210> SEQ ID NO 85
<211> LENGTH: 1338
<212> TYPE: DNA
<213> ORGANISM: Homo sapiens

<400> SEQUENCE: 85
caggtgcagc tggtggagtc tgggggaggc ttggtacagc ctggggggtc cctgagactc    60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaatattagg    300
tatagtgcag gctactgggg ccagggaacc ctggtcaccg tctcctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa    1338

<210> SEQ ID NO 86
<211> LENGTH: 648
<212> TYPE: DNA
<213> ORGANISM: Homo sapiens

<400> SEQUENCE: 86
tcctatgtgc tgacacagcc accctcagcg tctgggaccc ccgggcagag ggtcaccatc    60
tcttgttctg gaagcagctc caacatcgga agtaattatg tatactggta ccagcagctc    120
ccaggaacgg ccccccaaact cctcatctat aggaataatc agcggccctc agggtccct    180 gaccgattct ctggctccaa gtctggcacc tcagcctccc tggccatcag tgggctccgg    240
tccgaggatg aggctgatta ttactgtgca gcatgggatg accgcctgag tggttgggtg    300
ttcggcggag ggaccaagct gaccgtccta ggtcagccca aggctgcccc ctcggtcact    360

```
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca acaagtacgc ggccagcagc    540
tatctgagcc tgacgcctga gcagtggaag tcccacagaa gctacagctg ccaggtcacg    600
catgaaggga gcaccgtgga gaagacagtg gcccctacag aatgttca                648
```

<210> SEQ ID NO 87
<211> LENGTH: 446
<212> TYPE: PRT
<213> ORGANISM: Homo sapiens

<400> SEQUENCE: 87

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Arg Tyr Ser Ala Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 88
<211> LENGTH: 216
<212> TYPE: PRT
<213> ORGANISM: Homo sapiens

<400> SEQUENCE: 88

Ser Tyr Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Tyr Val Tyr Trp Tyr Gln Gln Leu Pro Gly Thr Ala Pro Lys Leu Leu
            35                  40                  45
Ile Tyr Arg Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Arg Leu
                85                  90                  95
Ser Gly Trp Val Phe Gly Gly Gly Thr Lys Leu Thr Val Leu Gly Gln
            100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
            195                 200                 205
Thr Val Ala Pro Thr Glu Cys Ser
    210                 215

<210> SEQ ID NO 89
<211> LENGTH: 1341
<212> TYPE: DNA
<213> ORGANISM: Homo sapiens
```

<400> SEQUENCE: 89

```
caggtccagc ttgtacagtc tggggctgag gtgaagaagc ctgggtcctc ggtgaaggtc    60
tcctgcaagg cttctggagg caccttcagc aactatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggccgtgt attactgtgc gagacgcggt   300
gggagctact ttgactactg gggccaggga accctggtca ccgtctcttc agcctccacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagccc aaatcttgt    660
gacaaaactc acacatgccc accgtgccca gcacctgaac tcctgggggg accgtcagtc   720
ttcctcttcc ccccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaaa ccgcggagg agcagtacaa cagcacgtac   900
cgtgtggtca gcgtcctcac cgtcctgcac caggactggc tgaatggcaa ggagtacaag   960
tgcaaggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa a                                            1341
```

<210> SEQ ID NO 90
<211> LENGTH: 648
<212> TYPE: DNA
<213> ORGANISM: Homo sapiens

<400> SEQUENCE: 90

```
tcctatgtgc tgactcagcc accctcagcg tctgggaccc ccgggcagag cgtcaccatc    60
tcttgttctg gaagcacctc caacatcgga agtcattatg tgttctggta ccagcagctc   120
ccaggaacgg cccccagact cctcatctat aggaatcatc agcggccctc agggtccct    180
gaccgactct ctggctccaa gtctggcacc tcagcctccc tggccatcag tgggctccgg   240
tccgaggatg aggctgatta ttactgtgca gtgtgggatg acaccctgag tggctgggtg   300
ttcggcggag ggaccaagct gaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc ggccagcagc   540
tatctgagcc tgacgcctga gcagtggaag tcccacagaa gctacagctg ccaggtcacg   600
catgaaggga gcaccgtgga agagacagtg gcccctacag aatgttca                648
```

<210> SEQ ID NO 91
<211> LENGTH: 447
<212> TYPE: PRT
<213> ORGANISM: Homo sapiens

<400> SEQUENCE: 91

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 92
<211> LENGTH: 216
<212> TYPE: PRT
<213> ORGANISM: Homo sapiens

<400> SEQUENCE: 92

```
Ser Tyr Val Leu Thr Gln Pro Pro Ser Ala Ser Gly Thr Pro Gly Gln
1               5                   10                  15

Ser Val Thr Ile Ser Cys Ser Gly Ser Thr Ser Asn Ile Gly Ser His
            20                  25                  30

Tyr Val Phe Trp Tyr Gln Gln Leu Pro Gly Thr Ala Pro Arg Leu Leu
        35                  40                  45

Ile Tyr Arg Asn His Gln Arg Pro Ser Gly Val Pro Asp Arg Leu Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Asp Thr Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 93
<211> LENGTH: 1350
<212> TYPE: DNA
<213> ORGANISM: Homo sapiens

<400> SEQUENCE: 93

```
caggtgcagc tggtggaatc tgggggaggc ttggtacagc ctggcaggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaggggccc     300
```

```
ggcgagggtc gagggcttgg agtggttatg ggccagggaa ccctggtcac cgtctcctca      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctggggggga     720 ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcggaggga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggatgag     1080
ctgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa                                      1350

<210> SEQ ID NO 94
<211> LENGTH: 645
<212> TYPE: DNA
<213> ORGANISM: Homo sapiens

<400> SEQUENCE: 94
caggctgtgg tgacccagga gccctcactg actgtgtccc caggagggac agtcactctc       60
acctgtgctt ccagcactgg agcagtcacc agtggttact ttccaaactg gttccagcag      120
aaacctggac aagcacccag gcactcatt tatagtacaa ccaacaaaca ctcctggacc       180
cctgcccggt tctcaggctc cctccttggg ggcaaagctg ccctgacact gtcaggtgtg      240
cagcctgaga cgaggctga gtattactgc ctgctctact atggtggtgc tcgggtgttc       300
ggcggaggga ccaagctcac cgtcctaggt cagcccaagg ctgccccctc ggtcactctg      360
ttcccgccct cctctgagga gcttcaagcc aacaaggcca cactggtgtg tctcataagt      420
gacttctacc cgggagccgt gacagtggcc tggaaggcag atagcagccc cgtcaaggcg      480
ggagtggaga ccaccacacc ctccaaacaa agcaacaaca gtacgcggc cagcagctat       540 ctgagcctga cgcctgagca gtggaagtcc cacagaagct acagctgcca ggtcacgcat      600
gaagggagca ccgtggagaa gacagtggcc cctacagaat gttca                      645

<210> SEQ ID NO 95
<211> LENGTH: 450
<212> TYPE: PRT
<213> ORGANISM: Homo sapiens

<400> SEQUENCE: 95

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
```

-continued

```
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Ala Gly Glu Gly Arg Gly Leu Gly Val Val Met Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
```

Gly Lys
    450

<210> SEQ ID NO 96
<211> LENGTH: 215
<212> TYPE: PRT
<213> ORGANISM: Homo sapiens

<400> SEQUENCE: 96

Gln Ala Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Phe Pro Asn Trp Phe Gln Gln Lys Pro Gly Gln Ala Pro Arg Ala
        35                  40                  45

Leu Ile Tyr Ser Thr Thr Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Arg Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 97
<211> LENGTH: 1365
<212> TYPE: DNA
<213> ORGANISM: Homo sapiens

<400> SEQUENCE: 97
caggtccagc ttgtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaacccta acagtggtgg cacaaactat     180
gcacagaagt ttcagggcag ggtcaccatg accagggaca cgtccatcag cacagcctac     240
atggagctga gcaggctgag atctgacgac acggccgtgt attactgtgc gagaggtacg     300
gtgactagga ttcagggccg ctctctctac ggtatggacg tctggggcca agggaccacg     360
gtcaccgtct cttcagcctc caccaagggc ccatcggtct tccccctggc accctcctcc     420
aagagcacct ctgggggcac agcggccctg ggctgcctgg tcaaggacta cttccccgaa     480
ccggtgacgg tgtcgtggaa ctcaggcgcc ctgaccagcg gcgtgcacac cttcccggct     540

```
gtcctacagt cctcaggact ctactccctc agcagcgtgg tgaccgtgcc ctccagcagc      600
ttgggcaccc agacctacat ctgcaacgtg aatcacaagc ccagcaacac caaggtggac      660
aagaaagttg agcccaaatc ttgtgacaaa actcacacat gcccaccgtg cccagcacct      720
gaactcctgg ggggaccgtc agtcttcctc ttccccccaa aacccaagga caccctcatg      780
atctcccgga cccctgaggt cacatgcgtg gtggtggacg tgagccacga agaccctgag      840
gtcaagttca actggtacgt ggacggcgtg gaggtgcata atgccaagac aaagccgcgg      900
gaggagcagt acaacagcac gtaccgtgtg gtcagcgtcc tcaccgtcct gcaccaggac      960
tggctgaatg gcaaggagta caagtgcaag gtctccaaca aagccctccc agcccccatc     1020
gagaaaacca tctccaaagc caaagggcag ccccgagaac cacaggtgta caccctgccc     1080
ccatcccggg atgagctgac caagaaccag gtcagcctga cctgcctggt caaaggcttc     1140
tatcccagcg acatcgccgt ggagtgggag agcaatgggc agccggagaa caactacaag     1200
accacgcctc ccgtgctgga ctccgacggc tccttcttcc tctacagcaa gctcaccgtg     1260
gacaagagca ggtggcagca ggggaacgtc ttctcatgct ccgtgatgca tgaggctctg     1320
cacaaccact acacgcagaa gagcctctcc ctgtctccgg gtaaa                     1365
```

<210> SEQ ID NO 98
<211> LENGTH: 645
<212> TYPE: DNA
<213> ORGANISM: Homo sapiens

<400> SEQUENCE: 98

```
gaaacgacac tcacgcagtc tccaggcacc ctgtctttgt ctccagggga aggagtcacc       60
ctctcctgca gggccagtca gagtgttaac aggaggtact tagcctggta ccagcagaaa      120
cctggccagg ctcccaggct cctcatctat ggggcatcca gcagggccac tggcatccct      180
gacaggttca gtggcagtgg gtctgggaca gacttcactc tcaccatcag cagactggag      240
cctgaagatt ttgcagtgta ttactgtcag cagtatggta gctcacccct cactttcggc      300
ggagggacca aggtggaaat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgt                      645
```

<210> SEQ ID NO 99
<211> LENGTH: 455
<212> TYPE: PRT
<213> ORGANISM: Homo sapiens

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Gly Thr Val Thr Arg Ile Gln Gly Arg Ser Leu Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 100
<211> LENGTH: 215
<212> TYPE: PRT
```

<213> ORGANISM: Homo sapiens

<400> SEQUENCE: 100

Glu Thr Thr Leu Thr Gln Ser Pro Gly Thr Leu Ser Leu Ser Pro Gly
1               5                   10                  15

Glu Gly Val Thr Leu Ser Cys Arg Ala Ser Gln Ser Val Asn Arg Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 101
<211> LENGTH: 5
<212> TYPE: PRT
<213> ORGANISM: Homo sapiens

<400> SEQUENCE: 101

Ser Tyr Ala Ile Ser
1               5

<210> SEQ ID NO 102
<211> LENGTH: 32
<212> TYPE: PRT
<213> ORGANISM: Homo sapiens

<400> SEQUENCE: 102

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 103
<211> LENGTH: 744
<212> TYPE: DNA
<213> ORGANISM: Homo sapiens

<400> SEQUENCE: 103

```
caggtccagc ttgtacagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcaccatg accagggaca cgtccacgag cacagtctac     240
atggagctga gcagcctgag atctgaggac acggccgtgt attactgtgc gagacgcggt     300
gggagctact ttgactactg gggccaaggg accctggtca ccgtctcctc aaagctttca     360
gggagtgcat ccgccccaaa acttgaagaa ggtgaatttt cagaagcacg cgtatcctat     420
gtgctgactc agccaccctc agcgtctggg accccgggc agagcgtcac catctcttgt      480
tctggaagca cctccaacat cggaagtcat tatgtgttct ggtaccagca gctcccagga     540
acggccccca gactcctcat ctataggaat catcagcggc cctcaggggt ccctgaccga     600
ctctctggct ccaagtctgg cacctcagcc tccctggcca tcagtgggct ccggtccgag     660
gatgaggctg attattactg tgcagtgtgg gatgacaccc tgagtggctg ggtgttcggc     720
ggagggacca agctgaccgt ccta                                             744
```

<210> SEQ ID NO 104
<211> LENGTH: 248
<212> TYPE: PRT
<213> ORGANISM: Homo sapiens
<400> SEQUENCE: 104

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Ser Tyr Val Leu Thr Gln
    130                 135                 140

Pro Pro Ser Ala Ser Gly Thr Pro Gly Gln Ser Val Thr Ile Ser Cys
145                 150                 155                 160

Ser Gly Ser Thr Ser Asn Ile Gly Ser His Tyr Val Phe Trp Tyr Gln
                165                 170                 175

Gln Leu Pro Gly Thr Ala Pro Arg Leu Leu Ile Tyr Arg Asn His Gln
            180                 185                 190

Arg Pro Ser Gly Val Pro Asp Arg Leu Ser Gly Ser Lys Ser Gly Thr
        195                 200                 205

Ser Ala Ser Leu Ala Ile Ser Gly Leu Arg Ser Glu Asp Glu Ala Asp
    210                 215                 220

Tyr Tyr Cys Ala Val Trp Asp Asp Thr Leu Ser Gly Trp Val Phe Gly
225                 230                 235                 240
```

```
Gly Gly Thr Lys Leu Thr Val Leu
            245
```

<210> SEQ ID NO 105
<211> LENGTH: 117
<212> TYPE: PRT
<213> ORGANISM: Homo sapiens

<400> SEQUENCE: 105

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser
        115
```

<210> SEQ ID NO 106
<211> LENGTH: 351
<212> TYPE: DNA
<213> ORGANISM: Homo sapiens

<400> SEQUENCE: 106

```
caggtccagc ttgtacagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcaccatg accaggaca cgtccacgag cacagtctac   240
atggagctga gcagcctgag atctgaggac acggccgtgt attactgtgc gagacgcggt   300
gggagctact ttgactactg gggccaaggg accctggtca ccgtctcctc a            351
```

<210> SEQ ID NO 107
<211> LENGTH: 22
<212> TYPE: PRT
<213> ORGANISM: Homo sapiens

<400> SEQUENCE: 107

```
Gln Pro Val Leu Thr Gln Pro Pro Ser Ala Ser Gly Thr Pro Gly Gln
1               5                   10                  15

Arg Val Thr Ile Ser Cys
            20
```

<210> SEQ ID NO 108
<211> LENGTH: 13
<212> TYPE: PRT
<213> ORGANISM: Homo sapiens

<400> SEQUENCE: 108

```
Ser Gly Gly Gly Ser Asn Ile Gly Arg Arg Phe Val Asn
1               5                   10
```

<210> SEQ ID NO 109
<211> LENGTH: 15
<212> TYPE: PRT
<213> ORGANISM: Homo sapiens

<400> SEQUENCE: 109

Trp Tyr Gln Gln Leu Pro Gly Thr Ala Pro Lys Leu Leu Ile Tyr
1               5                   10                  15

<210> SEQ ID NO 110
<211> LENGTH: 7
<212> TYPE: PRT
<213> ORGANISM: Homo sapiens

<400> SEQUENCE: 110

Arg Asn Asn Gln Arg Pro Ser
1               5

<210> SEQ ID NO 111
<211> LENGTH: 32
<212> TYPE: PRT
<213> ORGANISM: Homo sapiens

<400> SEQUENCE: 111

Gly Val Pro Asp Arg Phe Ser Gly Ser Lys Ser Gly Thr Ser Ala Ser
1               5                   10                  15

Leu Val Ile Ser Gly Leu Arg Ser Glu Asp Glu Ala Asp Tyr Tyr Cys
                20                  25                  30

<210> SEQ ID NO 112
<211> LENGTH: 11
<212> TYPE: PRT
<213> ORGANISM: Homo sapiens

<400> SEQUENCE: 112

Ala Ala Trp Asp Asp Ser Leu Ser Gly Trp Val
1               5                   10

<210> SEQ ID NO 113
<211> LENGTH: 744
<212> TYPE: DNA
<213> ORGANISM: Homo sapiens

<400> SEQUENCE: 113
caggtccagc ttgtacagtc tggggctgag gtgaagaagc ctgggtcctc ggtgaaggtc     60
tcctgcaagg cttctggagg caccttcagc aactatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagacgcggt    300
gggagctact ttgactactg gggccaggga accctggtca ccgtctcttc aaagctttca    360
gggagtgcat ccgccccaaa acttgaagaa ggtgaatttt cagaagcacg cgtacagcct    420
gtgctgactc agcccccctc agcgtctggg accccgggc agagggtcac catctcttgt    480
tctggaggcg gatccaacat cggaagaagg tttgtaaact ggtaccagca gctcccagga    540
acggccccca aactcctcat ctataggaat aatcagcggc cctcaggggt ccctgaccga    600
ttctctggct ccaagtctgg cacctcagcc tccctggtca tcagtgggct ccggtccgag    660
gatgaggctg attattactg tgcagcatgg gatgacagcc tgagtggttg ggtgttcggc    720

-continued ggagggacca agctgaccgt ccta                                                744

<210> SEQ ID NO 114
<211> LENGTH: 248
<212> TYPE: PRT
<213> ORGANISM: Homo sapiens

<400> SEQUENCE: 114

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Lys Leu Ser Gly Ser Ala Ser Ala Pro Lys Leu
        115                 120                 125

Glu Glu Gly Glu Phe Ser Glu Ala Arg Val Gln Pro Val Leu Thr Gln
    130                 135                 140

Pro Pro Ser Ala Ser Gly Thr Pro Gly Gln Arg Val Thr Ile Ser Cys
145                 150                 155                 160

Ser Gly Gly Gly Ser Asn Ile Gly Arg Arg Phe Val Asn Trp Tyr Gln
                165                 170                 175

Gln Leu Pro Gly Thr Ala Pro Lys Leu Leu Ile Tyr Arg Asn Asn Gln
            180                 185                 190

Arg Pro Ser Gly Val Pro Asp Arg Phe Ser Gly Ser Lys Ser Gly Thr
        195                 200                 205

Ser Ala Ser Leu Val Ile Ser Gly Leu Arg Ser Glu Asp Glu Ala Asp
    210                 215                 220

Tyr Tyr Cys Ala Ala Trp Asp Asp Ser Leu Ser Gly Trp Val Phe Gly
225                 230                 235                 240

Gly Gly Thr Lys Leu Thr Val Leu
                245

<210> SEQ ID NO 115
<211> LENGTH: 110
<212> TYPE: PRT
<213> ORGANISM: Homo sapiens

<400> SEQUENCE: 115

Gln Pro Val Leu Thr Gln Pro Pro Ser Ala Ser Gly Thr Pro Gly Gln
1               5                   10                  15

Arg Val Thr Ile Ser Cys Ser Gly Gly Gly Ser Asn Ile Gly Arg Arg
            20                  25                  30

Phe Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

```
Gly Ser Lys Ser Gly Thr Ser Ala Ser Leu Val Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu
            100                 105                 110

<210> SEQ ID NO 116
<211> LENGTH: 315
<212> TYPE: DNA
<213> ORGANISM: Homo sapiens

<400> SEQUENCE: 116 cagccccct cagcgtctgg gaccccggg cagagggtca ccatctcttg ttctggaggc      60
ggatccaaca tcggaagaag gtttgtaaac tggtaccagc agctcccagg aacgccccc    120 aaactcctca tctataggaa taatcagcgg ccctcagggg tccctgaccg attctctggc   180
tccaagtctg gcacctcagc ctccctggtc atcagtgggc tccggtccga ggatgaggct   240
gattattact gtgcagcatg ggatgacagc ctgagtggtt gggtgttcgg cggagggacc   300
aagctgaccg tccta                                                    315

<210> SEQ ID NO 117
<211> LENGTH: 1341
<212> TYPE: DNA
<213> ORGANISM: Homo sapiens

<400> SEQUENCE: 117
caggtccagc ttgtacagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tctttggtac agcaaactac   180
gcacagaagt tccagggcag agtcaccatg accaggaca cgtccacgag cacagtctac   240
atggagctga gcagcctgag atctgaggac acggccgtgt attactgtgc gagacgcggt   300
gggagctact ttgactactg gggccaaggg accctggtca ccgtctcctc agcctccacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagcc caaatcttgt    660 gacaaaactc acacatgccc accgtgccca gcacctgaac tcctggggg accgtcagtc   720 ttcctcttcc cccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcgggagg agcagtacaa cagcacgtac   900
cgtgtggtca gcgtcctcac cgtcctgcac caggactggc tgaatggcaa ggagtacaag   960
tgcaaggtct ccaacaaagc cctcccagcc ccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca gagcaggtg gcagcagggg  1260
```

-continued

```
aacgtcttct catgctccgt gatgcatgag gctctgcaca accactacac gcagaagagc   1320
ctctccctgt ctccgggtaa a                                              1341
```

<210> SEQ ID NO 118
<211> LENGTH: 648
<212> TYPE: DNA
<213> ORGANISM: Homo sapiens

<400> SEQUENCE: 118

```
tcctatgtgc tgactcagcc accctcagcg tctgggaccc ccgggcagag cgtcaccatc     60
tcttgttctg gaagcacctc caacatcgga agtcattatg tgttctggta ccagcagctc    120
ccaggaacgg cccccagact cctcatctat aggaatcatc agcggccctc aggggtccct    180
gaccgactct ctggctccaa gtctggcacc tcagcctccc tggccatcag tgggctccgg    240
tccgaggatg aggctgatta ttactgtgca gtgtgggatg acaccctgag tggctgggtg    300
ttcggcggag ggaccaagct gaccgtccta ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac acctccaaa caaagcaaca acaagtacgc ggccagcagc     540
tatctgagcc tgacgcctga gcagtggaag tcccacagaa gctacagctg ccaggtcacg    600
catgaaggga gcaccgtgga gaagacagtg gcccctacag aatgttca                 648
```

<210> SEQ ID NO 119
<211> LENGTH: 447
<212> TYPE: PRT
<213> ORGANISM: Homo sapiens

<400> SEQUENCE: 119

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
                195                 200                 205
Thr Lys Val Asp Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
    355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 120
<211> LENGTH: 216
<212> TYPE: PRT
<213> ORGANISM: Homo sapiens

<400> SEQUENCE: 120

Ser Tyr Val Leu Thr Gln Pro Pro Ser Ala Ser Gly Thr Pro Gly Gln
1               5                   10                  15
Ser Val Thr Ile Ser Cys Ser Gly Ser Thr Ser Asn Ile Gly Ser His
                20                  25                  30
Tyr Val Phe Trp Tyr Gln Gln Leu Pro Gly Thr Ala Pro Arg Leu Leu
            35                  40                  45
Ile Tyr Arg Asn His Gln Arg Pro Ser Gly Val Pro Asp Arg Leu Ser
        50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Val Trp Asp Asp Thr Leu
                85                  90                  95
Ser Gly Trp Val Phe Gly Gly Gly Thr Lys Leu Thr Val Leu Gly Gln
                100                 105                 110
Pro Lys Ala Ala Pro Ser Val Thr Leu Phe Pro Pro Ser Ser Glu Glu
            115                 120                 125
```

```
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Thr Glu Cys Ser
210                 215

<210> SEQ ID NO 121
<211> LENGTH: 1341
<212> TYPE: DNA
<213> ORGANISM: Homo sapiens

<400> SEQUENCE: 121
caggtccagc ttgtacagtc tggggctgag gtgaagaagc ctgggtcctc ggtgaaggtc      60
tcctgcaagg cttctggagg cacctttcagc aactatgcta tcagctgggt gcgacaggcc    120
cctggacaag gcttgagtg gatgggaggg atcatcccta tctttggtac agcaaactac      180
gcacagaagt tccagggcag agtcacgatt accgcgacg aatccacgag cacagcctac      240
atggagctga gcagcctgag atctgaggac acggccgtgt attactgtgc gagacgcggt    300
gggagctact ttgactactg gggccaggga accctggtca ccgtctcttc agcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg   1260
aacgtcttct catgctccgt gatgcatgag gctctgcaca accactacac gcagaagagc   1320
ctctcccctgt ctccgggtaa a                                             1341

<210> SEQ ID NO 122
<211> LENGTH: 648
<212> TYPE: DNA
<213> ORGANISM: Homo sapiens

<400> SEQUENCE: 122
```

-continued

```
cagcctgtgc tgactcagcc cccctcagcg tctgggaccc ccgggcagag ggtcaccatc      60
tcttgttctg gaggcggatc aacatcgga agaaggtttg taaactggta ccagcagctc      120
ccaggaacgg cccccaaact cctcatctat aggaataatc agcggccctc agggtccct      180
gaccgattct ctggctccaa gtctggcacc tcagcctccc tggtcatcag tgggctccgg      240
tccgaggatg aggctgatta ttactgtgca gcatgggatg acagcctgag tggttgggtg      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc      540
tatctgagcc tgacgcctga gcagtggaag tcccacagaa gctacagctg ccaggtcacg      600
catgaaggga gcaccgtgga agacagtgc ccctacag aatgttca                     648
```

<210> SEQ ID NO 123
<211> LENGTH: 447
<212> TYPE: PRT
<213> ORGANISM: Homo sapiens

<400> SEQUENCE: 123

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 124
<211> LENGTH: 216
<212> TYPE: PRT
<213> ORGANISM: Homo sapiens

<400> SEQUENCE: 124

Gln Pro Val Leu Thr Gln Pro Pro Ser Ala Ser Gly Thr Pro Gly Gln
1               5                   10                  15

Arg Val Thr Ile Ser Cys Ser Gly Gly Ser Asn Ile Gly Arg Arg
            20                  25                  30

Phe Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 125
<211> LENGTH: 5
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(5)
<223> OTHER INFORMATION: X = any amino acid

<400> SEQUENCE: 125

Xaa Tyr Ala Xaa Ser
1               5

<210> SEQ ID NO 126
<211> LENGTH: 5
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(1)
<223> OTHER INFORMATION: X= S or N
<220> FEATURE:
<221> NAME/KEY: VARIANT
<222> LOCATION: (4)..(4)
<223> OTHER INFORMATION: X= I or M

<400> SEQUENCE: 126

Xaa Tyr Ala Xaa Ser
1               5

<210> SEQ ID NO 127
<211> LENGTH: 17
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(17)
<223> OTHER INFORMATION: X= any amino acid

<400> SEQUENCE: 127

Xaa Ile Xaa Pro Xaa Xaa Gly Xaa Xaa Asn Tyr Ala Gln Lys Phe Gln
1               5                   10                  15

Gly

<210> SEQ ID NO 128
<211> LENGTH: 17
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(1)
<223> OTHER INFORMATION: X= G or A
<220> FEATURE:
<221> NAME/KEY: VARIANT
<222> LOCATION: (3)..(3)
<223> OTHER INFORMATION: X= I or S

```
<220> FEATURE:
<221> NAME/KEY: VARIANT
<222> LOCATION: (5)..(5)
<223> OTHER INFORMATION: X= I or S
<220> FEATURE:
<221> NAME/KEY: VARIANT
<222> LOCATION: (6)..(6)
<223> OTHER INFORMATION: X= F or G
<220> FEATURE:
<221> NAME/KEY: VARIANT
<222> LOCATION: (8)..(8)
<223> OTHER INFORMATION: X= T or S
<220> FEATURE:
<221> NAME/KEY: VARIANT
<222> LOCATION: (9)..(9)
<223> OTHER INFORMATION: X= A or T

<400> SEQUENCE: 128

Xaa Ile Xaa Pro Xaa Xaa Gly Xaa Xaa Asn Tyr Ala Gln Lys Phe Gln
 1               5                  10                  15

Gly

<210> SEQ ID NO 129
<211> LENGTH: 13
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(13)
<223> OTHER INFORMATION: X = any amino acid

<400> SEQUENCE: 129

Ser Gly Xaa Xaa Ser Asn Ile Gly Xaa Xaa Xaa Val Xaa
 1               5                  10

<210> SEQ ID NO 130
<211> LENGTH: 13
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (3)..(3)
<223> OTHER INFORMATION: X= S or G
<220> FEATURE:
<221> NAME/KEY: VARIANT
<222> LOCATION: (4)..(4)
<223> OTHER INFORMATION: X= T or G
<220> FEATURE:
<221> NAME/KEY: VARIANT
<222> LOCATION: (9)..(9)
<223> OTHER INFORMATION: X= S or R
<220> FEATURE:
<221> NAME/KEY: VARIANT
<222> LOCATION: (10)..(10)
<223> OTHER INFORMATION: X= H or R
<220> FEATURE:
<221> NAME/KEY: VARIANT
<222> LOCATION: (11)..(13)
<223> OTHER INFORMATION: X= Y or F

<400> SEQUENCE: 130

Ser Gly Xaa Xaa Ser Asn Ile Gly Xaa Xaa Xaa Val Xaa
 1               5                  10

<210> SEQ ID NO 131
<211> LENGTH: 7
<212> TYPE: PRT
<213> ORGANISM: artificial
```

```
<220> FEATURE:
<223> OTHER INFORMATION: consensus sequence
<220> FEATURE:
<221> NAME/KEY: VARIANT
<222> LOCATION: (1)..(7)
<223> OTHER INFORMATION: X= any amino acid

<400> SEQUENCE: 131

Arg Asn Xaa Gln Arg Pro Ser
1               5

<210> SEQ ID NO 132
<211> LENGTH: 7
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (3)..(3)
<223> OTHER INFORMATION: X= H or N

<400> SEQUENCE: 132

Arg Asn Xaa Gln Arg Pro Ser
1               5

<210> SEQ ID NO 133
<211> LENGTH: 11
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(11)
<223> OTHER INFORMATION: X= any amino acid

<400> SEQUENCE: 133

Ala Xaa Trp Asp Asp Xaa Leu Ser Gly Trp Tyr
1               5                   10

<210> SEQ ID NO 134
<211> LENGTH: 11
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (2)..(2)
<223> OTHER INFORMATION: X= A or V
<220> FEATURE:
<221> NAME/KEY: VARIANT
<222> LOCATION: (6)..(6)
<223> OTHER INFORMATION: X= S or T

<400> SEQUENCE: 134

Ala Xaa Trp Asp Asp Xaa Leu Ser Gly Trp Tyr
1               5                   10

<210> SEQ ID NO 135
<211> LENGTH: 5
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(5)
<223> OTHER INFORMATION: X= any amino acid
```

<400> SEQUENCE: 135

Xaa Tyr Ala Ile Ser
1               5

<210> SEQ ID NO 136
<211> LENGTH: 5
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(1)
<223> OTHER INFORMATION: X= S or N

<400> SEQUENCE: 136

Xaa Tyr Ala Ile Ser
1               5

<210> SEQ ID NO 137
<211> LENGTH: 11
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(11)
<223> OTHER INFORMATION: X= any amino acid

<400> SEQUENCE: 137

Ala Xaa Trp Asp Asp Xaa Leu Ser Gly Trp Val
1               5                   10

<210> SEQ ID NO 138
<211> LENGTH: 11
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (2)..(2)
<223> OTHER INFORMATION: X= A or V
<220> FEATURE:
<221> NAME/KEY: VARIANT
<222> LOCATION: (6)..(6)
<223> OTHER INFORMATION: X= S or T

<400> SEQUENCE: 138

Ala Xaa Trp Asp Asp Xaa Leu Ser Gly Trp Val
1               5                   10

<210> SEQ ID NO 139
<211> LENGTH: 117
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(117)
<223> OTHER INFORMATION: X = any amino acid

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Xaa Tyr
            20                  25                  30

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Xaa Thr Xaa Asp Xaa Ser Thr Thr Xaa Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Ser Tyr Phe Asp Tyr Trp Gly Gln Gly Thr Leu
                100                 105                 110

Val Thr Val Ser Ser
            115
```

<210> SEQ ID NO 140
<211> LENGTH: 110
<212> TYPE: PRT
<213> ORGANISM: artificial
<220> FEATURE:
<223> OTHER INFORMATION: consensus sequence
<220> FEATURE:
<221> NAME/KEY: VARIANT
<222> LOCATION: (1)..(110)
<223> OTHER INFORMATION: X = any amino acid

<400> SEQUENCE: 140

```
Xaa Xaa Val Leu Thr Gln Pro Pro Ser Ala Ser Gly Thr Pro Gly Gln
1               5                   10                  15

Xaa Val Thr Ile Ser Cys Ser Gly Xaa Xaa Ser Asn Ile Gly Xaa Xaa
            20                  25                  30

Xaa Val Xaa Trp Tyr Gln Gln Leu Pro Gly Thr Ala Pro Xaa Leu Leu
        35                  40                  45

Ile Tyr Arg Asn Xaa Gln Arg Pro Ser Gly Val Pro Asp Arg Xaa Ser
    50                  55                  60

Gly Ser Lys Ser Gly Thr Ser Ala Ser Leu Xaa Ile Ser Gly Leu Arg
65                  70                  75                  80

Ser Glu Asp Glu Ala Asp Tyr Tyr Cys Ala Xaa Trp Asp Asp Xaa Leu
                85                  90                  95

Ser Gly Trp Val Phe Gly Gly Gly Thr Lys Leu Thr Val Leu
                100                 105                 110
```

<210> SEQ ID NO 141
<211> LENGTH: 30
<212> TYPE: PRT
<213> ORGANISM: artificial
<220> FEATURE:
<223> OTHER INFORMATION: sequence from antibody which binds human CCR4

<400> SEQUENCE: 141

```
Glu Val Gln Leu Val Glu Ser Gly Gly Asp Leu Met Lys Pro Gly Gly
1               5                   10                  15

Ser Leu Lys Ile Ser Cys Ala Ala Ser Gly Phe Ile Phe Ser
            20                  25                  30
```

<210> SEQ ID NO 142
<211> LENGTH: 5
<212> TYPE: PRT
<213> ORGANISM: artificial
<220> FEATURE:
<223> OTHER INFORMATION: sequence from antibody which binds human CCR4

<400> SEQUENCE: 142

```
Asn Tyr Gly Met Ser
1               5

<210> SEQ ID NO 143
<211> LENGTH: 14
<212> TYPE: PRT
<213> ORGANISM: artificial
<220> FEATURE:
<223> OTHER INFORMATION: sequence from antibody which binds human CCR4

<400> SEQUENCE: 143

Trp Val Arg Gln Thr Pro Asp Met Arg Leu Glu Trp Val Ala
1               5                   10

<210> SEQ ID NO 144
<211> LENGTH: 17
<212> TYPE: PRT
<213> ORGANISM: artificial
<220> FEATURE:
<223> OTHER INFORMATION: sequence from antibody which binds human CCR4

<400> SEQUENCE: 144

Thr Ile Ser Ser Ala Ser Thr Tyr Ser Tyr Tyr Pro Asp Ser Val Lys
1               5                   10                  15

Gly

<210> SEQ ID NO 145
<211> LENGTH: 30
<212> TYPE: PRT
<213> ORGANISM: artificial
<220> FEATURE:
<223> OTHER INFORMATION: sequence from antibody which binds human CCR4

<400> SEQUENCE: 145

Arg Phe Thr Ile Ser Arg Asp Asn Ala Glu Asn Ser Leu Tyr Leu Gln
1               5                   10                  15

Met Asn Ser Leu Arg Ser Glu Asp Thr Gly Ile Tyr Tyr Cys
            20                  25                  30

<210> SEQ ID NO 146
<211> LENGTH: 12
<212> TYPE: PRT
<213> ORGANISM: artificial
<220> FEATURE:
<223> OTHER INFORMATION: sequence from antibody which binds human CCR4

<400> SEQUENCE: 146

Gly Arg His Ser Asp Gly Asn Phe Ala Phe Gly Tyr
1               5                   10

<210> SEQ ID NO 147
<211> LENGTH: 11
<212> TYPE: PRT
<213> ORGANISM: artificial
<220> FEATURE:
<223> OTHER INFORMATION: sequence from antibody which binds human CCR4

<400> SEQUENCE: 147

Trp Gly Arg Gly Thr Leu Val Thr Val Ser Ser
1               5                   10

<210> SEQ ID NO 148
<211> LENGTH: 21
<212> TYPE: PRT
<213> ORGANISM: artificial
```

<220> FEATURE:
<223> OTHER INFORMATION: sequence from antibody which binds human CCR4

<400> SEQUENCE: 148

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 149
<211> LENGTH: 23
<212> TYPE: PRT
<213> ORGANISM: artificial
<220> FEATURE:
<223> OTHER INFORMATION: sequence from antibody which binds human CCR4

<400> SEQUENCE: 149

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 150
<211> LENGTH: 16
<212> TYPE: PRT
<213> ORGANISM: artificial
<220> FEATURE:
<223> OTHER INFORMATION: sequence from antibody which binds human CCR4

<400> SEQUENCE: 150

Arg Ser Ser Arg Asn Ile Val His Ile Asn Gly Asp Thr Tyr Leu Glu
1               5                   10                  15

<210> SEQ ID NO 151
<211> LENGTH: 15
<212> TYPE: PRT
<213> ORGANISM: artificial
<220> FEATURE:
<223> OTHER INFORMATION: sequence from antibody which binds human CCR4

<400> SEQUENCE: 151

Trp Tyr Leu Gln Arg Pro Gly Gln Ser Pro Lys Leu Leu Ile Tyr
1               5                   10                  15

<210> SEQ ID NO 152
<211> LENGTH: 7
<212> TYPE: PRT
<213> ORGANISM: artificial
<220> FEATURE:
<223> OTHER INFORMATION: sequence from antibody which binds human CCR4

<400> SEQUENCE: 152

Lys Val Ser Asn Arg Phe Ser
1               5

<210> SEQ ID NO 153
<211> LENGTH: 32
<212> TYPE: PRT
<213> ORGANISM: artificial
<220> FEATURE:
<223> OTHER INFORMATION: sequence from antibody which binds human CCR4

<400> SEQUENCE: 153

Gly Val Pro Asp Arg Phe Ser Gly Ser Gly Ser Gly Thr Asp Phe Thr
1               5                   10                  15

```
Leu Lys Ile Ser Arg Val Glu Ala Glu Asp Leu Gly Val Tyr Tyr Cys
            20                  25                  30
```

<210> SEQ ID NO 154
<211> LENGTH: 9
<212> TYPE: PRT
<213> ORGANISM: artificial
<220> FEATURE:
<223> OTHER INFORMATION: sequence from antibody which binds human CCR4

<400> SEQUENCE: 154

```
Phe Gln Gly Ser Leu Leu Pro Trp Thr
1               5
```

<210> SEQ ID NO 155
<211> LENGTH: 10
<212> TYPE: PRT
<213> ORGANISM: artificial
<220> FEATURE:
<223> OTHER INFORMATION: sequence from antibody which binds human CCR4

<400> SEQUENCE: 155

```
Phe Gly Gly Gly Thr Arg Leu Glu Ile Lys
1               5                   10
```

<210> SEQ ID NO 156
<211> LENGTH: 825
<212> TYPE: DNA
<213> ORGANISM: artificial
<220> FEATURE:
<223> OTHER INFORMATION: sequence from antibody which binds human CCR4

<400> SEQUENCE: 156

```
gaggtgcagc tggtcgagag cggaggcgac ctgatgaagc ctggcggcag cctgaagatc      60
agctgcgccg ccagcggctt catcttcagc aactacggca tgagctgggt gcgccagacc     120
cccgacatgc ggctggaatg ggtggcaacc atcagcagcg ccagcaccta cagctactac     180
cccgacagcg tgaagggccg gttcaccatc agccgggaca cgccagaaa cagcctgtat     240
ctgcagatga acagcctgcg gagcgaggac accggcatct actactgcgg cagacacagc     300
gacggcaact tcgccttcgg ctactggggc agaggcaccc tggtgaccgt gtccagcaag     360
ctttccggca gcgcctccgc ccccaagctg gaagagggcg agttcagcga ggcacgcgtg     420
gacgtgctga tgacccagac ccctctgagc ctgcccgtgt ccctgggcga ccaggccagc     480
atcagctgca gaagcagccg gaacatcgtc cacatcaacg gcgacaccta cctggaatgg     540
tatctgcagc ggcctggaca gagccccaag ctgctgatct acaaggtgtc caaccggttc     600
agcggcgtgc ccgacagatt cagcggaagc ggctccggca ccgacttcac cctgaagatc     660
tcccgggtgg aggccgagga cctgggcgtg tactactgct ttcaaggcag cctgctgccc     720
tggaccttcg gcggaggcac acggctggaa atcaaagcgg ccgctggatc cgaacaaaag     780
ctgatctcag aagaagacct aaactcacat caccatcacc atcac                     825
```

<210> SEQ ID NO 157
<211> LENGTH: 275
<212> TYPE: PRT
<213> ORGANISM: artificial
<220> FEATURE:
<223> OTHER INFORMATION: sequence from antibody which binds human CCR4

<400> SEQUENCE: 157

```
Glu Val Gln Leu Val Glu Ser Gly Gly Asp Leu Met Lys Pro Gly Gly
1               5                   10                  15
```

-continued

```
Ser Leu Lys Ile Ser Cys Ala Ala Ser Gly Phe Ile Phe Ser Asn Tyr
            20              25              30

Gly Met Ser Trp Val Arg Gln Thr Pro Asp Met Arg Leu Glu Trp Val
        35              40              45

Ala Thr Ile Ser Ser Ala Ser Thr Tyr Ser Tyr Tyr Pro Asp Ser Val
    50              55              60

Lys Gly Arg Phe Thr Ile Ser Arg Asp Asn Ala Glu Asn Ser Leu Tyr
65              70              75              80

Leu Gln Met Asn Ser Leu Arg Ser Glu Asp Thr Gly Ile Tyr Tyr Cys
                85              90              95

Gly Arg His Ser Asp Gly Asn Phe Ala Phe Gly Tyr Trp Gly Arg Gly
            100             105             110

Thr Leu Val Thr Val Ser Ser Lys Leu Ser Gly Ser Ala Ser Ala Pro
            115             120             125

Lys Leu Glu Glu Gly Glu Phe Ser Glu Ala Arg Val Asp Val Leu Met
    130             135             140

Thr Gln Thr Pro Leu Ser Leu Pro Val Ser Leu Gly Asp Gln Ala Ser
145             150             155             160

Ile Ser Cys Arg Ser Ser Arg Asn Ile Val His Ile Asn Gly Asp Thr
                165             170             175

Tyr Leu Glu Trp Tyr Leu Gln Arg Pro Gly Gln Ser Pro Lys Leu Leu
            180             185             190

Ile Tyr Lys Val Ser Asn Arg Phe Ser Gly Val Pro Asp Arg Phe Ser
        195             200             205

Gly Ser Gly Ser Gly Thr Asp Phe Thr Leu Lys Ile Ser Arg Val Glu
    210             215             220

Ala Glu Asp Leu Gly Val Tyr Tyr Cys Phe Gln Gly Ser Leu Leu Pro
225             230             235             240

Trp Thr Phe Gly Gly Gly Thr Arg Leu Glu Ile Lys Ala Ala Ala Gly
                245             250             255

Ser Glu Gln Lys Leu Ile Ser Glu Glu Asp Leu Asn Ser His His His
            260             265             270

His His His
        275
```